United States Patent [19]
Thalhammer-Reyero

[11] Patent Number: 5,980,096
[45] Date of Patent: Nov. 9, 1999

[54] COMPUTER-BASED SYSTEM, METHODS AND GRAPHICAL INTERFACE FOR INFORMATION STORAGE, MODELING AND STIMULATION OF COMPLEX SYSTEMS

[75] Inventor: Cristina Thalhammer-Reyero, Framingham, Mass.

[73] Assignee: Intertech Ventures, Ltd., Wellesley, Mass.

[21] Appl. No.: 08/373,992

[22] Filed: Jan. 17, 1995

[51] Int. Cl.$^6$ .............................. G06F 9/455; G06F 17/30
[52] U.S. Cl. ........................... 364/578; 364/488; 707/100
[58] Field of Search ................................ 364/578, 222.3, 364/200, 513; 395/500, 800, 159, 157, 155, 600, 54, 161, 375; 382/199

[56] References Cited

U.S. PATENT DOCUMENTS

| | | | |
|---|---|---|---|
| 5,379,366 | 1/1995 | Noyes ........................................ | 395/54 |
| 5,443,791 | 8/1995 | Cathcart et al. ........................... | 422/65 |

FOREIGN PATENT DOCUMENTS

| | | |
|---|---|---|
| 0 367 544 | 5/1990 | European Pat. Off. . |
| 0367544 | 9/1990 | European Pat. Off. . |
| WO 91/06050 | 5/1991 | WIPO . |

OTHER PUBLICATIONS

Nilsson ("Object–Oriented chemical process modeling in Omola", IEEE, 1992 IEEE Symposium on Computer–Aided Control System Design, Mar. 17, 1992, pp. 165–172).
Stevenson et al. ("An intelligent approach to conceptual design automation of chemical processes", IEEE, IEEE Pacific Rim Conference on Communications, Computers and Signal Processing, vol. 2, May 19, 1993, pp. 650–653).
Uckun ("Model–Based Reasoning in Biomedicine," CRC Press, Inc., 1992), Jan. 1992.
Walther et al. ("Object–Oriented Data Management for Distributed Scientific Simulations," Society for Computer Simulation, Western Multi–Conference Proceedings, Jan. 1993).
Basila et al. ("A Model–object based expert system for real–time intelligent control of chemical processes", IEEE Comput. Soc. Press, Proceedings of the Fourteenth Annual International Computer Software and Applications Conference, Oct. 31, 1990, pages.

(List continued on next page.)

*Primary Examiner*—Kevin J. Teska
*Assistant Examiner*—Phallaka Kik

[57] ABSTRACT

The present invention describes an integrated computer-based graphical interface, methods and systems providing a shell environment for development and deployment for graphic information storage and retrieval, visual modeling and dynamic simulation of complex systems. In the current implementation the system comprises libraries of knowledge-based building-blocks that include sets of icons representing chemical processes, the pools of entities that participate in those processes, and the graphical description of those entities, encapsulating both information and mathematical models within the modular components, in the form of tables and in the form of component icons, and a plurality of methods are associated with each of the icons. The models are built by interconnecting each pool to one or several processes, and each process to one or several pools, resulting in complex networks of multidimensional pathways. A number of functions and graphical interfaces can be selected from the menus associated with each icon, to extract in various forms the information contained in the models build with those building blocks. Those functions include the creation of interactive networks of pathways, graphic selection of complex predefined queries based on the relative position of pools of entities in the pathways, the role that the pools play in the processes, and the structural components of the entities of those pools, and quantitative simulations. The system integrates inferential control with quantitative and semi-quantitative simulation methods, and provides a variety of alternatives to deal with complex dynamic systems and with incomplete and constantly evolving information and data.

76 Claims, 31 Drawing Sheets

OTHER PUBLICATIONS

Cinar et al. ("Reliable process control with a supervisory expert system", IEEE, Proceedings of the 29th IEEE Conference on Decision and Control, vol. 3, Dec. 5, 1990, pp. 1543–1544).

Bar et al. ("A Knowledge–based Flowsheet–oriented User Interface for a Dynamic Process Simulator", Computers & Chemical Engineering, vol. 14, No. 11, Jan. 11, 1990, pp. 1275–1280).

Biegl ("Knowledge–based Generation of Process Simulation Models", IEEE, Proceedings of the 19th Annual Southeastern Symposium on System Theory, Jan. 1, 1987, pp. 139–143).

Widman et al. ("Semi–Quantitative 'Close–Enough' Systems Dynamics Models: An Alternative to Qualitative Simulation," Artificial Intelligence, Simulation and Modeling, 1989), Jan. 1989.

Karp, P.D., et al., "EcoCyc User's Guide, Version 2.4," Nikos Drakos, Computer Based Learning Unit, University of Leeds, Oct. 17, 1995).

Pahwa et al. (Automatic database navigation: towards a high level user interface, IEEE, Proceedings of the 4th International Conference on Entity–Relationship Approach, Jan. 1, 1985, pp. 36–43).

Kravanja et al. ("PROSYN–an automated topology and parameter process synthesizer", Computers & Chemical Engineering, Jan. 1, 1993, 587–594).

Karp, P.D., et al., "EcoCyc: Encyclopedia of *E. Coli* Genes and Metabolism," http://www.sri.com/ecocyc/ecocyc.htme Oct. 1995.

Karp, P.D., et al., "Guide to the EcoCyc Schema," *Artificial Intelligence Center, SRI International,* 333 Ravenswood Ave., Menlo Park, CA 94025, pkarp@ai.sri.com (Sep. 1995).

Coppella, S.J., "A Mathematical Description of Recombinant Yeast," *Biotechnology and Bioengineering,* vol. 35:356–374 (1990).

Karp, P.D., et al., "Representations of Metabolic Knowledge: Pathways," Proceedings Second International Conference on Intelligent Systems for Molecular Biology, Menlo Park, CA, AAAI Press (1994).

Karp, P.D., et al., "Automated Drawing of Metabolic Pathways," Proceedings of the Third International Conference on Bioinformatics and Genome Research, H. Lim, C. Cantor and R. Bobbins eds. (Sep. 1994).

Karp, P.D., et al., "Representing, Analyzing, and Synthesizing Biochemical Pathways," *IEEE Expert,* pp. 1–27 (May 1994).

Reddy, V.N., et al., "Qualitative Analysis of Biochemical Reaction Systems," Dept. of Chemical Engineering, Northwestern University, Evanston, IL, pp. 1–9 (No date given).

Reddy, V.N., et al., "Petri Net Representations in Metabolic Pathways," *Proceedings ISMB–93, AAAI Press,* pp. 1–9 (1993).

Kazic, T., "Reasoning About Biochemical Compounds and Processes," Second International Conference on Bioinformatics, Supercomputing and the Human Genome Conference, Proceedings, pp. 1–17 (1993).

Ball, S.S., et al., "Senex: Symbolic Representation in Molecular Pathology," Department of Pathology, University of Mississippi, Jackson, MS, and Department of Neurology, Thomas Jefferson University, Philadelphia, PA (No date given).

Ball, S.S., et al., "Senex: Knowledge Representation in Molecular Pathology," Department of Pathology, University of Mississippi, Alpers Neuropathology Laboratory, Thomas Jefferson University, Philadelphia, PA (No date given).

Widman, L.E., "Semi–Quantitative "Close–Enough" Systems Dynamics Models: An alternative to Qualitative Simulation," *Artificial Intelligence Simulation and Modeling,* pp. 159–189 (1989).

Walther, S., et al., "Object–Oriented Data Management for Distributed Scientific Simulations," Society for Computer Simulation, Western Multiconference, Proceedings (Jan. 1993).

Uckun, S., "Model–Based Reasoning in Biomedicine," *Critical Reviews in Biomedical Engineering 19(4)*:261–292 (1992).

Kocabas, S., "Computational Models of Scientific Discovery," *The Knowledge Engineering Review,* 6(4):259–305 (No date given).

Kiezulas, C.J., et al., "Entwicklung von Expertensystemen," *XP000268407, Künstliche Intelligenz, Elektronik,* 40(22):122–123 128–134 (Oct. 1991).

FIGURE 16

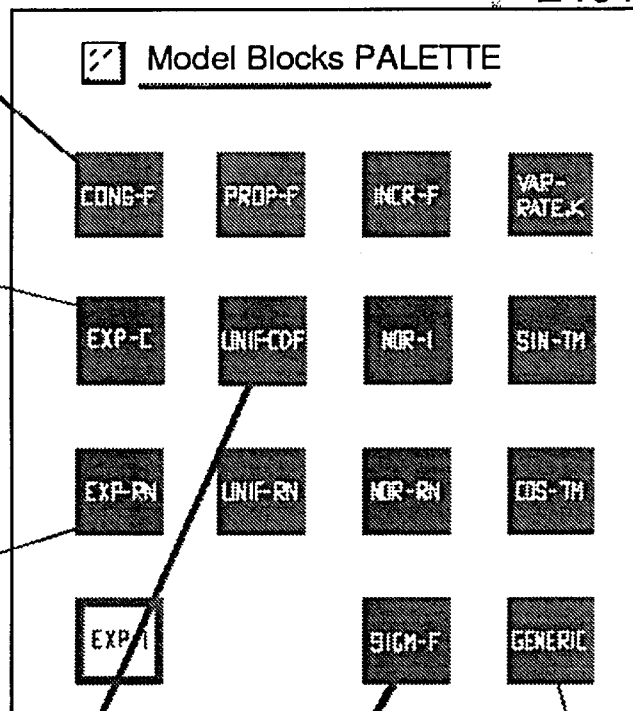

2402 — a constant.f

| Names | none |
|---|---|
| Label | "" |
| Model description | "" |
| Output 1 | 1.0e-19 |
| Constant | 1.0 |

2403 — an exp.c.pdf

| Names | none |
|---|---|
| Label | "" |
| Model description | "" |
| Output 1 | 1.0e-19 |
| Mean | 0.0 |
| X val | none |

2404 — an exp.rn.pdf

| Names | none |
|---|---|
| Label | "" |
| Model description | "" |
| Output 1 | 1.0e-19 |
| Mean | 0.0 |
| Min val | 1.0e-5 |
| Max val | 1.0 |

2405 — a unif.c.pdf

| Names | none |
|---|---|
| Label | "" |
| Model description | "" |
| Output 1 | 1.0e-19 |
| Min val | 1.0e-5 |
| Max val | 1.0 |
| X val | **** |

2406 — a sigmoid.f

| Names | none |
|---|---|
| Label | "" |
| Model description | "" |
| Output 1 | 1.0e-19 |
| Input 1 | none |
| Gain | 1.0 |
| Bias | 0.0 |

2407 — a generic.model.block.f

| Names | none |
|---|---|
| Label | "" |
| Model description | "" |
| Output 1 | 1.0e-19 |
| P.1 | 0.0 |
| P.2 | none |
| P.3 | 1.0 |
| P.4 | 0.0 |
| P.5 | none |
| V.1 | "" |
| V.2 | "" |
| V.3 | 1.0e-19 |
| V.4 | none |
| V.5 | 1.0 |

EXAMPLE OF DYNAMICALLY CREATED DISPLAY OF INTERCONNECTED PATHWAYS OF PROCESSES

EXAMPLE OF DYNAMICALLY
CREATED DISPLAY OF
PATHWAYS OF ALTERNATING
RESERVOIRS AND PROCESSES

COMPUTER-BASED SYSTEM, METHODS AND GRAPHICAL INTERFACE FOR INFORMATION STORAGE, MODELING AND STIMULATION OF COMPLEX SYSTEMS

NOTES

The body of the present application has sections that may contain some discussion of prior art teachings, intermingled with discussion of innovative and specific discussion of the best mode to use that prior art in this invention as presently contemplated. To describe the preferred embodiments, it is necessary to include in the discussion the capabilities offered by the shell used as development and deployment framework for this invention (hereafter referred to as "the Shell"). The applicant specifically notes that statements made in any of those sections do not necessarily delimit the various inventions claimed in the present application, but rather are included to facilitate the process to explaining how the workings of an existing set of tools is used to illustrate the preferred embodiments of the new tools and applications claimed in the claims section. The currently preferred embodiment of this invention, as described in the present application, is based on the definitions of a particular Shell: Gensym Corp.'s G2 Expert System. There are several other attributes that relate to the Shell's built-in performance and formatting capabilities, which are not shown in those examples. Some information included within the body of this application was extracted from various sources describing the characteristics of G2, including user manuals, and some of this material is subject to copyright protection.

III. BACKGROUND OF THE INVENTION

A. Field of the Invention

The present invention relates to computer-based interface, methods and systems for graphic information storage and retrieval, visual modeling and dynamic simulation of complex systems, that includes in general sets of processes and their participants, and more specifically chemical processes, and which result in complex networks of multidimensional pathways, encapsulating both information and mathematical models within modular components, and integrates inferential control with quantitative and semiquantitative simulation methods, providing a variety of alternatives to deal with complex dynamic systems.

B. Related Applications

This application is related to the patent entitled "Computer-Based System, Methods and Graphical Interface for Information Storage, Modeling and Simulation of Complex Systems Organized in Discrete Compartments in Time and Space" invented by the same inventor and filed with this application in the United States Patent and Trademark Office. This application is incorporated here by this reference.

C. Description of the Prior Art

1. Computer-Aided Physiological and Molecular Modeling and Artificial Intelligence in Molecular Biology a) Most computer-aided physiological and molecular modeling approaches have resulted in computer models of physiological function are numerical mathematical models that relate the physiological variables using empirically determined parameters. Those models, which can become quite complex, aim at modeling the overall system.

b) Both molecular biology and medicine have been fields of previous activity in the application of artificial intelligence (AI). In molecular biology, although there were some early systems such as Molgen and Dendral, the activity has intensified recently as a consequence of the explosion in new technologies and the derived data, mostly related with the Human Genome project and the handling of large amounts of sequence data generated, relating to both DNA and proteins. There has also been an increased interest in computer methodologies in 3D structural models of molecular interactions. As an example, the topics covered in symposia such as the recent Second International Conference on Intelligent Systems for Molecular Biology, 1994, Stanford University, CA. (see the reference to its Proceedings for a current state of the art, which here included by reference) cover areas as wide as machine learning, automatic generation of representations, inductive and deductive reasoning, case-based reasoning, computational linguistics applied to both text and DNA or protein sequences, constraint propagation, bayesian inference, neural networks, qualitative modeling, expert systems, object-oriented databases, simulation, knowledge acquisition technologies, and knowledge base maintenance. In those and many other published papers, there are as many objectives and as many approaches as there are teams. The projects, however, are in most cases of academic interest, and in few cases it has been attempted to develop finish products for commercial distribution. Here, only two projects will be mentioned that have some common objectives with the system that is the object of this invention. Discussions over other previous approaches are also included in those references.

c) The Molgen group at the Stanford University's Knowledge Systems Laboratory has been studying for several years scientific theory formation in the domain of molecular biology, as reported in by Karp, P. D. and Friedland, P. (included here by reference). This project relates to the system object of this invention in that both "are concerned with biochemical systems containing populations of interacting molecules . . . in which the form of knowledge available . . . varies widely in precision from quantitative to qualitative", as those authors write. However, the domain of Molgen is a small subset of the domain of the system object of this invention. Within the Molgen group, the Ph.D. dissertation of P. D. Karp (included here by reference), focused on applying that research to the design of a computer-assisted reasoning and hypothesis formation system. In the process, the author "developed a qualitative biochemistry for representing theories of molecular biology", as he summarizes in an abstract with the same name the AI Magazine, Winter 1990, pp 9–10. In particular, he developed three representation models to deal with the biochemical pathways related to the tryptophan operon in bacteria, called declarative device models, each having different capabilities and using different qualitative reasoning approaches. Only chapter 3, dealing with those models, have relevance in the context of this invention. The first model uses IntelliCorp's KEE (a commercial product) frames to describe biological objects and KEE rules to describe chemical reactions between the objects, which he recognizes to have serious limitations because is not able to represent much of the knowledge available to biologists. The objective of the second model, which is an extension of the fixed state-variable network of deKleer and Brown, is to predict reaction rates in a given reaction network, incorporating a combination of quantitative and qualitative reasoning about state-variables and their interdependencies. The drawbacks are that this model is not able to incorporate a description of the biological objects that participate in the reactions, and in addition it does not have a temporal reasoning capabilities, representing just an static description of the state variables and their relationships. The third model, called GENSIM and used for both prediction and hypothesis formation, is an extension of model 1, and is composed of three knowledge bases or taxonomical hierarchies of classes of a) biological objects that participate in the trp-operon gene-regulation system, b) descriptions of the biological reactions that can occur between those objects, and c) experiments with instances of those classes of objects. The GENSIM program predicts experimental outcomes by determining which reactions occur between the objects in one experiment, that create new objects that cause new reactions. GENSIM is also further used in conjunction with the HYPGENE hypothesis-formation program that will not be further discussed here. Characteristics of the GENSIM program that may be relevant, although different, for the system of this invention are:

- chemical objects are homogeneous populations of molecules, objects can be decomposed into their component parts, and identical objects synthesized during a simulation are merged;
- chemical processes are frames arranged in an inheritance class hierarchy, which represent reactions between those populations as probabilistic events with two subpopulations, one that participate in the reaction and one that does not;
- restrictions are specified in the form of preconditions for chemical reactions to happen.
- those Forbus-style processes can create objects and manipulate their properties, but cannot reason about quantitative state variables such as Quantities. In his words, "processes are described as KEE units . . . specify actions that will be taken if certain conditions hold", and in that sense are like production-rules;
- temporal reasoning is not available, resulting again in static representations and simulating only behavior in very short time intervals.

2. Knowledge-Based and Model-Based System Shells a) Several knowledge-based system shells have been used as tools allowing fast development of domain-specific applications. HERACLES, one of the first shells was developed by generalizing and separating the domain specific knowledge of NEOMYCIN from the underlying expert system methodology (see W. J. Clancey, "From GUIDON to NEOMYCIN and HERACLES in Twenty Short Lessons: ORN Final Report 1979–1985", in AI Magazine, August 1986, p.40–60, August 1986).

b) A knowledge-based system interprets data using knowledge added to the system by a human domain expert. This knowledge-base may contain diverse forms of knowledge, represented at each end by: a) shallow knowledge or heuristics, such as human experience and interpretations or rules-of thumb; and b) deep knowledge about the system behavior and interactions. The systems that mainly based in the first type of knowledge are in general referred to as knowledge-based expert systems, and the logic is represented in the form of production rules. In the more advanced real-time expert systems, inferencing techniques are usually data-driven using forward chaining, but can also employ backward chaining for goal-driven tasks and for gathering data. The inference engine searches for and executes relevant rules, which are separate from the inference engine and therefore, the representation is intrinsically declarative.

c) Model-based systems can be derived from empirical models based on regression of data or from first-principle relationships between the variables. When sufficient information to model a process—or part of it—is available, a more precise and compact system can be built.

d) Object-oriented expert systems allow a powerful knowledge representation of physical entities and conceptual entities. In those systems, data and behavior may be unified in the class hierarchy. Each class has a template that defines the types of attributes characteristic of that class and distinguish it from another types of objects. Manipulation and retrieval of the values of the data structures may be performed through methods attached to a object's class. The structure of the object system, typically hierarchical, maintains associations among facts and relations between objects.

e) There is a number of commercially available shells and toolkits that facilitate the development of domain-specific knowledge-based applications. Of those, real-time expert-system shells offer capabilities for reasoning on the behavior of data over time. Each of the real-time object-oriented shells from various vendors offers its set of advantages, and each follows a different approach, such as compiled versus interpretative, and offers a different level of graphic sophistication. The specific shell currently selected for the implementation of this invention is Gensym Corporation's G2 Version 3.0 system, which is designed for complex and large on-line applications where large number of variables can be monitored concurrently. It is able to reason about time, to execute both time-triggered and event-triggered actions and invocations, to combine heuristic and procedural reasoning, dynamic simulation, user interface, database interface capabilities, and other facilities that allow the knowledge engineer to concentrate on the representation and incorporation of domain-specific knowledge to create domain-specific applications.

f) G2 provides a built-in inference engine, a simulator, pre-built libraries of functions and actions, developer and user-interfaces, and the management of their seamless interrelations. A built-in inspect facility permits users to search for, locate, and edit various types of knowledge. The text editor interactively guides the expert in entering and editing knowledge. Among G2's Inference Engine capabilities are: a) a focus mechanism with meta-knowledge determines which knowledge structures to invoke, and allows concurrent focus and asynchronous events; b) data structures are tagged with time-stamp and validity intervals which are considered in all inferences and calculations, taking care of truth maintenance; and c) intrinsic to G2's tasks are managed by the real-time scheduler. Task prioritization, asynchronous concurrent operations, and real-time task scheduling are therefore automatically provided by this shell. G2 also provides a graphic user interface builder, which may be used to create graphic user interfaces which are language independent and allow to display information using colors, pictures and animation. Dynamic meters, graphics, and charts can be defined for interactive follow-up of the simulation. It also has debugger, inspect and describe facilities. The knowledge bases can be saved as separated modules as ASCII files. The graphic views are also saved in an ASCII format, and can be shared with networked remote CPUs or terminals equipped with X Windows server software.

IV. SUMMARY OF THE PRESENT INVENTION

A. The present invention in its broadest form is directed to a computer-based interface, methods and systems for graphic information storage and retrieval, visual modeling and dynamic simulation of complex systems. It provides a graphical interface and associated methods to develop domain-specific applications that can be used as a shell environment for both development and deployment of domain-specific visual databases, modeling and simulation applications.

B. In the current implementation of this invention the system is directed to a domain-specific, application-independent, knowledge-based development shell and deployment system capable of being used as an environment to construct specific visual databases, and modeling and simulation applications in the chemical and biochemical domains. The system comprises sets of knowledge-based building-blocks, hereinafter called libraries including tools arranged in hierarchies, that includes sets of chemical processes and their participants, and which result in complex networks of multidimensional pathways, encapsulating both information and mathematical models within modular components, and integrates inferential control with quantitative and semi-quantitative simulation methods, providing a variety of alternatives to deal with complex dynamic systems. A plurality of methods is related to and associated with those tools.

C. It is an object of this invention to provide a knowledge-base having a well defined structure for representing knowledge about chemical and biochemical entities, processes, pathways and interacting networks of pathways. It is a further object of the present invention to provide a system, graphical interface and associated methods capable of dealing with incomplete and constantly evolving information and data. The data structures and domain-specific knowledge-base are independent of application-specific use, allowing the application-specific knowledge-bases to expand without affecting the basic operation of the system. The structure of the domain-specific knowledge-base serves also as the infrastructure provided to store additional information about new tools and models.

D. This invention and its various embodiments describe systems, graphical interfaces and associated methods that combine with declarative object structures, with qualitative and quantitative modeling tools, and artificial intelligence, to model complex systems. Further important teachings of this invention comprise: a) the representation and storage of information and data about networks of interacting entities, together with information about the physical description of those entities, and the processes in which they participate, into a usable knowledge form; b) the graphical interface and associated methods to store the available information and data about those complex models into modular, modifiable, expandable and reusable knowledge structures; c) the graphical interface and associated methods for using the stored of information and data about interacting entities and the processes in which interact to dynamically generate and display at run-time organized cross-talking pathways, which may branch, merge, or loop forward or backward, and which provide interactive access to each of their components; d) the representation and storage of information and data about of the complex systems in graphic models that make use of several layers of encapsulation, which allows to hide the details in several layers and allows the user to display only the level of detail desired; e) the graphical interface and associated methods to perform queries that refer to either the structural composition of the entities involved, the position in the pathways downstream or upstream of the pool of entities taken as reference, the role of those pools of entities in the processes in which they participate, or any combination of the previous three; and e) the graphical interface and associated methods to dynamically simulate their continuous interactions and modifications.

E. More specifically, among the major teachings of this invention in its current embodiments are systems, graphical interface and associated methods used to:

1. interpret, represent and describe the attributes, characteristics and composition of chemical and biochemical entities, such as those participating in chemical, biochemical, cellular, physiological, pathophysiological or pharmacological reactions (hereinafter called chemical entities), as well as the parallel and serial sets of processes in which they interact and by which they are regulated;

2. compile such information and data and to store them in a more compact knowledge form, to construct a library of basic and reusable building blocks;

3. interactively integrate sets of building blocks, using the basic paradigm of "Clone, Connect and Configure", into more complex knowledge structures, constructing dynamic models of the behavior of those chemical entities and processes;

4. interactively integrate those simple models into more complex models that result in multidimensional networks of interacting pathways, which in turn can be reused as building blocks for even more complex models;

5. programmatically integrate those models into multidimensional networks of interacting pathways, including branching and merging of pathways, cross-talk between pathways that share elements, and feed-back and forward loops; and 6. dynamically simulate, optionally using the encapsulated absolute-valued or scaled-valued parameters and variables, the kinetic interactions represented in selected pathways, as defined within those more or less complex models.

F. More specifically, such entities, pools of such entities and the processes in which they participate, such as the synthesis, degradation, modifications, interactions and translocation processes, are visually represented by icons that encapsulate object-oriented knowledge-structures, hereinafter referred to as bioObjects. These bioObjects are composite objects that encapsulate a set of attributes, such as other component objects, attributes with set values, and variables and parameters which values can change dynamically at run time. A variety of methods, comprising rules, procedures, functions, relations, equations and qualitative and quantitative models, which are themselves object-oriented and are hereinafter referred to as methods, are either specified in a generic form, which apply to a class or group of classes of bioObjects or their attributes, or in a specific form, which apply to a particular instance of a tool or attribute.

G. Each of the building blocks used in the system of this invention is represented by an icon, and the knowledge stored in those bioObjects is encapsulated in three forms within different types of associated structures:

1. An Attribute Table contains information and data that describe the characteristics of that object in many different ways. It contains a set of slots that vary for different classes of objects. Each slot may have a simple value of the types integer, float, symbol, text, or truth-value, or it may contain parameters, variables or other objects, each with its specific Attribute Table. The values of parameters and variables are computed by generic formulas that apply to all the instances of a class. The values of a particular instance of a variable may also be computed by a formula defined in its Attribute Table. Simulated formulas may contain algebraic, difference and differential equations.

2. A Menu with various options which upon selection perform specific tasks related to that particular object. The options available vary for different classes of objects and, within each class, depend on the operation mode.

3. An optional Subworkspace that contains a set of other objects and/or other bioObjects, with their corresponding sets of associated structures.

4. With this architecture, interactive tasks are defined within the Menu, and biological information and data is encapsulated in two formats, either in the form of a table or visually by icons.

H. The current embodiment of this invention is based on an object-oriented, real-time development environment recently developed and used for very different types of industrial applications, which provides predefined, domain-independent, methods mapped to generic object-structures. The embodiments described herein comprise a layer of new domain-specific knowledge-structures, which contain chemical- and biochemical-expert knowledge and can be operated upon by the innovative graphical interface and associated methods here described, built on top of the capabilities provided and supervised by the Shell. The supervisor, the simulator, the inference engine, and process control units provide by the Shell, and the domain-specific knowledge-based system that is object of this invention can run in a single or in multiple networked computer systems, using a client-server approach.

I. It is also an object of this invention to provide a system that is easily and efficiently maintained, modified and expandable. Biological knowledge is represented in a declarative from, which is much easy to understand that knowledge embodied within a procedure of the more standard programming languages. A declarative language separates a domain-specific knowledge statement from the procedure about how that knowledge is used by the program. It also facilitated modularity by allowing to delete, modify or create part of the system without affecting the operation of the rest. The result is a system that is easy to maintain and modify. The knowledge can also be extended and reused under different contexts, and in different new applications. With the bioObjects provided, non-programmers can maintain, modify and extend the knowledge themselves. User configuration of the bioObjects in the system of this invention consists primarily of connecting graphical objects and filling out tables, which means that the building of models requires no programming other than the use of this graphical and natural languages.

J. The system of this invention combines a number of programming paradigms. The graphical interface and associated methods described herein define chemical and biochemical entities and processes as constrained objects represented as graphical structures or icons. These objects and their highly constrained relations and behaviors are defined by editing predefined, constrained and natural language templates, attached to the icons that represent instances of predefined classes of items. The templates are part of a standardized developers' interface, and the definitions entered can be revised and the knowledge modified at any time, without interference with the inference method. A characteristic of the system of this invention is that the chemical and biochemical knowledge is made explicit and open to direct manipulation and modification by the knowledge engineer or by the modeler, by using an interpreted approach rather than the more commonly used compiled approach. The domain-specific knowledge is represented in a declarative form, within the graphic knowledge-structures, independent from the procedural knowledge contained in the methods, which contain the code able to interpret the data entered in the knowledge-structures. The rules typical of an expert system, used by the inference engine for forward- and backward-chaining, and the more structured procedures, are transparent to the end user. In that way, the modelers do not have to deal with the restricted syntax of rules or procedures. Rather, they deal directly with icons representing items that already include rules and procedures in their definition frames, and knowledge engineers are not required. Both the developer's and user's input is translated automatically by the the Shell into an operational knowledge-based system. The result is a system that is easy to maintain and modify. With the provided by this system, non-programmers can maintain and modify the knowledge themselves.

K. The present system comprises several types of reasoning:

1. taxonomic reasoning, such as that used in the classification of entities and processes;
2. numeric algorithms,
3. graphic and connectivity reasoning, such as that used when referring to iconic objects and their connections;
4. default reasoning, such as that provided by the default values of variables and parameters, which are based either on available knowledge, informed assumptions, or guesses, and which are used in the absence of overriding information;
5. data-driven reasoning, which is propagated forward;
6. goal-driven reasoning, which is propagated backward;
7. event-driven reasoning, which propagates when a precondition is satisfied;
8. time-driven reasoning, which propagates when the specified time interval elapses; and
9. constraint propagation throughout the network.

L. It is a further object of the present invention to provide a mechanism for interactive communication between the program and the user, including prompting alert messages or requesting entry of user-defined values when any data or its source is missing. To access the knowledge implicit in the knowledge base, and to enter or modify explicit domain-specific knowledge, the present system comprises of a user interface that includes panels, user controls, messages and displays, which support communications and control activities.

M. It is a further object of the present invention to provide a mechanism for monitoring the system behavior and to provide explanations. The present system includes a graphical interface and associated methods that are used for development or for run-time operation of the system, but which are hidden from other users, and tools specifically available to developers, modelers, or other users. The user interface may be used by both developers and other users of the system of this invention, although part of it can be made accessible only to developers, to maintain integrity and proprietary control, while other parts may be made available only to modelers, to preserve the integrity of the models, and to prevent other users from modifying the system. Further, it is possible to restrict the simulation capabilities only to users that have acquired additional rights.

N. It is another object of the present invention to provide a system to enable the development of large knowledge-bases, computer models and simulations of very complex dynamic chemical and biochemical systems by non-programmers but domain-experts that are able to understand that complex knowledge, but who do not have expertise in the computer sciences. Major teachings of this invention are the graphical interface and associated methods of a system that allow the experts, such as chemists, biochemists and molecular or cell biologists, to encode modeling and simulation knowledge in the sets of icons connected in schematics. The overall chemical and biochemical knowledge-base is incrementally built as modules. Each of the modules can be maintained in a separate CPU, and all are seamless integrated by the Shell's supervisor.

O. Other teachings of this invention are related to methods to model changes in the states of chemical entities by defining each discrete state as a separate chemical entity, and by simulating the dynamic changes not as single entities, but rather as transfer of units from a pool of one state/entity, a reactant, to a pool another state/entity, a product. For that purpose, a class of objects is defined that represents a pool of entities with the same average attributes, which is characterized by a pool concentration, or other quantity, to describe its size. With this approach, when chemical entities change their structural and functional state they in fact are transferred from the pool of bioEntities in the original state to the pool of bioEntities in the new state.

P. The models here described can also be viewed as composed of two major components:

1. The functional structure of the system in consideration, which is constructed using experimentally obtained qualitative information, such as the identification of the chemical entities involved, the knowledge about their structural and functional characteristics, and about the relationships and qualitative interactions between those entities. This information is mapped into the knowledge structures represented by the different classes of bioObjects, and into the connections and relations that connect and relate these knowledge structures. The graphical environment merges data and information flow with sequential control, and the system supports both arithmetic and symbolic expressions.

2. The mathematical component is represented by a set of model differential and algebraic equations that define the system's variables and describe their behavior, together with the set of associated parameters that control the behavior of the variables and the system as a whole. The model can be then view as a set of embedded block diagram representations of the underlying equations that can be used to ask what if questions, and for dynamic numerical simulation and prediction of the effects of perturbations on the system.

3. The combination of both components allows the use of the same model for both symbolic and numerical simulations and predictions, and to reason about the origin and reasons of the outcome.

Q. The function of the present system is that of an interactive aid that allows users to integrate their experimental data with the knowledge derived from the work of thousands of other investigators, which can be integrated into this system using the bioObjects provided. Variations in multiple experimental parameters can be rapidly analyzed, either sequentially or simultaneously. Experimental conditions in silico that produce results of interest can then be tested either in vitro or in vivo. If the results coincide, the results validate the model. If they differ, the investigator can modify either the parameters or the model assumptions to meet the experimental data. By iterating this process, a level of confidence on the models is built and new hypothesis can be tested.

R. The present system allows the encoding and integration of large amounts of information and data in a very efficient manner. The bioObjects and methods included in the subject invention can be used in a variety of applications in different domains.

S. The accuracy and validity of knowledge-based systems correlates not only with the quality of the knowledge available to the developers but also with their ability to understand, interpret and represent that knowledge. Because of the complex interrelationships driving the processes in molecular cell biology, it is an objective of this invention to create an environment to allow such domain experts to directly enter that knowledge, and to create and modify models as needed based on experimentation, without the need of knowledge engineers as intermediaries. To provide the many options for knowledge representation required by those systems, the preferred embodiment of this invention presents a hybrid dynamic expert system that combines: a) the inheritance and encapsulation features characteristic of an object-oriented modeling approach, b) the procedural and rule-based inference capability of an expert system, and c) a model-based simulation capability. In the preferred embodiment of this invention, the knowledge-base is comprised of different types of knowledge, such as: facts and descriptions, associations and relations, interactions, conditions and constraints, rules and procedures, and symbolic and numeric equations and models. Logic is represented not only in the form of generic production rules encoded using a structured natural language, but also as defined within the bioObjects that incorporate specific rules. The combination of icon based graphical and intrinsically declarative representation allows development of models by biology experts who are not familiar with software programming.

T. Depending on the amount and type of information and data available about the system to be modeled, and the nature and size of the models to be developed, the present system's generated simulations may be quantitative or semi-quantitative. With well-known chemical reaction systems, or limited metabolic pathways, the simulation may be considered as close to quantitative. However, since in most biochemical systems both qualitative and quantitative information is incomplete, it may be difficult to simulate with accuracy such biochemical systems. However, the combination of quantitative and semi-quantitative methods integrated in the present system allows to gain insight from what-if simulations about the degree, direction and rate of change in the model variables. The simulation is not expected to predict with accuracy the absolute values of the variables. The present system is expected to be used by scientists as a new form of interactive research tool to integrate information and data into knowledge structures which characteristics and behavior can be modified and its parameters adjusted as new information and data pertinent to the system under study becomes available.

U. The application used to illustrate the current implementation of this invention is the functional modeling and dynamic simulation of the molecular mechanisms involved in intracellular signaling pathways, which interact with each other to form a multi-dimensional network. This is an example of the many potential applications of the system of this invention, however, and it should not be construed to limit the applicability of this system to the numerous other applications in the chemical, biochemical, biological, and environmental fields, which can be developed by minor modifications or additions of the system using the methodology here presented. Furthermore, the use of the prefix 'bio' to characterize most of the bioObjects of the system of this invention that are part of this invention does not preclude the use of this system for modeling and simulating other chemical reactions and pathways that are not of a biological nature.

V. The foregoing and additional objectives, descriptions, features, operations and advantages of the present invention will be understood from the following detailed description of the preferred embodiments in combination with the accompanying figures.

V. BRIEF DESCRIPTION OF DRAWINGS

FIG. 1 is an schematic representation of a partial view of the multiple layers of linked reservoir building blocks and process building blocks characteristic of the current implementation of this invention, representing populations of entities and the processes in which they participate, respectively, which together with the many other linked reservoir building blocks and process building blocks not shown result in a multidimensional network of interconnected pathways.

FIG. 16 shows a palette with exemplar prebuilt iconic model-blocks, as well as examples of their attribute/value tables holding their quantitative variables and parameters.

Figure 23:
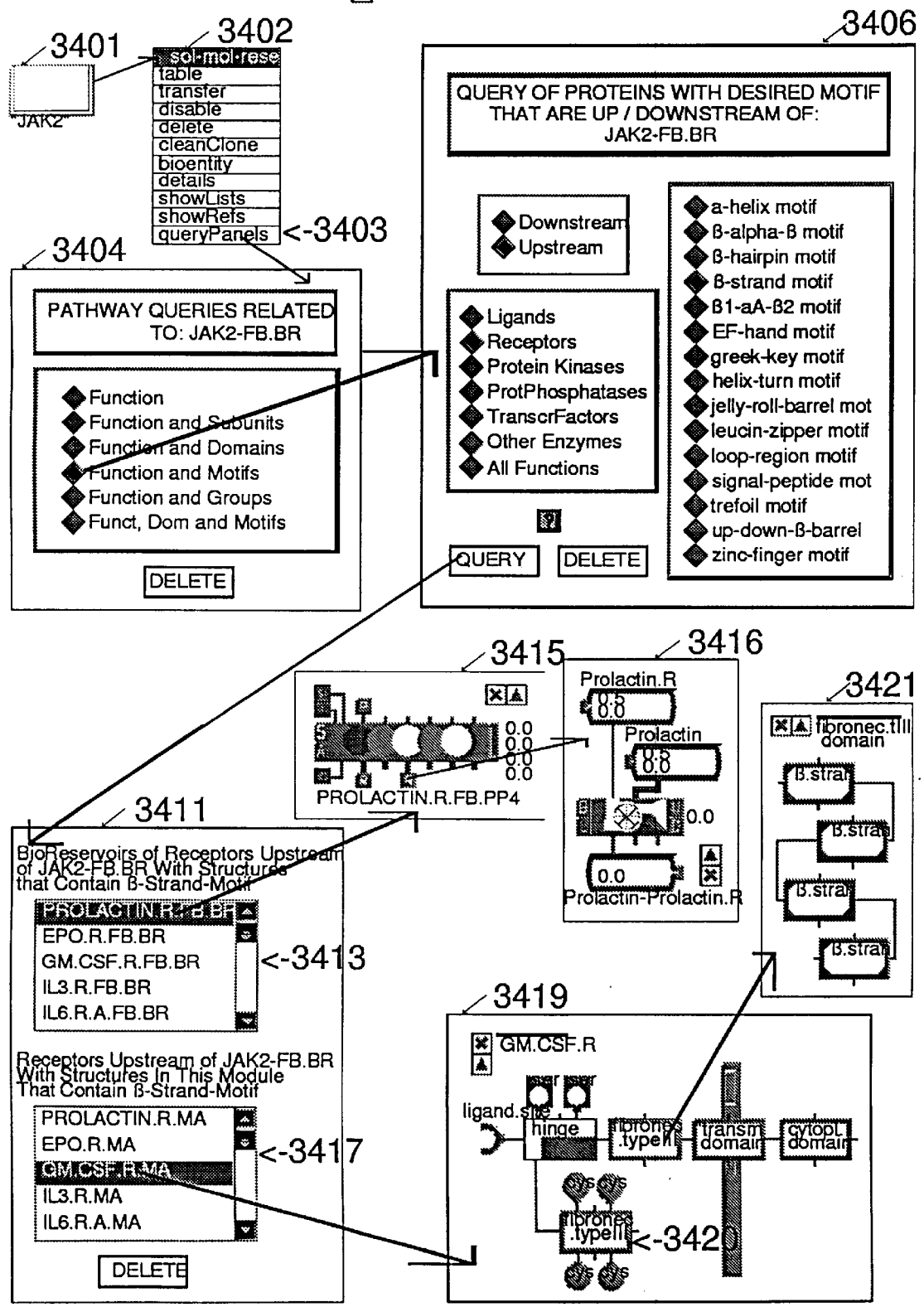

FIG. 23 shows exemplar prebuilt query panels, requestable from any reference instance of building blocks linked in a virtual model, enabling users to select combinations of one or more predefined search criteria based on relative downstream/upstream position, roles played as inputs, and/or structural components of their associated entity building blocks, as well as navigation means to display and access the results of said search.

Figure 24:
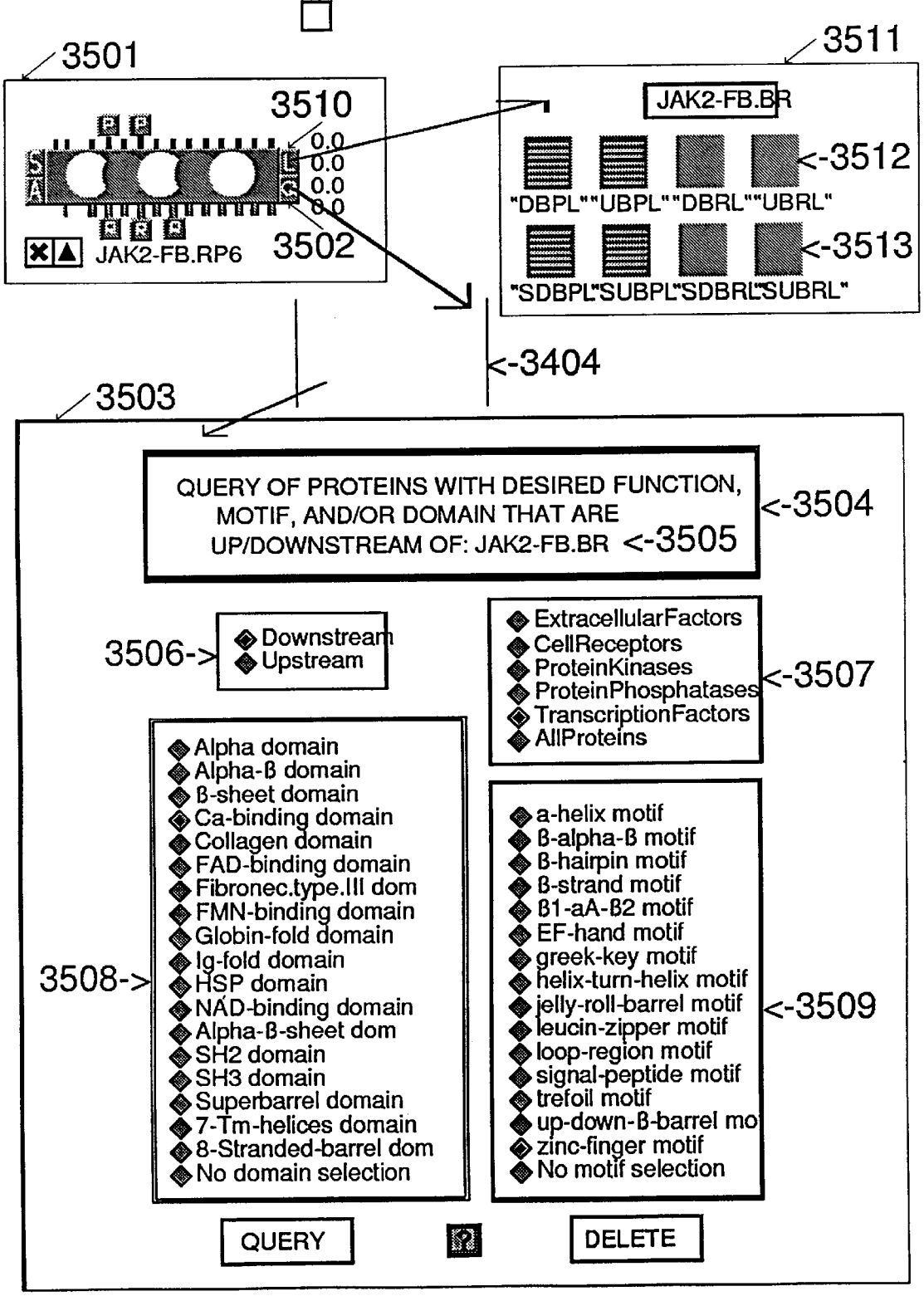

FIG. 24 shows exemplar means enabling users to request, from components of any reference instance of building blocks linked in a virtual model, lists of building blocks that are downstream and upstream from said reference as well as panels to perform relative queries.

Figure 25:
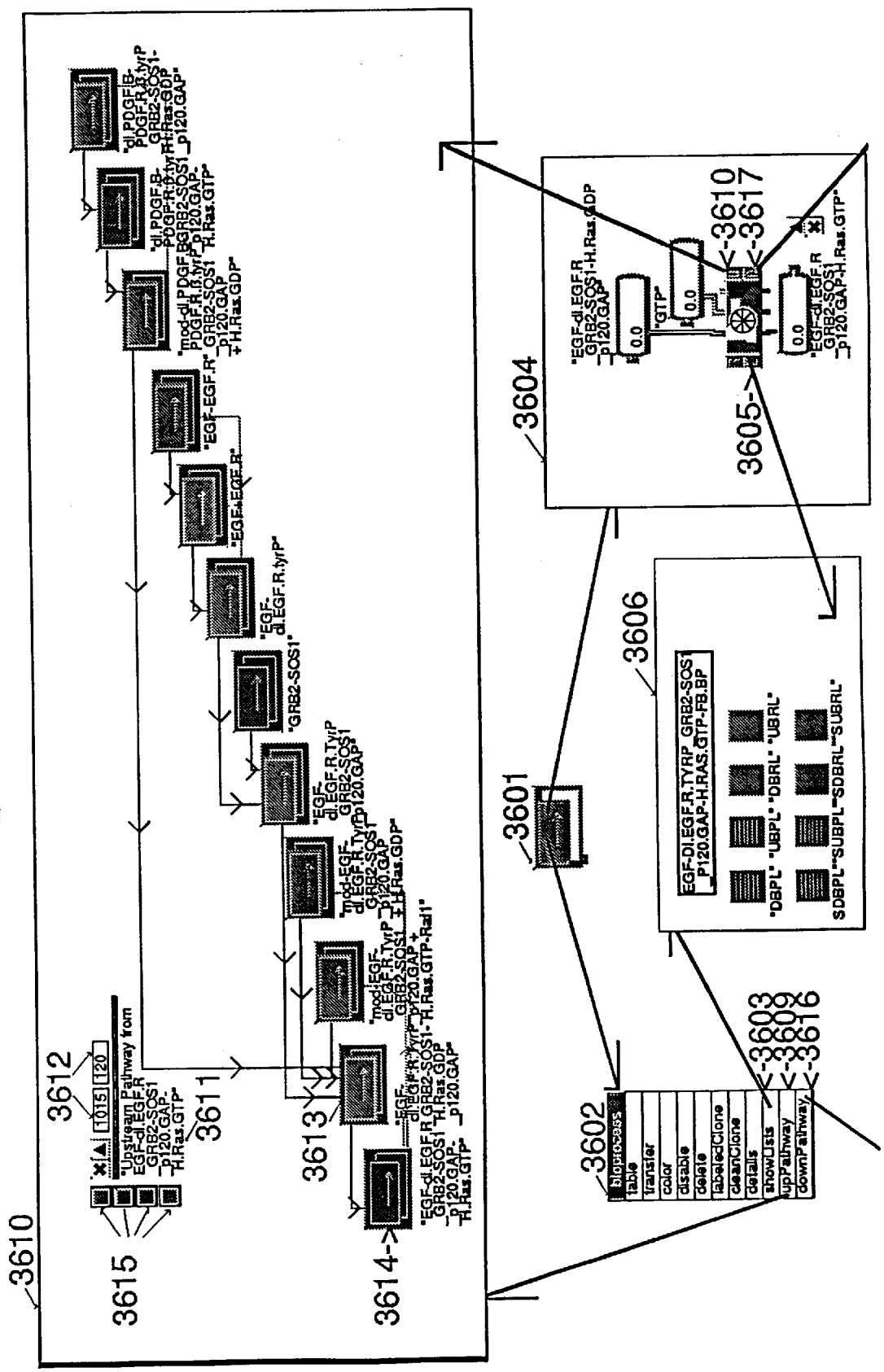

FIG. 25 shows exemplar means enabling to request, from any reference instance of building blocks linked in a virtual model or from its components, the dynamic generation and visual display of upstream or downstream pathways, as well as an exemplar display of pathways with instances of building blocks that are upstream of said reference.

Figure 26:
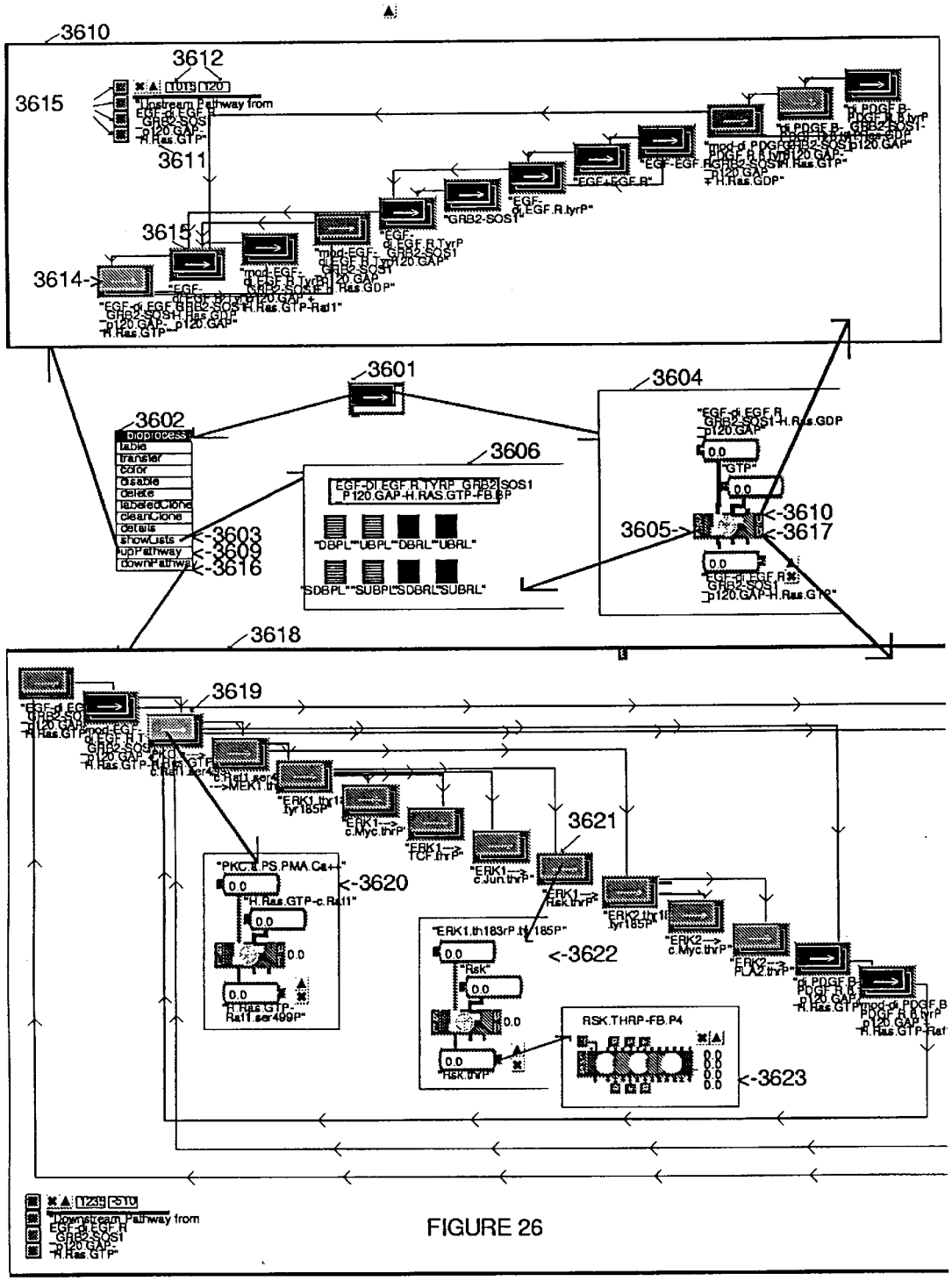

FIG. 26 is a continuation of FIG. 25 showing an exemplar display of pathways with instances of building blocks that are downstream of said reference, as well as how further navigation through the virtual model can be performed from said exemplar composite instances in said pathways.

Figure 27:
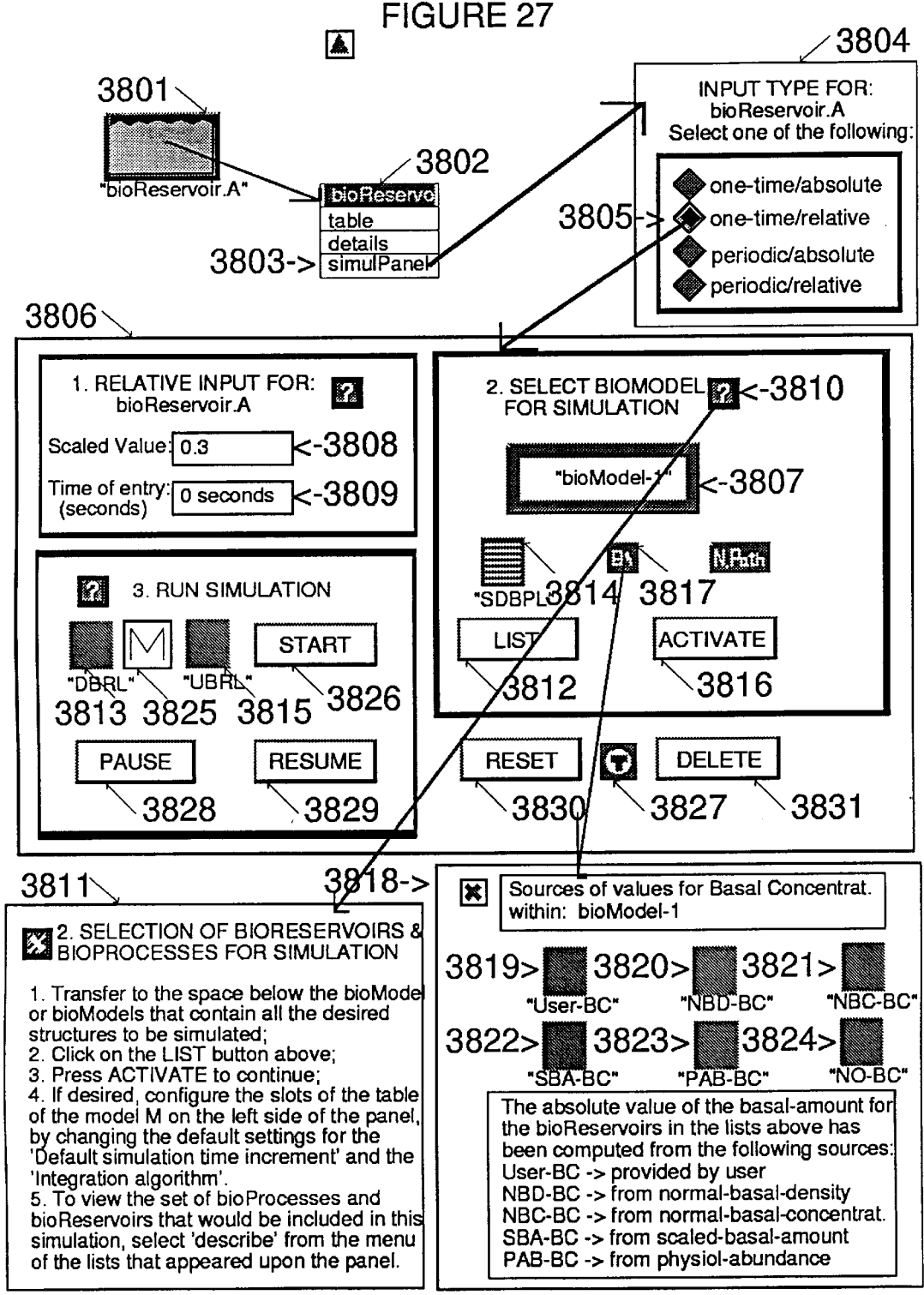

FIG. 27 shows an exemplar predefined simulation panel that users can request from any instance of building blocks linked in a virtual model, enabling users to select and control the dynamic simulation of the kinetic interactions of the populations of entities in the processes modeled by the pathways dynamically generated according to the user selected constrains and subsystem.

Figure 28:
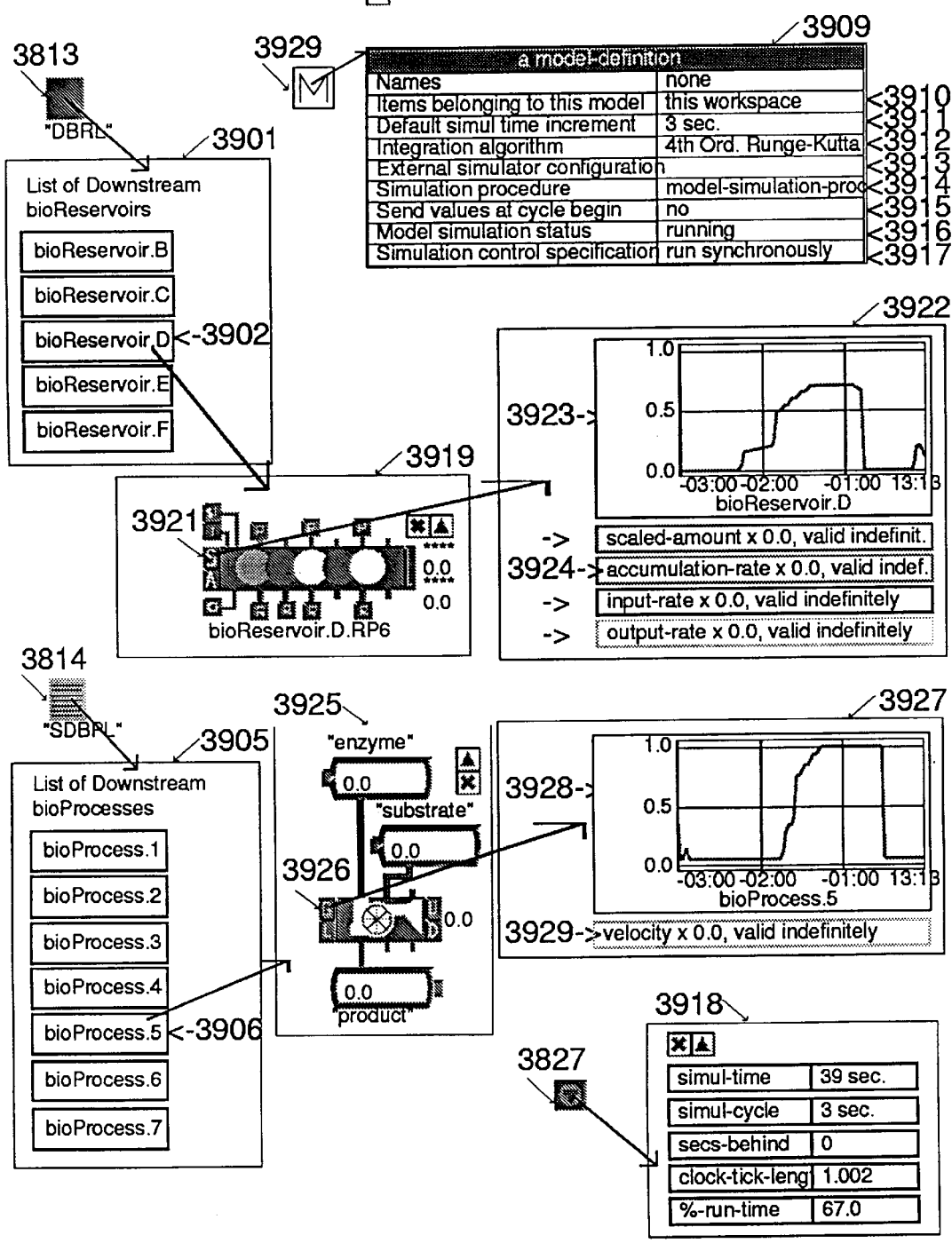

FIG. 28 shows exemplar means enabling the follow-up of said simulation by plotting the time-series of any of the quantitative values of any reservoir and process in the subsystem being simulated.

Figure 29:
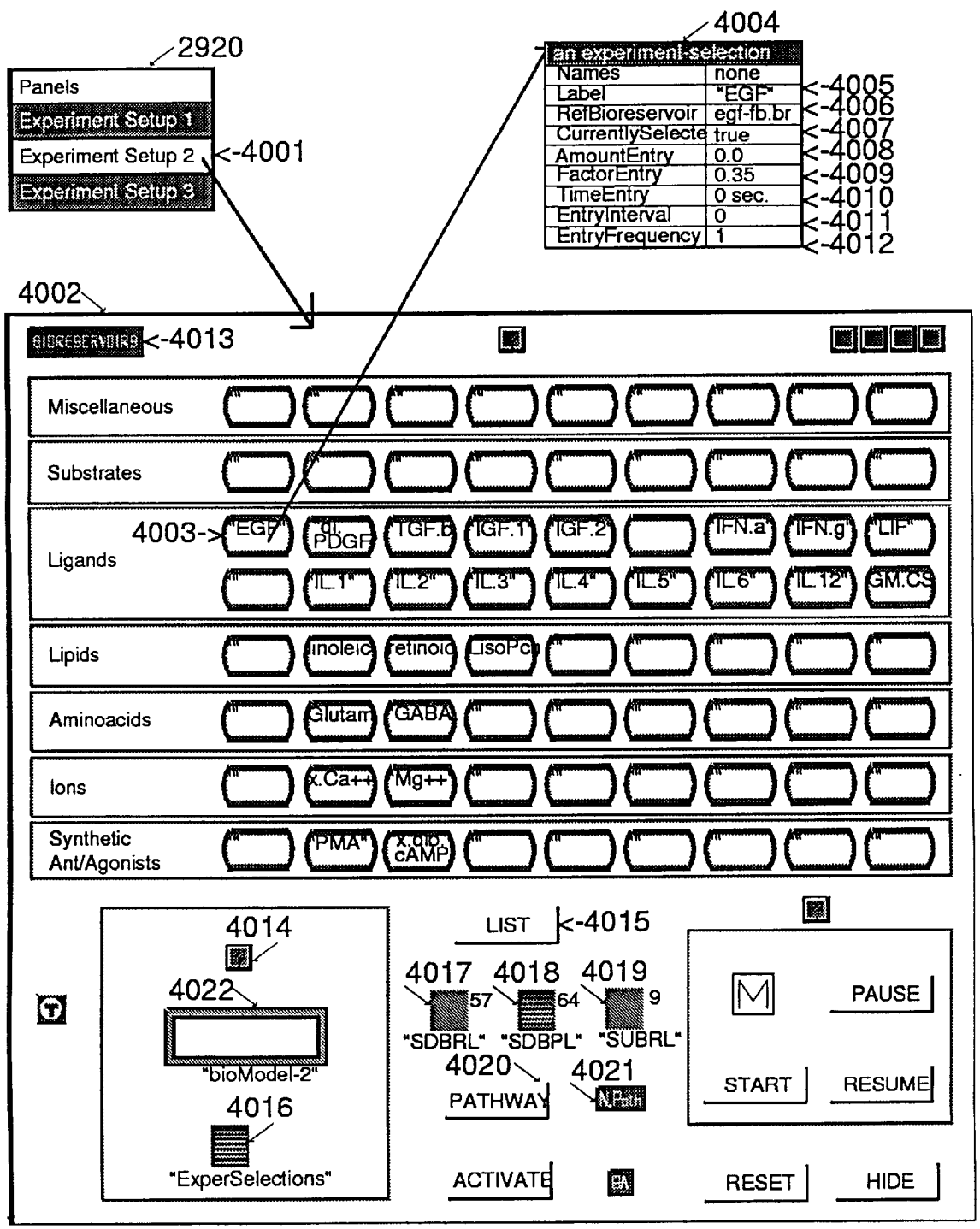

FIG. 29 shows exemplar predefined experiment panels that the user can select from the domain menus to request the dynamic generation of constrained pathways from multiple initial points and for the control of the dynamic simulation of the kinetics of those pathways.

Figure 30:
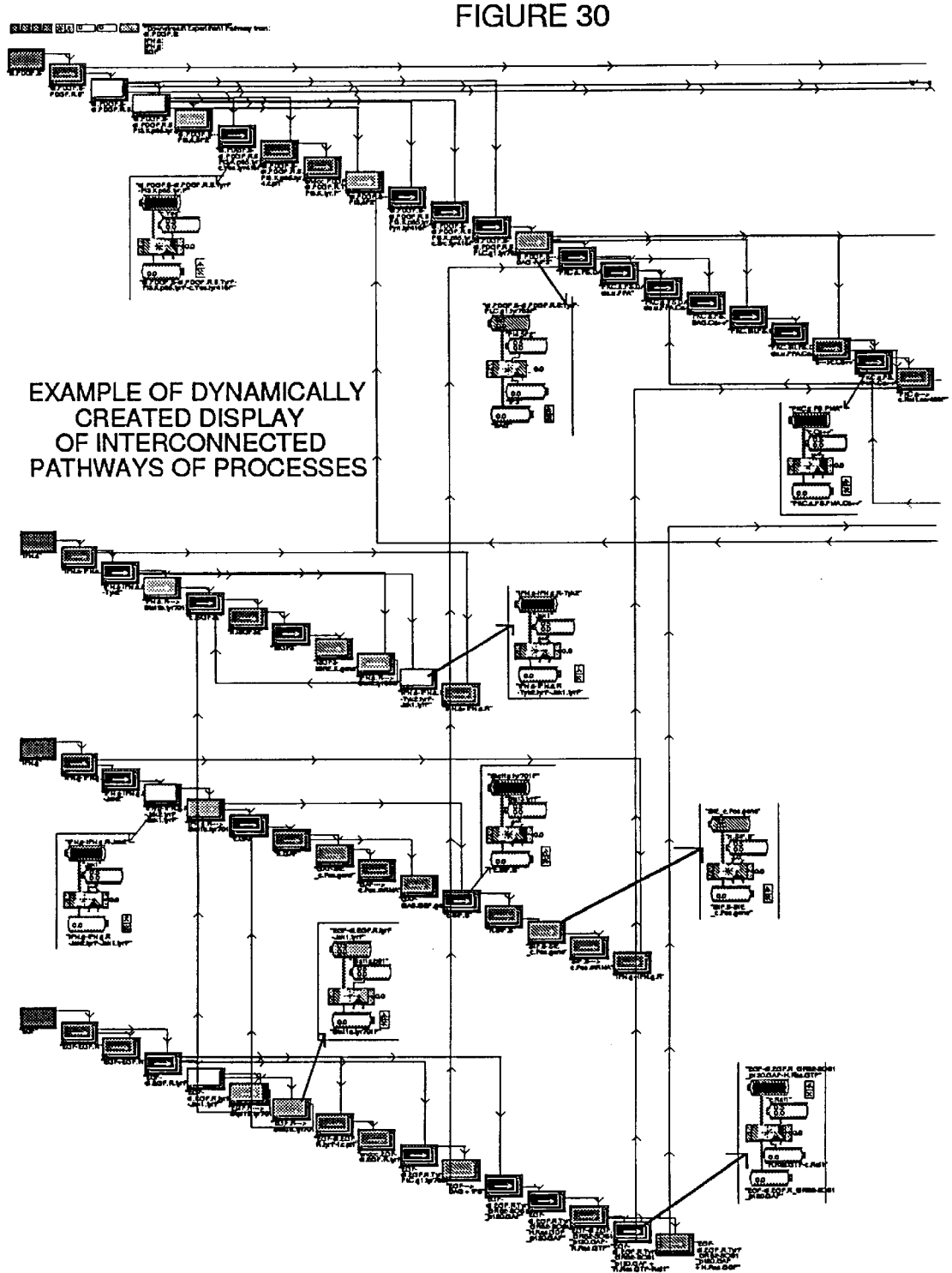

FIG. 30 shows an exemplar multidimensional network of interconnected pathways composed of instances of process building blocks that are downstream from multiple building blocks selected as initial points.

FIG. 30 shows an exemplar multidimensional network of interconnected pathways composed of instances of process building blocks that are downstream from multiple building blocks selected as initial points.

VI. DETAILED DESCRIPTION OF A PREFERRED EMBODIMENT

A. Introduction to the Underlying Methodology

1. The present invention is directed to a domain-specific, application-independent, knowledge-based and model-based real-time system capable of being used by modelers as a shell environment to construct specific object-oriented, visual and interactive information, modeling and simulation systems in the chemical and biochemical domains. The present invention also provides a variety of domain-specific, application-independent tools and graphical interface and associated methods to provide users the capability to extract, interactively or automatically, the integrated knowledge contained in those models build by the modeler, and to further use those models for quantitative real-time dynamic simulations. This system is comprised of a plurality of methods, hereinafter called "the methods" and diverse sets of objects, some representing biochemical entities or concepts, hereinafter called bioObjects, and other representing other auxiliary structures, which may in general may be referred as tools. Both objects and methods are arranged in object-class-hierarchies and workspace-hierarchies. Libraries of knowledge-based prebuilt generic bioObjects are provided as the building blocks that can be combined in prescribed ways to create diverse and new knowledge structures and models. A person using the underlying Shell to define the domain-specific application-independent but knowledge-based classes of objects, their associated methods, and the prebuilt knowledge-based building blocks is hereinafter referred to as a "developer", while the person using those building blocks to build application-dependent models, or expanding the libraries of prebuilt bioObjects, is hereinafter referred to as "modeler", and the person that extracts the accumulated knowledge and runs simulations, is hereinafter referred to as a "user". Other clarifications to note are: a) the current implementation of this invention is case insensitive, and what is referred in the description or in the text labels as bioObject or bioProcess, may be referred to in the code as bioobject or bioprocess, or the names may appear in the code in low case or all capitalized; b) the selection of a menu option is equivalent to clicking on that option, and both expressions are used in the following description of this invention; c) expressions similar to "selection of option A displays B" is a short form that means something similar to "selection of option A causes the invocation of the action or procedure specified in the definition of option A and, as a result of the execution of such action or procedure, B is displayed in the window from which option A was selected"

2. One of the several innovations of the present invention is the graphical interface and associated methods used to partition the domain knowledge into modular and interactive knowledge structures, represented as graphic objects, and the relations, behavior and interactions between those structures, incorporating declarative and procedural information. Each independent superior building-block, also called a composite bioObject, is decomposed into a set of different objects which, when combined, represent at either: a) the descriptive characterization of single units of molecular entities and molecular subcomponents, here called bioEntities; b) the aggregated behavior of a number of units with the same characteristics, defined as a population of such entities in specific states, here called bioPools, and c) their interactions and transitions from one molecular state to another over time, represented by the bioProcesses. As can be observed by comparison of the methods previously discussed in section V.A. with the description in the sections to follow, the model representation, bioObjects, graphical interface and associated methods and overall organization of the system object of this invention offers a very different and innovative approach that not only integrates the qualitative and quantitative description of biochemical objects with a set of state and dependent variables, including concentrations and reaction rates, but also incorporates temporal reasoning and generates dynamic simulations.

3. The principle followed in the design and implementation of the current embodiment of this invention is to break down the knowledge about chemical or biochemical entities and their components, processes and pathways into smaller functional units, to a level where the following requirements can be met: a) allowing their repeated use as building blocks in a variety of situations; b) allowing access to the structures and processes that are susceptible to control and regulation; and c) keeping the number of units manageable. Those functional units are further broken down into operational and standardized knowledge and data structures that add flexibility and facilitate the development of generic domain-specific graphic bioObjects that the user is able to open individually to input data, modify existing bioObjects, or create new bioObjects. Following that strategy, the system of this invention comprises a variety of domain-specific knowledge structures, all encoded as objects, which are either: a) graphic bioObjects that are represented by icons on workspaces, and are referred to as schematic bioObjects, b) graphic user interface objects such as buttons, data displays or input panels, c) non-graphic bioObjects which are either pointed to as attributes of other objects, such as domain-specific variables, parameters, lists or arrays, or d) methods, which refer to the bioObjects, such as the formulas, relations, rules and procedures and which are hereinafter referred to as the associated methods. All those types of knowledge structures are objects of the present invention, and they encode, in a distributed from, the data and the knowledge that enables the system to compute and to reason about conditions and events defined by the developer, modeler, or other external source, and/or generated during the dynamic simulation. Based on those conditions, the knowledge structures are used by the Shell to infer or simulate different behaviors, data, information and/or control are propagated and actions are executed.

4. The current embodiment of this invention provides a domain-specific interpretative environment approach that is easy to use and allows rapid building of prototypes and the continuous expansion and modification of the system, necessary for this type of applications. With its graphic format, the system can be easily browsed and understood by the user. The graphical programming capability is particularly important because it allows scientist modelers to further expand the system, to summarize and integrate their knowledge and data, and to convey it to others as graphic models, without the need for any formal programming skills. To further insure that applications built using the system of this invention are easily and efficiently maintained, modified and expandable by non-programmers, the domain-expert knowledge is represented in a declarative from, which is much easy to understand, separated from the methods that specified how that knowledge is used by the program. It also facilitates modularity by allowing to delete, modify or create parts of the system without affecting the operation of the rest of the system. The knowledge can also be extended and reused under different contexts, and in different new applications. User configuration of the tools in the system of this invention consists primarily of connecting graphical objects and filling out tables of attributes, which means that the building of models requires no programming other than the use of this graphical and natural languages.

5. To provide the many options for knowledge representation that chemical and biochemical systems require, the preferred embodiment of this invention integrates a variety of knowledge representation techniques which concepts will be introduced in the following paragraphs. The basic paradigm is that of the object-oriented approach, which provides a powerful knowledge representation of physical chemical and biochemical entities (such as DNA, enzymes, receptors, ligands, mediators, or ions) and conceptual entities (such as processes and interactions, concentrations and rates). In this system, data and behavior are unified in the objects. Like in other object-oriented systems, objects are here defined following class hierarchy in which each class has a template that defines the types of attributes characteristic of all objects of that class and distinct from other types of objects. Manipulation of the data is performed by operations and methods that can be either generic, attached to an object's class, or specific, attached to a specific instance.

6. The two characteristics of object-oriented environments, encapsulation and inheritance, are very important for the design and implementation of the system of this invention. Encapsulation permits to hide the details behind each object, and multiple levels of encapsulation are supported. Inheritance results from the hierarchic organization of objects, and the system of this invention takes advantage of this capability and systematically assigns all bioObjects and methods to several hierarchies of classes. In the current embodiment of this invention, the superclass at the top of each of these hierarchies of bioObjects or methods are in turn subclasses of one of the various classes of objects provided by the Shell, inheriting their predefined attributes and related methods. Broad classes of objects are defined to describe large families of bioEntities, bioPools, bioProcesses, and other tools. Within those classes, subclasses of more closely related bioObjects are further defined in successive inferior classes, until no more distinction between classes is necessary. At each level of the hierarchy, the information common for all the inferior classes is encoded just once, allowing a rapid encoding of domain-specific information. Each instance of a class is characterized by the set of attributes defined for the class, which can be inspected in the table of attributes attached to each object by selecting it with the mouse. Some attributes define configuration information, while other attributes describe the composition and characteristics of the object, and still others hold dynamic state information, such as the current value(s), data histories, and status. The value of some attributes of an object, such as the variables and parameters, can be dynamically modified at runtime.

7. The knowledge-based system and the bioObjects comprised in this invention constitute a hybrid 5th generation, domain-specific, shell that can be further used as the development and deployment basis for 6th generation user-defined applications in the areas of chemistry and biochemistry. This very powerful environment, that is easy to understand and maintain, combines the object-oriented modeling features characteristic of this invention, with the inference and simulation capabilities of a real-time object-oriented knowledge-based system provided by the 4th-generation underlying Shell, which combines the advantages of object-oriented systems and rule-based expert systems. The resulting domain-specific shell and knowledge-base comprise different types of knowledge associated with the basic object-oriented structure, such as qualitative and quantitative facts, different types of associations, rules, procedures, equations, models and time histories.

8. A knowledge-based modeling and simulation system interprets the information and data contained in the object data structures, based on additional knowledge added to the system in the form of rules or procedures. Additional knowledge, referred to as model-based, can be integrated in the form of structural, functional or behavioral models. Those models are defined qualitatively by the locations, connections, and relations and quantitatively, by mathematical models. The constants, parameters and variables that define those models are distributed through the different types of bioObjects, defined as their attributes, and the corresponding formulas and functions relate those data structures and characterize the particular system. Model-generated results are used as input information for the inference engine, and dynamic models can also reason about the historic values of its variables as well as projecting values of variables into the future. All those different types of knowledge are added by human domain experts to incrementally build an integrated knowledge-base.

9. The predefined bioObjects provided by the system object of this invention can be used by a chemist, biochemist or molecular biologist to build, using the basic paradigm of "Clone, Connect and Configure", more complex modeling algorithms in the form of multiple schematics. Any object in a schematic can have a subworkspace that may contain another schematic of desired complexity. This feature provides the foundation for encapsulation of schematics and a generic mechanism for hiding unwanted information or to facilitate the modularity resulting from a multilayered structure with increasing levels of detail, since multiple levels of encapsulation are supported. Reasoning and computations are performed on either the encapsulation bioObject, called here a composite bioObject, or the bioObjects that forms the encapsulated schematic. The combination of this graphical interface and associated methods allows the domain expert to construct reusable, user-defined libraries of simulation modules using only graphic programming. With the graphical interface and associated methods provided by the system object of the present invention, the same hierarchic architecture used to develop the bioObjects can be extended by the modeler to expand the bioObject libraries of the knowledge-base. Those functional knowledge structures, together with the innovative user-interfaces, permit domain-expert users to build specific applications. Any bioObject can be used to create new bioObject instances of the same type, by cloning, configuring and modifying, allowing the user to modified graphically create new object or modify existing ones. Furthermore, an original schematic on a workspace can then be referred to by a number of bioObjects, here called the master bioObject, and in that way only the original would have to be modified if required, and it will have to be stored only once.

10. In the current embodiment of this invention, objects are represented as graphic icons that can be dragged on a workspace (window) or transferred between workspaces. The attributes that define an object's composition and behavior can be viewed and modified by clicking a dialog box and editing the text in a table. Schematics are sets of connected objects that represent physical or abstract objects and their relationships. The domain expert can define new objects or instances by editing the attributes of existing objects, and the schematics can be edited graphically. The current embodiment of this invention incorporates and extends various abstract models of object-oriented representation, which implementation is inherent in the innovative representation and construction of the knowledge structures of this invention. These constructions comprise and integrate several methods, which are described in detail in the following sections and which are all important contributions of this invention:

a) Several of the basic components of object-relationship models are implicit in the architecture of the system of this invention in various forms, such as: the hierarchical structure of the object-class, the objects that are component attributes of other objects, the graphic connections between objects in a schematic or the distant connections between objects in different schematics, and the containment of objects upon the subworkspace of other objects, which are all permanent relationships; or they are explicit as defined relations, which are transiently established at run-time. Each of these relationships offer different forms of constrains, and provide inheritance, aggregation and association capabilities. The original use of such graphical interface and associated methods to represent biological entities, their pools and their interactions, and their combination to represent pathways and more complex graphic models is an important teaching of this invention.

b) The object-behavior models, which are equivalent to causal models, are integrated through several methods, such as; a) the rules and procedures that define the behavior of certain bioObjects depending on their specific states, or on the values of their quantitative variables, b) the representation and graphical interface and associated methods used to define and quantify the inputs and outputs, and the roles played by each bioObject; c) the methods to define the events or conditions that cause active processes to trigger the activation or inactivation of other knowledge structures; and d) the methods to integrate the causal and temporal knowledge representations, applying real-time constraints to the actions and triggers of knowledge structures. The overall behavior in the biochemical system represented is implemented as intrinsic population dynamics.

c) The object-interaction models are inherent in the current embodiment in the way that bioObjects interact with each other through their variables, which dependencies on each other are defined through the schematics. What is new in this invention are the specific encapsulated representations of various forms of interactions and the graphical interface and associated methods to encode the qualitative and quantitative knowledge about those interactions, while at the same time maintaining a graphic representation that is intuitive for scientists. The object-interactions models comprise: a) a graphical interface and associated methods related to the architecture of the schematic bioObjects and their specific connections, which establish the nature of the specific interactions between them; b) methods that relate the various numeric and symbolic variables and parameters of the connected knowledge structures; c) methods to pass control and data values between the appropriate bioObjects; and d) a graphical interface and associated methods that integrate data and information of different knowledge structures dispersed throughout several workspaces in the knowledge-base.

11. This system and its concepts, graphical interface and associated methods and architecture, which are all objects of this invention, can be implemented layered on top of any advanced real-time object-oriented expert-system development environment or shell that support the methodologies described throughout this application. This system and its concepts, graphical interface and associated methods and architecture, can also be developed from scratch or parting from any combination of hardware or software environments, either already existing or developed for this or other purposes, that provides the capabilities and means required for this implementation. In particular, and for the purpose of illustrating a preferred embodiment of this invention, this system is currently implemented on the G2 Version 3.0 Real-Time Expert System (G2) shell, an object-oriented development and deployment system produced by Gensym Corp. of Cambridge, Mass., and hereinafter referred to as the "Shell". It supports temporal reasoning, which is important to model and describe the causal mechanisms that drive chemical and biochemical systems. Many of the underlying capabilities referred to below are common to other static expert-system development environments, while some capabilities are only common to other real-time expert-system development environments. A few capabilities may be currently specific for G2, but equivalent capabilities can be expected to be developed by others. This Shell currently runs on several UNIX-based platforms, and it is being extended to other operating systems. G2 was designed for concurrent monitoring of thousands of variables in large on-line applications. For detailed information about the underlying capabilities of this system, Gensym Corp. should be consulted.

12. Some of the innovations of this invention comprises new uses and applications of a set of the development tools provided by the Shell, to construct different sets of domain-specific bioObjects to represent, model and dynamically simulate chemical and biochemical entities and processes, their states, relations, functions, behaviors, interactions and any other of their activities, as well as the concepts that make the simulation of this very complex system possible. Hereinafter, we will use the name "knowledge base" when we refer to the chemical or biochemical domain-specific knowledge-base, the word chemical or biochemical will be omitted and should be implied. The Shell provides a predefined object class, called "object-definition", which table of attributes provides a frame or template to define new classes of objects and to define, in the slot of the attribute "attributes-specific-to-class", the names, types and default values for new attributes for that class, which are added to or override the set of attributes inherited from the superior class. Associated with the class object-definition is the underlying code necessary to create a new class, and the menu options associated with its icon include, among others, "icon-editor" which provide access to the icon-editor, and "create-instance" which allows to create an instance of that class represented by an icon, as defined for that class or inherited, that sticks to the mouse-pointer and can be dropped by clicking on a workspace. Other instances can be created by repeating the procedure above, or by selecting the "clone" option from the menu of a previously created instance and transferred to a workspace for editing. Those available generic tools are not innovations of this invention. What are the objects of this invention are: a) the set of libraries of domain-specific graphic tools and methods that the user can use to encode application-specific knowledge, b) the domain-specific interface of this system, layered on top of the Shell, which allows the expert to use those bioObjects and methods without the need for programming or for a knowledge engineer.

13. Using G2 for the current implementation of this invention, rules and procedures are created in natural language, and may apply to a single object or a group of objects, or to a class or a group of classes, and may include references to connections and to connected objects. They may refer or apply to the values of attributes at different time points or to the behavior of variables or parameters over time. They can perform in response to: a) given events or conditions, b) at predetermined time intervals, or c) upon request from other rules or procedures. Rules and procedures can be executed in real-time, implementing different strategies concurrently and over extended periods of time. G2 supports arithmetic and symbolic expressions, and dynamic models include non-linear differential equations to logic expressions that can be used by objects over time to simulate analytic or heuristic behavior. References to time-based characteristics of variables, such as time series statistics, rate of change, and historical data can be expressed in structured natural language. Templates are provided to define object classes. heuristics, or other methods. G2 provides an inference engine that operates on information from different sources, such as: values compiled in the knowledge base, simulated values, and values received from the user, sensors or other external sources, and responds to events from the user, simulator, or external data servers.

14. There is a clear delimitation between the domain-specific tools and the graphical interface and associated methods comprised in this system that are innovations of this invention, described in detail in the following sections, and the generic, domain-independent, tools and capabilities provided by the Shell, which comprises:

a) a structured natural language, supported by a pop-up text editor, for encoding the object definitions as well as rules, procedures, functions, relations, formulas and values;

b) a graphical language, supported by an icon editor, based on a schematic representation of connected icons, and the capability to associate workspaces (windows) with objects, which allows to organize the knowledge at different levels of detail in objects within objects, each represented by icons. The Shell also allows to reason about those iconic objects, their connections, and their locations in the workspace hierarchy. Distant connections can be also maintained, and reasoned about, between objects in different schematics and different workspaces.

c) an inference engine, which interprets rules, relations, functions, rules and procedures;

d) a simulator, which may compute the values for three types of linear or non-linear systems:
      dependent variables or parameters, from algebraic equations;
      discrete-state variables or parameters, from difference equations; or
      continuous-state variables or parameters, from differential equations.

e) a supervisor, which controls operations, such as task prioritization, asynchronous concurrent operations, and real-time task scheduling. Other real-time features include time stamping and validity intervals for data, history-keeping, and real-time data interfaces;

f) a set of predefined generic object classes;

g) several inference methodologies, such as data-driven, event-driven, goal-driven or time-driven capabilities;

h) a graphic-interface development environment to create:
      user controls such as action buttons, radio buttons, check boxes, and type-in boxes; and
      graphic displays such as readout-tables, graphs and charts.

i) dynamic messages, to pass information to the developer and user;

j) an inspect facility, with various capabilities used in the current embodiment of this invention to allow developers and users to: a) show on a workspace the class hierarchies of any specified class, or all the members of any specified class, as well as the workspace hierarchy of any specified object, or the module hierarchy; b) go to any specified object in the knowledge base, displaying that object in the center of the screen; c) search for a set of objects that fit a set of specified characteristics; d) highlight or replace any word or expression within any specified class; and e) write to a file the text of the table of attributes of any named item, or of all the items upon a named workspace.

k) a describe facility allows, through the "describe" menu option to find out the relations between objects or the elements of dynamic lists, making possible to go to the icon of each element of the list, which provides a very useful facility to navigate to objects selected following desired criteria used to fill the list. The "describe" menu option, available in the Shell for every item, is restricted in the current embodiment of this invention to only a few classes, such as lists and arrays, when in any of the user-modes modeler, general, navigation, or simulation.

l) a tracing and debugging facility facilitates such developer's tasks;

m) the capability of breaking an application into a hierarchy of dependent modules;

n) the message board manage text messages generated by the system, such as configuration error messages, prompts generated at run-time, or explanations requested by the user. The system of this invention also use those facilities in some occasions to generate messages that show up on the screen to indicate a wide variety of abnormal conditions appearing during modeling or simulation, such as all those expressions used in many procedures listed in the tables as: inform the operator that " . . . ".

o) support for distributed applications, by allowing different knowledge-base modules to be located in several workstations. Communication between distributed modules is handled transparently by the Shell's built-in network protocols. A simulation application can be distributed among several workstations when the knowledge-base is distributed as well, allowing computer resources to be adjusted to achieve the necessary performance.

B. Domain Specific Knowledge-Representation

1. The computer-aided systems, methods, and interfaces that are the object of this invention can be applied to graphically model and quantitatively simulate any type of complex system involving any type of processes and their participants. The library of palettes of prebuilt building blocks is provided which together with the basic paradigm of "Clone, Connect and Configure" and other automated methods to facilitate the tasks of the modeler. A library of prebuilt query and simulation panels facilitate the tasks of the users to rapidly extract and dynamically use the knowledge and data contained in each specific application. The description that follows is based on one particular domain, that of chemistry, to illustrate one of the implementations of such computer-aided systems, methods, and interfaces. However, such computer-aided systems, methods, and interfaces can be implemented in a similar manner for domains other that of chemistry. For example, in a business domain, what in this description is called bioEntities can be substituted with different types of entities, such as employees or projects, and bioProcesses can be substituted with the different activities in which both interact, the bioReactants with the roles they play in such activities, that frequently may involve other participants. Employees are like enzymes, with the more capable having higher rate-constants. Projects are like the substrates, and employees may have higher affinities for some projects, with a likelihood that they will interact in a process in which a quantifiable measure of the outcome, such as quantity or level of quality, will depend on quantifiable measure of the employee, lets say amount of time put on that project and level of specific experience. The bioPool of each employee could be his/her time, and the max-amount could be set to a day, a month, a year, or any other amount. The bioPool of each employee could be his/her time, and the max-amount could be set to a day, a month, a year, or any other amount. The Contribution to each project would be the amount of time invested in that role, while the different activities will compete for the time left available.

2. Chemical and biochemical systems are complex, heterogeneous and non-linear systems, which involve an interplay between the processes of transport, reaction and conformational change. They are regulated by cybernetic flows of information. The system object of this invention uses a kinetic approach to model these chemical and biochemical systems, rather than a thermodynamic interpretation. The current approach, which focus on the quantities, such as concentrations, densities or other quantities of molecules or complexes, in a particular state, available within particular pools and the rates of transformation or transfer from one pool to another, as a continuous function of time, is close to the way of thinking of biochemists.

3. To represent chemical and biochemical systems, such as when referring to reactions between molecules, it is necessary to refer to populations of such entities with similar properties, and at the same time to refer to the characteristics and current state of single entities. In a small application for molecular genetics, Karp (1989) was only able to represent and implement the overall system as either a network of molecules or a network of processes, as separated systems, but he was not able to integrate both. Furthermore, his method of representation and implementation is quite different from that used in the present invention, since his representation was static and did not include temporal reasoning, having all processes represented as instantaneous reactions.

4. Pathways in the current implementation of this invention refer to sets of alternating bioReservoirs and bioProcesses connected to each other to indicate participation of the chemicals represented by the bioReservoirs in the reactions or processes represented by the bioProcesses, and to further indicate that the processes represented by the bioprocesses provide inputs to the pool of chemicals represented by the bioReservoirs. Furthermore, the term upstream is used to indicate those bioReservoirs, bioProcesses, or pathways that affect the inputs to a given bioReservoir or bioProcess, while the term downstream is used to indicate those bioReservoirs, bioProcesses, or pathways that are dependent upon the outputs to a given bioReservoir or bioProcess.

5. The following is an introduction to important concepts upon which much of the processing and reasoning of the current invention is based. A bioReservoir (201) is a graphic knowledge-structure that contains a bioPool, which refers to a population of a single type of molecule or complex contained within a limited space represented by the bioReservoir. The amount of such units comprised in a bioPool, represented by a variable such as Concentration or other appropriate quantity, is dynamically computed at run time, parting from an initial value or basal-amount set by the modeler, or in its absence, from a default value set by the developer. A chemical process is represented as a bioProcess (202), a graphic knowledge-structure that contains various components, including a bioEngine that controls the Velocity at which the input(s) of the bioProcess, the bioReactant (s) (203), are consumed and the output(s), the bioProducts (205), are produced. BioReactants can also be said to represent the participation of certain number of units of a bioPool as the input to a given bioProcess, and more specifically, the role that such number of units of the bioPool play in such bioProcess. BioProducts can also be said to represent the participation of certain units of a bioPool as output from a given bioProcess. Both types of knowledge-structures integrate bioProcesses with bioReservoirs in a complex architecture that allows to model the kind of complex systems and multidimensional pathways that are characteristic of the domain of this invention. In such integrated system, units from the bioPool of a consumable bioReactant, are transferred to the bioPool(s) represented by one of its bioProduct(s), at a dynamically computed rate. BioPools, bioReactants, bioEngines, and bioProducts are classes of basic bioObjects that further encapsulate a variety of knowledge structures, including quantitative attributes, parameters and variables, which values, provided by simulation formulas, can be dynamically simulated in real-time.

Figure 1:
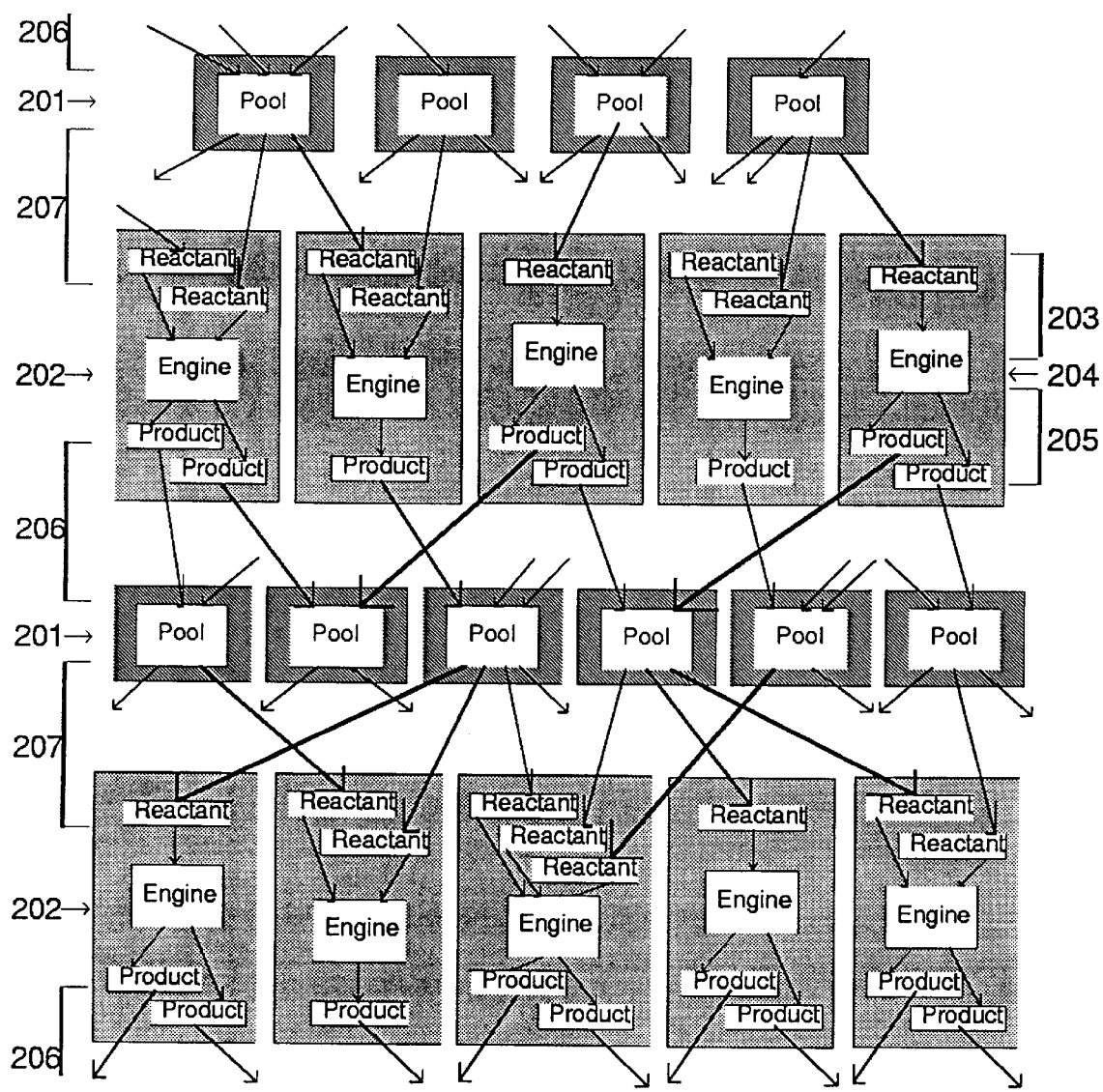

6. These concepts are expanded further in FIG. 1, where the different layers of arrows represent the direction of flow of information and data. Many layers of instances of the classes of bioObjects described above are connected among them in very specific ways, according to the knowledge about the system to be modeled. The result of those specific connections is a multidimensional network of interconnected biochemical pathways that determines the basic architecture of this system. That basic architecture also defines the resulting network of parameters and variables, and the specific arguments for the generic formulas that provide the values for those variables are determined by those connections. The arguments of the variables of these basic knowledge structures are the output values of certain other variables and/or parameters that are attributes of either: a) the same bioObject instance or b) instances of connected bioObjects of different classes. For instance, an argument for the Consumption-Rate of some bioReactants (203) and for the Production-Rate attribute of any bioProduct (205) is the value of the Velocity attribute of the connected bioEngine (204), while the values of the Contribution attribute of each bioReactant may be arguments of the Velocity attribute of the bioEngine. Furthermore, the Production-Rate of some bioProducts (206) and the Consumption-Rate of some bioReactants (207) are arguments for the Input-Rate and the Output-Rate attributes, respectively, of the bioPool (201) to which they are distantly connected, while the argument of the Contribution of any bioReactant (203) may be the value of the Concentration attribute of the connected bioPool. Told in a different way: a) the flow of data between the bioPool and a bioReactant is bidirectional, involving two variables in the bioPool and two in the bioReactant, b) the flow of data between a bioReactant and the bioEngine is bi-directional, involving two variables in the bioReactant and one in the bioEngine, c) the flow of data between the bioEngine and a bioProduct is unidirectional, involving one variable in the bioEngine and one in the bioProduct, and d) the flow of data between a bioProduct and the bioPool is unidirectional, involving one variable in the bioProduct and one in the bioPool. The reversibility of any binding can be represented in two alternative ways: a) implicitly reflected in the output of a single process, which is the balance in the predominant direction (as represented by the specific or global kinetic parameters), or b) explicitly modeled as two separated processes in the forward and reverse directions.

7. There are other parameters and variables defined in the system of this invention, which are also involved in the dynamic quantitative simulations of the graphically modeled systems, and which can be incorporated in two distinct and alternative forms of simulation reasoning, absolute or scaled, as will be described in more detail under the heading Simulation Mode. For example, the factors that affect and define the transformation rates, such as the catalytic, binding or transfer rate of a bioProcesses (here preferably encapsulated as the Velocity attribute of its bioEngine), are distributed as attributes of the various connected bioObjects and comprise:

a) the quantities of the bioReactants of different types, such as enzymes, substrates, inhibitors, and activators, or receptors, agonists and antagonists, or components of a complex (here preferably encapsulated as the Concentration or Density or Scaled-Amount attribute of the bioPool connected to each bioReactant, which values can be directly incorporated into the equation that gives the value of such Velocity, when using the absolute reasoning; or indirectly incorporated into the equation that gives the value of the Contribution attribute of each bioReactant, which holds an intermediary scaled value that is incorporated into the equation that gives the value of such Velocity, when using the scaled reasoning);

b) the values of specific kinetic parameters characteristic of each type of bioReactant (here preferably encapsulated as: the "effective-binding-sites" attribute of enzymes and receptors, and the "Michaelis-constant", "equilibrium-dissociation constant", or equivalent attribute of substrates, ligands, or other bioReactants, respectively, which values can be directly incorporated into the equation that gives the value of such Velocity, when using the absolute reasoning, or, alternatively, the "scaled-Michaelis.k", "scaled-equil.dissoc.k", or equivalent attribute of substrates, ligands, or other bioReactants, respectively, when using the scaled reasoning), or, alternatively, a global kinetic parameter specific for that bioProcess that replaces and represents the combination of the specific parameters of each of the bioReactants of that bioProcess (here preferably encapsulated as the "rate-constant-sec" attribute of its bioEngine);

c) the stoichiometric coefficients (here preferably encapsulated as the "stoichiometric-coeff" attribute of bioProducts and bioReactants); and d) the effects of environmental conditions such as temperature and pH are also specifically defined as attributes, and can be integrated into the simulation within the appropriate equations.

8. Chemical and biochemical reactions are continuous processes, within the time intervals that are dependent on the type of reaction and the environmental conditions, with the balance of the reaction favoring in general the forward direction. The strategy used in the system of this invention is to forward chain from inputs values from the user-interface or from databases. In the preferred embodiment of this invention, the specific way the bioObjects are connected specify the sequential or concurrent ordering of data flow, and the parameters of model equations are included as object attributes. Model-generated results may be used as input data for other simulated equations or as events to be used by the inference engine. These dynamic models can also reason about the behavior of variables in the past and project the behavior of variables into the future. Integrating the activities of the different parts of a model system requires the simultaneous solution of a set of non-linear ordinary differential equations and a set of dependent algebraic equations. In the current embodiment of this invention, this system takes advantage of the two methods of explicit integration supported by the Shell: either the first-order Euler scheme or the quadratic fourth-order Runge-Kutta scheme, depending of the desired accuracy of the computation. The updates of the different variables may be synchronous or asynchronous, as a result of the variables having equal or different update intervals. The dynamic values of variables or parameters may be displayed in both digital and graphic forms.

9. The default values and equations provided with the preferred embodiment of this invention, represent an steady-state modeling approach, since biochemical systems are better represented by steady-state than by equilibrium situations. The value for the Basal-Concentration of each population reflects the physiological normal steady-state value, when the rate of change is equal to 0 or equivalently when the sum of the inputs equals the sum of the outputs. Enzymes that are constitutively abundant and in their active form have no effect on the steady-state, since they are not rate limiting. However, regulated enzymes, such as kinases and phosphatases among others, may be constitutive only in their inactive form, and their Concentration influence the Production-Rate of the active form in the same way as the Concentration of a substrate controls its consumption rate. In the system of this invention, the activation-process of an enzyme (u other bioEntity) means consuming units of the bioReservoir of the inactive form and producing units of the bioReservoir of the active form, and therefore it is the same treatment as for any other substrate and product. The regulation of enzymatic activity is modeled through separate schematics that represent forward or feedback inhibition or activation processes or pathways. Each modification of molecules or complexes that results in relevant qualitative or quantitative changes in their function, is represented as separate bioEntities, which in turn are represented in separate bioPools and bioProcesses. Examples of those modifications comprise: a) gene mutations and other DNA modifications; b) post-transcriptional splicing and other modifications or degradation of RNA; c) post-translational modifications of proteins, including allosteric changes, phosphorylation, isoprenylation, and so on, and degradation; and d) modifications and degradation of other molecules. Synthesis and degradation, as well as allosteric changes or other modifications, may also be implicitly modeled within the parameters that affect the Velocity of a bioProcess (202), or as separate mathematical model-blocks connected to bioPools (201) as inputs or outputs.

10. In the currently preferred embodiment of this invention, a unit of a given chemical entity, referred to as a bioEntity, which describe the characteristics and state of a single molecule or complex, is considered a separated knowledge structure which is referred to as an attribute of a bioReservoir and can be accessed from the menu choices of this and other bioObjects, such as a bioReactant connected to its bioPool, which refers to a population of molecules with the characteristics described for such bioEntity. The information about the characteristics of particular functional states of a given molecule or complex is encoded as separate instances of classes of bioEntity, as will be described in detail in later sections. Different behaviors of each bioEntity are then explicitly defined through the mechanisms represented by the bioProcesses in which bioReactants that make reference to such bioEntity participate. In other words, it can also be said that bioProcesses represent the interactions of a bioPool of such bioEntity with bioPools of other bioEntities, as defined schematically through their connected bioReactants or bioProducts. Furthermore, in the present invention, a single molecule can be described in more detail by and ordered and connected set of instances of more elemental bioEntities, referred to as bioEntity-components, which represent molecular functional components such as subunits, domains, motifs, active sites, regulatory sites and mutation sites. The additional levels of detail are implemented in the current embodiment of this invention through the encapsulation of subworkspaces. In a similar way, sets of simple molecules can be components of other bioEntities representing a complex, or of a heter-mol-complex. Since unlimited levels of encapsulation are allowed, it is possible to start dealing with a topic with a very general overview schematic, and then successively "clicking" into objects of interest, to show the next level of detail.

11. As will be described in the following sections, in the system of this invention, the methods used to process the application-specific knowledge are separated from the application-specific knowledge itself. The domain-specific but application-independent knowledge is encoded in at least four different forms, characterized by: a) the selection, combination and specific connections of the simple knowledge structures that contain the variables and parameters that quantitatively define this system, within the subworkspace of a prebuilt composite bioObject; b) the selection and design of those simple structures and their interactions as components of the composite structures, which provide for the resulting transparently interconnected architecture underlying this system; c) the selection and definition of the specific attributes of each of those types of structures, which describe and characterize the potential behavior of those structures; and d) the methods in the form of procedures, rules, formulas, functions and relations that together provide for the monitoring, control and execution of the system. On the other hand, the application-specific knowledge is incorporated in at least two different ways: a) the selection, combination in different ways and connections of those prebuilt composite bioObjects and predefined structures; and b) the configuration of the values of the predefined attributes of those selected structures.

C. Description of the Functional Building Blocks and Overall Organization of the System 1. Table 1 shows the overall classification of the different groups of object classes that will be discussed in the detail description of this invention. The group of schematicTools will be here briefly introduced to facilitate the understanding of the system as a whole. These knowledge structures are novel constructions designed to deal with issues characteristic of the domain of this invention, and in addition to representing domain-specific entities and concepts, they are also part of the interactive user-interface. These, together with the auxiliary structures that are grouped under User Interface Tools, allow the user to interactively request, using the point-and-click paradigm, the performance of predefined complex tasks. Many of those tasks are context sensitive, depending on the current mode selected by the user, and the results generated or displayed are generated dynamically. The group of Variable-Structures are knowledge structures that are attributes of the schematicTools, while the group of Inference and Simulation Structures may refer to any of the above tools, determining their behavior, or providing their values, or monitoring and responding to the user's selections or inputs. The last three groups are domain-specific classes of more familiar knowledge structures that may be more dependent on the underlying operating system and flavor, and will be described later. It should be noted that there is a number of other capabilities and utilities, knowledge structures, and features that form part of the Shell, which may be mentioned here but not discussed in detail because they are used as they are offered, without further extensions. However, said capabilities may be necessary for the fully and efficient operation of this invention, and its is therefore assumed that a person skilled in the art has also access to said development Shell, or an equivalent development environment with comparable capabilities.

Figure 2:
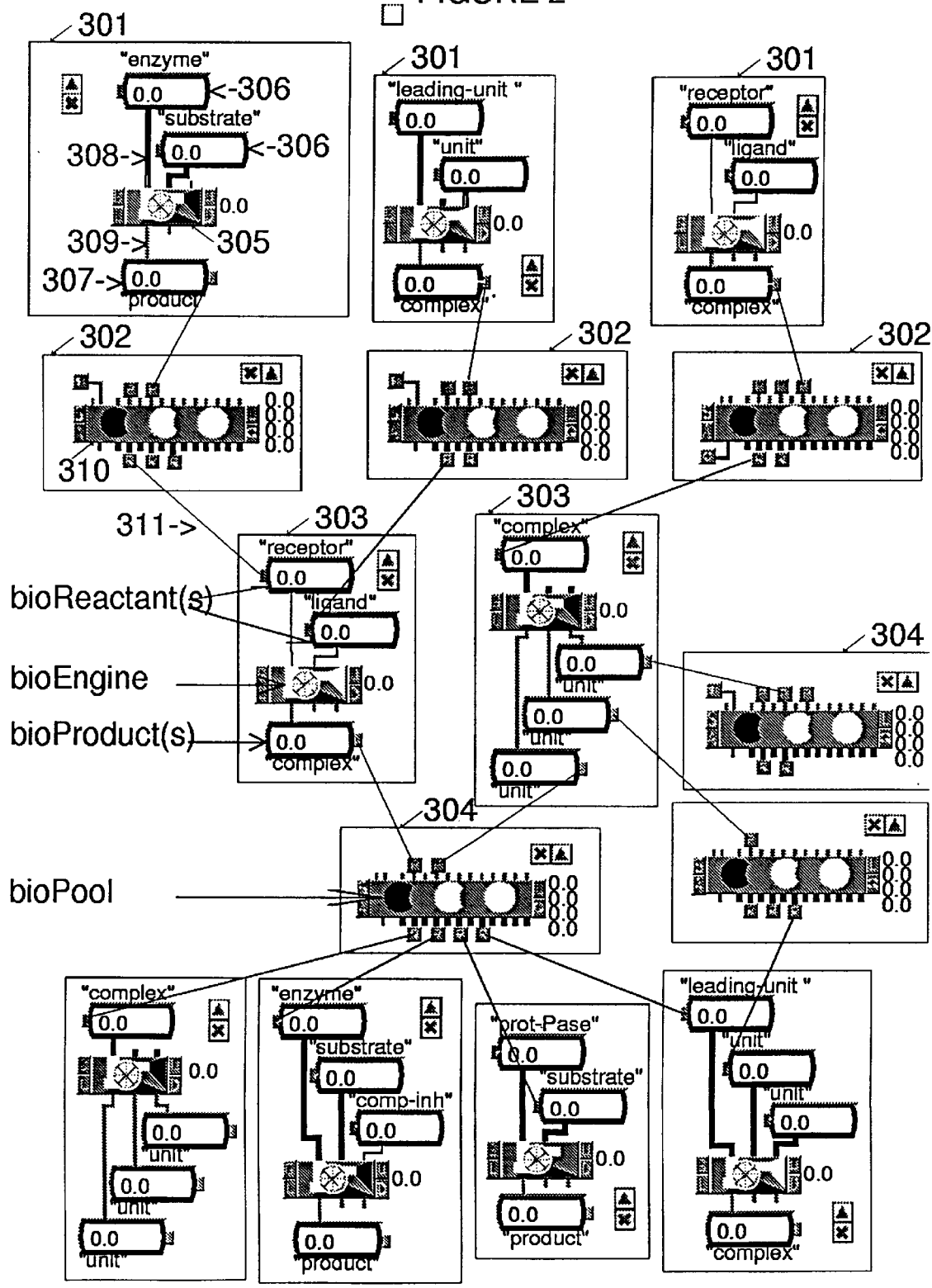
FIG. 2 shows an iconic representation used in the current implementation of this invention in the particular domain of biochemistry of a partial view as described in FIG. 1. This iconic representation is also used in the figures that follow as an exemplar and not necessarily as the preferred representation.

2. FIG. 2 shows how the concepts introduced in the previous section are implemented in the current embodiment of this invention, with the aid of additional graphic structures. The knowledge-base of this system is built on a hierarchy of windows, each called a workspace. Each workspace is represented in all drawings by the background rectangles. Subworkspaces are encapsulated within an object, such as the subworkspaces of bioReservoirs, bioProcesses, or bioEntities (607, 609), which contain each a complex set of components. The knowledge-base is in this way partitioned into modular bioSchematics on subworkspaces of other objects, that can be independently activated and deactivated at runtime when required by the simulation. Unlimited levels of encapsulation are allowed in structures such as bioEntities, where it is possible to start dealing with a bioEntity with a very general overview schematic, and then successively "clicking" into components of interest, to show the next level of detail. In other structures, such as bioReservoirs and bioProcesses, the levels of encapsulated are limited to those two defined in the generic bioObjects, as offered in the palettes.

3. To build graphic models of biochemical systems, icons of related bioProcesses and bioReservoirs are stored together in sets, in the subworkspace of another structure, a bioModel. The components of those sets are the modules that the program uses to dynamically generate interactive pathways. FIG. 2 shows as examples the subworkspaces of one such a set of generic bioReservoirs (301 and 303) and bioProcesses (302 and 304) with their encapsulated bioSchematics, to help the reader to visualize some of the basic types of graphical constructions and methods that are object of this invention. This schematic and all the schematics that follow are actual screen print-outs, showing the iconic representation used in the current implementation. Each bioProcess comprises a subworkspace (301), which contains only one bioEngine (305) connected to one or more bioReactants (306) and a one or more bioProducts (307) by specific types of r-connections (308) or by p-connections (309), respectively, in addition to other graphic structures to be introduced in following sections. The subworkspace of each bioReservoir (302) contains one bioPool (310) of chemical entities, in addition to other graphic structures to be introduced in following sections, including those that allow connections to a variety of bioProcesses, where the bioPools may participate as bioReactants (306) or bioProducts (307). The lines (311) in this schematic are imaginary and represent the distant connections that integrate the different schematics into a pathway. In FIG. 2, the bioProducts of the top layer of bioProcesses (301) provide the inputs to the layer of bioReservoirs (302) that follow, while the outputs of those bioReservoirs (302) provide the inputs to the next layer of bioProcesses (303), through their bioReactants, while their bioProducts feed the next layer of bioReservoir (304). A perturbation in the form of input data by the user or other sources, may be propagated by forward chaining of the newly inferred or computed values, which are interpreted in combination with the domain-specific knowledge implicit in the schematic. That flow of data and information passes through the variables from bioObject to bioObject along the graphical (308 and 309) and the distant (311) connections. It should be noted that: a) the distant connections (311) are invisible; the bioReservoirs and bioProcesses, not their subworkspaces, are organized in workspaces; c) neither the bioReservoirs and bioProcesses, nor their subworkspaces are usually organized in such layers, and d) the bioReservoirs and bioProcesses can be moved between different workspaces without affecting any of the connections.

4. The following set of Figures will be here used to introduce some additional graphic building blocks of the system of this invention, and to briefly describe in more detail the relationships between the major classes of bioObjects of this system. In all the figures that follow, the large unidirectional arrows are imaginary tools that represent the "click-and-display" paradigm that characterize most icons, menus and domain-menus, and tables in the current embodiment of this invention, where each arrow originate in the item, such as an icon, option or slot, respectively, that is "clicked-on" and points to the item being displayed as a result, such as a menu, workspace, or another table.

Figure 3:
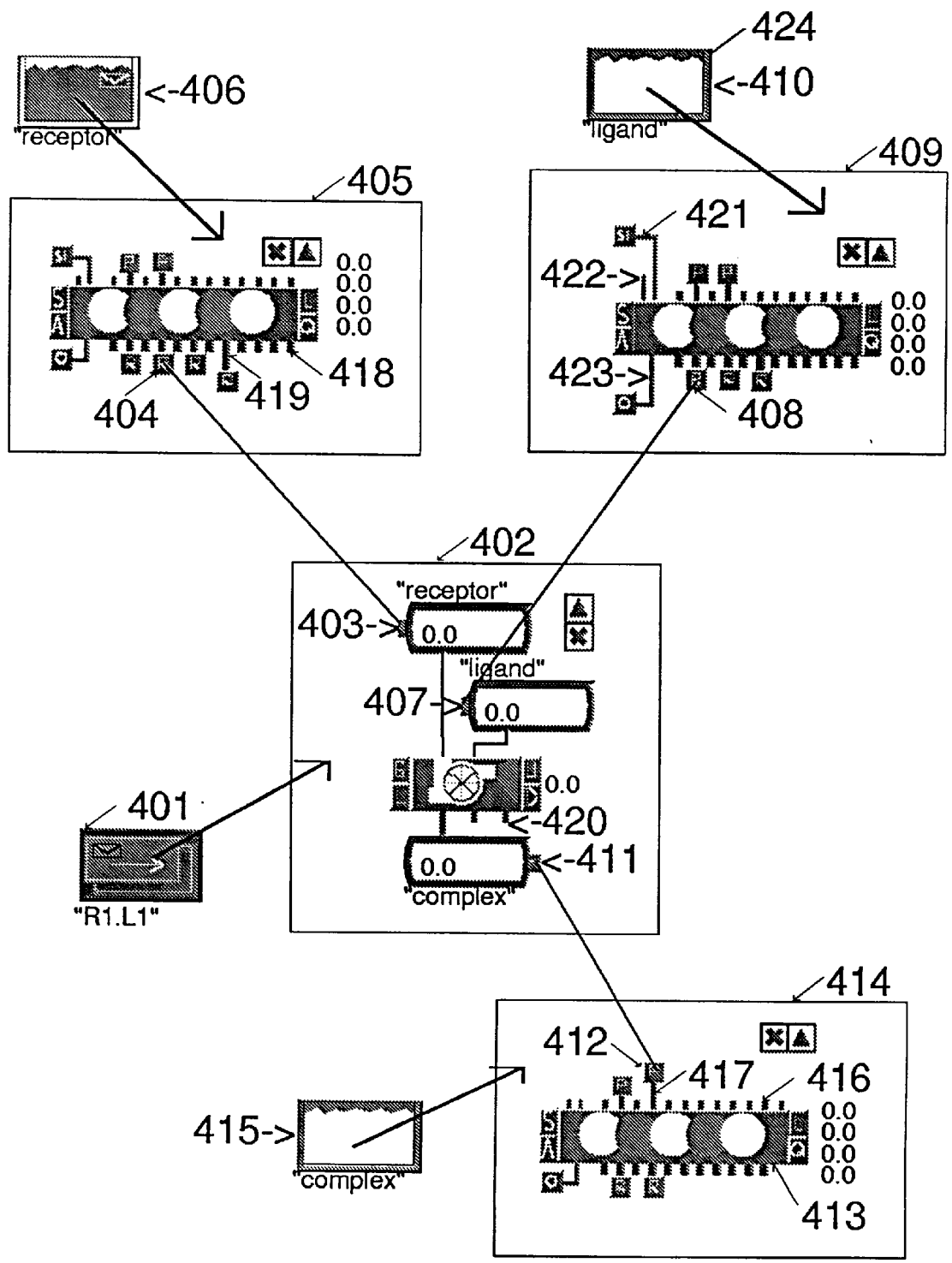
FIG. 3 shows in more detail exemplar iconic components of two-layered composite building blocks, focusing on an instance of process building block and some instances of reservoir building blocks that are the sources of its inputs and the targets for its outputs.

5. FIG. 3 focus on a bioProcess and the sources of its inputs and outputs. First it will be pointed out that clicking on the icons of any bioObject or any of its components shows different behaviors, depending on the operating mode settings or user-mode, as described below. Clicking on most icons in most user-modes displays a menu (not shown here). However, clicking on the icon of a bioProcess (401) or the icon of a bioReservoir (406, 410, and 415) in Navigation Mode results in automatically displaying their subworkspaces (402, 405, 409, and 414, respectively) with all their components, which is equivalent to displaying the menu and selecting the "details" option, as shown later. The bioProcess (401) shown here is a generic receptor bioProcess which contains in its subworkspace (402, similar to that introduced in FIG. 2 as the 303 on the left), a R1.L1.engine connected to two bioReactants, labeled "receptor" and "ligand", and one bioProduct labeled "complex". In addition, each bioReactant and bioProduct has an attached graphic appendix of the class bioRole-post (403, 407, and 411, respectively) which is connected by a connection of the class icon-wire which color is made transparent after the connection has been established, and therefore it is here not visible. The class bioRole-post has two subclasses, where each instance of the subclass bioReactant-post may be connected to only one bioReactant, and each instance of the subclass bioProduct-post may be connected to only one bioProduct. In addition each bioReactant-post (403 and 407) may be distantly connected to only one biopool-r-post (404 and 408, respectively), and each bioproduct-post (411) may be distantly connected to only one biopool-p-post (412), those bioPool-posts being located upon the subworkspace of bioReservoirs and connected to bioPools (413).

6. FIG. 3 can be summarized in terms that reflect the underlying architecture of the system of this invention by saying that, in a bioProcess of type receptor (401): a) the bioReactant of type receptor.r is transparently connected to a bioPool of molecules or complexes that may have, among others, a receptor function, through two complementary bioPosts (403 and 404); b) the bioReactant of type ligand.r is transparently connected to a bioPool of molecules or complexes that may have, among others, a function as ligand for the previous receptor, through two complementary bioPosts (407 and 408); a) the only bioProduct is transparently connected to a bioPool of molecular-complexes that result of the binding of the previous ligand to the previous receptor, through two complementary bioPosts (411 and 412). Such transparent distant connections determine, among others: a) the relative positions of the superior bioReservoir and bioProcesses within the resulting biochemical pathways, and b) the source of specific arguments for the formulas (equations) that provide the values for the parameters and variables of bioPools and their connected bioReactants and bioProducts and their connected bioEngines. Therefore, FIG. 3 can also be summarized in terms that reflect the dynamics of the system of this invention by saying that, a number of units contained in a bioReservoir (406) of a receptor interacts in a bioProcess (401) with a number of units contained in a bioReservoir (410) of one of the ligands specific for that receptor, resulting in the production of a number of units added to a bioReservoir (406) of a molecular-complex that results of the binding of that ligand to the receptor, in molar ratios specified by the stoichiometric-coeff attribute of the bioReactants and the bioProduct of the bioProcess (401), at a rate that is proportional to the dynamically computed value of the Velocity attribute of the bioEngine of the bioProcess, which in turn is proportional to the dynamically computed values of the quantities attributes of the bioPools that provide the inputs, which represent the available number of units remaining in the bioReservoirs of the receptor (406) and its ligand (410).

Figure 4:
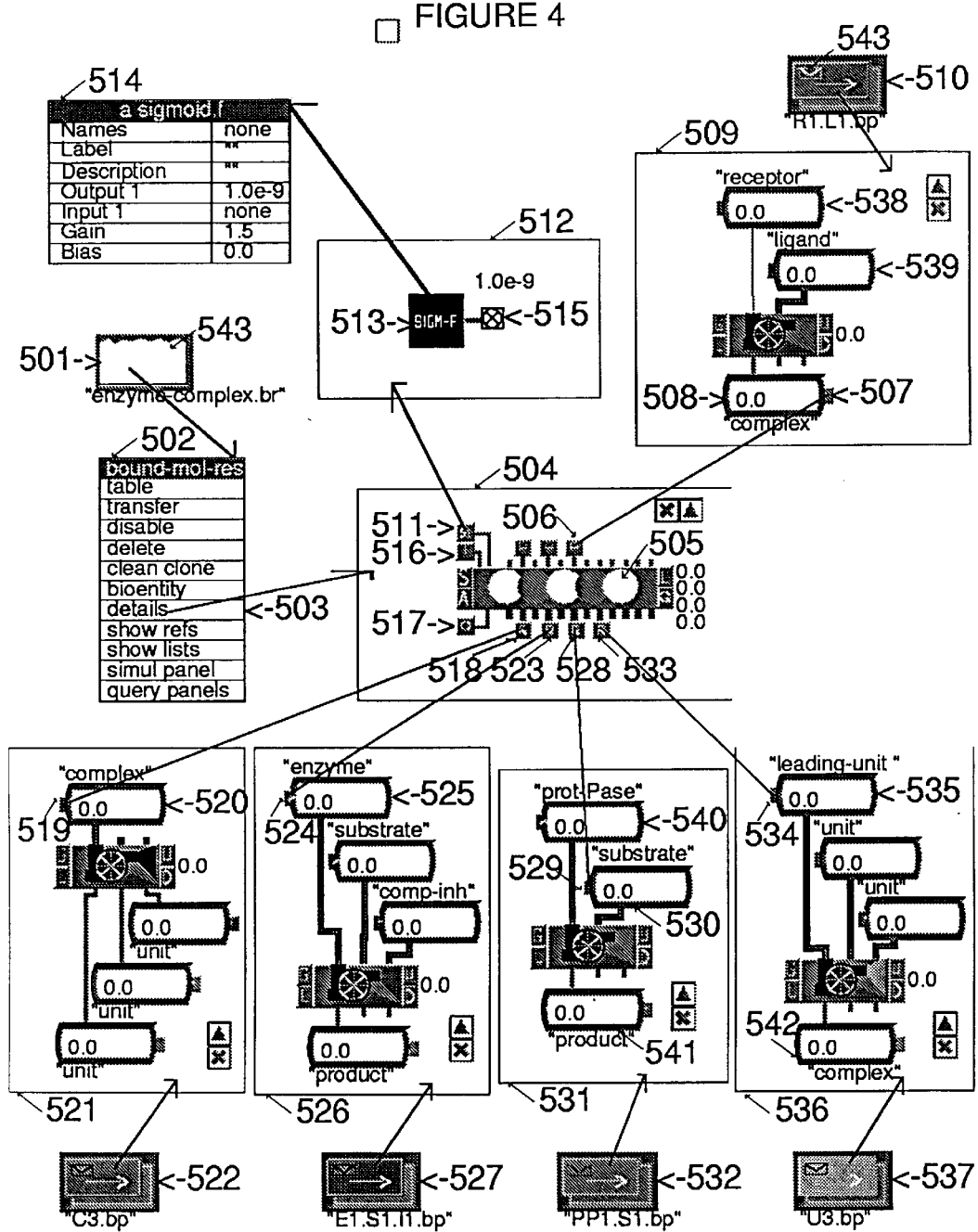
FIG. 4 shows in more detail exemplar iconic components of two-layered composite building blocks, focusing on an instance of reservoir and some instances of process building blocks that provide its inputs and receive its outputs, as well as a mathematically modeled input represented by a model-block.

7. Distant connections are here represented by lines which, like in FIGS. 2 and 4, are imaginary lines, and those connections are never visible. How those distant connections are established is described under the heading Modeler Mode. BioRole-posts and bioPool-posts are connection posts that, when distantly connected one-to-one, transparently connect the bioReactant or bioProduct to which one instance of the former is connected to the bioPool to which one instance of the latter is connected, and the result is that such bioReactant or bioProduct becomes connected to such bioPool, and the program can refer to those connections in rules, formulas, procedures, or other methods, by using expressions such as "the bioPool connected to bioReactant-A", or "the bioProduct connected to bioPool-B at inport-X". The program can also refer to "the bioReservoir superior to the bioPool connected to bioReactant-A" or "the bioProcess superior the bioProduct connected to bioPool-B at inport-X" or "the bioProcess superior to the bioProduct connected at inport-X to the bioPool upon the subworkspace of bioReservoir-B". In the narrative used to describe this invention, from time to time the following or similar expressions may be used as a short form instead of other more detailed and correct expressions, which also reflect the meaning of various relations defined in the current implementation, as described later and defined in Table 50:

a) "a bioProcess connected to bioReservoir-B" may be used to refer to "a bioProcess superior to any bioReactant or bioProduct connected to the bioPool upon the subworkspace of bioReservoir-B";

b) "the down bioProcesses of bioReservoir-B" refers to "all bioProcesses superior to any bioReactant connected to any bioReactant-post connected to the bioPool upon the subworkspace of bioReservoir-B", and a relation named a-down-bioprocess-of is defined between the classes bioProcess and bioReservoir that is used at run-time to relate each pair in that description, with the inverse relation defined as an-up-bioreservoir-of;

c) "the down bioReservoirs of bioProcess-A" refers to "all bioReservoirs superior to any bioPool connected to the bioproduct-post connected to any bioProduct upon the subworkspace of bioProcess-A", and a relation named a-down-bioreservoir-of is defined between the classes bioReservoir and bioProcess that is used at run-time to relate each pair in that description, with the inverse relation defined as an-up-bioprocess-of;

d) "the downstream bioReservoirs of bioReservoir-B" refers to "every bioReservoir superior to any bioPool connected to the bioproduct-post connected to any bioProduct upon the subworkspace of any bioProcess that is a-down-bioprocess-of bioReservoir-B, as well as every bioReservoir superior to any bioPool connected to the bioproduct-post connected to any bioProduct upon the subworkspace of any bioProcess that is a-down-bioprocess-of any bioReservoir that is a-downstream bioReservoir of bioReservoir-B", and a relation named a-downstream-bioreservoir-of is defined between the classes bioReservoir and bioReservoir that is used at run-time to relate each pair of bioReservoirs in that description, with the inverse relation defined as an-upstream-bioreservoir-of;

e) "the downstream bioProcesses of bioProcess-A" refers to "every bioProcess superior to any bioReactant connected to any bioReactant-post connected to the bioPool upon the subworkspace of any bioReservoir that is a-down-bioreservoir-of bioProcess-A, as well as every bioProcess superior to any bioReactant connected to any bioReactant-post connected to the bioPool upon the subworkspace of any bioReservoir that is a-down-bioreservoir-of any downstream bioProcess of bioProcess-A", and a relation named a-downstream-bioprocess-of is defined between the classes bioProcess and bioProcess that is used at run-time to relate each pair of bioProcesses in that description, with the inverse relation defined as an-upstream-bioprocess-of;

8. FIG. 4 describes a bioReservoir (501), with its associated menu (502) and its subworkspace (504). The menu associated with each object in the current implementation of this invention provides access to optional tasks associated with that particular object that the user can select. For example, when selecting the "details" option (503), the subworkspace of the bioReservoir is displayed (504), which contains, among other objects, a bioPool (505) connected to: a) several biopool-p-posts (506) on the top, which connect to the inputs to that bioPool from bioProcesses; b) several biopool-r-posts (518, 523, 528, and 533) on the bottom, which connect to the inputs of other bioProcesses that receive the outputs of that bioPool; and c) one scaled-input-model-box (511), one input-model-box (516), and one output-model-box (517), which allow modeling of inputs and outputs, as their names indicate, as mathematical models in the form of model-blocks. Each biopool-p-post (506) is connected to a bioproduct-post (507), as described above, connected to a bioProduct (508) upon the subworkspace (509) of a bioProcess (510), while each biopool-r-post (518, 523, 528, or 533) is connected to a bioReactant-post (519, 524, 529, or 534, respectively) which is connected to a bioReactant (520, 525, 530, or 535, respectively) upon the subworkspace (521, 526, 531, or 536, respectively) of other bioProcesses (522, 527, 532, and 537, respectively). The model-blocks are useful to bypass the detailed modeling provided by one or more bioProcesses or even a whole pathway, in situations when such detailed knowledge is not available or simply not desired. Model-blocks may refer to: a) any other variable or parameter, or sets of variables and/or parameters in the system, and they may also refer to the values of those variables or parameters at any given past point in time; b) the current or simulated clock time or time intervals; c) other variables and/or parameters external to the system; or d) any combination of the above. The subworkspace (512) of each such model-box provides an space for the user to place and connect any desired model-block (513), and any explanatory or other information. It can also contain a set of model-blocks to be alternatively tested at different times, with only the one model-block connected to the connection-post (515) being included in the computation of the Accumulation of the connected bioPool when a simulation is running. There are many classes of model-blocks defined in the system, as described later, and each has a characteristic associated table (514) that the user configures. The biopool-r-posts are connected to the bioPool through r-connections, biopool-p-posts through p-connections, and each class of model-box by scaled-input-box-connections, input-box-connections, and output-model-box-connections, respectively. Connections of different classes cannot be joined together, so that the user cannot by mistake make the wrong connections.

9. Each bioReservoir contains one and only one bioPool, and one bioPool is contained in only one bioReservoir. Therefore, in the description that follows, any attribute of a bioPool may be considered also considered as part of its bioReservoir, and may be referred to as a part of the bioReservoir. Each bioPool may be connected to an unlimited number of biopool-p-posts and biopool-r-posts, but each biopool-p-post may be connected to only one bioproduct-post and each biopool-r-post may be connected to only one bioReactant-post. Therefore, in the system of this invention, each bioReactant and each bioProduct of a bioProcess is said to represent, within that bioProcess, only one bioPool, and expressions like the bioPool (or the bioReservoir) of a bioReactant may be used in the description of the system. On the other hand, a bioPool may have, and usually do, several connected bioReactants and bioProducts, which may be expressed as the bioReactant(s) or the bioProduct(s) of, or connected to, the bioPool. When the definition of a pathway is completed, each bioReactant and each bioProduct have to always be connected, through specific connection-posts as described later, to a bioPool, resulting in a structure in which a bioReactant represents an input to a bioEngine and an output of the bioPool, while a bioProduct represents an output of the bioEngine and an input to the bioPool.

10. FIG. 4, while focusing on the bioReservoir, also summarizes an important part of the modular architecture used in this system that result in multidimensional pathways. Each bioPool may receive inputs from an unlimited number of bioProducts of different types of bioProcesses, which depend on the nature of the molecules represented by that particular bioPool. The bioPool can also receive an input in the form of the mathematical model, instead or in addition to the inputs from the bioProcesses. At the same time, the molecules contained in a bioPool can participate in many different types of bioProcesses, concurrently, sequentially, or both, through the connections of the bioPool to a variety of bioReactants. The generic example depicted in FIG. 4 could be described by a biochemist as following: A bioReservoir (501) contains a bioPool (505) of a molecular-complex generated (508), among other sources, in a bioProcess (509) by the binding of a receptor (538) to its ligand (539). Several bioProcesses of different classes can compete for the X number of units of such complex in the bioPool (505) at a particular point in time. The value X is given by the current value of the Concentration, Density, Scaled-Amount, or any other equivalent quantity (depending on the particular bioPool), that is an attribute of the bioPool. In the description of this invention the term "quantity" of a bioPool or bioReservoir may be used to generically refer to any of those more specific attributes or designations, which use varies with the class of bioPool involved and the type of reasoning. In a given bioProcess (522) the complex (520) dissociates into its subunits. In another bioProcess (527) the complex, where the potential enzymatic activity of the receptor component has been activated upon binding of the ligand, acts as an enzyme (525). In a third bioProcess (532) the complex acts a substrate (530) of another enzyme (540) that modifies it into the product (541), a modified and inactive form of the original complex. In a fourth bioProcess (537) the complex acts as a unit (535) of a yet larger complex (542). There are of course many other bioProcesses that could and do compete in this system, which are not represented in FIG. 4.

11. FIGS. 3 and 4 summarize the basis of an architecture that allows to model, using the basic paradigm of "Clone, Connect and Configure", very complex interactions. A bioPool and a bioEngine represent nodes where many pathways may merge, and where many pathway branches may originate. Any of the pathways that lead to any bioProcess where any of its bioProducts is connected to such bioPool, and any of the bioReservoirs and bioProcesses that are parts of such pathways, are referred to in this system as upstream pathways, upstream bioReservoirs and upstream bioProcesses, respectively. Any of the pathways that lead from any bioProcess where any of its bioReactants is connected to such bioPool, and any of the bioReservoirs and bioProcesses that are parts of such pathways, are referred to in this system as downstream pathways, downstream bioReservoirs and downstream bioProcesses, respectively. From a qualitative point of view, the defined bioProcess indicates which interactions are possible at some point in time, between the molecules or complexes characteristic of different bioReservoirs. Based on this architecture, the system of this invention is capable of establishing upstream and downstream relations between bioProcesses and bioReservoirs. This system is further able to use the knowledge of such relationships to dynamically build and draw pathways of multi-dimensionally connected bioProcesses, bioReservoirs, or a layered combination of the two structures. The elimination of one particular bioReservoir would cause the elimination of its downstream pathways.

12. From a quantitative point of view, the extent to which those interactions occur depend on the existence of adequate proportions of the interacting molecules or complexes at the adequate point in time. Any changes in the schematic architecture of the system, in the values of the initial conditions, such as the basal quantities, or any changes in the stoichiometric or kinetic parameters of the system can affect not only the quantitative but also the qualitative outcome of those interactions. Any of those changes that affect any of the components of any upstream pathway of a bioPool could effect changes in all of the downstream pathways of that bioPool. Furthermore, even changes in any pathway that affect downstream components of a bioPool can dramatically affect not only that branch but also all other pathways downstream of that bioPool. In the example in FIG. 4, any change in any pathway upstream of the active form of the protein-phosphatase enzyme that results in an increase of the amount of such active form available as prot-Pase (540) would cause the amount of the substrate (530) converted into product (541) to proceed at a faster rate, therefore leaving less amount X of complex units in the bioPool (505) to take part in the other bioProcesses. The net effect of more prot-Pase (540) would be an initial up-regulation of its bioProcess (532) and all its downstream pathways, and a down-regulation of other bioProcesses (522, 527, and 537) and all their downstream pathways, until the bioPool (505) is depleted, a new steady state is reached or other regulatory influences apply.

13. In the preferred embodiment of this invention, the basis of the system's dynamic simulation capability is the network of state variables and dependent variables and parameters, encapsulated as attributes of the bioPools and the different components of bioProcesses. A modeled system can be also abstracted as an interaction between bioPools as defined by the internal topology of bioProcesses, which could be viewed as representing the flow of materials from the bioPools of the bioReactants to the bioPools of the bioProducts, at rates determined by the appropriate algebraic equations associated with the variables of a bioProcess. The various inflows and outflows of materials to a bioPool are integrated through a set of variables of the bioPool, which output value is a quantity such as Scaled-Amount, Concentration or Density. A pathway could thus be defined as a set of consecutive and distantly connected bioReservoirs and bioProcesses. A pathway may be, and frequently is, branched, and branches of different pathways may, and frequently do, converge. Branching and convergence may, and usually do, happen at both the bioReservoir and the bioProcess levels. Therefore, when we refer to a pathway in the system of this invention, in reality we are more realistically referring to a more or less complex network of pathways.

Figure 5:
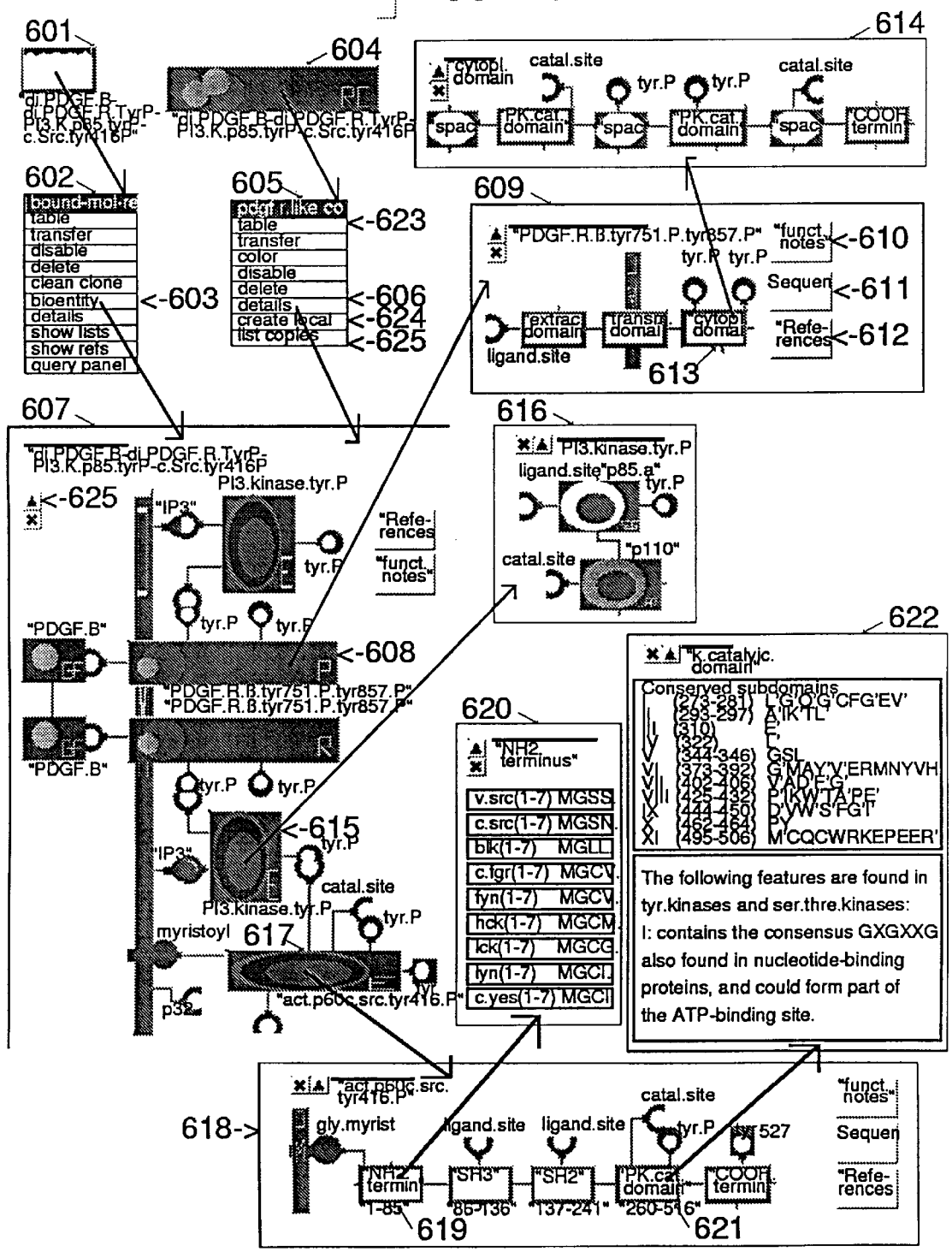
FIG. 5 shows various layers of an exemplar instance of iconic composite entity building block with a complex molecular structure built with instances of iconic entity building blocks representing its molecular components.

14. As illustrated in FIG. 5, instances of bioReservoirs may have a value for the "ref-bioentity" attribute, which holds a pointer to a named top-level (or superior) bioEntity, such as a molecule or a heter-mol-complex, in which case the menus (602) of such instances of bioReservoirs (601) and of their connected bioReactants and bioProducts (not shown) include the "bioentity" option (603). By selecting that option, the subworkspace of such bioEntity is displayed, which components represent the functional structure of the bioEntity which units are contained in such bioReservoir (501). The structure can also be displayed from the icon of the bioEntity (604), by selecting from its menu (605) the "details" option (606). The menus (602 and 605) shown are those that appear in Modeler Mode, while in General Mode some of those options are not available, and in Developer Mode more options are offered. In Navigation Mode and for some classes of objects, including complex-bioentity, clicking on their instances automatically causes their subworkspaces to be displayed or hidden, so that these menus (602 and 605) would be bypassed, and as a result, the structure of the bioEntity would not be accessible from the bioReservoir (601), while the structure (607) would be displayed directly upon clicking on the bioEntity (604), as is shown for the clicking of the other bioEntities in FIG. 5.

15. The subworkspace encapsulation approach used in the current embodiment of this invention to define the structure of a molecule, and the further details of instances of bioEntities can be explored by sequential clicking on the encapsulated icons. Each superior bioEntity represents the structure of a biochemical physical entity in a particular state, such as different chemical modifications, different states of association with other entities, or the products of different mutations or artificial manipulation or quimeric constructions, which corresponds to the concept that different bioReservoirs hold molecules or complexes in different states. The structural and other types of information about the units that form a bioPool, as provided in the corresponding bioEntities, is supplemental, and it is not necessary for creation or navigation thought the pathways, or for simulation. This information is used independently of the pathways, or they may be used in combination, in the complex queries.

16. The subworkspace (607) shown for a specific multi-unit receptor-complex (604) contains the icons of its various components. In turn, upon clicking on each of those components, their subworkspaces are displayed on the screen, showing their structural composition. The level of detail is optional, and components at different levels in the hierarchy of subclasses can be connected to each other. For example, clicking upon a subunit of the receptor (608) shows its structure (609) composed of domains, other simple-bioEntities, and other optional auxiliary structures, such as those that may contain: notes about its function (610), the sequence (611), or references (612). Any of those components may contain more detailed information, such as that displayed when clicking in one of those domains (613), which structure (614) is composed of other domains, spacers and other simple-bioEntities. Back to the main structure, clicking on a kinase (615) that form part of the complex, its structure (616) may be represented by its two subunits, a regulatory-subunit and a catalytic-subunit, each containing or pointing to additional detail (not shown). Or the structure can be directly represented directly by it lower level components, such as when clicking on other associated kinase (617), which structure (618) is composed directly by several domains and other simple-bioEntities. Any of those molecular components may contain in their subworkspace any type of other relevant information, when more detailed structure is not available or not desired. For example, clicking on one of the domains (619) shows (620) differences in the sequence of a functionally important homology region of that domain for different members of that family of molecules (which allows to represent all members of the family by just one structure, by describing additionally the differences between the different members), while clicking on another domain (621) shows more information (622) about conserved subdomains within that family. In general, simple-bioEntities may be linked to a motif, a domain or even to a subunit or a molecule. The structure may focus on only those parts of the structure that have functional relevance. If intermediary stretches within the structure are unknown or that detail is not desired, they may be represented by domains called spacers.

17. Many of the graphic structures used in the currently preferred embodiment of this invention to display information (equivalent to toggling buttons in many occasions, but not exclusively) have associated methods that cause to either dynamically create or destroy at run-time their subworkspace and a set of other graphic structures that are displayed upon such subworkspaces for further interactions by the user. This dynamic creation and destruction of structures is preferably for two reasons: a) the content of the knowledge-base and the relationships among its components may vary from one point in time to another, so the newly created structures show the information that is current when they are created, and depending on the type of structure this information may or may not subsequently be updated, and b) the applications that can be developed using the tools and methods of this invention may become very large, and this dynamic actions allow to cut considerable the amount of knowledge structures that are permanently stored in the knowledge-base. These dynamic actions put more demands on the system at run-time, and their effects on the overall performance of the system depends on many external factors, such as the availability of RAM, the number of windows or users that are using the system simultaneously, and also whether a simulation is running and the size of the model that is running, since this consume more computing resources.

18. The domain-specific interface of the system of this invention also comprises a variety of query-panels which facilitate query by the system, and entry-panels which facilitate user selections and inputs, such as the definition of initial conditions and the entry of user-defined inputs to start a simulation, as will be described in more detail in the appropriate sections below. The capabilities required to build these interactive panels are supported by the Shell's development and deployment environment, and facilitated by its graphical user interface, using devices such as mouse pointing, clicking, and dragging. The query-panels and entry-panels are created on demand upon selection by the user by selecting the appropriate options as offered in menus associated with bioObjects such as bioReservoirs or bioReactants, or from system-wide pull-down domain-menus. These query-panels and entry-panels, which are subclasses of dialogs, have all subworkspaces upon which specific layouts of any combination of standard user-interface structures (such as action buttons, type-in boxes, radio buttons, check boxes or sliders) are created at run-time, frequently by cloning existing master panels and/or by adding newly created structures. The data entry structures upon a entry-panel are associated with one of the variables or parameters that are attributes of the bioPool(s) selected for input.

19. All the definitions of object classes, some examples of instances of those classes, the definitions of the user-menu-choices associated with selected class definitions and the definitions of the procedures that those user-menu-choices invoke, the definitions of classes of variables and parameters, as well as the definitions of relations, formulas, rules and other procedures, to be discussed in the following sections of this application, are provided in the form of tables within the attached Appendix. In order to avoid disruption of the narrative, the fact that the table in parenthesis refers to the definitions of objects or methods that precede it, will be omitted. The number of the corresponding table will be given in parenthesis after the first time that class is mentioned. In the definitions of object classes, which are all those that start with the "class name" and "superior class" attributes, only incremental information new for that particular class is provided, omitting mostly parts of the definitions that are inherited from superior classes or parts that are obvious or not relevant. In the definitions of procedures, which are all those that start with its name followed by a parenthesis with the definition of its arguments, an english-like pseudo-code is used to describe the sequence of actions, loops, and so on. In that pseudo-code, the begin, end or equivalent delimiting signs have been eliminated, but an equivalent delimitation of groups of statements have been maintained in the structured indentation.

20. As shown in Table 1, the schematicTools described above are not all subclasses of a unique object class but rather of a set of classes, themselves classes or subclasses of object classes defined within the Shell, comprising the super classes bioObject (Table 2), connection (Table 4), and bioPost (Table 5). Furthermore, the class bioObject comprises the major classes of bioView-Object, bioNode-Object, bioRole-Object and bioEntity, which are important domain-specific components of this system. The composite bioObjects, which belong to the classes bioEntity and bioView-Object (which include bioReservoirs and bioProcesses), are defined not only through their attribute tables, but mainly graphically through the schematics in their subworkspace, which contain their internal component structures. These iconic objects described above are offered to the user as prebuilt tools in palettes, accessible through the domain-menus, to allow them to: a) create new instances of those existing bioObject classes, by using the clone, transfer to a workspace, and modify paradigm, and b) to graphically build their particular chemical or biochemical graphic databases and models to be used in experiments and simulations, by connecting the icons of existing or newly created instances.

21. The strategy used in organizing the following description of the numerous different types of objects and methods used in this invention is to divide the description into four major sections, following in a loose way the four user-modes of the system. User-modes are the defined values of a Shell-defined attribute of each window. The functionality of the system of this invention and the menu options available for different objects are constrained and defined differently for different values of such user-mode attribute, here referred in a generic way as user-modes. The Mode Selection Panel shows all the user-modes available to a developer, and is used to select and change to a desired user-mode. The user-mode can also be selected from options provided in the different user-mode specific domain-menus, as shown in the following sections. The Shell provides a facility to package and secure an application, which will not be discussed here in more detail, other than to say that it allows to restrict the access to different user-modes. The Administrator Mode option can be restricted to only a small number of people that should have wide access, while the Developer Mode is a proprietary mode that is not accessible to modelers or other users. Therefore, the Mode Selection Panel of an application packaged for only modelers and users would contain only the General, Navigation, Simulation and Modeler toggle-buttons (not shown). The application can be used concurrently by several users, and modified concurrently by several modelers or developers, by accessing the program from different windows (using X-windows-based or MS-Windows-based interfaces that are extensions of the underlying Shell) with the changes being immediately available to all of the concurrent users. To make concurrent use possible, the methods of the current implementation of this invention are encoded in reference to the current window (meaning screen, and not to be confused with a workspace of the current invention), to apply only within the window from which they are invoked. It is also possible for different windows to be operated concurrently in different user-modes, as selected by the user from the options available for each type of user, which depend on the rights acquired. In Simulation Mode, since the values of many attributes are dynamically changed, two alternative simulation methodologies are offered: one allows simulation runs concurrent with other users, but requires a system with more RAM, while the other allows only one user in Simulation Mode, but does not require the additional RAM. Which one should be used depends on the hardware configuration and user needs.

Figure 6:
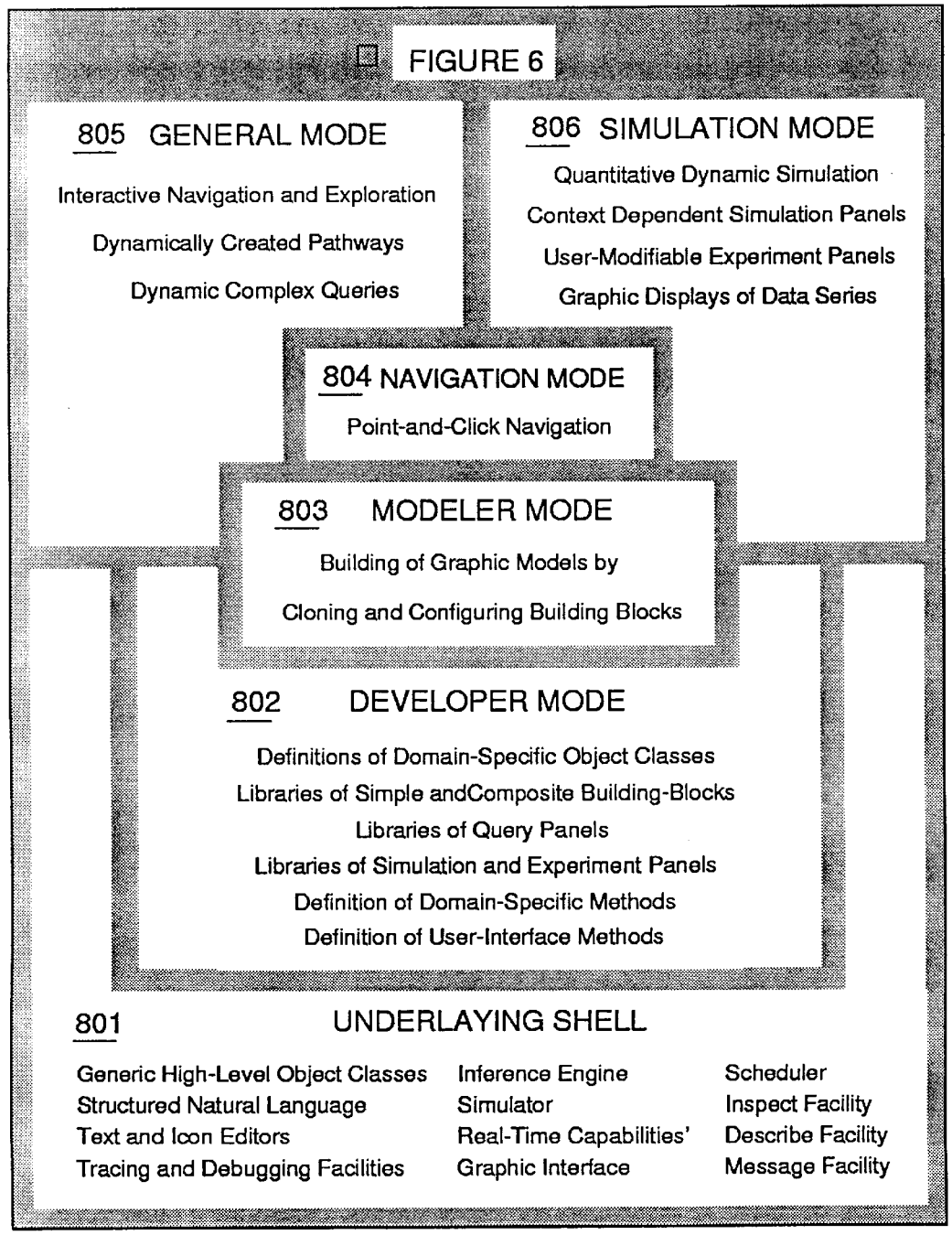
FIG. 6 shows some of the different capabilities and functions available under different selectable modes as provided by the means comprised in the systems and methods of this invention.

22. As shown in FIG. 6, the objects and methods that are necessary to perform the tasks characteristic of each user-mode are based on methods and knowledge-structures defined or build in the different user-modes that are layered below them. All modes use for deployment some of the facilities (801) provided by the underlying Shell, as described briefly in previous sections. Using those domain-independent facilities (801), all the objects classes and associated methods to implement all the domain-dependent capabilities comprised in the system of this invention are defined, and the palettes of prebuilt building blocks are constructed, in Developer Mode (802). Using the domain-dependent building-blocks, tools, and methods designed and built by the developer (802), the modeler can expand the library of building-blocks and build complex, application-specific, graphic models of biochemical systems in Modeler Mode (803). A user can then use those complex graphic models (803) to navigate through those biochemical systems when in Navigation Mode (804). A user can also use those complex graphic models (803), in combination with the inference engine and other facilities of the Shell (801) to: a) create dynamic interactive pathways that are context sensitive, and allow more targeted navigation and exploration, or perform complex predefined queries, that are context sensitive, and related to structure, relative position in the pathways, function, or any combination of them, when in General Mode (805); or b) running quantitative, absolute or scaled, simulations, with the additional use of the Shell's or external simulators, when in Simulation Mode (806)

23. Under the heading Developer Mode (FIGS. 7 through 11, Tables 1 through 102), we will first briefly discuss the definitions of the object classes and describe their attributes, as well as the methods associated with the high-level classes. After defining a few high-level classes, classes such as variables and parameters that will be referred to as attributes of other classes of objects will be briefly discussed first, so that can then be used as building blocks of the more complex objects. The user-menu-choices and associated methods for more specific subclasses of graphic objects will be discussed under the headings of the user-mode where such tasks are primarily used, even if operationally, the creation, coding, and modification of all those definitions and methods is restricted in the current embodiment of this invention to the Developer Mode.

24. Under the heading Modeler Mode (FIGS. 12 through 19, Tables 103 through 117), we will describe the tools and methods provided to the modeler, and how those tools are used to create, configure, and modify bioObjects, and how they can be organized to create graphic models of chemical pools of entities, the processes in which they interact and the functional architecture of those entities.

25. Under the heading General Mode (FIGS. 20 through 25, Tables 118 through 193), we will describe the tools and methods provided to the user that wants to interactively explore the system that the modeler has built, and to extract the knowledge incorporated into the system in a variety of forms. That knowledge includes not only the architecture of the models that the modeler has graphically composed, or the information and data that the modeler has entered into the attribute tables, but it more importantly includes the integration and amplification of that knowledge and the creation of new knowledge by the computer program, which: a) establishes relations between different components of the system, based on the graphic architecture, b) uses those relations and many other forms of reasoning to create and display specific answers to complex questions that the user pose by simply clicking on a variety of graphic structures within the rich user-interface provided by this system. Among the services that the user can request in this mode are various forms of queries, and the creation of downstream and upstream pathways containing the bioProcesses and/or bioReservoirs involved, from which further interactive exploration is possible. Cross-talk between different pathways can also be analyzed by requesting the creation of pathways from multiple initial points at once, and the program takes care of interconnecting the pathways where single elements are shared by more than one pathway. The tools provided for queries include a large library of predefined graphic query-panels, from very simple to very complex. Those queries are based on the structure of the bioEntities, the roles in which their bioPools participate in bioProcesses, their relative position within the pathways, or a combination of any or all of them. Those panels are dynamically created, to accommodate the context from which they are requested.

26. Under the heading Simulation Mode (FIGS. 26 through 30, Tables 194 through 231), we will describe the tools and methods provided to the user that wants to quantitatively simulate in real-time, or in simulation-time, the interactions between the different components within a pathway. Simulations can be initiated from a single point of input, through a simulation-panel dynamically created in association with the desired bioReservoir, or from multiple input points selected by the user through the user-modifiable experiment-panels.

D. Developer Mode: Definition of the Building Blocks and their Associated Methods 1. Domain-menus and Organization In the current embodiment of this invention, selecting any of the available user-modes changes, only for the window from which it is selected, the mode of operation and displays the specific domain-menus associated with that user-mode. Selecting Developer Mode displays the options "Object Definitions", "Variable Structures", "Rules Proc's & Relat's", and "Formulas & Functions". Selecting "Object Definitions" pulls down its options, which point to major groups of object classes. In a similar way, selecting "Variable Structures" displays its options, and further selecting "Variables" displays the additional pull-down menu headed by "Variables" which options refer to different groups of variables, and further selecting one of them, such as "Velocity pVariables" displays the workspace shown in FIG. 7 that contains the definitions of the class velocity-pVar and its various layers of subclasses.

2. Descriptions of General Groups and High-Level Classes a) The classification and definitions of the object classes will be here described. Table 1 shows the different classes and groups of tools and methods comprised in the current embodiment of this invention, which are all knowledge structures represented as objects. Those tools and methods are preferably organized into major groups, each comprising several object classes, which may each further comprise several levels of more specific subclasses, to be discussed in more detail in the following sections. Each top class of any of those groups is a subclass of one of the generic classes of objects defined within the Shell, inheriting a minimal set of attributes and capabilities. Several of those capabilities may be specific for that particular Shell and may be proprietary technology, and will not therefore be described. Some of the attributes and capabilities may not be mentioned here because they may not be necessary to describe this invention. However, these additional attributes and capabilities may facilitate the development task and improve the performance of this invention. The reader should contact the producer of the Shell for desired additional details. In this filing, only those Shell-defined attributes that are to be given values that are relevant for a clear definition of this invention will be considered, and these attributes or their equivalents may be common to other development environments. In the following discussion, attention will be focused mainly on those attributes that are newly defined and that are innovative and specific for the current embodiment of this invention.

b) There are several other basic classes defined within the Shell that the system of this invention makes uses of. One of those are workspaces, which are items used to hold and display other items. Workspaces can be independent higher-level workspaces, or subworkspaces subordinated to objects. The attributes of workspace are user restrictions, names, margin, and module assignment. Subworkspaces may also have the capability of being activatable, which means that the objects upon them are only active and visible to other parts of the system when such subworkspace is activated. If an activatable subworkspace is not activated, any item upon such subworkspace is ignored by the inference engine and the simulator, and as a consequence any structure upon it is not operational, and nothing happens when clicking on buttons or any other structure). In addition, several capabilities of the Shell, such as flashing of the icons, changing colors, or rotation of specific patterns can be used to animate a simulation and to indicate relevant events, such as showing the bioObjects and schematics that are activated, or which variables' values are out of range, and many other applications.

c) The Tables listed in the Appendix that contain object class definitions include only those attributes which provide new and relevant information, such as: a) "class name", b) "superior class", and c) "attributes specific to class". Other attributes are listed only when relevant, following the following rules:

"Capabilities and restrictions" describe which additional capabilities or restrictions apply to all the instances of all the subclasses of that class. The Shell-defined capabilities used in the current implementation of this invention comprise: "activatable-subworkspace", for the classes bioReservoir and bioProcess, and "subworkspace-connection-post" for the class model-box.

"Class restrictions" define which menu options and other non-menu choices are available or disallowed, or which attributes are visible in the table, in each particular user-mode for all the instances of all the subclasses of the class for which they are defined. The Shell-defined non-menu choices include: "move-object", . . . . The Shell-defined menu choices include: "table", "name", "transfer", "create-subworkspace", "change-size", "describe", "disable", "delete", "rotate-reflect", . . . .

"Inherited attributes" will usually not be listed, since they can be deduced by adding up the listings of "attributes specific to class" of each of the superior classes. On occasions, however, inherited attributes may be listed for the purpose of summarizing disperse definitions. When an attribute is defined in more than one object-definition, only the most proximal (or lower-level) definition applies.

"Menu option" refer to whether the name of the object class appears as an option within the new-object menu selection, or with other words, whether the class can have instances (if the value of this attribute is "a final menu choice") or whether the class is only a superior to other subclasses (if the value of this attribute is "not a final menu choice"). This attribute will be only listed for those high-level classes which are "not a final menu choice", and it is otherwise assumed that the class is a "final menu choice"

"Stubs" define each of the connections for that class, the position of the icon for that class at which they are connected, and optionally the direction of flow and/or the name of the connection port. The stubs can be inherited from superior classes, in which case the value of this attribute will be inherited, or the class may have no defined connections and the value is none, and in either case this attribute may or may not be listed. If it is not listed and the superior class have defined stubs, then it is assumed that the stubs are inherited, and if the superior class have no defined stubs, then it is assumed that the value of this attribute is none.

"Icon description" defines the graphic appearance of the icon characteristic of all the instances of the class. The icon can be inherited or be specific for that class, and usually contain differently colored layers, or color-regions, which color may change dynamically at run-time, to visualize the state of the objects, such as selected, or of their subworkspaces, such as activated. The detailed description of the icon is not included to save space, and in most occasions it will be referred to as the <name of the class>-pattern, followed by its dimensions (to have a reference for the stubs), and by the color-regions, which may be referred to by rules and/or procedures.

d) In addition to an attribute table and sometimes a subworkspace, each object has an associated menu with a set of options. Such actions may include starting one or more procedure. Some of those menu options, which are either domain-independent and defined within the Shell, perform standard tasks common to all objects, such as: change-size, clone, color, delete, describe, disable, go-to-subworkspace, move, and name. Many of those tasks are self-explanatory and will be not further described. Other menu options, are defined in the system of this invention as domain-specific user-menu-choices to provide interactive access by the user to important automatic or semi-automatic tasks related to the configuration of the knowledge structures and to requests for diverse forms of processing and display of such knowledge. User-menu-choices are defined for the specific class named in its applicable class attribute. They appear as options in the menu associated with the icon of every instance of every subclass of said applicable class, unless a class restriction defined for any of those classes for any particular user mode exclude that option from the menu. Selecting any particular options triggers one or more actions. All those domain-specific tasks provide a highly interactive user-interface and are important teachings of this invention. Those options and the methods invoked upon their selection will be discussed in later sections. Here we will focus on the definitions of all object classes and on the description of their attributes.

e) The first major group shown in Table 1 is that of schematicTools, which comprises three major classes, bioObject, bioPost, and bioConnection, and each of these major classes further comprises a hierarchy of classes and their subclasses, to be described in some detail below.

3. BioObjects a) The class bioObject comprises all the classes of knowledge structures necessary to represent the chemical and biochemical systems characteristic of this domain. These object classes are characterized by their assigned attributes, which can be: a) simple attributes of various types, such as text, symbols, integers, floats or truth values, or b) pointers to defined text, logic, symbolic or numeric parameters, variables, list or arrays, or pointers to other objects. The classes of the objects pointed to, including the variable structures (which are also defined as objects), have to be previously defined. The values for the parameters and variables can be provided by any of a variety of sources, such as the user-inputs, on-line sensors, or dynamically by the inference engine (for instance, through specific or generic formulas, rules or procedures), or a simulator (for instance, through specific or generic simulation formulas or simulation procedures), reflecting the changing values of the attributes defined within the knowledge structures and in the context selected by the user. In addition, the capabilities of the system of this invention is largely extended by the extensive use of the encapsulated mathematical models, which are made of simulated variables and parameters which values are computed by the Shell's or other external simulators. A user may create new instances of those knowledge structures by selecting and cloning icons from the domain-menus' palettes, transferring them onto desired workplaces, and configuring their attributes using the associated table.

b) The superior class of bioObject (Table 2) is object, a class defined within the Shell. Notice that this class can only have subclasses, not instances, and that they are some restrictions that apply to this class when in different modes. All bioObjects have at least three common attributes: a) "names", a Shell-defined attribute that binds one or more unique symbols to a knowledge structure; b) "label" a text attribute that allows to identify bioObjects that may not have a name; and c) "description" is an optional text string, entered by the user, that briefly describes the bioObject, or provides any additional information, notes or restrictions about it. While names are required for some bioObjects to be integrated into the pathways, labels offer more flexibility for identification when names are not required, because they require less memory than symbols, do not have to be unique, and their syntax is less restrictive and offers more attractive options for display.

c) Among the major subclasses of bioObject (Table 2), which subclasses are described in more detail in later sections, are:

the class bioNode-Object inherits all attributes and icon from bioObject and have no additional attributes specific to this class. However, there are methods that refer to and specifically apply to this class, and therefore, like with many other classes throughout this knowledge base, the differentiation between classes may not appear in their definitions, but rather on the methods that are applied to them. Notice that this class can only have subclasses, not instances.

the class bioView-Object inherits all attributes and icon from bioObject, and this class can only have subclasses, not instances. A user-menu-choice labeled "details" (Table 3) appears in the menu associated with the icon of every instance of every subclass of bioView-Object, unless a class restriction defined for any of those classes for any particular user mode exclude that option from the menu. Upon selection of that option from the menu of a bioView-Object by the user, the procedure go-to-view-proc is started. This procedure takes as among its arguments the bioView-Object from which it was invoked and the current window, where as a result of the actions of this procedure, the subworkspace of the bioView-Object is displayed or hidden, depending on the value of its "toggle-state" attribute, and the icon is configured to its pressed or depressed appearance, respectively. A characteristic of this class is that the subworkspace of each instance of those subclasses is activatable. New attributes defined for this class comprise:

"references", defined for several subclasses of bioObject, is an optional text that makes reference to the sources of information and data used to construct and configure that instance of any subclass of bioObject for which it is defined. Preferably, this attribute should list the short-ref attribute of the desired set of references, which are defined as separate structures of the class reference-block (described later). An alternative definition of the attribute "References" is: references is given by an instance of a reference-array. The initial-values attribute of a reference-array may be configured by the user to list the desired references, separated by commas, by referring to the short-ref attribute of the desired set of references. Procedures are provided to graphically display the references for each instance of the composite bioObject classes bioEntity, bioReservoir and bioProcess, as described below.

"warnings" is an optional simple text attribute which value is set by the modeler to warn the user about any particularities or data included, such as, for a bioReservoir, when that particular pool of molecules have not yet been observed experimentally, but can be assumed to exist by analogy to similar systems, or when the pool has been observed but the quantitative data has been assumed. This attribute is also defined for the class complex-bioEntity for similar purposes, and in all cases it is used in conjunction with an envelope design (424, 544) in the icons defined for all those classes and their subclasses as a separated color-region, called flag-color, that is changed to yellow to make the user aware of the existence of warnings, or back to any appropriate color. Those changes are automatically executed, as defined in the system of this invention, by procedures invoked during initialization, or any time while the application is running by two sets of three rules each to apply to each of those high-level classes, and which are equivalent to the following statements: "Whenever the warnings of any bioView-Object O receives a value V and when V/=" "then conclude that the flag-color of O is yellow" and "Whenever the warnings of any bioReservoir R receives a value V and when V=" "then conclude that the flag-color of R is medium-aquamarine"; and "toggle-state" is an attribute also defined for the class complex-bioEntity and other objects, such as the class button, which icons' appearance change upon selection by the user, depending on the value of this attribute, which alternatively switches between show and hide when the user clicks on the icon, and depending on the value of this attribute, a variety of procedures causes the subworkspace of the object to be displayed or hidden.

4. Connections and bioPosts a) In the current embodiment of this invention, a connection refers to an object that connects other types of schematicTools upon a workspace. Connections are established graphically, by the union of the stubs attached to the bioObjects involved, or by extending a stub of a bioObject and attaching it directly to another bioObject, if the class definition of the latter allows manual connections. Stubs are handles on the icons of objects that are clicked and dragged to create the connections. The class connection, defined within the Shell, has several domain-specific subclasses. They are used to define different abstract concepts such as relationships, links, inputs, outputs or information passed between objects. The definitions of the subclasses of bioEntity, bioPool, bioEngine, bioReactant and bioProduct and bioPost prescribe the class of connections that are allowed at each port of their icons, as defined in their stubs slot. They represent the different types of possible graphic connections defined for such structure, and direction of flow may also be specified in such definitions. The stubs are inherited, but they can also be modified. Those stubs that are not used can be graphically removed.

b) The definitions of all those subclasses (Table 4), include the descriptions of the "cross section pattern", that provide each with characteristic pattern and color to facilitate modeling tasks and visualization, and a predefined "stub length". Each of those classes is specific for connecting particular combinations of objects, as described in FIGS. 2 and 3. Stubs of different classes or subclasses cannot connect to each other to prevent the modeler from making erroneous connections. Connections comprise the following major classes:

the class p-connection represents the channel between a bioEngine and a bioPool, and more specifically a bioProduct's input to a bioPool, in terms of both unidirectional material flow and data flow. Several stubs for p-connections are defined at the top (416) of the class bioPool, which may graphically connected (417) to the one stub defined at the bottom of each biopool-p-post. Also several stubs for p-connections are defined at the bottom (420) of the class BioEngine, which may graphically connected (309) to the one stub defined at the top of each bioProduct.

the class r-connection represents the channel between a bioPool and a bioEngine, and more specifically a bioPool's input to a bioProcess, in terms of both unidirectional material flow and bidirectional data flow. Each instance of a r-connection may graphically connect (419) a biopool-r-post to the bottom of a bioPool, or may connect (308) a bioReactant to the top of a bioEngine. Several stubs for r-connections are defined at the bottom (418) of the class bioPool. In addition, the class r-connection has many subclasses which differ only in their characteristic cross section color pattern, and each connects a different class of bioReactant to a matching stub of the same subclass defined at the top of a bioEngine. The definition of each subclass of bioReactant specifies within the stubs attribute the specific subclass of r-connection, and the definition of each subclass of bioEngine specifies within the stubs attribute a set of specific subclasses of r-connections and their locations. The purpose of this implementation is to prevent users from making the wrong connections, while directing the user to make the appropriate connections by matching the color pattern.

the class icon-wire represents merely a programming tool, and each of its instances graphically connects a bioRole-post (403, 407, and 411) to its bioRole-Object.

Figure 8:
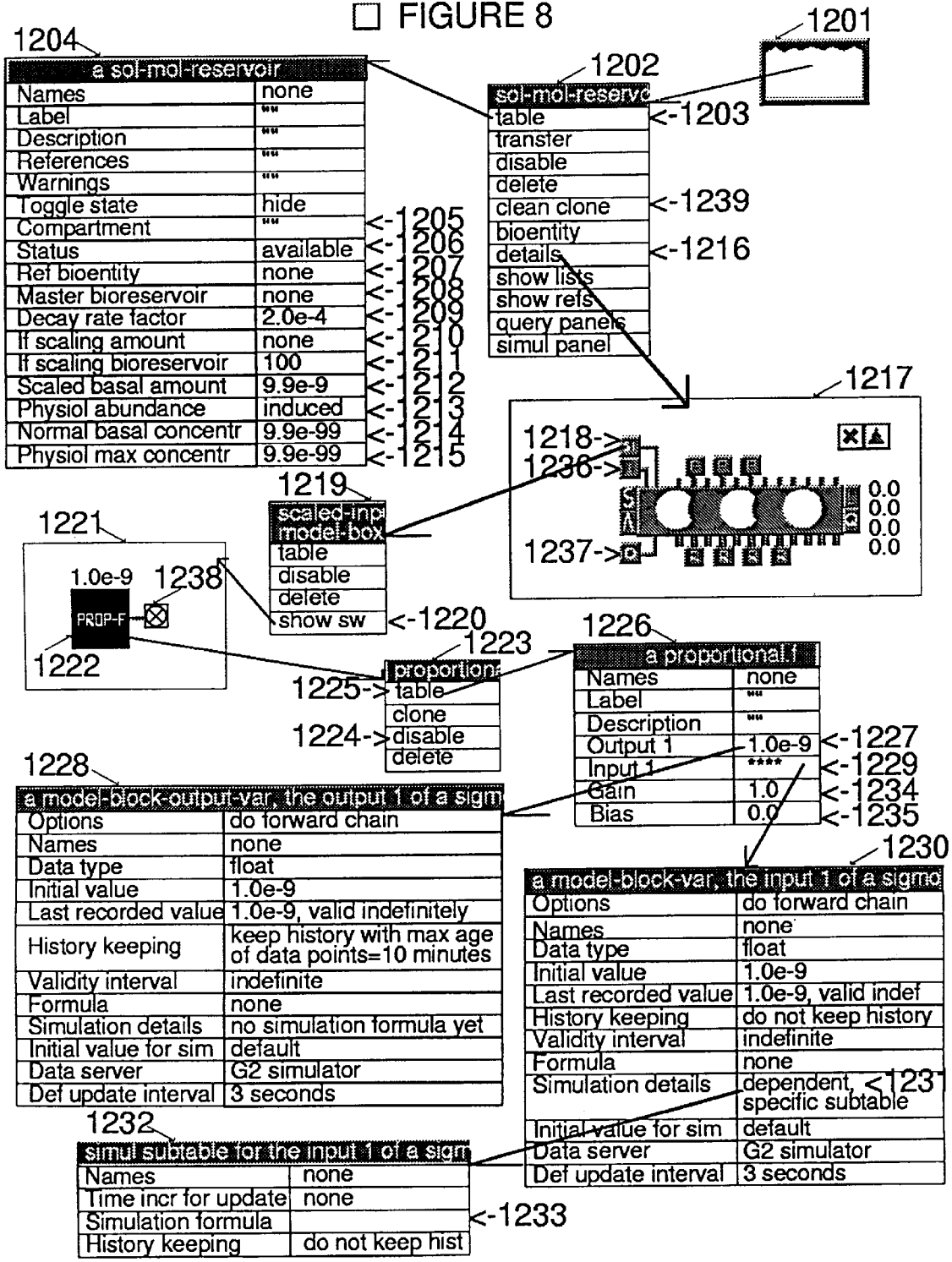
FIG. 8 shows an exemplar set of pop-up menus and attribute/value tables of an iconic instance of a two-layered composite reservoir building block and one of its inputs, with focus on the quantitative variables and parameters of a model-block modeling that input.

After the connection is made, this wire is made invisible by either: a) one of two rules (Table 55) invoked when the bioRole-Object is moved by the user, or b) by a procedure invoked at initialization (Table 123);

the class model-box-connection, which also represents a tool, has three subclasses, scaled-input-box-connection (421), input-box-connection (422), and output-box-connection (423), with instances of each graphically connecting, as shown in FIG. 8, instances of scaled-input-model-box (1218), input-model-box (1236), and output-model-box (1237), respectively, to predefined corresponding ports of a bioPool. Note that: a) the stubs for these specific connections are defined for each subclass of model-box, and for each subclass of bioPool at named ports; b) these subclasses are color coded to guide the modeler to match the color pattern when making the connections.

the class graph-link is merely a programming tool, each of which instances graphically connects various types of tracers, to be discussed later, to either a bioPool or a bioEngine. After the connection is made, this link is made invisible by either: a) one of two rules (Table 55) invoked when the bioPool or bioEngine is moved by the user, or b) by a procedures invoked at initialization (Tables 122 and 123);

the class link defines the connections between the bioEntities upon the subworkspaces (607, 609, 614, and 618) of other bioEntities, representing the continuity of an ordered sequence of structural components, such as: a) the subunits of a complex, or b) the bioEntity-components of a molecule. They represent a lumped class of chemical bond, and by defining further subclasses, specific types of bonds can be represented, such as covalent, —H—H-bridge, —S—S-bridge, and so on.

c) The class bioPost (Table 5) is a subclass of connection-post, itself a subclass of object defined within the Shell and from which it inherits all its capabilities. A very important teaching of this invention is the design and use of the different subclasses of bioPost, each referring to a graphic structure (403 or 411) that may be distantly connected to another bioPost (404 or 412, respectively) of a complementary subclass. To be distantly connected, those bioPosts must have the same name, and they are located upon different subworkspaces. These structures are components of the schematics located on the subworkspaces of composite bioObjects, and the overall function of the bioPosts is to integrate bioReservoirs and bioProcesses, wherever they are located. Any number of bioPosts with the same name may be connected to each other, however, in the current implementation, they are preferably connected one to one. There are several restrictions built into the system of this invention to prevent users from making the wrong connections, or to warn them that wrong connections have been made, such as when a bioReactant-post is given the same name as a bioPost that is not a biopool-r-post, or when a bioproduct-post is given the same name as a bioPost that is not a biopool-p-post. Warning messages are displayed when the connections are being established, as well at the next initialization time, when all the naming of bioPosts are checked, and any abnormalities found are reported to the user, as discussed later.

d) The definitions and descriptions of the various subclasses of bioPost, which hierarchy has been shown in Table 1, and their associated methods will be discussed in later sections, within the overall description of bioReservoirs and bioProcesses, where they are important components. Very important and novel teachings of this invention are the design, uses, and methods associated with the different subclasses of bioPost. This architecture allows various bioProcesses to simultaneously compete for the contents of a bioPool while also allows one bioPool to participate in various bioProcesses in different capacities, with different units within a bioPool behaving in different ways, as determined by the class of bioReactant to which they are distantly connected via the bioPosts. With this implementation, all bioEngines that input units into a given bioPool and all the bioEngines that get input units from that bioPool are integrated, even if they are part of different schematics. At the same time, all bioPools that input units into a given bioEngine and all the bioPools that get input units from that bioEngine are also linked, even if they are part of different schematics. The result is a very complex multidimensional network of composite bioObjects, which provides the matrix for further reasoning and simulation by the program. For example, the formulas that provide the values for the encapsulated sets of variables and parameters refer to connected bioObjects, both graphically or distantly, providing the capability of concurrently and dynamically compute as a large number of processors arranged both in parallel and in series within that matrix.

5. Buttons and other bioTools a) The class bioTool (Table 6), a subclass of the class object defined within the Shell, is defined to include a variety of auxiliary graphic structures used in this invention, and has no additional attributes. The class button (Table 7) is a subclass of bioTool, which only new attribute is toggle-state. A subclass of button is action-button (Table 8), which has a newly defined attribute, action-proc-name, that holds the name of the specific procedure invoked when that button is selected by the user. Clicking upon an action-button by the user triggers its "select" user-menu-choice (Table 9) which invokes the button-handler-callback, which in turn invokes the procedure defined as attribute of each subclass. Tables 10 through 17 show the definitions of each subclass of action-button together with the procedure named by its action-proc-name attribute, as well as a representative instance. Action-buttons play an important supportive role through the system of this invention by controlling the display, and in some cases the activation, of workspaces, allowing in that way the interactive navigation through the entire knowledge-base. The other subclasses of button play a support role as part of the domain-specific interactive user-interface.

b) In particular, the class go-to-sw-button (Tables 10) plays an important role in maintaining the different knowledge structures of this knowledge-base sorted or classified according to desired criteria. For example, a workspace named root.kb may contain a set of go-to-sw-buttons named defs-and-procs, rules, relations, formulas, and so on. In turn, the subworkspace of the button defs-and-procs may contain a set of go-to-sw-buttons named bioObjects-defs-procs, buttons-defs-procs, bioposts-defs-procs, connections-defs, an so on. In turn, the subworkspace of the button bioObjects-defs-procs may contain a set of go-to-sw-buttons named bioEntities, bioReservoirs, bioProcesses, and so on, upon which subworkspaces will be stored the definitions of said classes, their subclasses, their user-menu-choices and their associated procedures.

c) Change-mode-button (Table 18) is another subclass of action-button, which has the additional attribute "mode" and causes the invocation of change-mode-callback upon selection. A set of these buttons on a workspace called "Mode Selection Panel" allows the user to interactively change from one user-mode to another. User-modes are the defined values of a Shell-defined attribute of each window, and the mode and label attributes of each change-mode-button is set equal to each of the possible values of the user-mode attribute of the window within which this panel is displayed. The optional behaviors of many objects in this system are user-mode specific, and the availability of such behaviors also change with different user-modes. The different behaviors that apply to each user-mode are defined within the user-restrictions and class-restrictions attributes of the object-definition template for each class, or the mode-specific restrictions can be also applied at the workspace level, to all the instances of specified classes of objects that are upon such workspace.

d) The class resize-button (Table 19) is used in sets, usually of four, to change the size of the workspace upon which they are located, which is very useful when they get very large sizes, such as those displaying dynamically created interactive pathways.

e) The class lists-tracer (Table 20), a subclass of the class button, has no additional attributes but has subclasses and specific methods associated with this class and its subclasses. The user-menu-choice "show" (Table 21) associated with this class starts, upon selection by the user, the list-tracer-handler-proc, which on turn calls the configure-lists-tracer-proc and one of three optional procedures, depending on the class of the lists-tracer from which this procedure was invoked. These three procedures will be defined and described in later sections related to bioReservoirs and bioProcesses, where they play a support role as part of the interactive user-interface by controlling the dynamic creation and display at run-time of lists of either bioReservoirs or bioProcesses that are either upstream or downstream of the bioReservoir or bioProcess from which this procedure is invoked.

f) The class path-tracer (Table 22), a subclass of the class button, has no additional attributes but has subclasses and specific methods associated with this class and its subclasses. The user-menu-choice "show" (Table 23) associated with this class starts, upon selection by the user, the path-tracer-handler-proc, which on turn calls the configure-path-tracer-proc and one of three optional procedures, depending on the class of the path-tracer from which this procedure was invoked. These three procedures will be defined and described in later sections related to bioProcesses, simulation, and experiment, where they play a support role as part of the interactive user-interface by controlling the dynamic creation and display at run-time of interactive pathways of either bioReservoirs or bioProcesses or both that are either upstream or downstream of the bioReservoir(s) or bioProcess from which this procedure is invoked.

g) The class graph-tracer (Table 24), a subclass of the class button, has no additional attributes but has subclasses and specific methods associated with this class and its subclasses. The user-menu-choice "show-plot" (Table 25) starts, upon selection by the user, the transf-graph-tracer-handler-proc, which on turn calls the configure-graph-tracer-proc and one of three optional procedures, depending on the class of the graph-tracer from which this procedure was invoked. These three procedures, together with the definitions of the three subclasses of graph-tracer, will be defined and described in later sections related to bioReservoirs and bioProcess, where they play a support role as part of the interactive user-interface by controlling the dynamic creation and display at run-time of graphs that plot the values over time of key variables or parameters of those bioObjects. The actions performed by these procedures are similar, creating first a display with a graph and each a different set of predefined complex variables and then establishing relationships among those variables and the graph. The components of such display are discussed in more detail below.

h) Other subclasses of bioTool used in the current implementation of this invention include:

The class bioEntity-notes (Table 26) are auxiliary structures that serve as graphic containers for different types of specific information about the bioEntity upon which subworkspace they are located, which can be displayed by selecting the "details" menu option (Table 27).

The instances of the class bioObject-title (Table 28) are used to label subworkspaces, such as those of bioEntities, bioEntity-notes, submodels. A set of rules (such as the examples in Table 53) automatically set the text of those titles, based on the label of the object superior to such subworkspaces.

The instances of the class experiment-selection (Table 28) are auxiliary structures used upon the subworkspace of an Experiment Panel, to be discussed at the end, to allow selection of bioReservoirs that are to serve as the points of reference in such experiments, and also to allow the user to enter the input values for quantitative simulations of such experiments.

The instances of the class reference-block (Table 28) are used to represent each citation to published information that serve as the source for building the different parts of the models, and their attributes, including an abstract, mimic the fields used in commonly used public databases.

The classes reference-message and sequence-display are subclasses of message (Table 30) a class defined within the Shell used for display of text in the References Scroll.

6. Variable Structures:

a) Variables and Parameters:

In the present invention, the quantitative attributes of object classes may be defined as simple attributes, or as pointers to subclasses of parameters or variables. The values simple attributes can be modified through rules, procedures, or other actions of the inference engine. The values for the different classes of variable and parameters are provided from different sources. However, only the Shell's simulator is used in the current implementation to compute the values of variables and parameter that are part of this system's quantitative simulation (as described in later sections), including state variables (parameters) such as Accumulation. Those values are preferentially provided by generic simulation formulas, although users may also provide specific simulation formulas for variables. Users can also input values for the simulator through the input-panels described below. and the inference engine can update simulated values based on values received from other sources. To standardize the units used during, the absolute values are entered by convention in Molar, M/sec, moles/liter, or seconds, as pertinent.

There are large number of subclasses of parameters and variables involved in this system, as defined in Tables 31 through 40. Only a few of them are used as independent parameters or variables represented by their icon, and usually they have auxiliary functions, such as the x-pos () and y-pos () used to aid in the graphic drawing of pathways on a workspace. Most of them are used encapsulated as attributes of the various classes of bioObjects or other objects, such as modelblocks, as well as attributes of other variables. Aside from the high-level classes, most of the other subclasses do not have additional specific attributes, but many have distinctive default settings, as specified in their listed definitions. The many separate subclasses allow to attach specific methods to each class, either in the form of formulas, or by referring to all members of the class in rules, procedures or other actions. Since it would be tedious and repetitious to discuss each subclass of parameter and variable that are referred to in the listed definitions of other objects, they are instead listed in lumped groups by similarities, and only a few that are representative or important to the understanding of the operation of the overall system will be discussed in the section where they are relevant.

In the currently preferred in this embodiment, domain-specific variables and parameters are subclasses of various subclasses of the class parameter, as defined within the Shell, such as float-parameter or integer-parameter. Those that represent domain-specific parameters are grouped under the domain subclasses int-par (Table 31) or float-par (Tables 32 and 33), depending on their value types. Those that represent domain-specific variables are grouped under the domain subclass float-pvar (Tables 34 through 37). This invention also provides a set of subclasses of float-var (Tables 38 through 40), a subclass of the shell defined class float-variable, which represent alternative data structures for domain-specific variables, such as velocity (which by default are represented by pvars, as discussed in more detail in the next section) or parameters, such as a variety of kinetic constants (which by default are represented by simple float attributes). The reason for these discrepancies is that In the currently preferred underlying Shell, the classes parameter and variable do not correspond to the common distinction between the concepts of variables and parameters, and they are simply two different data structures with different constraints and capabilities. One of the advantage of the Shell's variables is that they allow the user to define simulation or general formulas specific for a particular instance of a variable, by writing the formula directly in the corresponding slot for the formula in the variable's simulation subtable, while the Shell's parameters cannot receive values from specific formulas, only from generic simulations formulas that apply to all instances of a class. Because the Shell's variables are larger structures that require more memory space, in the current embodiment of this invention, subclasses of the Shell's parameters are used by default as attributes of bioObjects, but various classes of alternative but equivalent subclasses of variables are also provide, allowing the user to delete the default parameter and replace it with the equivalent variable, allowing the user to then write any customized specific simulation (values provided by the simulator) or general (values provided by the inference engine) formula to model that particular variable. The Shell's parameters and variables differ also in the following ways: a) variables can have two values, the inferred and the simulated values, while the parameters have only one value that can be inferred or simulated; b) the values of variables can expire and therefore variables may have no values, while parameters always have a value; c) parameters cannot backward-chain to seek its values, and can receive values only from generic formulas, in addition to conclude actions in rules, procedures, or other action-causing items; and d) variables cannot be directly referenced by procedures. When using a different Shell with only one type of variables, or with variables with different attributes and capabilities, some modifications may be necessary.

The velocity-var is an example of how the attribute table of a variable contains specific information to define and control each particular variable, such as the methods of inference allowed, its name, data type allowed, initial value, if desired; last recorded value, the number of data points or the time period for keeping the values of the most recent history of that variable, if desired; the period of time for which each value is valid, the formula slot is where the user may write a specific formula for the inferred value of that particular instance, if desired; details about its optional simulated value, which may include an additional simulation subtable, which contain slots that allow the user to control the simulation of that particular instance, such as the time increment for update, a specific simulation formula, and the number of data points or the time period of values to be stored, the main table also provides for the initial value for simulation, whether its value is provided by the inference engine or any simulator, and the default update interval.

The system of this invention utilizes the capability, provided by the Shell, of keeping the history of the values of relevant parameters and variables, and to reason about those historic values. Specific parameters and variables of interest, as specified in their listed definitions, are set to store a desired number of the most recent values, together with their time stamps (the times at which those values were collected). The user can decide to display those values in charts or other display forms. The historic values, as well as their maximum, minimum, average values, or rates of change can be not only be displayed, but also used by the user in different ways, such as storing them in external files or databases. Therefore, after each simulation run, the values of desired variables over time throughout a simulation can be further analyzed.

Velocity:

Each instance of the class rate-pvar provides the value for the Velocity attribute of an instance of the class bioEngine, and represents a mathematical model to dynamically simulate the velocity of its superior bioProcess, propagating its current values by forward-chaining. The Velocity attribute of the subclasses of bioEngine is treated as an special case because is the one that admits more variability in the current embodiment of this invention, since there are not only many types of chemical processes, depending on the participants in each case, but there are also many opinions about what is the most fitting equation to compute the Velocity of each type. In addition, there are two types of simulation provided by the system of this invention, as discussed under the Simulation Mode heading. One is semi-quantitative, in the sense that it operates using scaled (dimensionless) variables, and the other type makes use of variables with absolute values. The currently preferred embodiment of this invention is defined by default with a matching set of scaled variables, each with its associated simulation formula. For the Velocity attribute, depending on the bioEngine subclass, one of the following subclasses of rate-pvar (Table 36) is used: catalytic-rate-pvar, binding-ratepvar, dissociation-rate-pvar, modification-rate-pvar, or transfer-rate-pvar.

Figure 7:
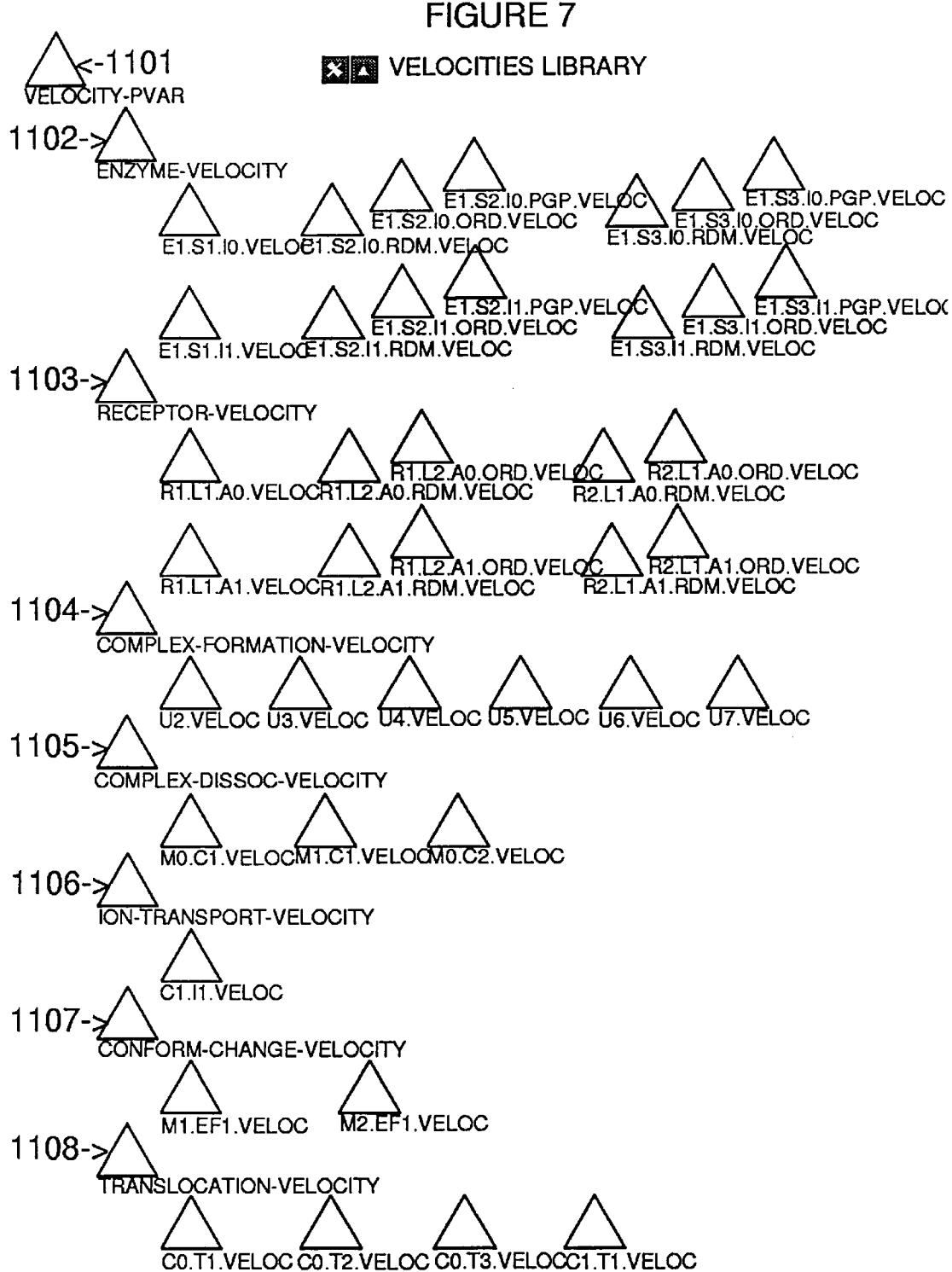
FIG. 7 shows an exemplar of a defined hierarchy of different types of quantitative dependent variables with associated functions to compute their values which instances may be comprised in instances of corresponding types of process building blocks.

However, an alternative set of more specific classes of bioEngines can be defined having as default a more specific set of pvars. As shown in FIG. 7, the current embodiment of this invention provides a large library of variables, subclasses of velocity-pvar (Table 41) that can be used for that purpose, or they can be used by the user to replace in each desired individual instance the default rate-pvar with the equivalent velocity-pvar. Each subclass of velocity-pvar (1101), which include enzyme-velocity (1102), receptor-velocity (1103), complex-formation-velocity (1104), complex-dissoc-velocity (1105), ion-transport-velocity (1106), conform-change-velocity (1107), and translocation-velocity (1108), has more specific subclasses, and each of those subclasses has its associated simulation formula. The nomenclature used for naming each subclass indicates all the participating components and the reaction type. For example, 1E.2S.1I.ORD.velocity is meant for a bioengine.1E.2S.1I, which means that its icon has at the top four specific stubs connected to one enzyme.r, two substrate.r and one inhibitor.r, and the formula for that variable reflects the fact that the reaction happens in an ordered fashion, that is substrate1.r binds before substrate2.r, and the inhibitor is a competitive inhibitor of the first substrate.

The subclasses of velocity-pvar, and their associated formulas, represent only the more typical cases, but they are only a fraction of all possible cases that user may need to represent. Therefore, another alternative is provided for the user to write the simulation formula that most appropriately fits the system to be modeled: the class velocity-var, a subclass of float-var, as described above (Table 38).

b) Arrays and Lists

Arrays and lists are structures that hold a number of values in an ordered manner. The subclasses of arrays and lists have all the characteristics of their parent classes, as defined in the Shell as subclasses of the class g2-array, itself a subclass of object, and they may have additional attributes within the system of this invention, as specified in their definitions. Arrays are indexed, and therefore each of its elements can be directly referred to by referring to its index, while lists may be indexed or not. The length of arrays have to be predetermined, before additional values are added, while the length of lists increase automatically, as more elements are added. The values of the elements of both arrays and lists are transient, are not stored as part of the permanent application, and their values are lost upon resetting the application. However, the current implementation of this invention uses arrays to permanently store the values of its elements by setting the "initial-values" attribute of an array equal to the desired values to be stored, separated by commas, which may be the current values of the elements of that particular array at any point in time, the elements of an auxiliary list, as described in the section describing the methods for queries, or any other desired set of values.

In the current invention, one of the important classes of arrays used is a subclass of symbol-array, query-array (Table 41), which instances are created when query init is selected by the user. Those query arrays are used to store the tables of all the instances of each class of molecular components in the system, as described later. The instances of a subclass of text-array, references-array (Table 42), are attributes of instances of bioEntities, bioReservoirs or bioProcesses. When the show-references option is selected by the user from the menu of instances of any of those bioObjects, a display is created that shows dynamically created copies of the references referred to (by the value of one of the references' attributes) by the values of that array. In addition, and instance (Table 43) of the subclass float-array can be used to store all the values of a desired parameter or variable during a simulation run, which can then be stored to a file or passed to another external device for further analysis or processing.

The current embodiment of this invention makes more extensive use of lists at run-time, which are used as auxiliary structures in processing information. Instances of query-list (Table 44), a subclass of symbol-list, are used as auxiliary structures in the creation of the more efficient query-arrays, as described below. Instances of scroll-text-list (Table 45), a subclass of text-list, are used as auxiliary structures in the creation of scroll-areas, to be described later. Both types are not seen by the user. All classes of lists used in this invention have the default setting for the "allow-duplicate-elements-for-list" set to no, which means that when a new element is added to the list, if the same element is already listed it will not be added again. In numerous occasions in this invention, this feature of lists is used to clean-up the output of some processing before it is displayed, as it is the case for example with such scroll-text-lists Bioitem-list (Table 46) is a subclass of item-list with no additional attributes, but with a class restriction. The different subclasses of bioitem-list are restricted to instances of particular classes of objects, such as experiment-selection (Table 46), bioReservoir (Tables 47 and 48), and bioProcess (Table 49). The icons of the instances of most subclasses of bioitem-list are visible to the user, providing additional information and direct access to the objects listed. The restriction defines that upon clicking on that icon by the user, the elements of the list are described, which means that a temporary workspace is created were pointers to each of the items that are elements of that list are displayed. The menu of each pointer allows to select, among other things, to display the attribute table of that object, or to display the object itself, as shown in FIG. 27 and described later.

c) Scroll-Areas

Scroll-areas are part of the graphic user-interface provided by the Shell which, in the current embodiment of this invention, are created dynamically and used in various ways. As it will be described later in more detail, a scroll-area can be requested from an experiment panel (4013) to list, in a scrollable fashion, all bioReservoirs defined in the system. Scroll-areas are also used extensively (FIGS. 21 and 22), to list and directly access, the bioEntities or bioReservoirs that meet the requirements defined by means of interactive queries, where they are also created dynamically. The scroll-messages which form the scrollable components of the scroll-area, and which refer to the objects of interest, can be ordered in different ways, and in the previous examples are ordered alphabetically. No subclasses of scroll-areas are defined within the system of this invention. The particular instances are dynamically configured by giving values to the attributes defined within the Shell.

7. Relations, Rules, Formulas, and Functions a) Relations are defined associations between two items which can be dynamically concluded and reasoned about, and in the current implementation of this invention, they represent physical and abstract relationships between objects, such as a-downstream-bioReservoir-of and the-downstream-BR-list-of. After being defined by the developer, relations are established transiently at run-time by the inference engine. The existing relations for a particular object can be also be listed using the "describe" option of the menu of any object, a Shell-defined capability. The creation or breaking of relations are treated as events that can forward chain to rules, and are sometimes used in this system to trigger rules that refer to those relations in their antecedent. Relation definitions are shown in Tables 50 and 51.

b) Domain-specific rules are used to conclude or to respond to the changing conditions in the world defined by the domain-specific knowledge structures. In the current embodiment, a rule has, in addition to its body that encodes the rule itself, a set of attributes that can be configured to establish its mode of operation and to define its restrictions, such as: whether it can be invoked by forward chaining and backward chaining, whether it may cause data seeking or forward chaining, focal classes and focal objects, priority, and its scan interval. Different types of rules may lack some of those capabilities. For example: a) whenever rules have no focal objects or classes, and cannot be invoked by forward or backward chaining, being only event driven. One such event may be the a relation being established or broken, such as those shown in Table 52. Other such event may be moving the icon by the user, which is frequently used in this application to either trigger the automatic configuration of the value of some attribute, such as those shown in Table 53, or the appearance of the icons, such as those shown in Table 54, or the position of the icons, such as those shown in Table 55; and c) initially rules are first and only invoked when a knowledge-base is started, or when a subworkspace is activated. Therefore, the situations to which those rules applied, and the conditions under which they can be invoked, can be very much constrained by the generic and specific sets of options and attributes of each particular instance.

c) Formulas in this system can be defined as expressions that define the relationships of a variable or parameter to other variables or parameters, in a way that when one variable or parameter changes the formula predetermines in which way other variables or parameters will be changed, either by the inference engine, in the case of general formulas, or by the simulator, in the case of simulation formulas. Generic simulation and general formulas are created as statements on workspaces and provide values for a whole class or group of bioVariables or bioParameters, in contrast with the specific simulation and general formulas, which are attached to the definition of one variable and apply only to that variable. The definitions of generic simulation formula for sets of scaled-valued variables, mixed-type variables and absolute-valued variables are shown in Tables 56 through 60, and will be discussed under the Simulation Mode heading.

d) Functions are statements that define a sequence of operations that are performed when the function's name and arguments appear as part of an active expression. The tabular-function-of-one-argument, a class defined within the Shell, has an important use in the domain of this invention. It allows to deal with situations when the algebraic relationship between two variables is not known, but the experimental data is available, and straight-line interpolation is optional. Tabular functions can also be used in other expressions, such as the rule: if the [Product1]([Substrate1]) decreases then inform the operator that "[Substrate-1] may be inhibitory at high concentrations". For example, Table 61 defines the Concentration of product as a function of the Concentration of substrate.

8. BioEntities a) The class bioEntity has numerous subclasses, organized in a hierarchical structure with different levels, according to the way a biochemist would classify different molecules, by taking into consideration their commonalties in chemical composition in the upper levels of the hierarchy, such as protein, nucleic acid, or lipid, followed by a reference to their function, such as, within the class protein, active-polypeptide, receptor, or enzyme. Table 62 shows a partial listing of the hierarchy defined in the current embodiment of this invention, with some examples of the subclasses at different levels.

b) In the current embodiment of this invention, a bioEntity is a graphic knowledge structure that represents any chemical and biochemical entity or their components, at different levels of structural complexity. Each bioEntity may have information encoded in two different ways: a) that information and data stored in its table of attributes, and b) each bioEntity may have a subworkspace upon which the components that represent its functional architecture are graphically defined, as described before and shown in FIG. 5. In the current implementation, functional components represent structural components that are relevant for the bioEntity's function and regulation, that allow the user to visualize the schematic structural composition. The graphic composition is also used for reasoning during the processing of queries that involve the structure. That reasoning may be in the form of procedures that refer to bioEntities that have certain components in their subworkspace. Each functional component of a bioEntity belongs by itself to a bioEntity class, either molecule or bioEntity-component or any of its hierarchy of subclasses.

c) The class bioEntity (Table 63), a subclass of bioObject, has a set of class restrictions that define which user-menu-options and other non-menu choices are available in each user-mode for all the instances of all the subclasses in the hierarchy of bioEntity. Its additional attributes are: "references" is a simple text attribute, unless otherwise defined for some of its subclasses. There are two major subclasses of bioEntity:

simple-bioEntity (Table 64) includes all the subclasses with simple structures that are not further graphically described, in the current implementation, and they do not generally have subworkspaces with additional components. This class has two subclasses, each with its additional subclasses: protein-site (Table 65), and protein-modified-group (Table 66). The class simple-bioEntity has its additional set of user-mode restrictions, and the following additional attributes:

"id" is a simple attribute that is used to hold a text to identify the instance instead of using a unique name;

"position" is a simple attribute text that indicates the position of that component within the molecule when applicable, such as the position of an aminoacid in the sequence of a protein, and is usually displayed; and "superior-bioentity" is a simple indexed attribute that holds the name of the first superior bioEntity in the workspace hierarchy that has a name, if any, a value that is computed by the program within the query reasoning and, as explained later, this mechanism is provided to avoid repetition of structures that are shared by various instances of the same family or of other families that share regions of homology.

complex-bioEntity (Table 67) includes all that subclasses that can be further described by their components in their subworkspaces. The additional not previously described attributes are:

"master-bientity" is a simple indexed attribute that holds the name of the bioEntity that is displayed when the user request to see the "details", which may be itself if it has a name. This value is set by the program upon cloning an existing bioEntity using the create-local menu option, as described later. BioEntities with no names which "master-bientity" names another bioEntity, the master bioEntity, can be considered as only a copy or "pointer" to the subworkspace, or "master-details", of the master bioEntity, but it can also hold additional information in its table of attributes or in its own subworkspace, or "local-details".

d) The major subclasses of complex-bioEntity are defined in this invention to deal with multiple levels of biochemical structural complexity.

The lower-level, represented by the class bioEntity-component (Table 68) and its subclasses represent molecular functional components such as: dna-component and its subclasses (Table 69) such as dna-domain, promoter, operator, and so on; protein-component and its subclasses (Table 70), such as protein-domain, protein-motif, and so on; and membrane and its subclasses (Table 68). The subclasses of this class have 4 stubs of the class link, located each on the top, right, bottom and left of the icon, which may be used to link different bioEntity-components upon the subworkspace of a molecule, on the schematics that represent their structure. The architecture allows for branching, and those stubs that are not used can be quickly dragged away. Additional attributes are: "superior-bioentity" and "position", defined above, for the class bioEntity-component; and "size", with default value 0 base-pairs, for the class dna-component.

The next level of complexity is represented by the class molecule (Table 71) and its successive level of subclasses such as protein (Tables 72 through 74), nucleic-acid (Table 75), and so on.

A higher level of complexity is represented by the class heter-mol-complex and its subclasses (Table 76), such as nucleosome, tf-dna-complex.

e) In addition to the structure in the subworkspace, additional information about that instance of bioEntity can be stored in its table of attributes, such as those shown for default instances of subclasses of enzyme, receptor and dna, namely a p.tyr.kinase (Table 73), a pdgf.r.like.complex (Table 74, corresponds to the table (605) of the example bioEntity (604) shown in FIG. 5), and a gene (Table 75). Taking the table of the instance of tyr.kinase shown in Table 73 as an example, we will comment briefly on some of the successively added and inherited attributes, through the superior classes molecule, protein, and enzyme:

"synonyms" is a simple text attribute provided to list the different names by which a molecule or complex may be known;

"in-species" is a simple text attribute provided to list the species or common name of living organisms in which that molecule or complex has been found, such as all, human, mouse, Drosophila, C. elegans, S. cerevisiae, and so on;

"in-tissues" is a simple text attribute provided to list the tissues in which that molecule or complex has been found, and it may take predefined values for those elements, such as connective-tissue, smooth-muscle, endothelium, and so on.

"inCells" is a simple text attribute provided to list the cell types in which that molecule or complex has been found, and it may take values such as T-lymphocytes, nerve-cells, fibroblasts, and so on.

"inOrganelles" is a simple text attribute provided to list the organelles within a cell in which that molecule or complex has been found, and it may take values such as plasma-membrane, cytosol, nucleus, and so on.

"cas-number" is a simple text attribute provided to indicate the CAS number assigned to that molecule, which is indexed to allow for faster searches and has a default value to indicate the preferred format;

"mol-weight" is a simple integer attribute provided to indicates the molecular weight of a single molecule or complex, preferably expresses in Daltons;

"isoelectric-point" is a simple float attribute provided to indicates the isoelectric point of the molecule or complex;

"sequence" is a simple text attribute provided to contain the sequence of a molecule, if relevant, or any other information about its composition;

"substrates-info" is a simple text attribute provided to contain any information about the known specific substrates or groups targeted by this enzyme;

"inhibitors-info" is a simple text attribute provided to contain any information about the known specific inhibitors of this enzyme;

"ligands-info" is a simple text attribute provided to contain any optional additional information about any other ligand that may bind to this enzyme and regulate its catalytic activity;

f) The structure of a heter-mol-complex or of a complex-molecule may be represented by an ordered set of bioEntities of the class molecule in its subworkspace. For example, a tf-dna-complex may have a dna or a gene icon in association with one or more icons of specific transcription-factors. In turn, the structure of a simple molecule is represented by an ordered set of bioEntities of the class bioEntity-component in its subworkspace. As shown in FIG. 5, and previously discussed in some detail, a protein may have a set of domains or motifs, or a combination of both, and it may have in addition one or more protein-sites, or protein-modified-groups, connected to the domains and or motifs at approximate locations, with the more accurate position displayed in the "position" attribute. A protein-domain may also have in its SW a set of smaller domains or motifs, or a combination of both, and it may have in addition one or more protein-sites, or protein-modified-groups, including copies of those connected to the icon of the domain. It is preferred that all parts of the structure that define functional differences between two bioEntities are represented, such as phosphorylations, isoprenylations or methylations at specific sites, or by cleavage of fragments of different sizes. For example, if a protein-kinase-3 is only active when the tyrosine residue at position 87 is phosphorylated, and inactive when it is dephosphorylated, then two bioentities are represented: a) PK.3 has an explicitly represented tyr-site with position 87, and has no kinase activity, and b) act.PK.3.tyr.P has an explicitly represented tyr.P-group with position 87.

g) Therefore encapsulation is an important feature utilized in the present invention to keep the level of detail of the structural composition of a bioEntity manageable. Each component can be cloned and reused repeatedly as a building block for a variety of bioEntities with increasing degree of complexity. This modular and reusable building block structure gives the system great flexibility and transparency, while allowing to build very complex structures of bioEntities. The components on the subworkspace of a molecule may be used by the user to reason about its function, since the presence of given domains, motifs, or simple-bioEntities usually is associated with described function, therefore directing the scientist's attention to further focus on those functions. An additional very important feature of this invention is that the knowledge graphically stored in that composition within the hierarchy of subworkspaces of bioEntities is used by the program to process queries about molecules containing certain component or combination of components.

9. BioModels a) In the current embodiment of this invention, any reference to a bioModel means a graphic knowledge structure used as a tool to contain and organize sets of bioProcesses and/or bioReservoirs, depending of the subclass. It can be also said that a bioModel represents the set of bioReservoirs and/or bioProcesses that are the components or modules of a fragment of a biochemical pathway, as delimited by the modeler. The class bioModel (Table 77) is a subclass of bioView-Object and has three subclasses, submodel, bioReservoir-Bin, and On-Hold-Bin, which have no additional defined specific attributes, but inherit the attributes "names", "label", "description", "references", "warnings", and "toggle-state". The subworkspace (1830) of a submodel contains a set of related bioProcesses and also a bioReservoir-Bin (1832), which in turn contains a set of related bioReservoirs connected to those bioProcesses. The class On-Hold-Bin (2308) is characterized by having an activatable-subworkspace, which is usually maintained deactivated. The instances of On-Hold-Bin are used to store within a submodel (not shown) bioReservoirs and/or bioProcesses that are either substitutions for the bioReservoirs and/or bioProcesses contained in such submodel, or additional bioReservoirs and/or bioProcesses to extend the pathway represented by such submodel, which are appropriately connected, but which the user wants to exclude from a simulation or other uses. By having the subworkspace deactivated, all those structures are ignored by the inference engine and the simulator. The user may have those structures included or excluded from a simulation or other uses at will, as described under the Modeler-Mode heading. The table of attributes (2311) of each instance of an On-Hold-Bin allows to store and access additional information. All instances of On-Hold-Bin have either one of two alternative menu options (Table 77b): a) if the subworkspace of the On-Hold-Bin is activated, then the "deactivate-sw" is available, which upon selection by the user deactivates such subworkspace; or b) if the subworkspace of the On-Hold-Bin is deactivated, then the "activate-sw" is available, which upon selection by the user activates such subworkspace.

10. BioReservoirs a) Class bioReservoir

Figure 9:
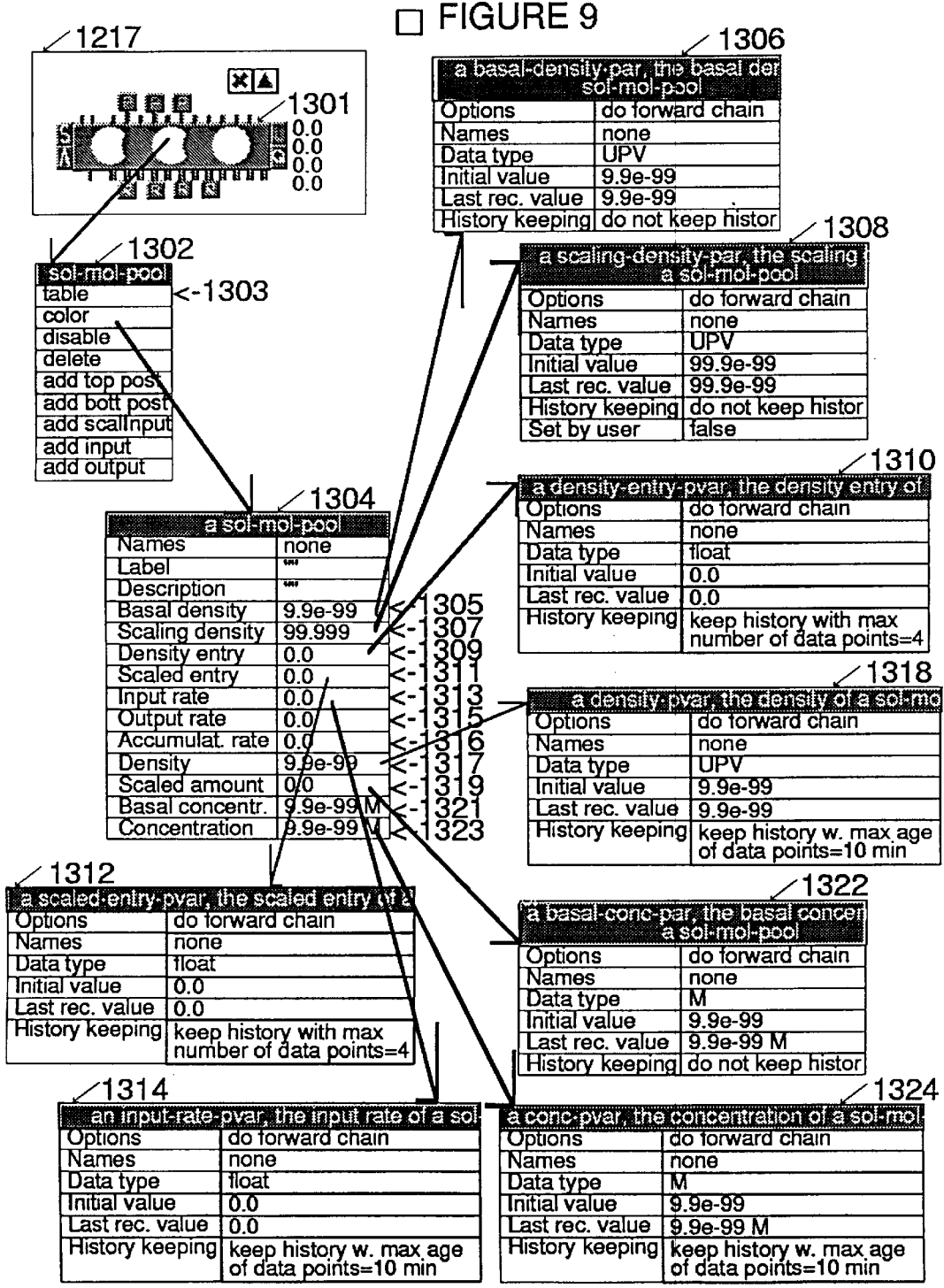
FIG. 9 shows exemplar attribute/value tables of an iconic component of an instance of a reservoir building block and some of its quantitative variables and parameters.

As shown in FIGS. 8 and 9, any reference to a bioReservoir (1201) in the current embodiment of this invention means a predefined graphic object that represents an imaginary container of a bioPool (1301) of a number of units of a molecule or complex, which boundaries may be indicated by the value of its compartment attribute, if any. A bioReservoir has several operational functions and encapsulates several forms of knowledge, and each instance of bioReservoir has an associated menu (1202) which options provide access to other forms of knowledge that more specifically characterize each particular instance, and to a variety of other tasks which, together with the methods invoked upon selecting those options, will be discussed in later sections. Here we will focus on the definitions of all the components involved, and on the description of their attributes. The "table" option (1203) invokes the display of its table of attributes (1204), which serves, among other functions, to hold: a) attributes that characterize that particular bioReservoir, which values are set by the modeler, and which are used by the program to set the initial conditions before a simulation model is run, when in Simulation Mode, and in addition each of these values provides useful quantitative or semi-quantitative information to the user. The values of these attributes are something characteristic of the system, and are stored as part of the permanent database (Parameters and variables of a bioReservoir which values are computed when a simulation model is running, but which do not usually require to be set by the modeler, are encapsulated as attributes of the bioPool contained in each bioReservoir, as described below); b) a pointer to the specific bioEntity that populates that bioReservoir; and c) other auxiliary attributes which values are set and used only by the program at run-time, and which are usually hidden from modelers and users.

The class bioReservoir (Table 78) is a subclass of bioView-Object and has two subclasses, sol-mol-reservoir and bound-mol-reservoir. All instances of bioReservoir have an activatable-subworkspace, which means that any object upon such subworkspace are not recognized by the inference engine or the simulator, and therefore, any of the tasks associated with their icons are not functional, unless the subworkspace is activated. When the application is started, all those subworkspaces are deactivated, and in the current implementation of this invention they are activated when the general initialization procedures are invoked, as described under the General Mode heading. Attributes newly defined for this class and its subclasses that were not previously described will be described here in conjunction with the table of attributes (1204) of an instance not yet configured, shown here with its default values. Note the unlikely default value of 9.9e-99 given to some of those attributes, which provides a) a signal that an adequate value has not been entered yet by the modeler, and b) a branching criteria for the inference engine. Those attributes include:

"compartment" (1205) is an optional simple attribute which value is set by the modeler to represent the physical boundaries of the contained biopool;

"status" (1206) is a symbolic attribute which value is set and used at run time by the simulation and other procedures, as an aid in the activation of pathways and in the creation of interactive pathway displays. It can take any of the values specified in the definition table and it is not visible to the modeler or other users.

"ref-bioentity" (1207) is an optional attribute which value, if any, is a pointer to the bioEntity instance that describes the structure of one unit representative of those units that populate that bioReservoir, and that value is set by the modeler. This value is used by the program when the user selects the "bioEntity" option from the menus of either the bioReservoir itself or any of the bioReactants and bioProducts distantly connected to its bioPool, and that option appears on those menus only when the value of this attribute is not the default value none;

"master-bioreservoir" (1208) is set only by the program when copies of named bioReservoirs are made, such as those used in the creation of interactive pathway displays, and is used by the program to display the subworkspace of the bioReservoir referred to by the value of this attribute, when the "master-details" menu option is selected by the user. This attribute is not visible to the modeler or other users.

"decay-rate-factor" (1209) is a parameter which value may be entered by the modeler or can be modified at run time by rules or procedures. Its default value is 2.0e-4, a value small enough not to cause dramatic changes, but in line with some experimental observations in the domain of this invention, but it should preferably be modified by the modeler to better reflect individual cases;

"if-scaling-amount" (1210) is a simple attribute set by the modeler to indicate to the program the value to be used to interconvert between the absolute-valued and the scaled-valued variables or parameters of bioPools and their connected bioReactants. The complex methods used for this conversions differ, depending on the classes of bioPools and bioReactants involved, as discussed in more detail under the Simulation Mode heading. Its default value of 100 is used if not modified by the modeler, if the value of the if-scaling-bioreservoir attribute is none;

"if-scaling-bioreservoir" (1211) is a simple attribute which value may optionally be set by the modeler to indicate to the program that the value of the if-scaling-amount should be taken from the bioReservoir named by this attribute. This value is only required or used when the value of the if-scaling-amount attribute is the default, otherwise, the later value is used and this attribute is ignored. This and the previous attribute are not visible in General Mode;

"scaled-basal-amount" (1212) is a float simple attribute set be the modeler that represents the scaled value of the amount of units in the contained bioPool under normal or basal conditions, equivalent to a fraction of the maximum amount that this bioPool can reach under optimal physiological conditions. Since in many occasions in the domain of this invention neither the basal nor the maximum amounts can be measured or known with certainty, this value represents in such occasions the best estimated guess, and it is an important semi-quantitative knowledge component. The default is the unlikely value of 9.9e-99.

"physiol-abundance" (1213) is a symbolic attribute which value is set by the modeler to indicate the physiological level of abundance of the corresponding bioEntity in the compartment covered by that bioReservoir. It is a symbolic replacement of the previous attribute when the 9.9e-99 has not been modified by the modeler. The values allowed for this attribute in the current embodiment of this invention are: highest, abundant, steady-state, low-induced or only induced, which currently correspond to the scaled values of 1.0, 0.9, 0.5, 0.1, and 1.0e-9, respectively. However, this default scale can be changed to different values, and additional symbols and values can be added to the scale. As and alternative, fuzzy-sets can be defined for the values of this attribute, and fuzzy-logic can then be applied to those values. The reasoning for using the values of either the previous or this attribute, in conjunction with one or more of the following attributes, are discussed in more detail under the Simulation Mode heading.

"normal-basal-concentration" (1214) is a float simple attribute set be the modeler that represents the physiological average value of the Concentration of the units in the bioPool of a sol-mol-reservoir;

"normal-basal-density" is a float simple attribute set be the modeler that represents the average value of the Density of the units in the bioPool of a bound-mol-reservoir.

"physiol-max-concentration" (1215) is a float simple attribute set be the modeler that represents the physiological maximum value of the Concentration of the units in the bioPool of a sol-mol-reservoir;

"physiol-max-density" is a float simple attribute set be the modeler that represents the physiological maximum value of the density of the units in the bioPool of a bound-mol-reservoir.

Selecting the "details" option (1216) displays the sub-workspace (1217) which contain the components that characterize a bioReservoir. The classes of those components that are used in the modeling process are defined below, while other auxiliary structures are described in later sections.

b) Class bioPool

The class bioPool (Table 79) has two subclasses: sol-mol-pool and bound-mol-pool (Table 80). A bioPool is defined with a characteristic icon with two sets of stubs of two classes of connections: a) the p-connection stubs are located at the top of the icon, and b) the r-connection stubs are located at the bottom of the icon. In the current embodiment of this invention, each p-connection stub (416) is to be connected (417) to a biopool-p-post (412) and each r-connection stub (418) is to be connected (419) to a biopool-r-post (404) on the subworkspace of the bioReservoir, which allow to establish distant connections to a bioReactant and a bioProduct, respectively, and allow bidirectional flow of data and control between them. As shown in FIG. 9, every instance of bioPool (1301) has an associated menu (1302), and selecting the "table" option (1303) causes the display of the table of attributes (1304). The values of several of the attributes of a bioPool are pointers to variables or parameters, which include a density-related set and a concentration-related set, which values do not have to be set by the modeler (with the exception of the values of the basal quantities, which are preferably set by the modeler, if known, but they are not required, since they can be computed from the set values of other attributes of the bioReservoir, or their defaults), since they are inferred or simulated, as described under the Simulation Mode heading. The units of all the parameters and variables of all bioPools connected to the same bioProcess have to be appropriately matched. Newly defined attributes of bioPool comprise:

"Basal-Density" (1305) is given by a basal-density-par (1306). The subclass sol-mol-pool has additionally a "Basal-Concentration" (1321) given by a basal-conc-par (1322). The values of either of these attributes may be set by the user to indicate: a) the normal physiological steady state density or concentration, or any other appropriated measured or assumed value, for physiological molecules or complexes, or b) 0.0 for pharmacological or other experimental molecules that are added to the system from an external environment. This value is required for any bioReservoir that participates in a simulation, and if its default value has not been overridden by the user with a new value, the inference engine sequentially pursues other sources of the Basal-Density value, as determined by a generic basal-density-procedure which is called during the activation process of a simulation, only for those bioReservoirs that have been activated for a simulation;

"Scaling-Density" (1307) is given by a scaling-density-par (1308) which value is inferred by a procedure invoked at initialization, as discussed under the Simulation Mode heading. This value is used by simulation formulas to inter-convert scaled values and absolute values.

"Density-Entry" (1309) is given by a density-entry-pvar (1310). It takes the value of a user-input at a time, or different times intervals, during simulation as defined by the user in an input-panel, during the simulation set-up process. It has a default value of 0.0, and a new value may be inferred and set by a procedure called when the simulation is started, and, after the new inferred value has been propagated, it reverts back to the default value of 0.0. This value is an argument to the Accumulation, where it is summed to other inputs and outputs;

"Scaled-Entry" (1311) is given by a scaled-entry-pvar (1312), and it is the scaled equivalent of the Density-Entry, with its value set and used in a way similar to that described above;

"Input-Rate" (1313) is given by a input-rate-pvar (1314), which value is given by a simulation formula that sums all the graphically defined inputs, including: a) all the schematically modeled inputs, that is, the current values of the Production-Rate of all the bioProducts connected to the biopool-p-posts of the bioPool, if any; and b) the input modeled by means of a model-block contained in any connected input-model-box, if any;

"Accumulation" (1316) is given by an accumulation-pvar, a time variant and continuous state variable which represents a quantity in the classical systems dynamics sense, that is the time integral of its time-dependent inputs and outputs, given an initial value, here set to be equal to either the scaled-basal-amount or the basal-amount, as discussed under the Simulation Mode heading. The inputs included in the default simulation formulas are: a) all the schematically modeled inputs, that is, the current values of the Production-Rate of all the bioProducts connected to the biopool-p-posts of the bioPool, if any; b) the input modeled by means of a model-block contained in any connected input-model-box, if any; and c) the input entered by the user through an input-panel, if any. The optional outputs included in the default simulation formulas are: a) all the schematically modeled outputs, that is, the current values of the Consumption-Rate of bioReactants connected to the biopool-r-posts of the bioPool, if any; b) the output modeled by means of a model-block contained in the connected output-model-box, if any; and c) the decay term, which is a function of the current value of the Concentration or Density as specified by the decay-rate-factor (a decay rate constant in sec^(-1)), and which represents a variety of outputs not modeled schematically or through a model-block, including the degradation and diffusion components. Since at steady-state the overall rate of output is equal to the overall rate of input, then, by definition, the Accumulation should approach 0.0 in a closed system, in the absence of additional external disturbances, such as user-inputs or inputs modeled by model-blocks.

"Density" (1317) is given by a density-pvar (1318) which value, in UPV (units per volume), represents the number of molecules or complexes per liter, or any other unit of volume, such as the volume of the reaction mixture in a test tube. The subclass sol-mol-pool has the additional attribute Concentration (1323) is given by a conc-pvar (1324), which value in M (Molar) represents moles per liter. In the implementation used to illustrate this invention, simulations operate by default based on the Density of the bioPools involved. In the case of sol-mol-pool, where the quantities used by scientists may be most commonly given as Concentrations, the second set of concentration related variables is defined to facilitate user-input, but those quantities are preferably transformed into density-related variables by the inference-engine before integration with other quantities. Those values can be inter-converted by using Avogadro's number (6.023e23 molecules per mol). However, several other types of quantities could be used as well, with little conversions to other units of measure, such as activity (X-units times Y-unit), amount (X-units), or others types of densities (such as X-units per Y-unit). The same concepts and the same type of formulas, rules and procedures, apply to other-quantities, and a variety of units may also be allowed for entries from the user or other external sources, by providing lookup-tables or any other standard methods for automatically converting any of those units to the desired target units. Hence, the modeler has the option to design and define a system totally or partially based on a different quantity measurement, as long as proper care is taken to maintain consistency throughout the system. In those cases, the quantities entered by the user in the attribute slots of the bioReservoir that refer to physiological levels would also have to reflect those different sets of units.

"Scaled-Amount" (1319) is given by a scaling-density-par (1320), which value represents an scaled, dimensionless, alternative to Density, Concentration, or any other quantity. This attribute is used in the default scaled reasoning, which is the preferred method when dealing with biological systems, when absolute quantitative data is incomplete, and much of the data available is from relative measurements. The Scaled-Amount can be converted into a Density, and vice-versa, by using the value of the Scaling-Density of the bioPool.

c) Class bioPool-post

In the current embodiment of this invention, any reference to a bioPool-post means a bioPost to be located upon the subworkspace of a bioReservoir which function is to connect a bioPool to a bioRole-post. The class bioPool-post is a subclass bioPost (Table 5), itself a subclass of connection-post, a basic class defined within the Shell and from which it inherits all its capabilities. Connection-posts are like extensions of connections that permit to physically interrupt a graphic connection and continue it on another workspace, but without interrupting the flow. The class bioPool-post (Table 81) has two subclasses: biopool-p-post (412), which is to be connected to an input p-connection at the top of a bioPool's icon, and its name is to be given to one bioproduct-post to establish a distant connection; and biopool-r-post (404, 408) which is to be connected to an output r-connection at the bottom of a bioPool's icon, and its name is to be given to one bioReactant-post to establish a distant connection. BioPool-posts are interactively created an named by selecting a menu option of the closest bioPool, as described below. The new attributes for this classes are:

"id" is a simple text attribute used as a unique identifier, instead of the unique name, in some types of processing, such as in the alternative simulation procedures described in that section;

"ref-bioprocess" is a pointer to the bioProcess instance that contains the bioProduct or bioReactant to which the biopool-p-post or biopool-r-post, respectively, are distantly connected. The value is interactively set by selecting the "set-refs" menu option of the bioproduct-post or bioReactant-post to which it is distantly connected;, and it is used by the program for interactive navigation through bioReservoirs and bioProcesses, as described below.

d) Classes model-box and model-block

In the current embodiment of this invention, any reference to a model-box means a graphic programmed object to be located upon the subworkspace of a bioReservoir, which function is to hold optional model-blocks. The class model-box is a subclass of bioTool (Table 6), a generic class that includes a variety of auxiliary tools used in this invention, and which is itself a subclass of the Shell's class object with no additional specific attributes. The class model-box (Table 82) has three subclasses, which definitions differ only in the icon description, but which play different roles, as their name indicate: scaled-input-model-box (1218), input-model-box (1236), and output-model-box (1237). Model-boxes are interactively created by selecting a menu option of the closest bioPool, as described below. The menu options available for all subclasses of model-box are different, depending on the user-mode. When clicking on a model-box (1218) in any of the user modes bypasses its menu (1219) and selects the "show-sw" option (1220), which causes its subworkspace (1221) with a model-block (1222) to be displayed.

In the current embodiment of this invention, any reference to a model-block means a graphic programmed object, to be used upon the subworkspace of a model-box, which function is to hold the components of a mathematical model as defined by its attributes, where the value of one or more of those attributes (here called outputs) depend on the values of one or more such attributes (here called inputs). The class model-block (Table 83), a subclass of the class bioTool, may have as many subclasses as needed to represent the different mathematical models needed by the domain modeler, and some representatives subclasses are shown as examples, together with the simulation formulas used to compute the value of their output (Tables 83 through 85). Included is a generic-model-block that is a place holder for new parameters and/or variables to be added by the modeler, to define any desired number of the slots provided, and to write specific general or simulated formulas for those newly added variables. The only new attribute for the class model-block, inherited by all subclasses, is "output.1", which value is given by a model-block-output-var (Table 39), and each subclass have additional specific attributes, which number and type vary, and which are either simple attributes or parameters or variables. The values of the inputs may be constant or may be changed at run time according to procedures, rules or their associated formulas, and may depend on other variable values.

As shown in FIG. 8, clicking on a model-block (1222) displays its menu (1223). The "disable" option (1224) is used when a set of alternative model-blocks is configured and placed in the same model-box, keeping enabled only the one to be modeled, or none, and disabling all others not currently in use. Selecting "table" (1225) displays the table of attributes (1226) and provides access to its variables. Two classes of variables are defined to be used as attributed of model-blocks: model-block-var and model-block-output-var (Table 39), which differ only in the default settings: only the former has by default a simulation subtable and only the latter keeps history of its value, while both have an initial value and indefinite validity interval, so that they always have a value, and therefore can be used by the simulator. Clicking on the slot (1227) of the attribute "output.1" displays its subtable, which is the table of attributes of an instance of model-block-output-var (1228). Although each of the predefined model blocks classes has an associated generic formula to compute the value of the output.1, which applies to each instance of the class, the modeler may want to override it. The modeler can request, by clicking on the slot of its simulation details attribute, the addition of a simulation subtable. The slot (1229) of the attribute "input.1" displays its subtable, an instance of model-block-var (1230), and clicking on the slot of the attribute "simulation-details" (1231) displays its simulation subtable (1232) which displays additional attributes, among them a slot (1233) to hold the simulation formula to be written by the modeler. The particular subclass selected in this example, a proportional.f, is defined with two additional attributes given by simple float attributes with default values of 1.0 for "gain" (1234) and 0.0 for "bias" (1235), which represent what their names indicate.

Each subclass has a characteristic icon with no stubs, so that the connection is made manually by extending the stub of the connection-post (1238) which comes with the subworkspace of a model-box, becoming in this way of the class specified by the connection of the model-box. The superior connection of such connection-post is that defined by the stub of the model-box that contains it, and therefore, the model-block (1222) connected to it is distantly connected to the bioPool to which the model-box (1218) is connected. Tables 83 through 85 show the partial definitions of some of the many subclasses of model-box, a default instance, and the formulas that provide the values for their output-1. Table 85 shows the partial definition of a generic model-block with a large number of slots to allow the user to use as many of those slots as desired by entering a value, or by selecting an instance of one of the variables or parameters already defined in the knowledge-base, and the customized formula for output-1 is in this cases user-defined. These subclasses are just a number of representative examples, and a person skilled in the art can define numerous other subclasses following the general principles described in this invention.

11. BioProcesses a) Class bioProcess

Figure 10:
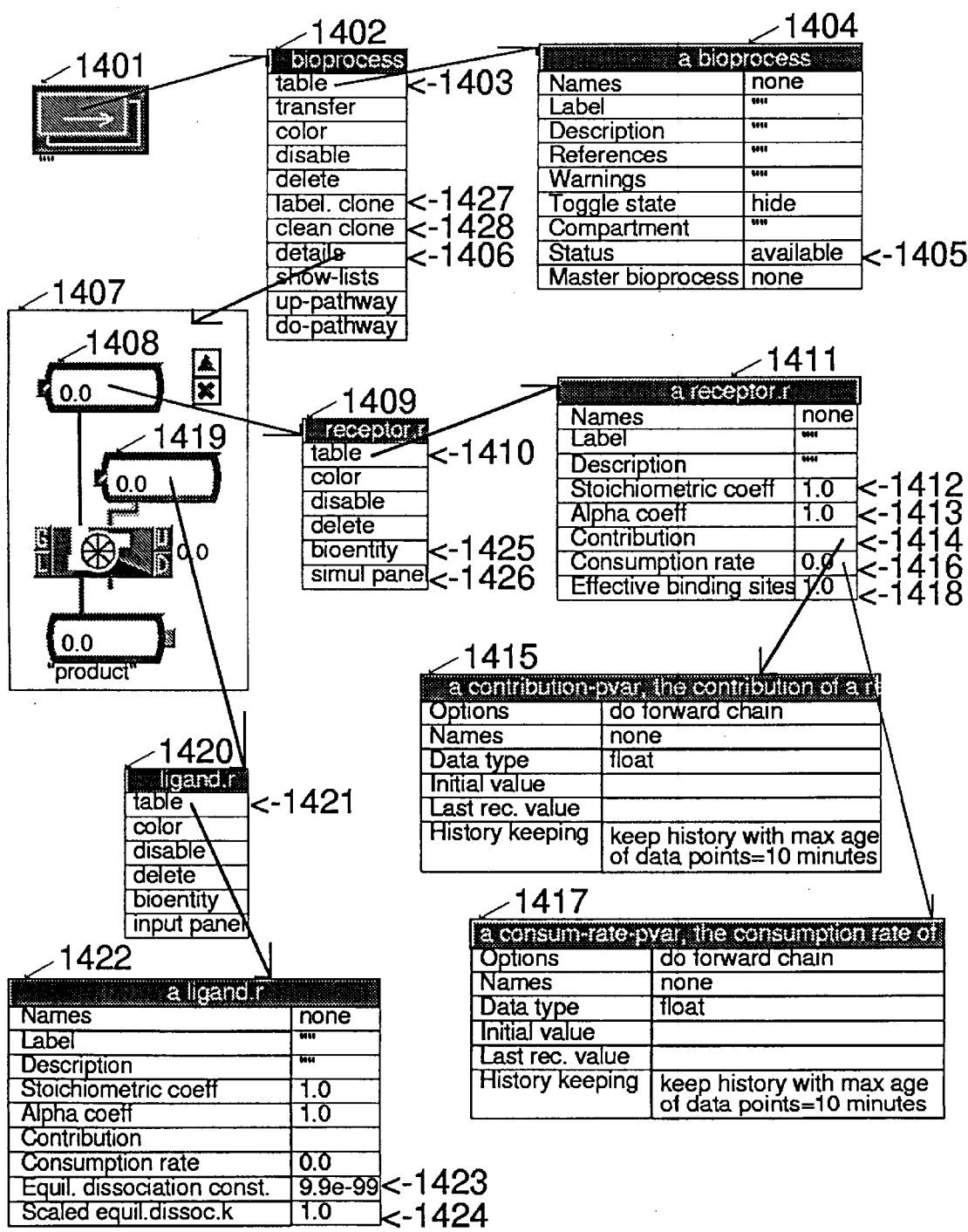
FIG. 10 shows an exemplar set of pop-up menus and attribute/value tables of an iconic instance of a two-layered composite process building block and two of its different types of inputs with their quantitative variables and parameters.
Figure 11:
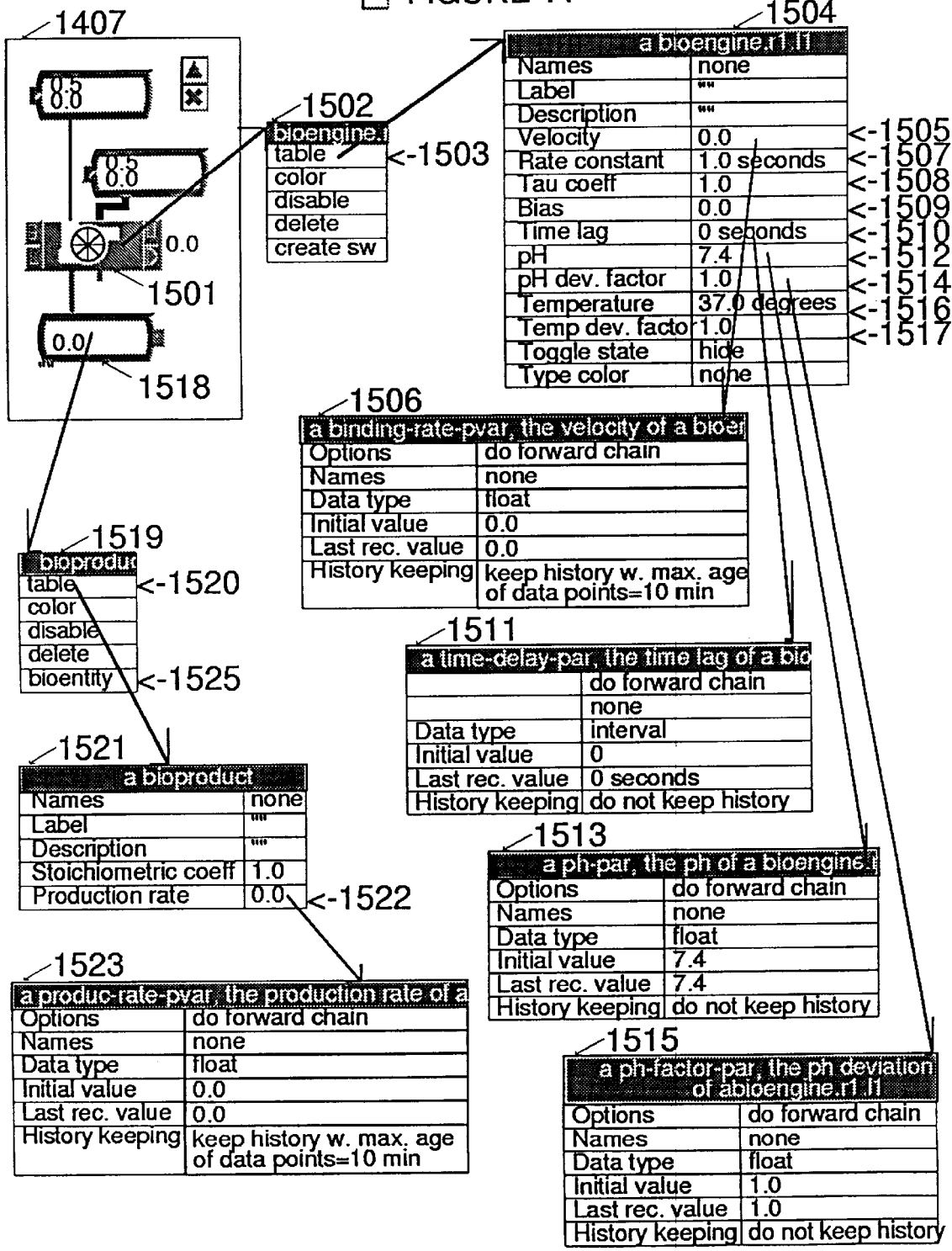
FIG. 11 shows additional exemplar attribute/value tables of other iconic components of an instance of process building block, with focus on their quantitative variables and parameters.

As shown in FIGS. 10 and 11, any reference to a bioProcess (1401) in the current embodiment of this invention means a predefined knowledge structure that integrates a variety of knowledge forms, from qualitative heuristic information to quantitative mathematical models. It can be said that a bioProcess is a graphic object with a subworkspace (1407) in which a schematic graphically represents the preconditions (bioReactants), the reaction (bioEngine) and the effects (bioProducts) of a chemical process as separate but connected objects that contain the variables and parameters, which together describes the system qualitatively and quantitatively. The class bioProcess (Table 86) is a subclass of bioView-Object, and has no additional subclasses. All instances of bioProcess have an activatable-subworkspace, which means that any object upon such subworkspace are not recognized by the inference engine or the simulator, and therefore, any of the tasks associated with their icons are not functional, unless the subworkspace is activated. When the application is started, all those subworkspaces are deactivated, and in the current implementation of this invention they are activated when the general initialization procedures are invoked, as described under the General Mode heading. The different types of bioProcesses are all instances of that class, and differ in the schematics in their subworkspace, which have different components. The different types are also visually distinguished by different colors for the type-color region of their icon, which is changed by the inference engine to be the same color as the color of the type-color region of the bioEngine they contain.

A bioProcess has several operational functions and encapsulates several forms of knowledge, and each instance of the class bioProcess has an associated menu (1402) which options provide access to other forms of knowledge that more specifically characterize that particular instance, and to a variety of other tasks which, together with the methods invoked upon selecting those options, will be discussed in later sections. Here we will focus on the definitions of all the components involved, and on the description of their attributes. The "table" option (1203) invokes the display of the table of attributes (1404) for that instance, which serves to hold various attributes, some of which have values that are set by the modeler and provide information for the user, and others are auxiliary attributes which values are set and used only by the program at run-time, and which are usually hidden from modelers and users. The values of the former attributes are something characteristic of the system, and are stored as part of the permanent database. Most attributes specific for this class have been previously described for other classes, the new description is:

"master-bioprocess" (1405) is set only by the program when copies of named bioProcesses are made, such as those used in the creation of interactive pathway displays, and is used by the program to display the subworkspace of the bioProcess referred to by the value of this attribute, when the "master-details" menu option is selected by the user. This attribute is not visible to the modeler or other users.

The "details" option (1406) invokes the display of the subworkspace (1407) for that instance, which holds all its schematic components. In addition to other auxiliary structures to be discussed in latter sections, those components comprise a single bioEngine (1501) which serve as the site where all inputs or bioReactants (1408 and 1419) interact with each other and where the bioProduct(s) (1518) are generated, which more detailed description follow.

b) Class bioEngine

As shown in FIG. 11, any reference to a bioEngine (1501) in the current embodiment of this invention means a graphic programmed object to be located upon the subworkspace of a bioProcess that represents the dispatcher of any chemical, biochemical or physical process, such as synthesis, modification, translocation, diffusion, degradation, and so on. The class bioEngine (Table 87) comprises a hierarchy of subclasses (Table 88), a few examples of which incremental definitions are shown for subclasses of amplifier-bioengine (Table 89), binding-bioengine (Table 90), and lumped-bioengine (Table 91). Each subclass is characterized by its set of different types of connections defined in the stubs slot, and also by the class of the variable that gives the value to its Velocity attribute, as discussed earlier quite in detail under Velocities. Each bioEngine, graphically represented by a rectangular icon, has a number of stubs at the top, belonging to subclasses of the r-connection class, to be connected only to bioReactants, and a number of stubs of the p-connection class at the bottom, to be connected only to bioProducts. The number and class of stubs define the specific r-connections to the different classes of bioReactants, such as enzyme.r, substrate.r, inhibitor.r, receptor.r, agonist.r, antagonist.r or unit.r, or the p-connections to the class bioProduct. The bioEngines of the class lumped-bioengine, including those with two S or more enzymes, are in reality lumped models of a two or more reactions in series, and are used to model stretches of pathways which detail is either not desired or not known, and only the rate limiting reactions are represented. There are a number of different class restrictions for this class that depend on the user-mode. Like other objects, every instance of a bioEngine (1501) has an associated menu (1502), and selecting the "table" option (1503) causes the display of its table of attributes (1504). The values of several of the attributes of a bioEngine are pointers to variables or parameters, including newly defined attributes not previously described, which will be here described while referring to such a table (1504) of a newly created instance that shows the default values. Those attributes comprise:

"Velocity" (1505) is an attribute specific for each class which value is a pointer to an instance of any of the subclasses of velocity-pvar, described above, which for the receptor-bioengine shown is a binding-rate-pvar (1506). The values for this dependent variable are provided by generic simulation formulas that model the rate of the interactions of the bioReactants connected to a given bioEngine with each other. Its arguments may be the Contributions of each of its bioReactants, when using the scaled set of variables and formulas, or the bioReactant's kinetic-coefficients and the Concentrations or other quantities of the bioPools connected to the bioEngine through the bioReactants, and its output is an argument for the Consumption-Rate and Production-Rate of the connected bioReactants and bioProducts, respectively. Therefore, this attribute may take as arguments either a set of absolute-valued variables and/or parameters, in which this attribute would be also absolute-valued, or a set of scaled-valued variables and/or parameters, in which this attribute would be also scaled-valued.

"rate-constant-sec" (1507) is a simple float attribute which value may optionally be set by the modeler to provide the rate-constant in seconds for the overall process. This value is used by the set of generic simulation formulas that use the scaled set of variables, which is currently the default mode of operation. The default value is used if no other value is set by the modeler.

"tau-coeff" (1508) is a simple float attribute which value may optionally be set by the modeler to modify by a factor the rate-constant-sec, for testing the effects of a modification of such parameter on the simulation of the system, without having to change the value of such attribute, which may have been obtained experimentally and direct changes of its value may not be desired. This value is incorporated by default in the generic formulas provided, and if not configured by the modeler, multiplying by its default value of 1.0 has no effect on the system.

"bias" (1509) is similar to the above attribute, a simple float attribute which value may optionally be set by the modeler to modify by a constant amount the rate-constant-sec, for testing purposes, without having to change the value of the later attribute. This value is incorporated by default in the generic formulas provided, and if not configured by the modeler, adding its default value of 0.0 has no effect on the system.

"time-lag" (1510) is an optional time-interval attribute which may be useful for certain instances of bioEngines, and which value, given by a time-delay-par (1511), is set by the modeler to indicate the period of time by which the forwarding of the computed output of the Velocity of a bioEngine is delayed. It represents a time delay, equivalent to holding an amount from a bioPool for the specified period of time, which is returned after that time has elapsed. An example of its use is when a bioReactant and a bioProduct of this process are both connected to the same bioPool, and the forwarding of the output value of the Velocity is delayed. The value of this attribute may also be modified at run time, as a result of dynamic events related to this or other processes, and may be simulated or inferred by means of modeler-defined formulas, rules, or procedures;

"pH" (1512) and "temperature" (1516) are optional float attributes which values are given by a ph-par (1513) and a temperature-par (not shown) and which, as their name indicate, represent the environmental conditions under which the process takes place. The values of these parameters may vary at run time, as a result of dynamic events related to this or other processes, and may be simulated or inferred by means of modeler-defined formulas, rules, or procedures;

"pH-deviation-factor" (1514) and "temp-deviation-factor" (1517) are optional float attributes which values are given by a ph-factor-par (1515) and a temp-factor-par (not shown) and which are used in conjunction with "pH" or "temperature", respectively, and represent a correction factor that either accelerates or decelerates the process when the values of either the pH or the temperature deviates from their defined default values. If used, the values of these parameters may remain constant or may vary for different values of the pH or temperature, as defined by a tabular function similar to a look-up table.

To accommodate the many different types of processes in which molecules and complexes participate, the class bioEngine is taxonomically divided into different levels of subclasses (Table 88) in the currently preferred embodiment of this invention. The major classes are arranged according to the type of reaction or process they represent, indicated by their names. The next level of classes usually refers to the type of activity of the members of the class and is usually characterized by the class of the variable that defines its Velocity attribute, such as for example: the Velocity of a enzyme-bioengine (Table 89) is a catalytic-rate-pvar, while the Velocity inherited by receptor-bioengine (Table 90), as well as all other subclasses of binding-bioengine, is a binding-rate-pvar, the Velocity of a complex-dissoc-bioengine (not shown) is a dissociation-rate-pvar, and the Velocity of a translocation-bioengine (Table 91) is a translocation-rate-pvar. Further subclasses of each of those classes are defined according to the number and type of their defined stubs, which in turn determines the number and classes of connected bioReactants, and further by color coding the icons to show further specialization, such as using different type-color for different types of enzymes, such as protein-kinases, protein phosphatases, and so on. Further differentiation between particular instances can be generated by selecting as the value of their Velocity attribute an instance of different subclasses of velocity-pvar. The nomenclature used for each subclass refers to the defined bioReactants, such as:

bioengine.E1.S2.I1.Em is an enzyme-bioengine that represents an enzymatic reaction and which icon has at the top four stubs: one for the enzyme.r, two for substrate1.r and substrate2.r, and one for an inhibitor.r.

bioengine.R1.L1.An1.Rm is a receptor-bioengine which icon has at the top three stubs: one for the receptor.r, one for ligand.r, and one for an antagonist.r;

bioengine.M1.Ef1.An1.CCm is a conform-change-bioengine that represents an induced conformational change process which icon has at the top three stubs: one for modifier.r, one for effector.r, and one for an antagonist.r;

bioengine.U2.CFm is a complex-formation-bioengine that represents the formation of a complex from two previously independent bioEntities (which may themselves be complexes) and which icon has at the top two stubs: one for unit1.r and one for unit2.r;

bioengine.C1.M1.CDm is a complex-dissoc-bioengine that represents the dissociation of one complex induced by a mediator into two or more independent bioEntities (which may themselves be complexes) and which icon has at the top two stubs for complex.r and mediator.r.

bioengine.ch1.ii1.L1.ICm is a channel-bioengine which icon has at the top three stubs: one for channel.r, one for ion-Input.r, and one for antagonist.r;

bioengine.C1.In1.Tm is a translocation-bioengine that represents a translocation between different compartments and which icon has at the top two stubs: one for carrier.r and one for input.r;

c) Class bioRole-Object

As previously discussed, a bioRole-Object is a graphic programmed object that represents the role that a bioPool plays in a bioProcess, either as a different types of bioReactants, such as: enzyme.r, substrate.r, inhibitor.r, subunit.r, receptor.r, agonist.r, antagonist.r, carrier.r, and so on, each representing the specific roles of the inputs that different bioReactants provide to the bioEngine, or as a bioProduct. The class bioRole-Object (Table 92) is a subclass of bioObject, and has two subclasses: bioReactant and bioProduct.

As shown in FIG. 10, a bioReactant (1408 or 1419), is connected to an input r-connection at the top of a bioEngine, and represents the material contribution from a bioPool to the bioEngine to which it is connected. To be operational, the bioReactant-post connected to a bioReactant must have the same name as one of the bioPool-r-posts connected at the bottom of a bioPool. The two bioReactants shown are representative examples of a pair of two interacting molecules or complexes with complementary roles or functions: a receptor and its ligand. As described earlier, may other combinations of two, three or any other number of interacting participants are possible, to represent other types of processes, such as combinations of enzyme and substrate(s), units that form a complex, and so on. These combinations may also include antagonists or inhibitors, which may alternatively be represented as competing in a separate process, the latter being the preferred alternative in the default implementation using the scaled set of variables and simulation formulas.

The class bioReactant (Table 93) comprises a hierarchy (Tables 95 through 100) of subclasses, with a few examples of their incremental definitions shown for subclasses amplifier-bioreactant (Table 95), source-bioreactant (Table 96), leading-bioreactant (Table 97), binding-bioreactant (Table 98), inhibitor-bioreactant (Table 99), and single-bioreactant (Table 100). There are several attributes common to all subclasses of bioReactant, while each subclass has one or two specific attributes. Every instance of a bioReactant (1408 or 1419) has its associated menu (1409 or 1420), and selecting its "table" option (1410 or 1421) causes the display of its table of attributes (1411 or 1422). Those tables, showing the default values for their attributes, will be referred to while describing the new, and not previously described, specific attributes defined for any of the subclases comprise:

"stoichiometric-coeff" (1412) is a simple float attribute of all subclasses of bioReactant and bioProduct, which constant value represents the characteristic stoichiometric coefficient of that participant in that particular bioProcess. In other words, the set of the stoichiometric-coeff of all bioReactants and bioProducts of a particular bioProcess indicates the relationship between the number of units of each bioProduct produced per number of units of each bioReactant;

"alpha-coeff" (1413) is a simple float attribute which value may optionally be set by the modeler to modify by a factor the Contribution, which value is computed by the program. This is of interest for testing the effects of a global modification of such variable on the simulation of the system. This value is incorporated by default in the generic formulas provided, and if not configured by the modeler, multiplying by its default value of 1.0 has no effect on the system. Alternatively, the modeler may delete the alpha-coeff-par and provide instead a simple float value "Contribution" (1414) is an attribute of every subclass bioReactant which value is given by a contribution-pvar (1415), which value is dynamically computed while a simulation is running. The meaning and use of this attribute is a novel teaching of this invention, designed to meet some of the challenges posed by the domain of this invention, where both qualitative and quantitative knowledge is frequently scattered and incomplete. This attribute represents, as its name indicates, the Contribution of each bioReactant to determining the overall rate of the transformation that the bioProcess, as represented by the Velocity of its bioEngine. the contribution is a variable that can take values from 0.00 to 1.00, and represents a dimensionless scaled concentration (or other equivalent quantity variable). The scaling of the concentration is done at the bioReactant level, rather than at the bioPool level, to allow for additional flexibility. In this way, the absolute concentration can be scaled differently for each bioEngine, centering around the specific constant that characterized the molecular interactions between each specific pair of bioReactants. The type of constant may be different for different bioReactants representing the same BioPool depending on the role played by each bioEntity in a given bioEngine, such as a Km for each substrate, the Ki for an inhibitor, the Ks for ligands or complex-subunits. The default values for all types of contribution are equal to: a) 0.5 for normal steady-state physiological conditions (for that particular compartment); b) 0.0 for bioPools of inducible proteins or non-physiological molecules; or c) 1 for constitutive and repressible proteins. The user can either directly override a relative value or leave the default values. A generic formula specific for each of the bioReactant classes determines how the value of each contribution class is computed.

"Consumption-Rate" (1416) is an attribute of every subclass of bioReactant which value is given by a dependent consum-rate-pvar (1417), which value is dynamically computed while a simulation is running, and indicates the rate of consumption of units of the connected bioPool in such bioProcess. Its arguments are the bioReactant's stoichiometric-coeff and the Velocity of the bioEngine, and its value is an argument for the Output-Rate of the connected bioPool. For those classes of bioReactants that are not consumed in a reaction, the value of this attribute remains 0.0. In the current embodiment of this invention, an enzyme.r or an inhibitor.r are preferably not consumed in the enzyme-processes. However, they may be retained, by modeling them with a time-delay-var with its specific formula. The connected bioReservoir may be configured for the quantity of the bioPool to decay dynamically, representing their degradation and diffusion components, and it also may be consumed in oth☐☐☐er bioProcesses;

"effective-binding-sites" (1418) is a simple float attribute of the subclasses of bioReactant that refers to molecules or complexes that have binding activity, such as all the subclasses of amplifier-bioreactant and leading-bioreactant, and its value is set by the modeler to indicate the number of effective binding sites per unit.

Kinetic-parameters are by default simple float attributes specific for some subclasses of bioReactants, which values are optionally set by the modeler to indicate the value of the kinetic parameter characteristic for that particular instance. A set of two attributes is provided for each of such subclasses, one to hold the absolute value and the other to hold a scaled value of such kinetic parameter, which are used by the set of absolute generic simulation formulas used in conjunction with the absolute-valued variables, or by the currently default set of scaled generic simulation formulas used in conjunction with the scaled-valued variables, respectively. Alternatively, in cases where the value the kinetic-parameter is time-variant and dependent on other variable values, the modeler may choose for individual instances to have the value of that attribute to be given by an instance of one of the different subclasses of kinetic-parameter-var (as defined in Table 38), in which case the modeler has to define the specific simulation formula to provide the value for that particular instance. To add a variable or parameter of the desired class as an attribute, the modeler can select the "add subtable" from the menu that appears when clicking on the slot of the value that attribute, and then navigate through successive menus to follow the hierarchy of subclasses of variable or parameter, in this case of float-variable, until the desired subclass can be selected, which results in the creation of an instance of that subclass that gives the value to the attribute from which slot it was requested. To define the specific simulation formula the same process has to be followed as that previously described in FIG. 8 for a model-block-var (1230), were clicking on the slot of the attribute "simulation-details" (1231) displays its simulation subtable (1232) with a slot (1233) where the simulation formula may be written by the modeler. Some examples of such attributes comprise:

"catalytic-constant" and "scaled-catalytic.k" (not shown) are simple float attributes of the subclasses of enzyme.r (Table 95) which value is optionally set by the modeler to indicate the absolute or a scaled value, respectively, of the characteristic kp of that enzyme (where kp is the equivalent of the units of activity per catalytic center, or kp=Vmax/[E]t (t−1));

"Michaelis-constant" and "scaled-michaelis.k" (not shown) are simple float attributes of the subclass substrate.r (Table 96) which value is optionally set by the modeler to indicate the absolute or a scaled value, respectively, of the Km characteristic of that substrate (where Km is the dynamic constant equivalent to the substrate concentration that yields half-maximal velocity, or Km=(k−1+kp)/k1, used when the bioEngine is treated under steady-state conditions, which the preferred treatment in this invention). This attribute may optionally be considered to represent the Ks (where Ks represents the intrinsic dissociation-constant, or Ks=[E][S]/[ES]= k−1/k1 (M)=1/Keq, may be used when the system modeled is under rapid equilibrium conditions, which is usually not required because of the dynamic nature of the simulation system of this invention), which may be used in a formula in conjunction with the catalytic-constant or scaled-catalytic.k, respectively, of the interacting enzyme.r;

"equilibrium-dissociation-constant" (1423) and "scaled-equil.dissoc.k" (1424) are simple float attributes of the subclasses of binding-bioreactant (Table 98) which value is optionally set by the modeler to indicate the absolute or a scaled value, respectively, of the Ks characteristic of that agonist or complex-subunit; and "inhibition-constant" and "scaled-inhibition.k" (not shown) are simple float attributes of the subclasses of inhibitor-bioreactant (Table 99) which value is optionally set by the modeler to indicate the absolute or a scaled value, respectively, of the Ki characteristic of that inhibitor or antagonist (where the factor (1+[I]/Ki) may be considered as an [I]-dependent statistical factor describing the distribution of enzyme between the E and EI forms).

The class bioProduct (Table 101) has no subclasses. As shown in FIG. 11, a bioProduct (1518) is connected to an output p-connection at the bottom of a bioEngine, and represents the material contribution from a bioEngine to the bioPool to which it is connected. To be operational, the bioProduct-post connected to a bioProduct must have the same name as one of the bioPool-p-posts connected at the top of a bioPool. Every instance of bioProduct (1518) has its associated menu (1519), and selecting its "table" option (1520) causes the display of its table of attributes (1521), which in this case shows the default values for its attributes, and which will be referred to while describing the new, and not previously described, specific attributes of this class:

"Production-Rate" (1522) is an attribute of the class bioProduct which value is given by a dependent produc-rate-pvar (1523), which value is dynamically computed while a simulation is running, and indicates the rate of production of units to be added to the connected bioPool from such bioProcess. Its arguments are the bioProduct's stoichiometric-coeff and the Velocity of the bioEngine, and its value is an argument for the Input-Rate of the connected bioPool.

d) Class bioRole-post

In the current embodiment of this invention, any reference to a bioRole-post means a bioPost to be located upon the subworkspace of a bioProcess which function is to connect a bioRole-Object to a bioPool through a bioPool-post. The class bioRole-post (Table 102) is a subclass of bioPost, from which it inherits all its capabilities, and has two subclasses: bioReactant-post (403 or 407), which together with a biopool-r-post (404 or 408) distantly connects a bioReactant to a bioPool; and bioProduct-post (411), which together with a biopool-p-post (412) distantly connects a bioProduct to a bioPool. The new attribute defined for these classes is:

"ref-bioreservoir" is a pointer to the bioReservoir instance that contains the biopool-r-post or biopool-p-post to which it is distantly connected. The value is interactively set by selecting the "set-refs" menu option, and it is used by the program for interactive navigation through bioReservoirs and bioProcesses, as described below.

12. Prebuilt Building Blocks and Panels a) The encoding of domain-knowledge in this invention is achieved by first defining the hierarchies of new classes of required structures, with their specific sets of attributes. Then, those object definitions are used to create instances that are combined in specific ways to build generic types of composite bioObjects, that are them made available organized in Palettes. Palettes are created by the developer by cloning the Master-Palette, a named and special instance of go-to-sw, which subworkspace has the value of its "user-restrictions" attribute set to "unless in developer-mode: selection of any bioObject upon this workspace implies clone; non-menu choices exclude additionally: move-object". There are several alternatives for building each generic type of composite bioObject, such as those provided in the palettes as prebuilt building-blocks, and several steps are necessary. One alternative method comprises the following steps: a) an instance of the desired class, such as bioProcess, is created (by selecting from the menu of the object-definition of that class the "create-instance" option) and transferred to a workspace; b) the subworkspace of such instance is created (by selecting from its menu the "create-subworkspace" option); c) the characteristic set of instances of several classes of schematicTools are created (by selecting from the menu of the object-definition of each class the "create-instance" option, or by cloning an existing instance by selecting from its menu the "clone" option) and transferred to such subworkspace; d) the different newly created instances are positioned and connected in specific ways, to conform to the designs specified in the current embodiment of this invention, such as those designs shown in FIGS. 2 through 5 and throughout other exhibits of this invention, resulting in a modular schematic that is encapsulated. An alternative way is to clone an existing composite bioObject that is similar to the desired one, and delete and/or add components, as desired. The so created generic but distinctive types of composite structures are organized in palettes, which are made accessible through the domain-menus, and are used to create new instances of the same type by cloning such generic structures. Cloning an object in the current embodiment of this invention means cloning also its subworkspace, and all objects upon its subworkspace, and any objects upon the subworkspace of each of those objects, and so on. The modeler can then further individualized each newly cloned instance by configuring the attribute tables of the superior object, or by configuring the attribute tables of the objects encapsulated within that superior object, either as attribute objects or as objects upon successive subworkspaces. The relationships between those various data structures may be established either graphically by the modeler, through the permanent connections, or abstractly by the inference engine, by establishing at run-time transient relations that have been previously defined.

b) In addition of the previously described methods to manually create instances of objects, where the developer or modeler interactively selects different menu options, it is possible in the current embodiment of this invention, to create transient objects by including appropriate actions in procedures or other methods that are invoked at run time. There are two alternative and different ways to create transient objects at run-time: a) by using the "create a <class-name>" and "transfer" actions, which is equivalent to the "create-instance" option of the object-definition described above; or b) by using the "create a <class-name> by cloning <instance-name>" and "transfer" actions, which is equivalent to the "clone" option of an instance described above. Transient objects are sometimes made permanent by using in addition the "make <instance> permanent" action after the instance has been transferred to a workspace. Both manually and at run-time, simply creating an instance (first alternative) only creates that, an instance without a subworkspace, while cloning an instance (second alternative) that has a subworkspace clones the instance with its subworkspace and anything upon the subworkspace.

Therefore, the second is the preferred alternative in the current embodiment of this invention, where extensive use is made of prebuilt sets of objects encapsulated in the subworkspace of other objects. In addition, the current embodiment of this invention makes extensive use of dynamically creating objects at runtime, by cloning, such as when creating dynamic pathways, dynamic query-panels, dynamic query-output-panels, dynamic entry-panels, dynamic graphs, dynamic lists, and so on. A set of partially prebuilt complex sets of structures, such as those required for the different types of panels, are organized and stored in the subworkspaces of objects called bins, and used as master structures to be cloned and completed with additional context-dependent structures at runtime, as will be described under the General Mode and Simulation Mode headings below.

c) The classes query-panel and entry-panel are both subclasses of uil-tailored-dialog, a class defined within the Shell and from which they inherit several attributes, used by procedures that are proprietary to the Shell and used for run-time processing, and are therefore not listed here. The relevant attributes used in the current embodiment of this invention are listed in Table 29. Neither class has additional subclasses. The different types of query-panels and entry-panels are important components of the domain-specific graphic interface implemented in this invention. The different types are designed as master structures, built by transferring to the subworkspace of individual instances of the desired class different sets of a variety structures, arranged in specific designs depending on the intended use, as will be discussed together with their use in later sections. The prebuilt query-panels are stored in the subworkspace of the query-panel-bin and the prebuilt entry-panels are stored, together with other prebuilt structures in the subworkspace of the master-structures-bin. Those different types of partially prebuilt panels are used as master structures that are dynamically cloned and completed at run-time, following requests from the user. The dynamically created entry-panels are used to interactively set-up and start simulations comprising a desired set of schematics. It is a facility that permits the user to select the workspaces to be included in a simulation, and to enter the entry-value and entry-time. The dynamically created query-panels are used to interactively perform predefined complex queries, based on structure, function or relative position within the pathways.

E. Modeler Mode

Figure 12:
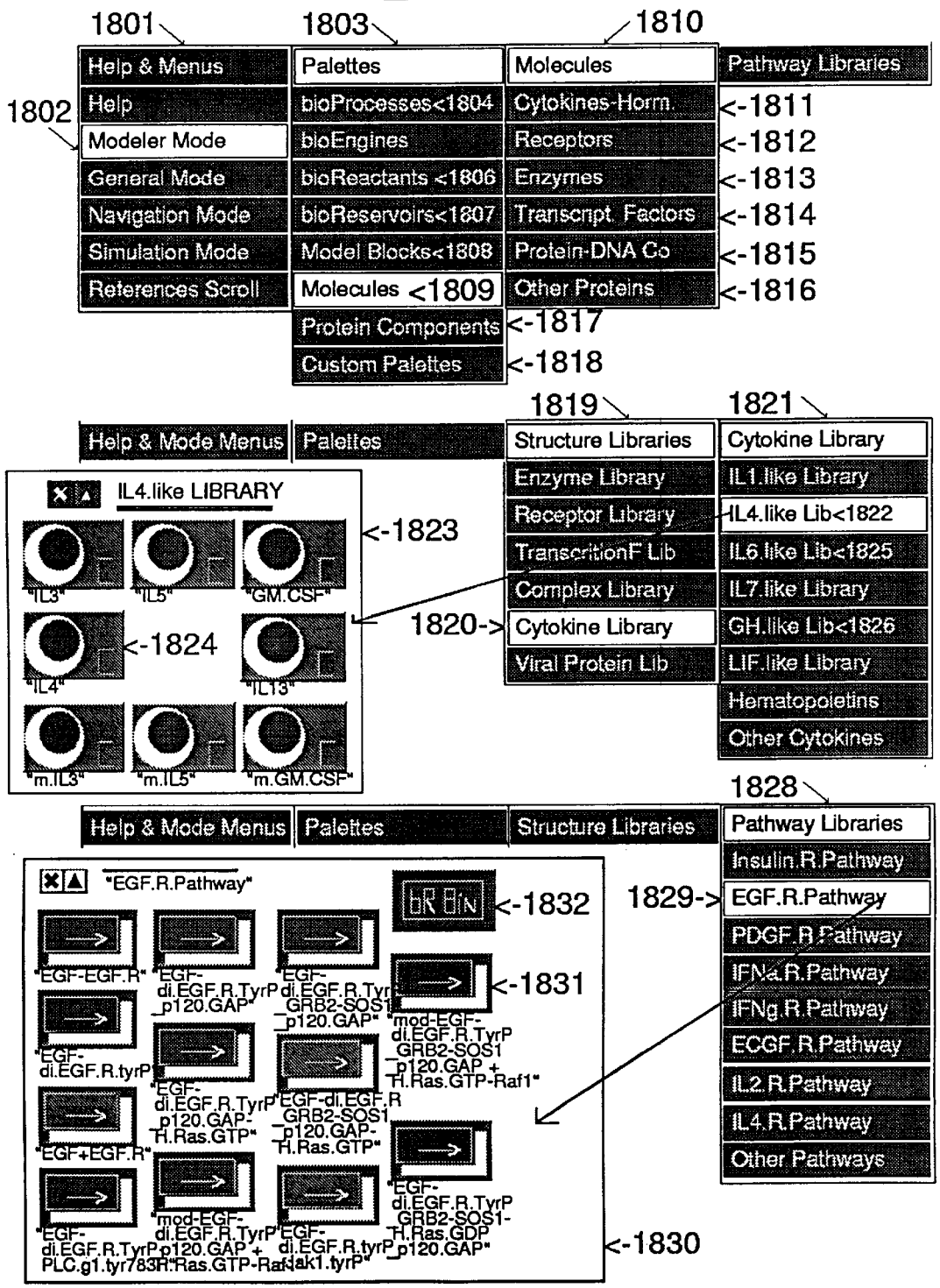
FIG. 12 shows exemplar domain menus enabling modelers to access the different palettes of prebuilt building-blocks as well as the libraries of built visual models.
Figure 20:
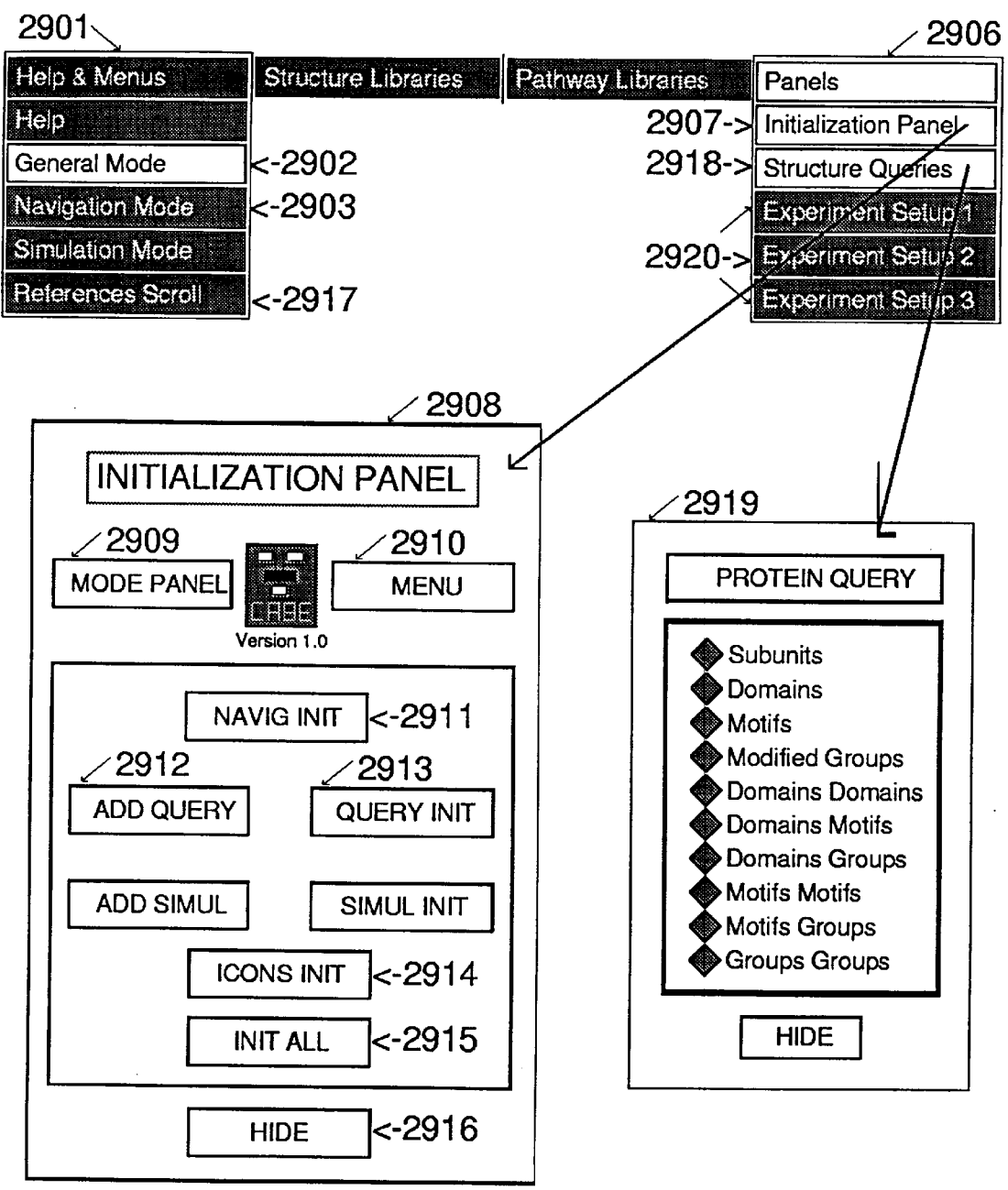
FIG. 20 shows exemplar domain menus enabling users to access different user modes as well as prebuilt panels to control the different tasks to be performed on the virtual models, including exemplar initialization and query panels.

1. Menus, Palettes and Libraries a) The Modeler Mode is available only to those users that have rights to build or modify graphic models or applications, in which case it is the default mode when the application is started. The modeler's tasks are all based on the basic paradigm of "Clone, Connect and Configure", and consist of building and configuring graphical models of the structure of bioEntities, as well as to design and build graphical models of complex networks of cross-talking pathways, which result from the modeler's actions of cloning, connecting and configuring sets of bioProcesses, bioReservoirs, and bioEntities. To facilitate the modeler's tasks, the Modeler-Menu provides a way to organize and access the different components of the system.

b) FIG. 12 shows the domain-menus associated with this mode in the current embodiment of this invention, which are shown here again in an overly expanded (pulled-down) way, for demonstration purposes. Selecting the "Help & Mode Menus" option (1801) allows access to the available user-modes, which upon selection causes a change to that mode of operation and displays the specific domain-menus associated with that user-mode, only for the window from which it is selected. Selecting Modeler Mode (1802) displays the contracted top layer of menu heads shown in the lower menu display, which additionally comprise the options "Palettes", "Structure Libraries", and "Pathway Libraries". The following discussion of this menu system also serves the purpose of discussing how the building-blocks are organized in Palettes and how the graphic models build by the modeler are organized and stored in Libraries. The difference between Palettes and Libraries is that Palettes contain domain-specific and generic building-blocks built by the developer and to be used by the modeler, while Libraries contain application-specific models built by the modeler and to be used by different types of users. Palettes are provided to allow the modeler to quickly create new instances from prebuilt generic bioEntities, bioReservoirs or bioProcesses, or any of their components, which comes with their corresponding default or no values, to be then configured by editing their tables of attributes. Libraries may be of two types: a) "Structure Libraries" (1823), which are hierarchically organized workspaces (which means subworkspaces of objects contained in subworkspaces of objects, and this repeated as many times as necessary) containing models of high-level bioEntities, or b) "Pathway Libraries" (1830), which are related sets of bioProcesses (1831) contained in the subworkspace of a submodel, which also contains a bioReservoir-Bin (1832) with the bioReservoirs connected to those bioProcesses, where those bioProcesses and bioReservoirs are the modules or nodes of the modeled multidimensional pathways that result from sets of those pathways organized in one or more submodel. The highlighted options with white background are selected options.

c) The Palettes provide a large number of characteristic types of bioObjects, grouped by subclasses and organized in special subworkspaces of named go-to-sw buttons organized in the subworkspaces of another go-to-sw named "Palettes-Bin". Palettes are accessible through the domain-menus, and because of their defined user-restrictions, selection of any bioObject upon a Palette in Modeler Mode implies clone, which means that upon selection of a bioObject from a Palette by the modeler automatically results in a clone of such bioObject (including its subworkspace and all structures upon it, and all the further levels of encapsulation contained in their subworkspaces) to be attached to the mouse-pointer and ready for the modeler to transfer it to the desired subworkspace. Selecting "Palettes" (1803) pulls down its options, which in most cases point directly to the palettes of important classes of bioObjects and also model-blocks (1804 through 1808 point to the Palettes shown later as 2501, 2701, 2301, and 2401, respectively). In the case of classes with large number of building-blocks, those may be grouped further by subclasses in a number of palettes that can be accessed through walking menus, such as when selecting "Molecules" (1809) displays an additional pull-down menu headed by "Molecules" (1810), which options may now point directly to Palettes, small samples of which are shown in FIG. 20, such as when selecting "Cytokines-Hormones" (1811 points to 2104), "Receptors" (1812 points to 2106), "Transcription Factors" (1814 points to 2102), "Protein-DNA-Complex" (1815 points to 2105), or "Other Proteins" (1816 points to 2101). Again it is possible that an option referring to a large class may lead to another walking menu, such as when selecting "Enzymes" (1813) leads to a walking menu (not shown), one of which various options points to a palette such as that shown as 2103.

d) New empty Palettes may be also created by the modeler, to allow them to expand and complement the built-in library of building-blocks to satisfy their more specific needs. Selecting the "Modeler-Defined" (1818) option of "Palettes" displays the subworkspace of a regular instance of a go-to-sw button named Modeler-Palettes-Bin, which contains: a) a clone of a regular go-to-sw button, labeled "original-bin", to be cloned when additional bins are needed, or when additional levels in the workspace hierarchy are required, in which case the new bin will be transferred to the subworkspace of the desired existing bin; and b) a clone of the Master-Palette labeled "original-palette", which the modeler may clone to add new palettes at the desired level in the workspace hierarchy.

e) Selecting the main menu head "Structure Libraries" (1819) displays its options, which point of sets of high-level bioEntities that model the functional structure of molecules or molecular-complexes at various levels of complexity. For example, further selecting the option "Cytokine Library" (1820) displays the menu headed by "Cytokine Library" (1821), which options refer to libraries of different families of cytokines, and further selecting one of them, such as "IL4.like Library" (1822) displays the library (1823) of the IL4 family, which contain several cytokines (instances) with similar structures, which prototype is IL4 (or interleukin 4, 1824), which structure is shown as 2203.

f) Selecting the main menu head "Pathway Libraries" (1828), pulls-own its options, which in this case points directly to submodel which subworkspaces are displayed. For example, selecting the option "EGF.R.Pathway" (1829) displays the components of a short pathway (1830) containing bioProcesses (1831) and a bioReservoir-Bin (1832). When the size of the submodel increase to a point that it is not conveniently handled, it can be partitioned into two or more submodel, by simply transferring related sets of bioProcesses and their corresponding bioReservoirs to the subworkspace of a newly cloned submodel, without affecting the connectivity of the pathways in any way. When the application grows larger and the number of submodel increase, those direct domain-menus options are replaced by other options that lead instead to walking menus offering as many hierarchical levels as necessary. Modelers can also clone submodel, in which all the bioProcesses organized in its workspace, together with the contained bioReservoir-Bin and all the bioReservoir organized in its workspace, are also cloned preserving the labels and any other attributes, but with no names, since names are unique. This means that all new bioReservoirs and bioProcesses have to be named (with the same basic named but different tags), and the connections have to be reestablished by naming the bioPosts and setting the ref-attributes, as discussed elsewhere for new sets.

Figure 13:
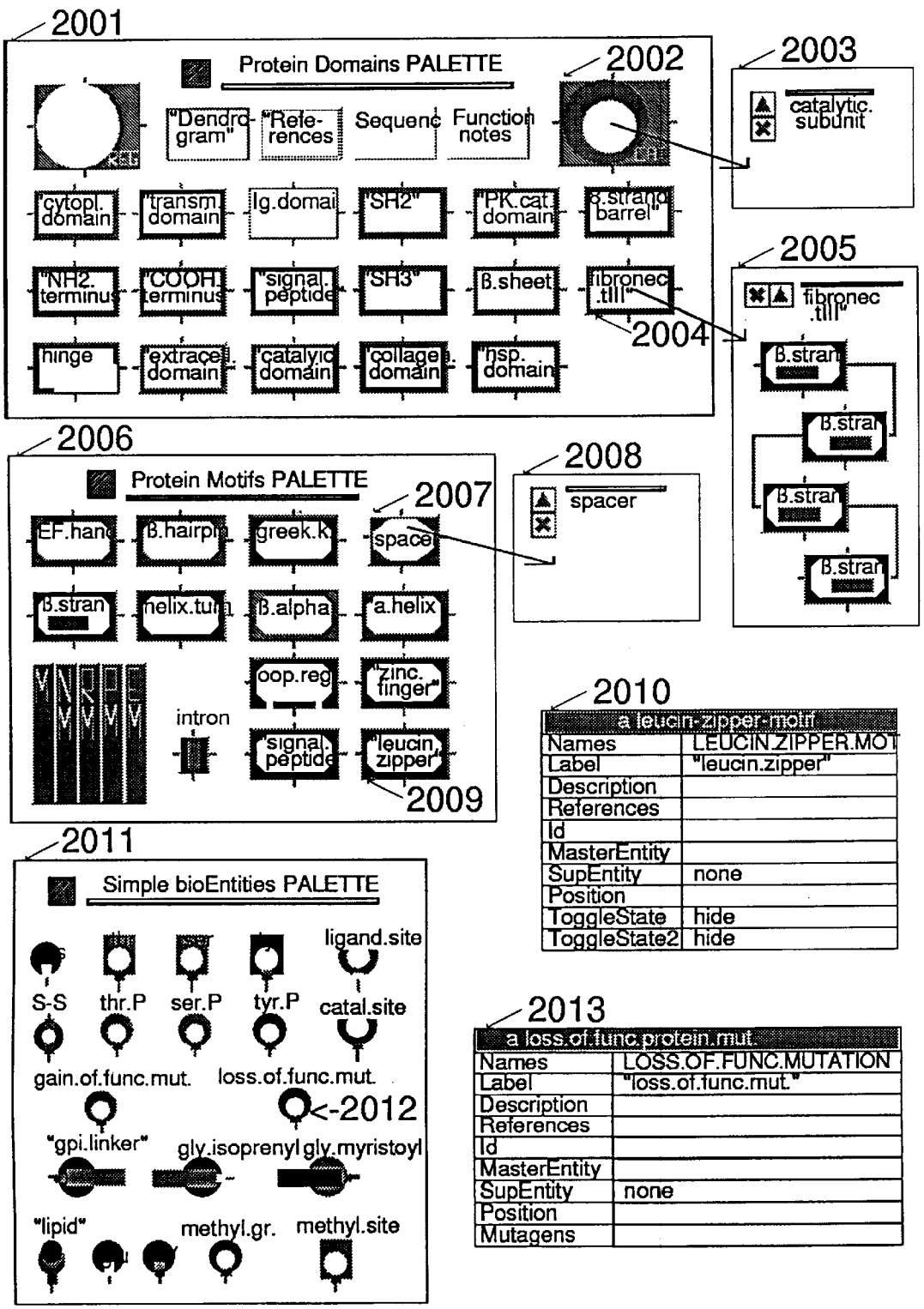
FIG. 13 shows exemplar palettes of simple iconic entity building-blocks to be used to build more complex structures, as well as examples of their attribute/value tables used for configuration or data storage.
Figure 14:
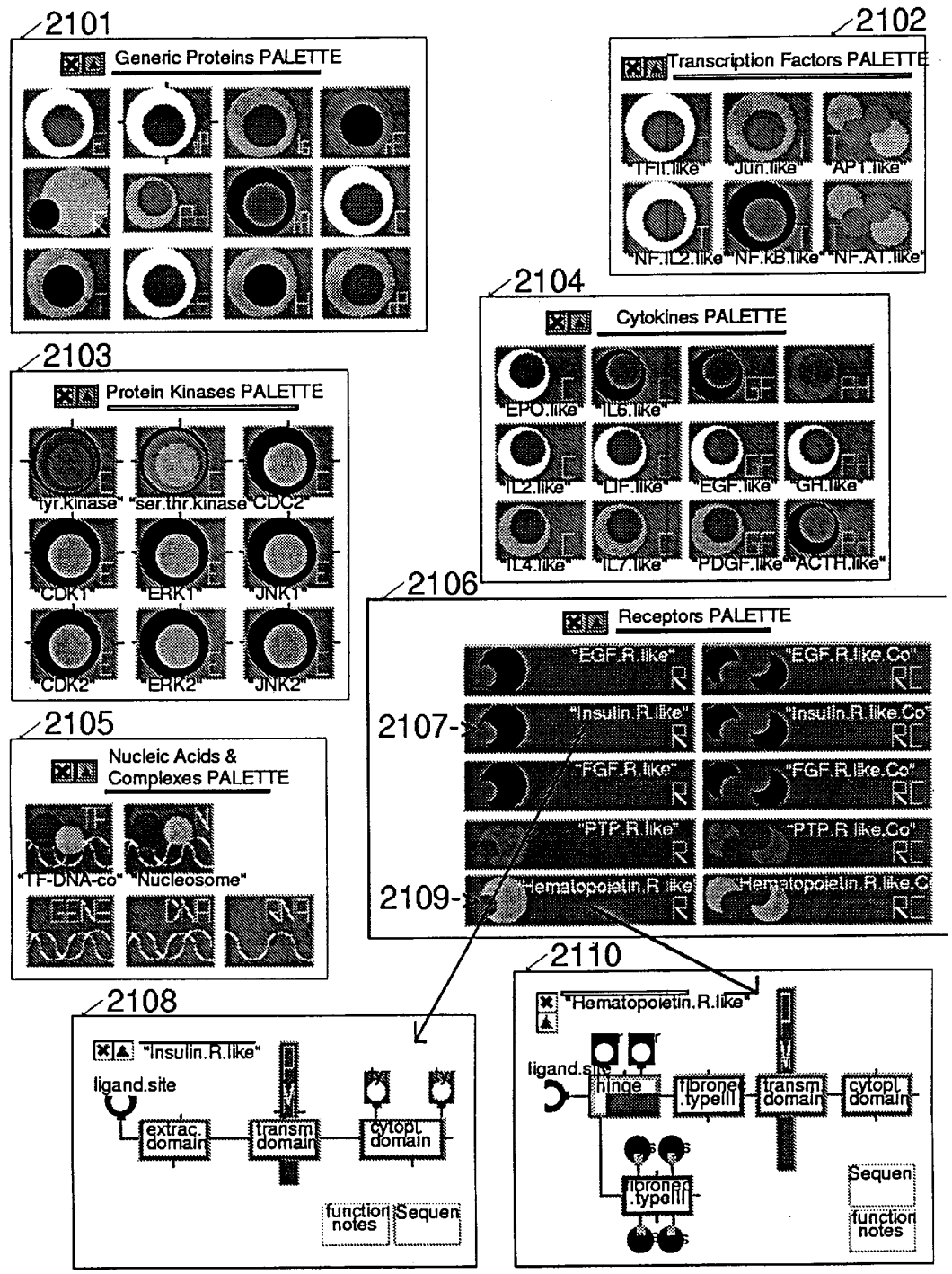
FIG. 14 shows exemplar palettes of prebuilt complex iconic entity building-blocks to be used to build entity structures of further high levels of complexity.

2. Modeling bioEntities a) FIG. 13 shows the Palettes with representative examples of master instances of some of the different subclasses of protein-domain (2001), protein-motif (2006), and simple-bioEntity (2011), accessed through the walking menu (not shown) displayed when selecting the "Protein Components" option (1817). Some of those building-blocks are very generic or "empty" structures, such as the examples shown of the subworkspaces (2003 and 2008) of catalytic-subunit (2002) and spacer (2007), respectively, while others may contain more or less detailed prototypic structures, in which case they are named master-structures, which may be referred to by the master-bientity attribute of its copies (to avoid redundancy and save computer memory resources), such as the example shown of the structure (2005) of a fibronectin.type.III-domain (2004). In addition, like any other bioEntity, each instance of these components have an associated menu (605) from which options specific for each class can be selected to perform generic or specific tasks. Selecting the "table" option (623) shows their tables of attributes, such as the examples shown for the tables (2010 and 2013) of a leucin-zipper-motif (2009) and a loss.of-.function.protein.mutation (2012), respectively, provides additional options for the modeler to include additional information, which in this case is specific for each instance, including copies. Clones of those instances can be combined in different ways to model, using the basic paradigm of "Clone, Connect and Configure", at the desired level of detail, the structure of a bioEntity. A high-level bioEntity such as a protein, may be composed with:

- diverse instances of subclasses of protein-component and simple-bioEntity, such as those which form part of the Cytokine Library and correspond to prototypes of families of cytokines mentioned earlier (1826, 1825, 1822). Having prototypes for each family, speeds up the modeling process, allowing the modeler to clone the prototype and them made the required modifications, rather than starting from the palettes for each new instance. And even prototypes can be derived from other prototypes.
- diverse instances of subclasses of molecule, which may also be combined with simple-bioEntities, such as the example shown in FIG. 5 and previously discussed, which represents the structure of a molecular complex b) FIG. 14 shows small sets from some of the Palettes with representative examples of master instances of: cytokine (2104), receptor (2106), p.tyr.kinase and p.ser.thr.kinase (2103), transcription-factor (2102), nucleic-acid and hetermol-complex (2105), and some of the different subclasses of high-level subclasses of protein (2101, which instances the modeler can use for less common types of proteins which more specific subclasses may not be defined in the system). Those palettes, accessed through the options (1811 through 1816, respectively) of the "Molecules" menu (1810), as described above, contain master-structures with more or less detail, such as the examples shown here of the structure (2108) of insulin.r.like (2107), or the structure (2110) of hematopoietin.r.like (2109). These master-structures may be referred to by the master-bioEntity attribute of its copies. In addition, the tables of attributes of those molecules, such as the examples shown for default instances of p.tyr.kinase (Table 73), a pdgf.r.like.complex (Table 74), and a gene (Table 75), provide additional options for the modeler to include additional information, which is specific for each instance, including copies.

c) The structural representations that are novel teaching of this invention allow to represent the modular patterns so frequently used by nature. Abstraction is obtained in part by selectively hiding some detail in the subworkspaces of other components. That representation focuses on components and the way they are arranged that relate to their function, to offer the scientists (users) visual models that facilitate their reasoning about structure-function relationships. Furthermore, each of those graphic instances of bioEntities have their associated tables of attributes, where the modeler can include additional information, data, and references to access other sources of information about those models, which can provide to the user a wealth of knowledge in the form of an intuitive and interactive visual database. The knowledge extracted from those models can be integrated in the current embodiment of this invention with other forms of knowledge, related to the function of those bioEntities, provided by the pathways related models. For example, the members of each family may be involved in similar mechanisms but result in very different and even opposing effects, due to the participation of their bioPools in different pathways. That knowledge integration is performed sometimes interactively by the user, and sometimes programatically as a result of an interactive request by the user, depending on which of the many offered capabilities, to be discussed in the following sections, is used.

d) In addition, to the standard "clone" capability which applies to every object, as defined within the Shell, there is a novel domain-dependent capability associated with the class complex-bioEntity, and therefore with all its subclasses. Selecting the "create-local" menu option (624) from any instance of any of its subclasses invokes the et-createlocal (Table 103) which is restricted to Modeler Mode, allows the modeler to create local copies. Local copies are used to point to a master-bioEntity, which subworkspace with the prototypic structure may be displayed upon request, while also allowing to include additional private details in the subworkspace of the local copy. That is, a copy of any complex bioEntity (including bioEntity-components), may have its own specific information in its table of attributes and in its subworkspace, while it is also able to cause the display the subworkspace of its master bioEntity. Simple-bioEntities do not have a subworkspace and do not have master-bioEntity attribute, and the concept of copy does not apply to them. The term clone means in this invention a complete reproduction of the original, while the term copy means an incomplete reproduction that is usually stripped from the contents of the subworkspace of the original, but contains a pointer to the original and is used in conjunction with it.

Figure 15:
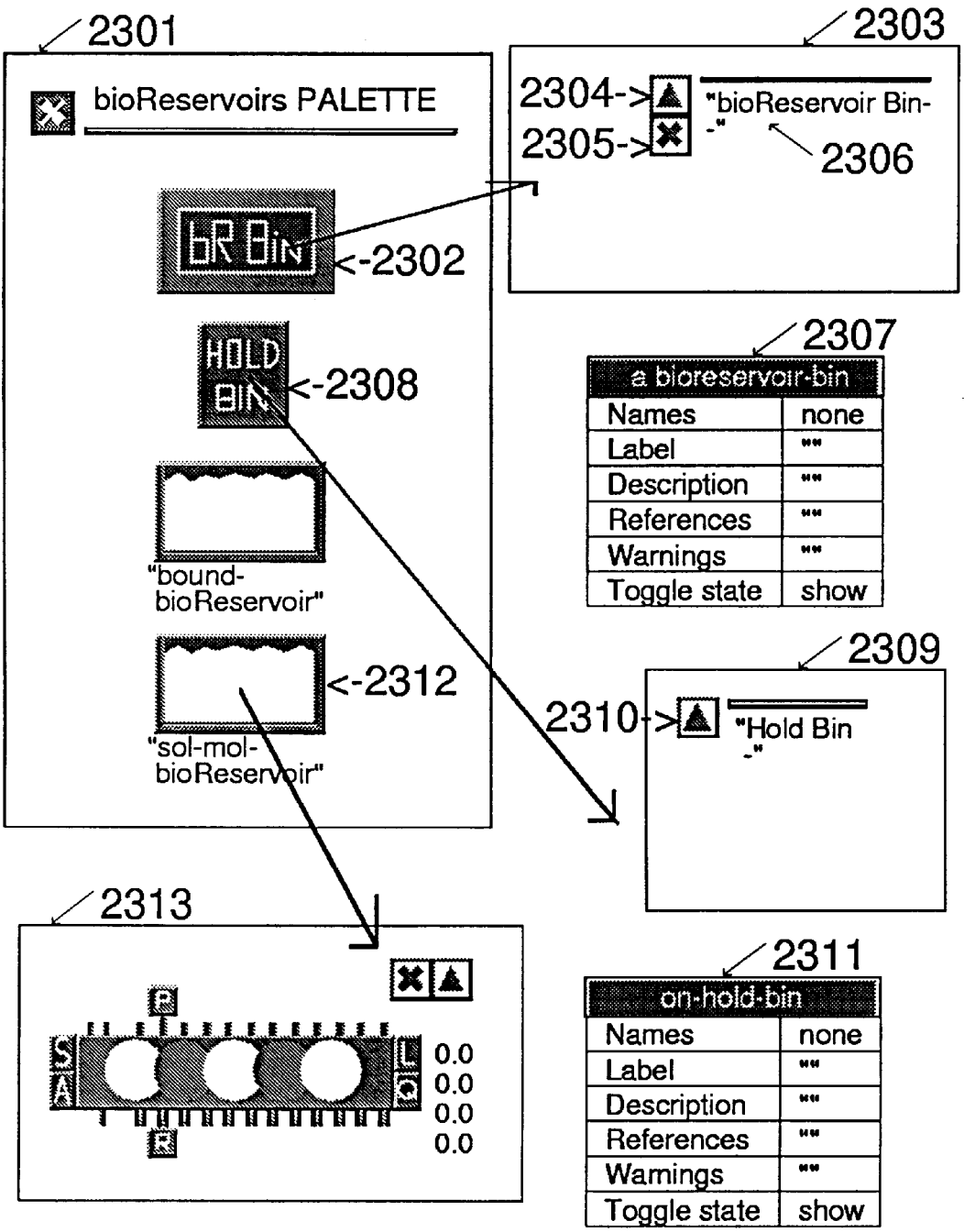
FIG. 15 shows a palette with exemplar iconic reservoir building-blocks and their containers, with a view of the iconic components including a default input and output.
Figure 17:
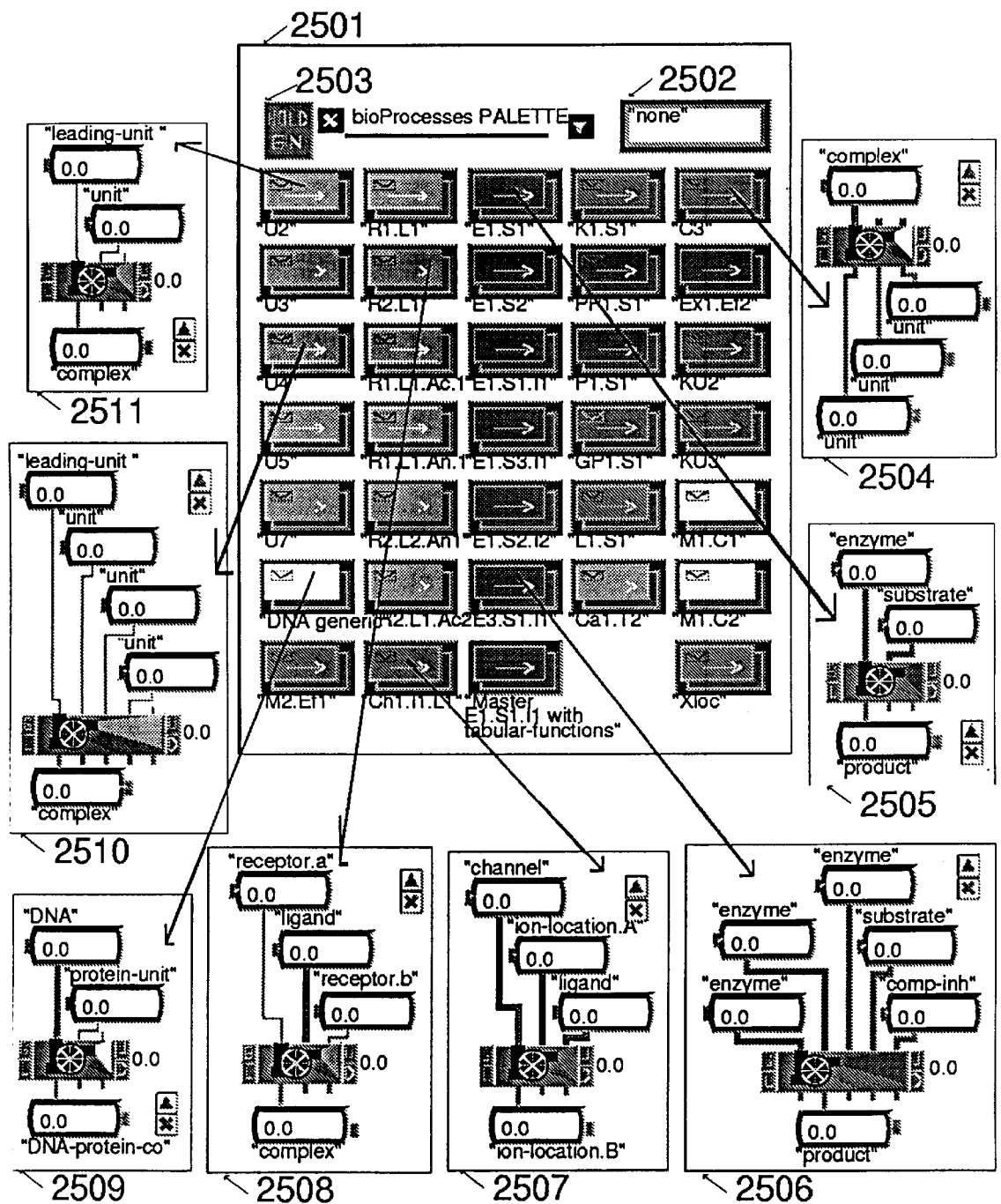
FIG. 17 shows a palette with exemplar prebuilt iconic composite process building-blocks, with views of their iconic components including different types of inputs and outputs.
Figure 18:
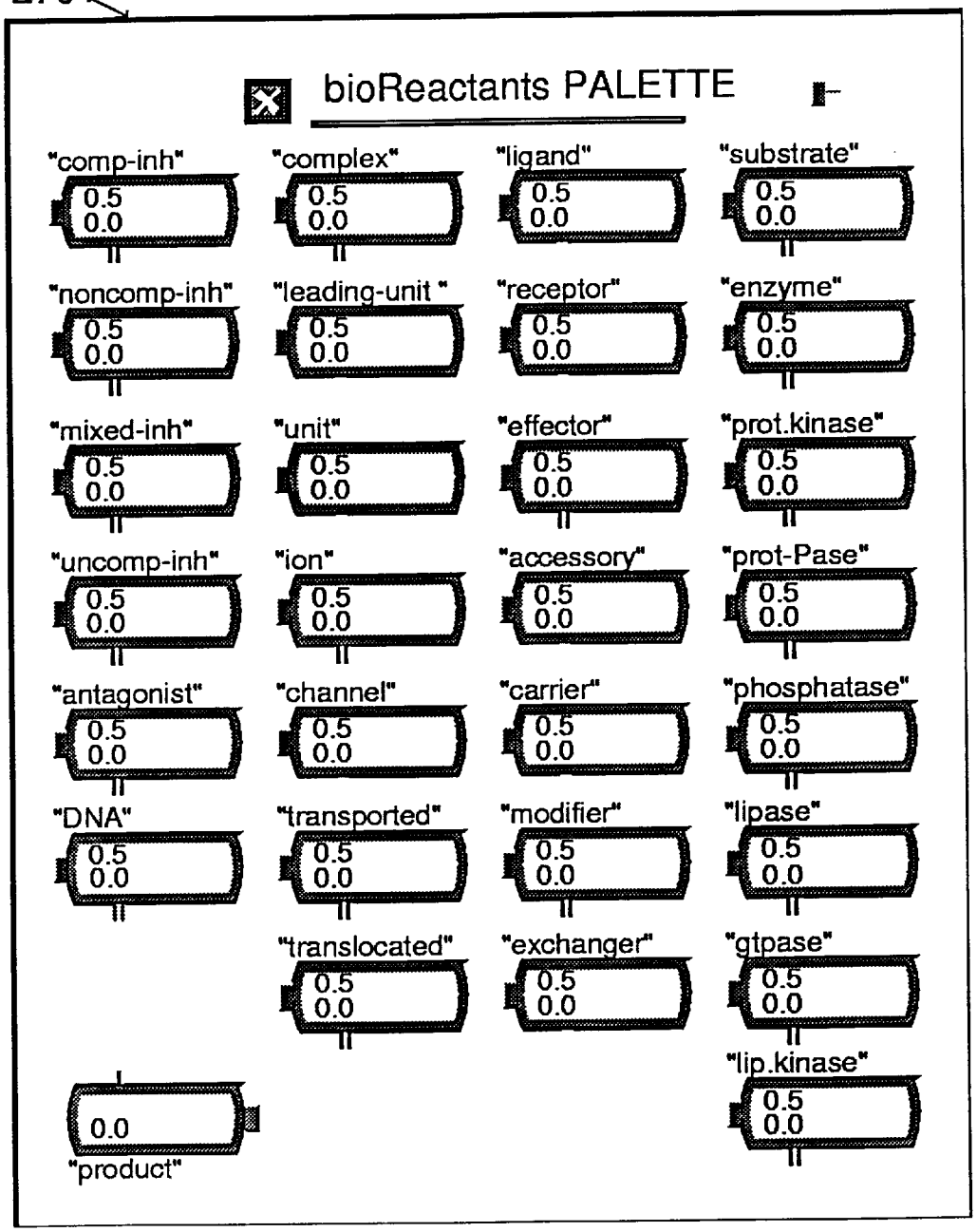
FIG. 18 shows a palette with exemplar different types of iconic inputs to be used as components of composite process building-blocks.
Figure 19:
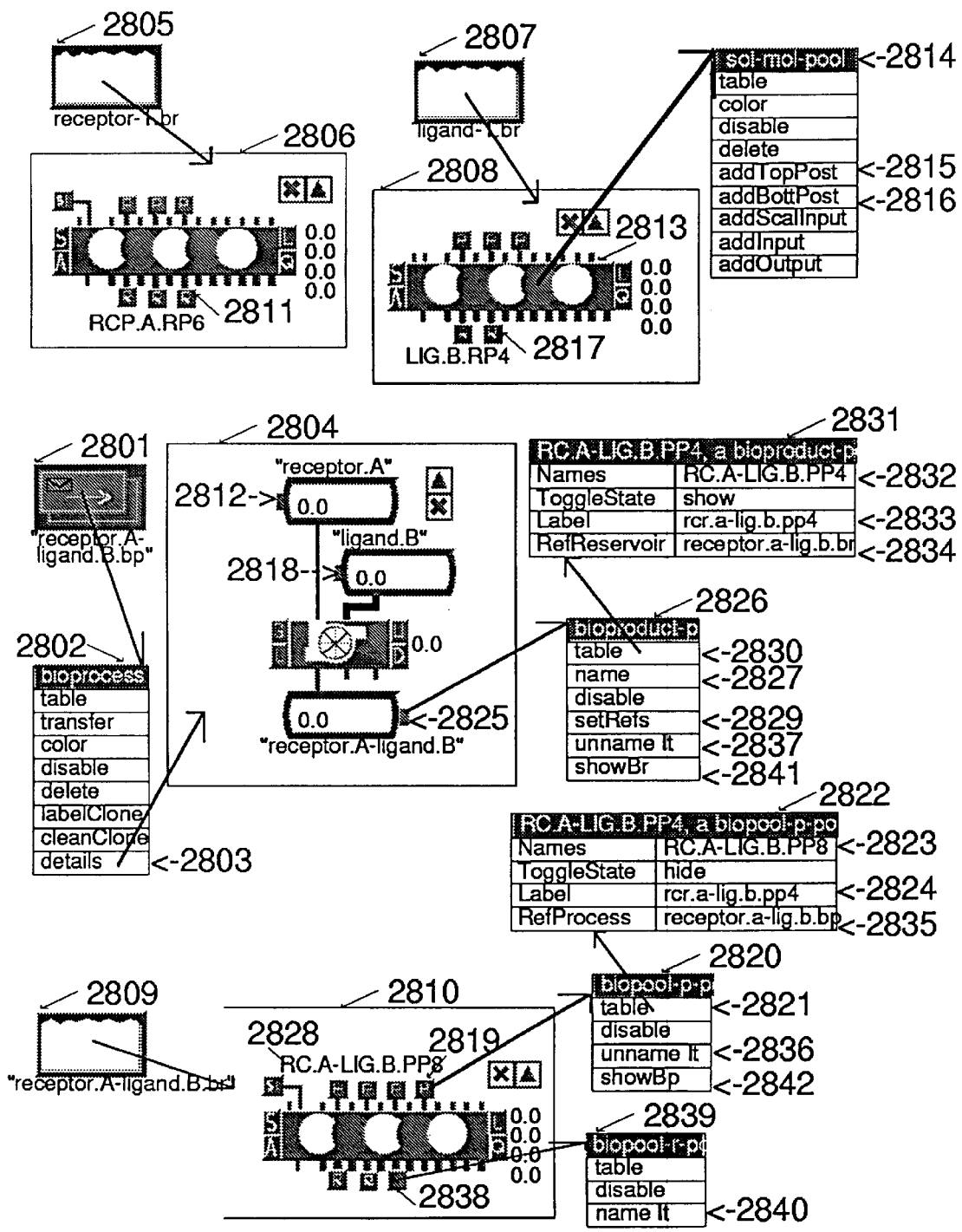
FIG. 19 shows exemplar means for interactively establishing links between corresponding iconic components of process and reservoir building-blocks.

3. Modeling Pathways a) FIG. 15 shows the Palette (2301) of bioReservoirs that contains prebuilt "empty instances" of:

- A bioReservoir-Bin (2302) used to store a set of related bioReservoirs upon its subworkspace (2303), which is prebuilt with: a) the standard set of navigation buttons used on most subworkspaces, consisting of a go-to-sup-obj-button (2304) and a hide-sup-ws-button (2305), and b) a bioObject-title (2306), which is standard for the subworkspaces of all bioModels as well as of all complex-bioEntities. The table of attributes (2307) of each instance of a bioReservoir-Bin allows to store and access additional information.
- An On-Hold-Bin (2308) to be used to store, upon its subworkspace (2309), connected bioReservoirs and/or bioProcesses that the modeler may want to offer as alternatives, and which the user may include or exclude from a simulation or other uses at will, by using any of three alternatives: a) desired individual structures can be moved out of the On-Hold-Bin and transferred to the subworkspace of such submodel, or its bioReservoir-Bin if bioReservoirs; b) if all structures are desired for inclusion, the subworkspace of the On-Hold-Bin can be activated and deactivated at will; or c) two On-Hold-Bins can be used to transfer those structures between them at will, one to be permanently deactivated and the other be activated and to hold only those structures desired for inclusion. If any of those structures are substitutions for other bioReservoirs and/or bioProcesses contained in such submodel, then those structures they are replacing should be removed to a deactivated On-Hold-Bin. This subworkspace is prebuilt with a hide-and-deact-sup-ws-button (2310), instead of the standard set of navigation buttons, which upon clicking on it when the subworkspace is activated, hides and deactivates such subworkspace, and its table of attributes (2311) allow to store additional information.

two different prototypes of bioReservoirs, representing the two subclasses, which differ only in the instance of the bioPool they contain upon their subworkspace, which is in turn of one of the two corresponding subclasses of bioPool, and in the color of the type-color region of their icon. Each of those prototypic bioReservoirs comes with a minimal set of basic structures, as shown here for the subworkspace (2313) of the sol-mol-bioReservoir (2312), and additional structures can be added interactively upon request by the modeler, as described in the following paragraphs. By cloning a bioReservoir of the appropriate class from its Palette, transferring it to a workspace and clicking on its icon and repeating a similar sequence of clicking, selecting and configuring operations, it can be connected to any of the bioRole-Objects of the bioProcess by simply giving the same name to a matching pair of bioPosts, one from each structure, always keeping in mind the required restrictions. Another alternative is to clone an existing bioReservoir that has similar characteristics, directly from the schematics, by selecting the "clean-clone" option from its menu, and configure the new name and desired attributes.

b) The "clean-clone" option (1239) appears in the menu of every bioReservoir, and starts the BR-clean-clone-proc (Table 104) upon selection by the modeler, which creates a clone of such bioReservoir, including its subworkspace and all structures upon it, and then sets the values of all the attributes of all structures involved, including the bioReservoir, to their default values. This capability is useful to create clean bioReservoirs of desired types that are available on the displayed workspace, without the need to open the palette of generic bioReservoirs.

c) With the bioReservoir's architecture used in the current embodiment of this invention, the details of the bioPool and its attributes are hidden in a different layer. The modeler can add, modify or remove connections to bioProcesses, by creating and naming the corresponding bioPosts, but the modeler does not need to access the table of attributes of the bioPool. That established distant connectivity is independent of the location of bioProcesses and bioReservoirs throughout the knowledge-base or the workspace hierarchy, and no additional changes are required when moving those structures from one location to another. Various menus options and associated methods are offered to automate the task of establishing those connections, which will be described after the discussion of the creation of bioProcesses d) The modeler can also model inputs or outputs to a bioPool as mathematical models using model-blocks held in model-boxes, as previously discussed with the description of FIG. 4. An additional set of menu options, defined for the class bioPool, are provided to automate the task of adding a scaled-input-model-box, input-model, or output-model-box, respectively, when desired. The menu options (1302) labeled "add-scaled-input", "add-input", and "add-output", start their associated methods, create-scaled-input-model-box-proc (Table 105), create-input-model-box-proc (Table 106), and create-output-model-box-proc (Table 107), respectively, when selected by the modeler, which result in the cloning of one of the prebuilt master model-boxes, as indicated by their name, and then transferring the new instance to its specified position in relation to the bioPool. The modeler has only to extend its stub to join it with the color-matched stub of the bioPool, which is the closest to it. Each of those named master structures is simply a generic model-box, each of the subclass referred to by its name, with a color-coded subworkspace containing, in addition to instructions for the modeler on how to proceed, a connection-post which attribute "superior-connection" has been set to refer to the only connection stub of the superior model-box. The capability obtained by using this construction is that any model-block connected to such connection-post upon the subworkspace of a model-box is connected also with any object to which the model-box is connected through such superior connection. In the currently preferred embodiment of this invention, the novel methods and use of this capability results in the generic ability for the modeler to establish a connection between an encapsulated model-block and a bioPool, by cloning the desired model-block from the palette of generic model-blocks and connecting to the unique connection-post upon the subworkspace of a interactively created model-box connected to that bioPool. As described in a later section, the generic formulas that provide the value for the Accumulation of each bioPool already integrates the output of any such connected model-block as either an absolute input, a scaled input or an output, depending on the class (each connected at its predefined specific port) of the model-box that contains the model-block.

e) As shown in FIG. 16, a Palette (2401) of predefined standard model-blocks are provided to the modeler, each being a default instance of each of the subclasses of model-block. All those subclasses have a set of common attributes that include "model description" and "output-1", the latter holding the output value of that model. The value of the output-1 of each subclass of model-block is computed by a separately defined generic simulation formula, which take as arguments the values of the other attributes that are specific for each subclass. Some examples of those attributes with their default values, which meaning is self-explanatory, are shown through the tables of attributes (2402 through 2407) of default instances of: constant.f, exp.c.pdf, exp.rn.pdf, unif.c.pdf, sigmoid.f, and generic.model.block.f, respectively. The latter is a very generic block that allows the modeler to create instances and configure as many attributes as required by defining their slots with any desired type of value, including instances of model-block-var, in which case their specific formula would also have to be defined. The output-1 of this block is also a model-block-var, and the modeler also has to write its formula, to incorporate as arguments the newly configured attributes f) As shown in FIG. 17, the bioProcesses Palette provides the most representative types of generic bioProcesses, pre-built and ready to be cloned and further configured. These pre-assembled (2504 through 2511) and stored structures allow the repeated use of bioProcesses as building blocks of more complex pathways. Like in chemical systems, some bioProcesses are relatively simple, and some may become more complex, but all are built with the basic building blocks. The modeler can, for example, clone a bioProcess labeled R2.L1.A1, which subworkspace comprises one receptor-bioengine connected with two receptor.r (which may each be connected to different bioPools, if the active receptor is an homodimer of two equal molecules, or to the same bioPool, if an homodimer of two equal molecules), one ligand.r, and one antagonist.r at the top, and one bioProduct at the bottom. After transferring the clone to the desired workspace, the bioProcess can now be configured, by clicking on its icon and selecting its table of attributes. Selecting "details" from its menu displays its subworkspace and provides access to all its components, which can now be configured by accessing the tables attributes of the bioEngine, each bioReactant and each bioProduct, and each bioReactant-post and bioproduct-post. BioProcesses have activatable-subworkspaces, which means that any object upon such subworkspaces are not recognized by the inference engine or the simulator unless the subworkspace is activated. When a new bioProcess is created using the "clone" menu option, the new subworkspace is deactivated, and it has to be activated using the "activate-sw" menu option (Table 108) that is available only when the subworkspace is deactivated.

g) Another alternative is to clone an existing bioProcess that has similar characteristics and labels directly from a submodel, without the need to access the bioProcess Palette, and then transferring them to the desired workspace and making any other desired changes in the configuration of any of its components. To facilitate that task, two menu options are provided. The user-menu-choices labeled "clean-clone" (Table 109) and "labeled-clone" (Table 110), appears in the menu of every bioProcess that has a subworkspace, and upon selection by the modeler, either BP-clean-copy-proc or BP-labeled-copy-proc, respectively, are started. The second procedure creates a clone of the bioProcess, including its subworkspace and all structures upon it, and then sets the values of all the attributes except the label of all structures involved, including the bioProcess, to their default values. The first procedure call the second one, and therefore the actions are the same, but in addition it sets the values of the label attribute of all structures involved, including the bioProcess, to their default values.

h) The bioEngines Palette and the bioReactants Palette shown in FIG. 18 are provided for the purpose of allowing the modeler to: a) modify individual instances of bioProcesses cloned from the Palette, to accommodate particular infrequent needs; and b) to design new prototypic bioProcesses, by starting from a done of an existing bioProcess and adding or removing bioReactants or bioProducts, or by exchanging the bioEngine for another of compatible type. Such newly designed bioProcesses may be stored as building-blocks in the appropriate Palette within the Modeler Palette Bin. One of the major differences between those bioEngines in the Palette, each representing a different subclass, is the subclass of the rate-pvar that by default gives value to their Velocity attribute. For example, a bioengine.E1.S1 has a catalytic-rate-pvar, a bioengine.R1.L1 has a binding-rate-pvar, a bioengine.C3 has a dissociation-rate-pvar, and a bioengine.Ex1.Ef2 has a modification-rate-pvar.

i) The modeler is also allowed to modify the Velocity attribute of instances of any subclass of bioEngine. As discussed in the Velocities section, the modeler can replace the instance of that subclass of rate-pvar for an instance of the equivalent subclass of velocity-pvar, or even for an instance of velocity-pvar, in which case the modeler would have to provide the specific simulation formula to provide its value. Another major differences between those bioEngines is the number and specific combinations of subclass of r-connection stubs. Finally, the color of the type-color region of their icon is characteristic for each class. To provide the values for the Velocity, any desired equation that best describe the process being modeled can be used. A selection of those equations frequently used by biochemists are provided within the generic formulas (Tables 56 through 60) of the system of this invention, which each applies to a subclass of velocity-pvar. However, modelers can also define for particular instances of variables, each an attribute of a particular instance of a bioEngine, specific formulas to represent their favorite equations, which can then be used as of the appropriate type, with the matching number and type of connected bioReactants. Those specific instances of bioEngines can be created as instances of an existing bioEngine subclass, where the class of the variable providing the Velocity is changed from its table of attributes to velocity-var, as described earlier under the Velocities subheading.

j) In addition, the modeler may use a tabular-function as a look-up-table from which the program is able to interpolate, to model a process by entering experimental pairs of values of the independent and the dependent variables in such table, such as a dose response. To facilitate that task, a user-menu-choice (Table 111) is defined that starts the create-sw-for-bioengine-proc. By selecting such "create-sw" option from the menu of a bioEngine, its subworkspace is created by cloning the subworkspace of bioengine-sw-master, which contains a tabular-function-of-1-argument, and instructions for the modeler about how to use such a tabular-function.

k) As shown in FIG. 19, several steps are required to establish the distant connection between a bioReactant or a bioProduct and a bioPool. To facilitate this process, and more importantly, to reduce the sources of error while entering those values by the modeler, various methods are offered to automate the tasks of: creating and naming, or removing the names, of bioPool-posts, removing the names and the references of of bioRole-posts, and to set the appropriate values for the ref-bioprocess of bioPool-posts and ref-bioreservoir of bioRole-posts, as following:

The first step is to select the bioProcess (2801) and bioReservoirs (2805, 2807, and 2809) to be connected, if already in existence, otherwise they are created by cloning from the Palettes and named. BioProcesses and bioReservoirs have to be named before their bioPosts can be named. By selecting the "details" option (2803) from the menu (2802) of the bioProcess, and such of the bioReservoirs (not shown), their subworkspaces (2804, 2806, 2808, and 2810, respectively) of each of them are displayed.

The next step is to connect each of the bioRole-posts (2812, 2818, and 2825) to a complementary and not yet connected bioPool-post of the appropriate bioReservoir. Here the first pair (2811 and 2812) has been already connected, which is not apparent to the user. In most cases, this process will first require to create a new bioPool-post of the appropriate subclass, by selecting from the menu (2814) of the bioPool (2813) either the "add-top-post" option (2815) or like here, the "add-bottom-post" option (2816), which results in the automatic creation of an appropriately named bioPool-post, and its transfer to the appropriate position (2817), which is close to the next available free stub with the same cross-section pattern on the bioPool. The modeler has now to establish the connection to the bioPool by extending its stub and joining it to the closest free stub on the bioPool, and then establish the distant connection to the bioReactant-post (2818). Here is shown how such distant connection is established between and already named and connected bioPool-p-post (2819) and the bioProduct-post (2825). Clicking on the bioPool-p-post (2819) in Modeler Mode displays its menu (2820), and selecting the "table" option (2821) shows its table of attributes (2822). The tables shown here for a bioRole-post (2831) and a bioPool-post (2822) are shown with all the values already set, as they would appear for fully functional bioPosts. However, at this point in the connection process, the values shown for the "ref-bioprocess" (2835) would be the default value none, while the values of the "names" (2823) and the "label" attributes (2824), will be already set. The value of the "label" attribute, is set to be the same as its name in the case of all bioPosts, and is used at run-time when using the alternative simulations procedures, as discussed under the Simulation Mode heading.

The next step is to give the bioRole-post (2825) the same name as the name of the bioPool-post (2819) to which is to be connected. Here, this is accomplished by selecting either the "name" menu option (2827) or the "names" attribute value slot (2832) of the bioRole-post (2825) and clicking on the name-display (2828) of the bioPool-post (2819). Note also that any time the name of any object is edited, its name-display (2828) appears in the proximity of that object, and that name-display has text-insertion capabilities, in a way that whenever the text-editor is opened (which happens among other occasions when clicking on the "name" option of any object or on the value slots of the tables of attributes), clicking on such display automatically inserts its text into the slot or at the position of the cursor. In the current implementation of this invention, most name-displays are hidden by the developer or modeler after they are used, since the labels are used instead to provide a more flexible and user friendly method of recognition for those objects when one is desired. In the case under discussion, all the names of bioRole-posts are hidden, while only the name-display of the last bioPool-post is left as a means of also providing a reference to the name of the superior bioReservoir.

The previous step completes the basic connection process that allows the inference engine and the simulator to reason about those connections. The additional step that follows adds information to those connected bioPosts that is used by the program to quickly access the components on the subworkspaces of those connected bioReservoirs or bioProcess, even when the subworkspaces of those connected bioReservoirs or bioProcess are deactivated, which may be the case when in Simulation Mode, and which would cause the system to not recognize those connections, since the system would not recognize the connected bioPosts upon such subworkspaces. A method is provided to facilitate and reduce the sources of error in setting such additional information. Once the bioRole-post (2825) and the bioPool-post (2819) are equally named, the "ref-bioreservoir" attribute (2834) of the bioRole-post and the "ref-bioprocess" attribute (2835) of the bioPool-post are automatically set to refer to each other's superior bioObjects, as their names indicate, by just selecting the "set refs" menu option (2829) of the bioRole-post, which is only available when it has a name. The "ref-bioreservoir" and "ref-bioprocess" attributes are in turn used by the program when the user selects the "show-br" option (2841) or the "show-bp" option (2842), which are available in the menus (2826 and 2820) of bioRole-posts and bioPool-posts, respectively, only when those attributes have a value different than none.

Alternatively, connections can be changed and previously connected bioPosts can be recycled by using consecutively the following set of menu options: "unname-it" (2836) of the bioPool-post which only appears if it has a name, "unname-it" (2837) of the bioRole-post which only appears if it has a name, and "name-it" (2840) of the bioPool-post which only appears if it has no name, which tasks are obvious and described below, followed by clicking the name of the bioPool-post into the name slot of the bioRole-post and selecting the "set-refs" (2829) of the bioRole-post, as described above for new connections.

l) A more detailed description of those methods, with references to their definitions follow:

the user-menu-choices labeled "add-top-post" (Table 112*a*) and "add-bottom-post" (Table 113*a*) are associated with the class bioPool. Upon the selection of either of them by the modeler, either the create-biopool-p-post-proc (Table 112*b*) or the create-biopool-r-post-proc (Table 113*b*), respectively, is started. Each of those procedures do the following: it first scans for the first free stub (of its specified class of connection) of those defined at an even-numbered port (p02 to p12, or r02 to r12, respectively), and: a) if one is found, it creates an instance of its specified class of bioPool-post, and transfers it to the workspace of the bioPool from where it was invoked, aligned opposite to such stub within the first layer of such bioPool-posts, and then calls the poolpost-name-it-proc Table 114) and returns; or b) if none is found, it then scans for the first free stub (of its specified class of connection) of those defined at an uneven-numbered port (p01 to p11, or r01 to r11, respectively) and, if one is found, it creates an instance of its specified class of bioPool-post, and transfers it to the workspace of the bioPool from where it was invoked, aligned opposite to such stub within a second layer (more distant from the bioPool) of such bioPool-posts, and then calls the pool-post-name-it-proc (Table 114) and returns. If none is found, then: a) it moves the existing bioPool-post connected at the first port (p01, or r01) to a more distant position, to start the next layer, b) it creates an instance of its specified class of and returns, and transfers it to the next free predefined position within that layer; c) it calls the poolpost-name-it-proc (Table 114); and d) it sends a message to the modeler with instructions to connect the stub of the new bioPool-post directly to the connection of such bioPool-post connected at the first port, creating in that way a connection-junction which does not interfere with the reasoning about those connections, and returns.

a the user-menu-choice labeled "name-it" (Table 114) is associated with the class bioPool-post.

This option is only available in the menu when the bioPool-post has no name, and upon its selection by the modeler the pool-post-name-it-proc is started. This procedure gives the "names" attribute of the bioPool-post a name composed of the base name of the superior bioReservoir (removing the ending BR tag) followed by the default value of the "label", which is a reference to the class and relative position of that bioPool-post, such as PP4 referring to bioPool-p-post connected at port p04, and also colors the face-color region of its icon.

the user-menu-choice labeled "unname-it" (Table 115) associated with the class bioPool-post defines an option which is only available in the menu when the bioPool-post has a name. Upon its selection by the modeler it starts the poolpost-remove-name-proc, which changes the values of the names and the ref-bioprocess attributes of the bioPool-post to their default value none, removes the base-name from the value of the "label" restoring it to its default value, and resets the face-color of its icon to gray.

the user-menu-choice labeled "set-refs" (Table 116) is associated with the class bioRole-post. It defines an option which is only available in the menu when the bioRole-post has a name, and upon its selection by the modeler it starts the rolepost-set-refs-proc, which changes the values of the "ref-bioreservoir" of the bioRole-post and the "ref-bioprocess" of its connected bioPool-post to equal the names of the bioReservoir superior to such bioPool-post and the bioProcess superior to the bioRole-post, respectively.

the user-menu-choice labeled "unname-it" (Table 117) associated with the class bioRole-post defines an option which is only available in the menu when the bioRole-post has a name. Upon its selection by the modeler it starts the rolepost-remove-name-proc, which changes the values of the "names", "label", and "ref-bioreservoir" attributes of the bioRole-post, and the "ref-bioprocess" attribute of the bioPool-post, to none.

4. Biochemical Modeling Techniques a) To be connected to each other and integrated into pathways, bioReservoirs and bioProcesses must have unique names.

b) For bioReservoirs that represent the input into the system of a synthetic agonist or antagonist: a) the Concentration has: a) a normal default initial value of 0.0, b) has no modeled inputs from bioProcesses, and c) it may be modeled by a model-block. However, quantities of that compound may be transferred to another bioReservoir in a different compartment, and that latter bioReservoir is a regular one.

c) It may not be desired in most occasions that the synthesis of macromolecules, such as DNA, RNA, and proteins be schematically modeled by bioProcesses, because of its complexity and the large number of steps or components involved. In these situations, the synthesis component may also be modeled by adding a model-block to one input-box connected to the bioPool, which is represented by the additional term already integrated in the Accumulation equation. The output of this model-block may define a global synthesis-rate (rs(t)) that may be made dependent on the values of any other variable of the system multiplied by a synthesis-rate-constant (krs) parameter, a separate attribute of the model-block. The krs may also be dynamically increased or decreased (by multiplying by appropriate factors) as defined in rules or procedures, which are fired or called as a result of the activation or deactivation of other bioProcesses, which directly or indirectly regulate the processes of DNA-transcription into mRNA, mRNA-splicing, mRNA-translation into protein precursors, or the processing of the precursors into the active-form of the proteins (all or part of which may or may not be schematically modeled).

d) When degradation or diffusion are important components of the model, they can be separately modeled by: a) using additional bioProcesses to model those processes; or b) adding a model-block to the output-box connected to the bioPool; or c) using additionally defined degradation-rate or diffusion-rate parameters, respectively, and modifying the formula accordingly by adding the corresponding terms. The first two approaches are recommended because they are more flexible and modular.

e) Processes in which the binding step is the limiting factor (the catalytic or other actions are fast so that the ES complex is very short-lived), are usually modeled by a single bioProcess. If the complex stays around exposed to other interactions, two bioProcesses may be used: a) complex-formation and b) catalytic or other action, each with its respective constants. Inhibitors and antagonists should as frequently as possible be modeled by separate bioProcesses.□ f) In the system of this invention, the intermediary complexes that are formed in enzymatic reactions, and their concentrations such as [ES1] or [ES1S2], are preferably not explicitly represented, unless they are the specific targets of regulation or translocation to different compartments. Otherwise they are implicitly represented within the model equation of the bioEngine.

g) Reaction systems with two or more substrates of the ordered or ping-pong types, may be represented by either one bioProcess with two substrate.r, in conjunction with the appropriate Velocity equation, or by two separated bioProcess in series. Preferable, these types of reactions are modeled by two bioProcesses in which the participants are represented as following: a) the enzyme and the first substrate are the enzyme.r and substrate1.R of the first bioProcess, b) the bioPool of the enzyme-substrate1 complex is represented by both a bioProduct of the first bioProcess and by the enzyme.r for the second bioProcess, c) the second substrate is the substrate.r of the second bioProcess, and d) one bioProduct of the second bioProcess may be represent the bioPool of the enzyme. To be more accurate, in the ping-pong case the bioProcess cannot be said to be first or second, since the enzyme oscillates between the "free" and the "complexed" states.

h) In reactions with cooperativity, such as allosteric reactions of an enzyme with n equivalent substrate binding sites, can be either modeled by: a) one bioProcess with a 1E.nS.1I.HMME bioEngine with each of the n substrate.r representing the same bioPool, each with a stoichiometric coefficient equal to 1, but each with a different effective Km corresponding to each additionally bound molecule, and a Velocity formula representing a Henry-Michaelis-Menten equation, or b) one bioProcess with a 1E.1S.1P.0I.HE bioEngine with one substrate.r with stoichiometric coefficient equal to n, and the Velocity formula representing a Hill equation. In that case, the overall affinity constant $(K=\psi*K'A^\wedge(n)$, where $(\psi=\alpha*\beta*\delta* \ldots \xi)$ is equivalent to the product of the K1' of the first bound site times the series of Ki' times the coefficients by which each molecule of ligand bound modifies the affinity of the other sites.

i) Allosteric reactions of an enzyme with binding sites for two or more different ligands, either substrates, inhibitors or modifiers, can be either modeled by: a) one bioProcess in which each ligand is represented in the formula for appropriate class of variable providing the Velocity, or b) two or more bioProcesses, in series or parallel or both, when the mechanism of the reaction is known and information is available. The latter case is preferred where separate bioProcess, one for each ligand, compete with each other for the common component(s), with an strength dependent on their respective affinities and Concentrations. In addition to the cases above, it is in general preferable to model several complex-form-process in the following cases, as described in more detail below:

all types of inhibitions in which an irreversible complex is formed, such as E+I→EI, or E+S+I→SEI, the effects of antagonists, such as R+Ant→R-Ant, and the feedback activation or inhibition by products, such as E+X+P→P+Y+Z, where P is the product of either this reaction or a downstream reaction.

j) Different types of inhibitors may be modeled in a variety of ways to show different behaviors, usually involving a complex-form-process in which the resulting complex would have different characteristics:

A competitive inhibitor and the substrate are mutually exclusive, which means that EI does not bind S, but it may result in E+S+I←→ES+EI→P. This type of reversible competition is best modeled as one enzymeEngine comprising enzyme.r, substrate.r and inhibitor.r, and a bioProduct, with its matching standard kinetic equation. The intermediary complexes may be modeled if desired by editing the value of the time-lag, to account for the time the E, S and I spend in the complex forms ES and EI, not explicitly modeled otherwise. The same approach can be applied to any other class or type of bioProcess, when appropriate.

An irreversible inhibition is equivalent to enzyme removal from the system, with the Vmax reduced, and it is therefore best represented by two parallel bioProcesses, of different classes: a) an enzymeProcess for E+S→P, and b) a complex-form-process for E+I→EI. The production rate of P is influenced by the Concentration of S, directly, and I, indirectly, while the production rate of EI is indirectly influenced by the Concentration of S. It may also be represented by one enzyme-process containing enzyme.r, substrate.r and inhibitor.r, and two bioProducts (E+S+I→P+EI), with its matching standard kinetic equation.

An uncompetitive inhibitor may bind reversibly to the ES complex yielding inactive ESI complex, but it does not bind to enzyme alone. This model needs some modifications of the regular bioProcesses, because it requires access to an intermediary complex that is not explicitly modeled in the system of this invention in a standard enzyme-process (E+S+I→P). This type of reaction may be represented by three bioProcesses, first in series and then in parallel: a) complex-form-process: E+S→ES; b) enzymeProcess: ES→E+P; and c) complex-form-process: ES+I→ESI. It may also be represented by one enzyme-process comprising enzyme.r, substrate.r and inhibitor.r, and one bioproduct (E+S+I→P), with its matching standard kinetic equation.

A noncompetitive inhibitor and the substrate do not affect each other's binding to the enzyme, however the trimmeric complex SEI (ES+I→SEI or EI+S→SEI) may be inactive. The main effect is a sequestering of either enzyme or both enzyme and substrate, and the Vmax is reduced. This type of reversible competition is best modeled by three different bioProcesses: an enzyme-process E+S→P (a), and two complex-form-process: E+I→EI (b), and E+S+I→SEI (c), where (a) and c) have the same Ks and (b) and (c) have the same Ki. It may also be represented by one enzyme-process comprising enzyme.r, substrate.r and inhibitor.r, and three bioProducts (E +S+I→P+EI+SEI), with its matching standard kinetic equation.

A mixed-type inhibitor I is such that reversible binding of either I or S to E changes the Ks or Ki of the other by a factor a, yielding ES, EI and inactive ESI complexes. It may be best represented by three different bioProcesses: an enzyme-process E+S→P (a), and two complex-form-process: E+I→EI (b), and E+S+I→SEI (c), where (a) and (c) have different Ks and (b) and (c) have different Ki. The Ks' of (c) may equal the Ks of (a) multiplied by $\alpha$, or similarly, the Ki' of c=a*Ki, where a is a cooperativity-coefficient that may be introduced as a factor in the formulas of the respective Ks or Ki.

k) Different types of feedback regulation by downstream products are represented by different sets of bioProcesses. As examples are given the following cases of feedback inhibition by more than one product:

Cooperative or synergistic inhibition is when mixtures of $P_1$ and $P_2$ at low concentrations are more inhibitory than the sum of inhibitions by each at those concentrations, and at saturating levels of either one of the products $P_1$ and $P_2$, the velocity of the reaction may be driven to zero. It means that both $P_1$ and $P_2$ can combine with E simultaneously to form $EP_1P_2$ complexes. This system may be represented by 4 bioProcesses: an enzyme-process: E+S→P (a), and three complex-form-processes: $E+I_1 \rightarrow EI_1$(b), $E+I_2 \rightarrow EI_2$(c) and $E+I_1+I_2 \rightarrow_{EI1}I_2$(d), where $I_1=P_1$, and $I_2=P_2$, and where (d) have different $Ki_1$ and $Ki_2$ than (b) and (c) (the K'$i_1$ of (d)=$\alpha$*$Ki_1$, and the K'$i_2$ of (d)=$\beta$*$Ki_2$, where $\alpha$ and $\beta$ are cooperativity-coefficients).

Cumulative or partial inhibition is when each end product is a partial inhibitor, and a saturating level of one alone cannot drive the velocity to zero. Each of $I_1$ or $I_2$ alone, either increases the Ks of S (partial competitive inhibition) or decrease kd of E (partial non-competitive inhibition) or both partial mixed-type inhibition). True cumulative inhibition results in the second case, where the total inhibition factor is $i_T=i_1+i_2*(1-i_1)$. This type of reversible competition is best modeled by three different bioProcesses: an enzyme-process: E+S→P(a), and two complex-form-processes: $E+I_1+I_2 \rightarrow EI_1I_2$(b), and $E+S+I_1I_2 \rightarrow ESI_1I_2$(c), where (a) and c) have the same Ks and (b) and (c) have the same $Ki_1$ and $Ki_2$. It may also be represented by one enzyme-process comprising enzyme.r, substrate.r, inhibitor1.r and inhibitor2.r, and three bioProducts ($E+S+I_1+I_1 \rightarrow P+EI_1I_2+ESI_1I_2$), with its matching standard kinetic equation.

Concerted or multivalent inhibition is when both end products have to be present to be inhibitory, and either alone has no effect on E. It means that either $EI_1I_2$ does not bind S or $ESI_1I_2$ is inactive. It may be represented in two alternative ways, either by: 1) two bioProcesses: one enzyme-process: E+S→P(a) and one complex-form-process $E+I_1+I_2 \rightarrow EI_1I_2$(b); or 2) one enzyme-process: $E+S+I_1+I_2 \rightarrow ESI_1I_2$(c) In both (b) and (c), the matching standard kinetic equations include a term to represent the concerted effect of $I_1$ and $I_2$, that is proportional to the Concentration of $I_1$ multiplied by the Concentration of $I_2$.

Additive inhibition implies the presence of two distinct enzymes or catalytic sites, each sensitive to only one of the feedback inhibitors. This type of reversible competition is best modeled by three enzyme-processes: a) $E+S_1+S_2 \rightarrow P$; b) $E+S_1+S_2+I_1 \rightarrow P$; and c) $E+S_1+S_2+I_2 \rightarrow P$. It may also be represented by one enzyme-process comprising enzyme.r, substrate1.r, substrate2.r, inhibitor1.r and inhibitor2.r, and one bioProduct ($E+S_1+S_2+I_1+I_2 \rightarrow P+EI_1I_2+ESI_1I_2$), with its matching standard kinetic equation.

Sequential inhibition is when downstream of $E_1$ and $S_1$, one product $P_1$ inhibits enzyme $E_2$ and another product $P_2$ inhibits enzyme $E_3$ of another pathway of utilization of $S_1$. When both $P_1$ and $P_2$==are at high levels, $S_1$ accumulates, and $S_1$ may also inhibits $E_1$. This type of feedback inhibition is best represented schematically by a combination of the appropriate bioProcesses, as described above, in parallel and in sequence as required.

l) Lumped Enzymatic Pathways: In occasions, it may be desirable to model a pathway, such as an enzymatic pathway, for which: a) the details may be unknown or not desired, b) only the inputs and the outputs are relevant, and c) sufficient quantitative or qualitative information is available about the rate limiting enzymes and the inputs. Because of metabolic and energy/mass conservation constraints, only a few of their net conversion rates are independent variables, and the others are mutually dependent, various of those reactions can be combined and the pseudo-steady-state approximation of the combined process can be used instead. For these cases, the currently preferred embodiment of this invention provides enzyme-bioEngines classes with templates and stubs for two or more enzymes, and which formulas consider only those enzymes, together with the substrates that are inputs to the pathway and the products that are outputs of the pathway, ignoring the intermediaries and other participating enzymes.

m) Black-box-bioProcesses: The metabolic pathways of cells and organisms are composed of a large number of chemical reactions and compounds, that, assuming normal physiological conditions, maintain the steady-state of the system. To simplify the overall structure of the system, in the currently preferred embodiment of this invention many of such metabolic pathways are considered as a black box with inputs and outputs connected to other modeled pathways or two other black boxes, and are generally not modeled. The black boxes are considered, until better defined, as a collection of constitutive bioEntities interacting under steady-state conditions. If and when it is desired to model disturbances at specific points in the pathway, the black-box can be split into the pathway before and the pathway after (both of which remain like black boxes), and the segment where the disturbance occurs to be defined and modeled.

F. GENERAL AND NAVIGATION MODE

1. Menus and Panels a) FIG. 20 shows the domain-menus associated with the General Mode in the current embodiment of this invention, which is the default user-mode when the application is started by regular users, with no modeler or developer rights. The change between the different user-modes available to users can be requested in two ways: a) from the domain-menus by selecting the "Help & Mode Menus" option (2901) and then the option for the desired mode, in this case General Mode (2902), or b) a "Mode Selection Panel" can be requested by selecting the "Mode Panel" button (2909) from the Initialization Panel (2908) which is displayed by default as a result from an action from an initially rule (Table 118) invoked when the application is first started. Selecting Navigation Mode (2903) changes the value of the user-mode of that window, and therefore the behavior that certain classes of items display when selected will change, but the domain-menus are the same as these General Mode.

b) The Initialization Panel (2908), which is used to request or initiate tasks, associated with each of its buttons, that are very important to the proper functioning of the current embodiment of this invention, since the relations between different components of the interrelated graphic models are established during this process, and those basic relations are frequently used by the inference engine and the simulator at run-time. Other relations may also be established later during the processing of specific tasks. Here we will discuss the methods associated with each of those buttons, with the exception of "Add Simul" and "Simul Init", which are only required when intending to run quantitative simulations, and are therefore discussed later under the Simulation Mode heading.

c) Among those tasks requested from the Initialization Panel is the creation of the domain-menus, which may be requested by clicking on the "Menu" button (2910), that calls the basis-menu-head-callback (Table 119). This procedure calls another procedure defined within the Shell and, depending on the current value of the user-mode of the window from which the request has been made, it passes as argument the name the menu-structures specific for that mode. A menu-system-template is a facility provided by the Shell that allows to build permanent schematic designs of connected structures or menu-templates of different classes (such as those instances of each class which tables of attributes are listed in Table 120), each corresponding to a different menu option, and each containing attributes that hold information about the "label" to be displayed by such menu option, the name of the procedure to be invoked, and depending on the class of such menu object, it may hold either the name of the object which subworkspace is is to be displayed, or the name of a new menu system to be displayed. When an option is selected from the menu, the procedure named in its corresponding template is started, which may take as arguments the values of some of those other attributes. The domain-menus are transient sets of workspaces and messages that are dynamically created mirroring the ordered design of the named permanent schematic menu-structure.

d) The options of the menus headed by "Structure Libraries" (2904) and "Pathway Libraries" (2905) are the same as those (1819 and 1828, respectively) available in Modeler Mode which were previously discussed, since all such libraries of graphic models are build by the modeler to offer such information to the user, although the modeler may choose not to make accessible through the domain-menus those sets of models that are under construction or not yet validated. The new menu for this mode is that headed by "Panels" (2906), which options include panels of various types used to access tasks that are not initiated from one single bioReservoir or bioProcess, or their components, but which are instead application-wide, or including more that one starting points, including the Initialization Panel can also be displayed by selecting that option (2907).

e) Selecting "References Scroll" (2917) displays the subworkspace of the References Panel discussed below. Selecting "Structure Queries" (2918) creates a clone of Master-General-Structure-Query-Panel and displays its subworkspace (2919) discussed in more detail below in relation to FIG. 22. Selecting any of the "Experiment Setup #" (2920) displays the subworkspace of the corresponding "Experiment Setup Panel", which are various clones of the Master-Experiment-Setup-Panel, one of which will be discussed in more detail under the Simulation Mode heading in relation to FIG. 29, since part of the capabilities provided within this type of panels can be used under the General Mode, and all the capabilities can be used in Simulation Mode.

2. Initialization a) The following description of the initialization procedures, as well as the simulation procedures and other complex processing described later, are meant to only highlight the overall major tasks accomplished, and is not meant to substitute for the more detailed descriptions provided in the pseudo-code listings provided in the form of tables in the Appendix, as referred to within this text section.

b) Selecting the "Navig Init" button (2911) calls the navig-init-callback, which in turn calls the navig-init-proc (Table 121), which results in the activation of the subworkspaces of all bioProcesses and bioReservoirs (which are all deactivated when the application is initially started), and then successively calling the following procedures:

the br-initialization-proc (Table 122) sets the appropriate values of the "master-bioReservoir" attribute of all bioReservoirs, highlights the flag-color region of the icon of those bioReservoirs that have "warnings", sets the appropriate values of the "ref-bioprocess' attribute of all bioPool-posts of all bioReservoirs, and establishes all the appropriate "a-down-bioProcess-of" and "an-up-bioProcess-of" relations between bioProcesses and bioReservoirs, making then those changes permanent (relations are transient and cannot be made permanent, and therefore they are lost when the application is restarted).

the bp-initialization-proc (Table 123) changes the color of the type-color region of the icon of each bioProcess to equal that of the bioEngine it contains, sets the appropriate values of the "master-bioprocess" attribute of each bioProcess, highlights the flag-color region of the icon of those bioProcesses that have "warnings", sets the appropriate values of the "ref-bioreservoir" attribute of all bioRole-posts of each bioProcess, establishes "an-upstream-bioReservoir-of" and "a-downstream-bioReservoir-of" relations between certain pairs of bioReservoirs that are separated only by one bioProcess, and establishes "an-upstream-bioProcess-of" and "a-downstream-bioProcess-of" relations between certain pairs of bioProcesses that are separated only by one bioReservoir.

the downstream-chaining-proc (Table 124) completes the downstream chaining process by extending those relations to distant bioReservoirs and bioProcesses, by establishing the appropriate "a-downstream-bioReservoir-of" relations between any bioReservoir A and each other bioReservoir that is positioned downstream of A in any pathway, and establishes all the appropriate "a-downstream-bioProcess-of" relations between any bioProcesses B and each bioProcess that is positioned downstream of B in any pathway.

the upstream chaining-proc (Table 125) completes the upstream chaining process by extending those relations to distant bioReservoirs and bioProcesses, by establishing the appropriate "an-upstream-bioReservoir-of" relations between any bioReservoir A and each other bioReservoir that is positioned upstream of A in any pathway, and establishes all the appropriate "an-upstream-bioProcess-of" relations between any bioProcesses B and each bioProcess that is positioned upstream of B in any pathway.

c) Such upstream and downstream relations are also created and broken at run-time by a set of rules (Table 52 and a parallel set for bioReservoirs, not shown) that monitor whenever any such chaining relation is newly established or broken, and in response to such events they establish or brake other relations, according to similar criteria, which in turn trigger the same rules for a chain of other bioReservoirs or bioProcesses. The use those rules makes sure that if a modeler or user deletes a bioReservoir or bioProcess that is part of one such chain of relations, then the chain is broken between the elements of both sides on the breaking point. Similar sets of rules are used for establishing relations whenever new connections between bioReservoirs and bioProcesses are made by the modeler.

d) The "Add Query" button (2912) is to be selected only after the "Navig Init" was been successfully concluded. If changes to the database have been made by the modeler since the "Navig Init" was last concluded, or if the application has been restarted, then the "Query Init" button (2913) should be selected, since it comprises the methods of the other two. The common purpose of both buttons is to organize knowledge about the structure of all the bioEntities in the application, and to create a set of structures to hold that knowledge, to be used any time that the user request a predefined query that involves that kind of knowledge. Selecting the "Add Query" button calls the add-query-callback (Table 126), which in turn calls the two procedures that follow. Selecting the "Query Init" button calls the query-init-callback (Table 127), which in turn calls the navig-init-proc (Table 121) and the two procedures that follow:

the et-initialization-proc (Table 128) scans the loaded application for every copy of each named complex-bioEntity, and then assigns a value to the "id" attribute of each such copy that is equal to the name of such bioentity complex-bioEntity ended by the copy number. Copies are numbered consecutively, in the order found, with the original being –0.

a the init-query-tables-proc (Table 129) activates the subworkspace of the Query-Arrays-Bin and deletes any old array upon it, and also deletes any old list upon the Query-Lists-Bin, and then call the following procedures:

the find-bioentity-definitions-proc (Table 130) scans the Bioentities-Defs-Bin, which contains all the object definitions of all the subclasses of the class bioEntity, and for each of those subclasses it calls the create-query-array-proc (Table 131) which creates a query-array, sets its "major-class" attribute equal to the name of the superior-class of such subclass, sets its "ref-component-class" attribute equal to the name of such subclass, and sets its "name" attribute equal to the name of such subclass followed by the ending -query-array, and transfers such query-array to the Query-Arrays-Bin at a location specific for each superior-class;

the create-query-lists-proc (Table 132) creates a query-list to correspond to each query-array in the Query-Arrays-Bin, and transfers the list to the corresponding location upon the Query-Lists-Bin, sets its "ref-array" attribute equal to the name of such array, and sets its "ref-component-class" attribute equal to the "ref-component-class" attribute of such array;

then, for each of those lists and for each bioEntity of the subclass named by the "ref-component-class" of such list, it calls the find-named-bioentities-with-component-proc (Table 133) which in turn, if such bioEntity has a name it directly calls for such bioEntity the procedure that follows, otherwise it calls first the find-named-bioentity-proc (Table 134) to scan the hierarchy of bioEntities superior to such bioEntity, until one is found with a name, in which case, it now calls for the named bioEntity the procedure that follows:

the seek-bioentity-copies-proc (Table 135), inserts the argument bioEntity in such list, and then scans the application for any copy of such bioEntity, and if any is found then it loops back for such bioEntity by calling the find-named-bioentities-with-component-proc (Table 132) mentioned above, which will repeat the cycle back to this procedure, as described, until the various loops for each bioEntity of every list are completed.

When this process is completed, the list for each bioEntity subclass contains, with no duplicated elements, all the named bioEntities that contain one such bioEntity, either directly or by reference. To give an example, that means that if a named protein instance-A contains a protein-motif instance-B, then every named protein complex-instance-C that contains an unnamed copy of instance-A (which does not itself contain a copy of instance-B, but rather points to its master-bioEntity, instance-A, which contains instance-B) will also be included in the list of all bioEntities that contain a protein-motif. After all such lists are completed, it calls the following procedures:

the complete-query-proc (Table 136) simply transfer the values of the elements from each of those lists to their corresponding arrays, by fist setting the length of the array to match the the length of the list, and then setting the text of the initial-values attribute of each array to equal a text string that mentions all elements of the list separated by commas, as illustrated in the example listed in Table 136*b*, which shows a pair of corresponding instances of a query-list and a query-array of the subclass sub-et-array, which list named instances of bioentities that contain an a-helix-motif, which in this small demo application consists only of a few master-structures from the library. In the table of attributes listed, the initial-values attributes is displayed, and the list of elements of either the list or the array can be displayed by selecting the "describe" option of their menus.

the create-auxiliary-query-arrays-proc (Table 137) adds a few empty arrays corresponding to the no-selection options of each query panel, which are simply programming aids and to conclude it deactivates and activates again the subworkspace of the Query-Arrays-Bin for the purpose of initializing the query-arrays upon activation, which means that the elements of the array take the values given by the set initial values.

e) The "Icons Init" button (2914) calls the init-icons-callback (Table 138), which function is not essential for the functioning of this system, but which provides a very useful cosmetic function, by realigning the tracers in the subworkspaces of bioReservoirs and bioProcesses and making their connections invisible. Selection of this button is not necessary every time the application is started, and it can be selected any time thereafter, when problems are detected, in any mode other than Simulation Mode (where those subworkspaces may be deactivated). The same effect is achieved for individual bioReservoirs or bioProcesses by slightly moving and repositioning their bioPool or bioEngine, respectively, which triggers their respective icon-movement rules, as defined in Table 56, which also apply to repositioning the bioRole-posts any time a bioReactant or bioProduct is moved.

f) Selecting the "Init All" button (2915) calls all-init-callback (Table 139), which in turn calls the all the initialization procedures mentioned above, and selecting the "Hide" button (2916) calls the hide-workspace-callback, which hides this Panel.

Figure 21:
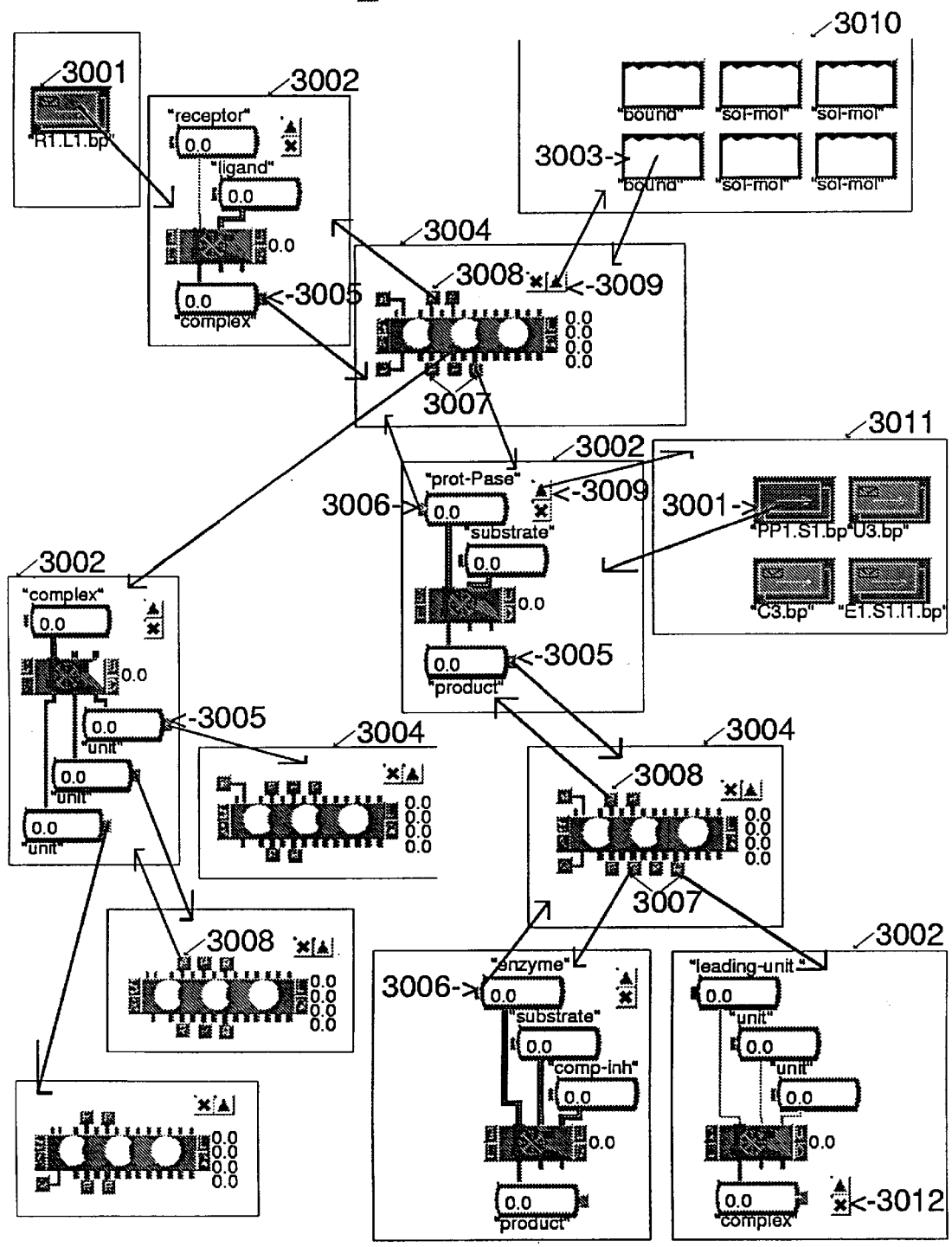
FIG. 21 shows exemplar means for interactive navigation through the views of series of linked composite iconic process building-blocks and reservoir building-blocks, and to/from their containers.

3. Navigation a) Navigation in general may refer to the capability of displaying from one knowledge structure other related knowledge structures. This definition includes generic tasks provided by the Shell, such accessing Tables of Attributes and their subtables. In the current embodiment of this invention, the definition of navigation is restricted to the domain-specific tasks of displaying and hiding either related bioObjects or their subworkspaces. The concept of related object include various types of associations, including some that are permanently stored in the knowledge base, as defined by either graphic or distant connections, or containment in subworkspaces at any level in the hierarchy, and some that are transient such as relations, which are established and may be broken at run-time (in the system of this invention it is also possible to store run-time versions or snap-shots of the application, which also include transient objects, such as relations). Navigation tasks may may be performed in any mode, but Navigation Mode has that name because the behavior of certain object classes, including the classes bioReservoir, bioProcess, and complex-bioEntity, is restricted to do just that. This means that a navigation task is automatically performed upon clicking on the instances of any such classes, instead of displaying a menu with various other options as well, and therefore all those other tasks offered by the other options are not available in this mode. Therefore, a user in Modeler or General Mode may want to quickly switch to Navigation Mode when intending to do just that, because it is much faster, for example when exploring and navigating through the pathways, and then switch back to the other mode to perform other tasks. Navigation tasks are usually simplified, in the following discussion and elsewhere in this filing, by expressions "selection of A starts proc-B which displays C", but in reality these processes do more than that in the current embodiment of this invention: selection of A invokes proc-B which takes as arguments A (the item) and the current window, and causes C to be either displayed or hidden on the current window, depending on the value of the "toggle-state" attribute of A, and in addition, the icon appearance of A is configured, switching between its pressed or depressed configuration, respectively, and the value of the "toggle-state" attribute of A is alternated between on and off. In such cases, A may be either a button or any of the bioObjects that has a subworkspace, which in this regard behave similarly.

b) FIG. 21 will be described to summarize some of those navigation tasks when in Navigation Mode, while also referring to the definitions of the methods involved, as listed in the form of tables in the Appendix. Any navigation task that is directly performed in this mode may be performed in any other mode as well but, depending on the previously defined class restrictions for each mode, they may have to be selected from the menu instead, requiring two steps rather than one. Selecting any bioProcess (3001) in Navigation Mode implies selecting its "details" option which starts the details-bp-proc (Table 140) which displays its subworkspace (3002), in the same way that selecting any bioReservoir (3003) implies selecting its "details" option which starts the details-br-proc (Table 141), resulting in the subworkspace (3004) of the bioReservoir being displayed or hidden, depending on whether the value of the "toggle-state" of the bioReservoir is hide or show, respectively. With both procedures, the icons of the tracers on the corresponding subworkspace are restored to their default relative positions before such subworkspace is displayed.

c) When selecting the "details" option of any bioProcess that has a master-bioprocess but has no subworkspace, conditions which when combined are characteristic of a copy bioprocess used in the creation of Pathways, causes such first procedure to call the bp-master-details-proc (Table 140) which in this case displays or hides the subworkspace of the original (master) bioProcess, in addition to configuring the icons of both the original and the copy bioProcess to their pressed or depressed appearance, respectively. In a similar way, when selecting the "details" option of any bioReservoir that has a master-bioReservoir but has no subworkspace, characteristic of a copy bioReservoir, causes the first procedure to call the br-master-details-proc (Table 141) which in this case displays or hides the subworkspace of the original bioReservoir, in addition to configuring the icons of both the original and the copy bioReservoirs to their pressed or depressed appearance.

d) BioEngines do not have subworkspaces by default, by the modeler can create one, as described, to store tabular functions. In such cases, a "show-sw" option is available, and selecting such bioengines in Navigation Mode implies "show-sw", which starts the show-bioengine-sw-proc (Table 142) which displays or hides its subworkspace (not shown) and toggles the configuration of its icon.

e) The behavior of complex-bioEntities in Navigation Mode is similar, as it was shown in FIG. 5, where selecting any bioentity (608, 613, 615, 617, 619, or 621) implies selecting the "details" option which starts the et-details-proc (Table 143) which displays or hides its subworkspace (609, 610, 616, 618, 620, or 622, respectively) and toggles the configuration of its icon. The combination of this option with the go-to-sup-obj-button (625) upon each subworkspace allows to navigate up and down in their workspace hierarchies.

f) Selecting any bioProduct-post (3005) or any bioReactant-post (3006), in General, Navigation, or Simulation Modes, implies selecting its "show-br" option which starts the rolepost-show-br-proc (Table 144) which displays the subworkspace (3004) of the bioReservoir named by its "ref-bioreservoir" attribute. Similarly, selecting any bioPool-r-post (3007) or any bioPool-p-post (3008) implies selecting its "show-bp" option which starts the poolpost-show-bp-proc (Table 145) which displays the subworkspace (3002) of the bioProcess named by its "ref-bioprocess" attribute. This option is only available in the menu when the bioPool-post has a name. Selecting any go-to-sup-obj-button (3009) displays, as described (Table 11), the object superior to its workspace, and one instance of this class is a standard feature for the subworkspaces of every bioObject. In this example, selecting such button from the subworkspace of a bioReservoir shows such bioReservoir (3003) upon its workspace (3010), while selecting such button from the subworkspace of a bioProcess shows such bioProcess (3001) upon its workspace (3011). Selecting any hide-sup-ws-button (3012) hides its workspace (3002), as described (Table 11). The combination of those capabilities allow to follow all the distant connections through the pathways of bioReservoirs and bioProcesses, and also up and down in their workspace hierarchies.

g) Selecting any model-box (511, 516, or 517) in General, Navigation, and Simulation Modes, implies selecting its "show-sw" option, available only if the model-box, which starts the show-model-box-sw-proc (Table 146) which displays or hides its subworkspace and toggles the configuration of its icon. This option is used to access the model-block upon that subworkspace.

h) Other important navigation task performed through the menu in any mode, include the "bioentity" option (Table 147) appears in the menus of bioReservoirs, bioReactants and bioProducts only when the "ref-bioentity" attribute of the bioReservoir has a value different from the default value of none, and upon selection of this option by the user, or hides, depending on whether the initial value of the toggle-state attribute of the bioReservoir is hide or show, respectively, the subworkspace of the bioEntity named by said ref-bioentity attribute. The "ref-bioentity" attribute is defined only for the class bioReservoir, for storage economy, and the menu options of bioReactants and bioProducts refer to that attribute when connected. However, this attribute can be defined for those other classes as well, allowing access to a bioEntity independently of a bioReservoir.

4. References a) Every bioObject has the attribute "references" in which references are made to the published sources of information from which the modeler obtains information and data contained in the structural and pathway related models. This is an important issue for scientists that may want to corroborate the validity of that data, or find out more about the context in which that data was obtained. Such references are to be entered in a standard uniform format, also used by widely used online databases such as Medline, separated from each other by commas. This attribute is defined in most bioObjects as a simple text attribute, which the user may consult to perform independent searches, or each of the references may be highlighted and copied over to other database search facilities, such as the Reference-Scroll to be described below. But first will be described an alternative way to handle the references, which is applicable in the current implementation of this invention only to the class bioReservoir, as defined for its "references" attribute. This alternative way could be defined as well for any other class of high-level bioobject, such as bioProcess or molecule, just by defining as an attribute: references is given by a reference-scroll, and by defining a user-menu-choice labeled "show-references" for any such desired class, to start the same procedure (Table 148). However, it requires more memory resources to store an array for each of those instances, instead of the simple text currently used.

b) The menu of a bioReservoir may have the option "show references". This user-menu-choice (Table 148) is defined for the class bioReservoir and is available only when the array that gives the value to its "references" attribute has any element. Upon selection of this option, the show-references-of-array-proc (Table 148) is started, which creates a clone of Reference-WS-Master, stores it in the Temporary-Panel-Bin and displays its subworkspace, after ordering upon it, in columns, copies of all the original reference-blocks referred to by the elements of the reference-array of such bioReservoir. Selecting one of those copies displays its table of attributes, which correspond to several of the fields of a Medline file, including the abstract, and which values were copied over from such file. Selecting the buttons "Print" or "Delete" starts the procedures (Table 149) print-this-ws-callback, which makes a postscript file of such subworkspace, or delete-sup-obj-callback, which deletes such subworkspace together with its superior object.

c) The subworkspace of Master-Reference-Panel, with the Reference-Scroll at the top, which set of scroll-messages list short references to published sources, equivalent to the field with the same name in a Medline file, and to the "short-ref" attribute of a reference-block, and to the standard uniform format used in the has the "references" attribute of bioObjects. The Reference-Scroll can be used in two different ways: a) to list all the references in the application ordered alphabetically, or b) to contain only those references currently needed, which can be quickly copied over by highlighting the desired text of the "references" attribute of any bioObject. The definitions of some of the tools listed in this processing are listed in Table 150. Selection of any of those scroll-messages starts the ref-search-proc (Table 151) which in turn calls several procedures, several of them proprietary system procedures defined within the Shell, and others include: the ref-search-progress-indicator-proc (Table 152), which monitors the progress of the search and reports it to the user by changing the value of a displayed text; the ref-get-file-proc (Table 153) localizes the directory and text file to be read, which are external to this application, and which values have to be entered by the user as attributes of the Ref-File-Location tool provided. The main function of the procedure is to read such file and when a text equal to the text of the selected scroll-message is found in such file, then it reads that text that follows line by line until some feature signals the end of file. The ref-text-formatter-proc (Table 155) prepares that text to be displayed in a formatted and scrollable form upon that panel. The processing can be interrupted at any time by selecting the "Cancel" button, which calls the ref-system-cancel-search-proc (Table 154). Selecting the buttons "Print" or "Quit" start the procedures (Table 156) ref-print-callback, which makes a postscript file of such subworkspace or ref-reset-scroller-proc, which resets the system and clears all the messages from the lower scroll.

Figure 22:
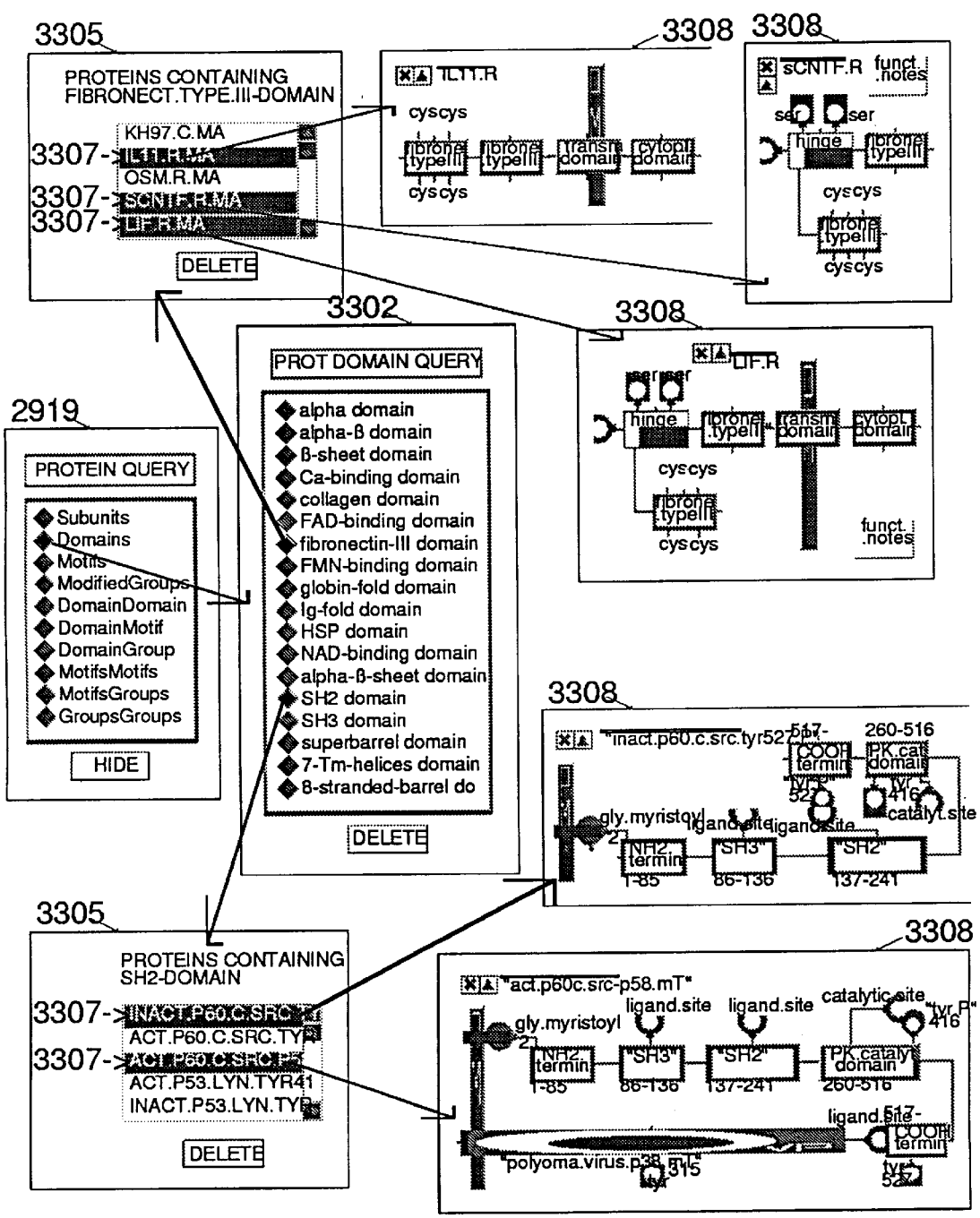
FIG. 22 shows exemplar prebuilt query panels enabling users to select predefined search criteria based on the components of entity building blocks, as well as navigation means to display and access the results of said search.

5. Structure Related Queries a) FIGS. 22 through 24 illustrate a few examples of the types of predefined Queries that the user can perform by just selecting the desired buttons from the many options offered in the graphic panels. The Query Panels are also built hierarchically, with each radio-button from the first Selection Panel leading to another more specific Query Panel, where now the user can compose a selection and then initiate the Query. There are two major groups of Queries, to be described below in more detail: a General-Query is application wide while a BR-Query is in reference to the bioReservoir from which it was initiated.

b) As shown in FIG. 20, a General-Query may be requested by selecting from the "Panels" menu head (2906) the "Structure Queries" option (2918) which, as previously mentioned, calls its named procedure (Table 120), the create-general-structure-selection-panel-callback (Table 157), which in turn creates a clone of Master-General-Structure-Query-Panel, stores it in the Temporary-Panel-Bin, configures its radio-box with the aid of the set-radio-box-id-proc (Table 158) and displays its subworkspace (2919).

c) As shown in FIG. 22, the user may now use that Query Selection Panel so created to select any radio-button (3301) from its radio-box, which calls the select-general-structure-selection-panel-callback (Table 159) with such button as one of its arguments, which in turn: a) gets the value of the radio-button selected, and depending on the value of the "on-value" attribute of such button, clones the corresponding master-panel, then calls the create-general-query-panel-proc (Table 160) with such value and the new panel among its arguments, which in turn completes such panel by scanning the panel for the presence of specifically labeled radio-boxes (related sets of radio-buttons) and configuring the radio-boxes with the aid of the set-radio-box-id-proc (Table 158), and b) displays the subworkspace (3302) of the new panel.

d) The user may now use that Query Panel so created to select any combination of one radio-button (3303) per radio-box (in this example shown is only one, and the procedure is associated with the radio buttons, but there could be two or more), and then selecting a "Query" button calls the query-general-structure-callback (Table 161), which in turn calls first the query-general-structure-proc (Table 162), which scans such panel for the presence of specifically labeled radio-boxes and then calls find-specific-array-proc (Table 163), with such label as one of its arguments, to find the value of the selected radio-button and the matching array within the Query-Arrays-Bin (those arrays are created when the "Add Query" or "Query Init" are selected from the Initialization Panel, as described in the Initialization section above). An auxiliary scroll-text-list is created and, if only one radio-box is present in the Query Panel, then the elements of the corresponding array are transferred to such list. If two radio-boxes are present in the Query Panel, then two such arrays should be found, in which case the merge-two-structure-lists-proc (Table 164) is called, which scans those arrays against each other to find the common elements, which are transferred to such scroll-text-list. A specific text-string is developed (TX2 in Tables 162 and 164) which includes references to the selected options and to the outcome of the search, which is then given as a value to a free-text structure which is displayed as a heading for the results of the search. The callback calls then the create-general-query-output-panel-proc (Table 165) with such scroll-text-list and free-text among its arguments, which creates an output panel by cloning the Master-Molecular-Query-Output-Panel and stores it in the Temporary-Panel-Bin, then creates a scroll-area to display in a scrollable and interactive format the elements of such scroll-text-list, and transfers to the subworkspace (3305) of such output panel both the free-text and the scroll-area listing the results of the search, which is them displayed.

e) The user can now use the scroll-area (3306) upon the Query Output Panel (3305) so created to interactively display or hide the structure of any number of bioEntities named by the options listed. Selecting any option (3307) of such scroll-area changes the color of that message to the selected configuration and calls the procedure named by the message-selection-method of the scroll-area, in this case the query-message-selection-proc (Table 166), which results in the display of the subworkspace (3308) of the named bioEntity; while unselecting the option resets the color and calls the query-message-unselection-proc (Table 167), which hides the subworkspace. Once the subworkspaces of such bioEntities are displayed, they can be used to navigate up and down the workspace hierarchy, by combining the "details" menu options of the objects with the go-to-sup-obj-buttons, or they can also be directly hidden using the hide-sup-ws-button, as described earlier. All the Query Selection Panels, Query Panels, and Query Output Panels are dynamically created and transient, and when the search is completed they are no longer needed and they are deleted, as well as their associated lists, by selecting the "Delete" button (3304), which calls the delete-query-panel-callback (Table 168).

6. Pathway Related Queries a) Any reference to a query-tracer means a graphic programmed object (Table 20), to be located upon the subworkspace of a bioReservoir and connected to a bioPool at a lateral position, where it plays a support role as part of the interactive user-interface by controlling the dynamic creation and display at run-time of a Pathway Query Selection Panel, which offers a wide spectrum of options that allow to request other more specific Pathway Query Panels, selected from those predefined options. All the searches generated from this type of panels, include bioReservoirs that are located anywhere within any pathway that is either upstream or downstream, depending on the selection, of such initial bioReservoir, and in addition, the bioEntities referred to by any of those upstream or downstream bioReservoirs. Those upstream or downstream queries can be further restricted by the type of roles that those bioReservoirs play in different bioProcesses, as defined by the major classes of bioReactants to which their bioPools are distantly connected, which is referred here as function-related search. In complex queries of mixed type, such bioEntities can be further restricted to those containing any particular component, similar to the Structure Related Queries described above. In such cases, the methods pertinent to the pathway search are applied first to generate the pathway-related set, followed by the function search, which is applied only to the pathway-related set and generates the function-related set, and finally the structure search, which is applied only to the function-related set, or to the pathway-related set if no function search has been selected, and generates the structure-related set. The structure search applies only to the bioEntities for the purpose of displaying the results, in the sense that all bioReservoirs that meet the selected pathway, and optionally function, requirements are listed in the scroll-area listing the bioReservoirs, regardless of whether they meet any of the bioEntity related criteria. This implementation of this invention is currently preferred because the "ref-bioentity" of a bioReservoir is an optional attribute, and it is expected that many of the bioReservoirs will not have a corresponding defined bioEntity, particularly in the growing stages of an application, before it matures and more complete overall picture is obtained. This alternative provides a more complete search in terms of relative position and function of bioReservoirs, without being influenced by the implementation of an option. It also allows to judge the completeness of the Structure Library for that particular part of the application, by comparing the lists of bioReservoirs and bioEntities, which should have the same base name, in their respective scrolls. Note also that the word Panel is frequently used in a more general sense to refer to the subworkspace of an instance of the class query-panel.

b) As shown in FIGS. 23 and 24, a BR-Query may be requested in two different ways: a) from a bioReservoir (3401) by selecting from its menu (3402) the "query panels" option (3403); or b) from the subworkspace (3501) a bioReservoir by selecting the query-tracer (3502), which implies selecting from its menu the "show" option. Each of those options starts the create-br-related-selection-panel-callback (Table 169), which creates a clone of Master-BR-Molecular-Query-Panel, stores it in the Temporary-Panel-Bin, configures it, and displays its subworkspace (3404). For this and any other panel that follows during the processing of br-related queries, configuring a panel always includes to set the value of the "related-item" attribute of the panel equal to the name of the bioReservoir from which the query was initiated, and this name is passed along when a new panel is originated from such panel That is, any callback invoked from a button of a panel, takes the name of the bioReservoir from the "related-item" of the panel upon which subworkspace it is located, and passes that name as an argument when calling other procedures.

c) The user may now use that Pathway Query Selection Panel (3404) so created to select any radio-button (3405) from its radio-box, which calls the select-br-related-query-panel-callback (Table 170) with such button as one of its arguments, which in turn: a) gets the value of the radio-button selected, and depending on the value of the "on-value" attribute of such button, clones the corresponding master-panel, then calls the set-br-related-query-panel-proc (Table 171) with such value and the new panel among its arguments, which in turn configures and completes such panel with the aid of the set-radio-box-id-proc (Table 158), and b) displays the subworkspace (3406 or 3503) of the new panel.

d) The user may now use that Pathway Query Panel so created to select any combination of one radio-button per radio-box. The example in FIG. 24 shows one such complex panel, which composed of: a) the title (3504) which specifies the type of search being made from that panel and names the bioReservoir (3505) that is the point of reference for the search; b) the set of radio-buttons (3506) of the radio-box labeled "direction", defining the two possible alternatives; c) the set of radio-buttons (3507) of the radio-box labeled "function", which defines the possible alternatives available for function, which in this case we only show a small but important subset that is of high relevance to scientists; d) the set of radio-buttons (3508) of the radio-box labeled "domains", which defines the possible alternatives available for subclasses of protein-domain; and e) the set of radio-buttons (3509) of the radio-box labeled "motifs", which defines the possible alternatives available for subclasses of protein-motif.

e) As shown in FIG. 23, selecting the "Upstream" option (3407) (or the "Downstream" option, not shown) calls the or the upstream-query-lists-callback ( or downstream-query-lists-callback ) (Table 172) which in turns calls the upstream-function-query-lists-proc (Table 174) (or downstream-function-query-lists-proc, Table 173), which do: a) it first calls repeatedly the create-br-query-list-proc (Table 175) to create a set of two lists per predefined type of function, one to contain names of bioReservoirs and the other the names of bioEntities; b) then, it loops over all bioReservoirs that are upstream (or downstream) and scans for their connections to certain classes of bioReactants, which define their function, and enters their name in the corresponding one of those bioReservoirs lists, for example, if the bioPool of a bioReservoir is connected to both a kinase.r and a transcription-factor.r, then the name of such bioReservoir will be added to each of the two corresponding lists, so that a bioReservoir may be named in more than one function list, but is not duplicated within one single list; and c) for each pair of one of those bioReservoirs lists and its corresponding bioEntities list, it calls the fill-br.et-list-proc (Table 175) which scans all the bioReservoirs in the fist list for the value of their "ref-bioentity" attribute, which if available is added to the second list. All those lists, to be used by the procedures described below, are associated by a relation to the panel from which they are created, are valid only for the bioReservoir giving the related-item of that panel, and are deleted when the panel is deleted.

f) The user can now select any combination of one radio-button per radio-box, such as receptors (3408) and β-strand-motif (3409), and then select the "Query" button (3410) to complete the processing and display the results of the query. The processing from the "direction" button is independent and previous to the processing from the "Query" button, and if the user selects the "Query" button before the "direction" button, then processing cannot occur, because the lists do not exist, and an error message is displayed to the user to that effect. Selecting the "Query" button calls the query-br-related-callback (Table 177), which first obtains the values of the selected radio-buttons of the "direction" (3407) and "function" and then calls the get-br-function-list-proc (Table 178) with those values among its arguments, which uses those values to obtain and return the corresponding set of two lists from the bioReservoirs lists and bioEntities lists created and filled in the previous processing, as discussed above. Such bioReservoirs list is going to be used to directly pass its values to the bioReservoirs scroll-area for final display, while such bioEntities list is going to be used as the basis for the complex further processing that follows.

g) The callback scans now the Panel to find whether there are structure related radio-boxes, such as the "domains" radio-box in this example, in which case it calls the query-br-structure-lists-proc (Table 179) with those previous values and the bioEntities list among its arguments, which does a complex processing as following: a) it finds the label of such structure related radio-box(es) and calls find-specific-array-proc (Table 163) to find the value of the selected radio-button for such box(es), such as B-strand-motif (3309), and its matching array(s) in the Query-Arrays-Bin (as described above in the Structure Related Queries section); b) if there is only one structure related radio-box, like in FIG. 23, then it calls merge-br-function-structure-proc (Table 180), or if there are two structure related radio-boxes, like in FIG. 24, then it calls merge-br-function-structure-structure-proc (Table 181), passing among its arguments the values of all selected radio-buttons, as well as the corresponding bioentities list filled earlier, and the array(s) now found. These procedures create a new list, the bioentities scroll-text-list, and then, taking into consideration the type and value of the arguments: a) they select a text specific for each situation, to be displayed as a title for the results, b) they call the br-fill-et1-list-proc or the the br-fill-double-et1-list-proc (Table 182), which enter the common elements of both the bioEntities list and the array(s) in the scroll-text-list, and c) they return the text and the scroll-text-list to the previous procedure from which they where invoked, which in turn returns them to the callback.

h) The callback passes such text to a free-text structure, and finally calls the create-double-query-output-panel-proc (Table 183) with the bioReservoirs list mentioned in paragraph f), the bioentities scroll-text-list, and their two corresponding free-texts among its arguments, which creates an output panel by cloning the Master-Molecular-Query-Output-Panel and stores it in the Temporary-Panel-Bin, then transfers the two free-texts to it, creates two scroll-areas to display the elements of each of those lists in a scrollable and interactive format, and calls the complete-br-panel-proc and complete-br-panel-proc (Table 182), which configure those scroll-areas and transfers them to the subworkspace, which is them displayed (3411).

i) The user can now use the Pathway Query Output Panel (3411) so created to scroll through the lists bioReservoirs and bioEntities that are the output of the query. Selecting and unselecting any option of such scroll-areas allows to interactively display or hide subworkspace of the named structure by, in addition to changing the color of that message to the selected configuration, calling the query-message-selection-proc (Table 166) or the query-messageunselection-proc (Table 167). Each of the titles (3412) are directly related to the scroll-area below them and vary with the results of each part of the search, and they may omit naming those groups of buttons where not selection was made, or indicate that some search or part of the search was empty. The scroll-area (3413) on the top shows the bioReservoirs that meet the direction and function requirements, which are those named by the options listed, and selecting any of its options (3414) displays the subworkspace (3415) of the named bioReservoir. The scroll-area (3417) on the bottom shows the bioEntities that meet the combination of direction, function and structure requirements, as selected, which are those named by the options listed, and selecting any option (3418) displays the subworkspace (3419) of the named bioEntity. Those structures displayed can be used to navigate in any way previously described, including up and down the pathways from bioReservoirs (3415) to bioProcesses (3416) and so on, from bioReservoirs or bioReactants or bioProducts to their bioEntities as shown in FIG. 5, or up and down the workspace hierarchies (3420,3421), by combining the variety of tools and methods previously described. As before, all the Pathway Query Selection Panels, Pathway Query Panels, and Pathway Query Output Panels are dynamically created and transient, and when the search is completed they are no longer needed and they are deleted, as well as their associated lists, by selecting the "Delete" button, which calls the delete-query-panel-callback (Table 168).

7. Interactive Lists and Pathways a) In addition to the various query methods previously described, the current embodiment of this invention provides several other tools and methods to enable the user to extract the knowledge build entered into the system by the modeler, in addition to the new knowledge created by applying the methods of this invention to analyze and integrate the knowledge provided by the modeler.

b) One of those capabilities is provided by means of the "list copies" menu option (625) defined for the class complex-bioEntity, which upon selection calls the et-list-local-copies-callback (Table 185), which creates a scroll-text-list and then calls the list-local-bioentities-copies-proc (Table 186), which in turn scans all the bioentities of the same major subclass as the one bioEntity from which the request originated to find if the master-bioentity of any of then matches the name of such bioEntity, in which case the value of the "id" attribute of each of those copies is added to the list. If there is any element in that list, then the callback creates an Output Panel by cloning the Master-Local-Bioentity-Copy-Panel, creates a specific title and a scroll-area, which are then added to the Panel and configured, and finally the Panel is displayed. This Panel is not shown, but looks very much the same as the Query Output Panel (3305) discussed above, with a different title. An unseen difference between them is that when selecting and unselecting any option of such scroll-area, the procedures called are different: the et-copies-message-selection-proc and the et-copies-message-unselection-proc (Table 187) interactively displays or hide the subworkspace of the structures referred to by their "id", rather than by name. This also provides an example of how, in general, instances of bioEntities as well as bioReservoirs, bioProcesses and bioModels, or any other structure, can be referred to by the value of any attribute, rather than by their names, which have to be unique and sometimes inconvenient, but they can be avoided. Referring to attributes, defined for such or any other purpose, also allows to refer to groups of instances within a class, without having to refer to each individual member of the group.

c) Another novel teaching of this invention is the capability of creating lists (3511, 3606) of downstream and upstream bioReservoirs and bioProcesses. By selecting the icon of any of those lists (3512, 3607), the user can display on a workspace the elements of that list, which are pointers to all the bioReservoirs or bioProcesses that meet the criteria set for each specific list, and each pointer further allows to either display the table of attributes of such object, or displays the object itself upon its workspace, as described in more detail later (FIG. 39). Navigation can be now initiated from those objects as well as any other tasks described in the current embodiment of this invention This capability is accessible through the "show lists" options from the menus of bioReservoirs and bioProcesses (3603), which appear in the menus only when they are named and their subworkspaces are activated, as well as from the list-tracers in their subworkspaces, as described below.

d) As illustrated in FIGS. 24 and 25, in the current embodiment of this invention, references to BR-chaining-tracers or a BP-chaining-tracers mean the graphic programmed objects (as defined in Table 20), located upon the subworkspace (3501) of bioReservoirs and connected (3510) to a bioPool, or located upon the subworkspace (3604) of bioProcesses and connected (3605) to a bioEngine, where they play a support role as part of the interactive user-interface by controlling the dynamic creation and display at run-time of a set of such lists of either bioReservoirs or bioProcesses that are either upstream or downstream of the bioReservoir upon which subworkspace such list-tracer is located. The user-menu-choice labeled "show" (Table 21) is defined for the class list-tracer and is inherited by all its subclasses, including BR-chaining-tracer and BP-chaining-tracer. In most user modes, selecting any such list-tracer by the user implies "show", which starts the list-tracer-handler-proc (Table 21), which in turn, configures the buttons and depending on the subclass of list-tracer, either calls the BR-chaining-proc (which is also started upon selection of the "show lists" option of the bioReservoir, Table 188), or calls the BP-chaining-proc (which is also started upon selection of the "show lists" option of the bioProcess, Table 189). The major actions performed by both of these procedures comprise: a) if the list-tracer already has a subworkspace, then it is displayed with its contents, otherwise a subworkspace for the BR-chaining-tracer or BP-chaining-tracer, respectively, is created by cloning the subworkspace of BR-Chaining-Lists or BP-Chaining-Lists, respectively, which in both cases contain two sets of four predefined lists each, one set (3512 or 3607) is meant to be used in any user mode, while the second set (3513 or 3608), meant to be used only in simulation mode since otherwise these lists will be empty, contain elements from the first set that are further restricted to those which have been activated as a result of their inclusion in a simulation model (to be described in later sections), and then such subworkspace with the those newly created lists is displayed; and b) those lists are populated by using for each list of the set, having always as point of reference the bioReservoir or bioProcess from which they were requested, the following criteria: the elements of DBPL and SDBPL are downstream bioProcesses, the elements of UBPL and SUBPL are upstream bioProcesses, the elements of DBRL and SDBRL are downstream bioReservoirs, and the elements of UBRL and UDBRL are upstream bioReservoirs.

e) A further novel teaching of this invention is the capability to create and display interactive pathways of complex chemical processes, where these pathways comprise a chain of downstream, or upstream, bioReservoirs or bioProcesses or both, orderly arranged in a graphic format with connections drawn between them to indicate those that are adjacent. By visually following those connections, the user can follow the pathways that indicate a dependency relationship between those bioReservoirs or bioProcesses or both. The capability to display interactive downstream pathways is accessible from several different types of structures: a) from an individual bioProcess, in which case such bioProcess is the point of reference; b) from a Simulation Panel (to be discussed in conjunction with FIG. 27), in which case a bioReservoir is the point of reference; and c) from an Experiment Panel, (to be discussed in conjunction with FIG. 29), in which case one or more bioReservoirs are the points of reference.

f) As illustrated in FIG. 25, now we will refer to accessing such capability from an individual bioProcess, or from icons in its subworkspace that have such specific functions, to display either upstream or downstream pathways, and in either case the bioProcess is the point of reference. Any reference to up-path-tracer and down-path-tracer means the graphic programmed objects (as defined in Table 22) located upon the subworkspace (3604) of a bioProcess and connected (3610 and 3617) to its bioEngine, where they play a support role as part of the interactive user-interface by controlling the dynamic creation at run-time of a graphic display of such interactive upstream or downstream pathway, respectively, from the bioProcess from which it was requested. The user-menu-choice labeled "show" (Table 23) is defined for the class path-tracer and is inherited by all its subclasses, including up-path-tracer and down-path-tracer. In most user modes, selecting any such path-tracer by the user implies "show", which starts the path-tracer-handler-proc (Table 23), which in turn, configures the buttons and depending on the subclass of path-tracer, and if from an up-path-tracer it calls the draw-up-pathway-proc (Table 190), which is also started upon selection of the "up pathway" option (3609, which is available only when it subworkspace is activated) from the menu (3602) of the bioProcess (3601), or if from a down-path-tracer it calls the draw-down-pathway-proc (Table 192), which is also started upon selection of the "down pathway" option (3616, which is available only when it subworkspace is activated) from the menu (3602) of the bioProcess (3601). The major actions performed by each of these procedures comprise:

it creates a subworkspace for the up-path-tracer (3610) (or down-path-tracer, 3617), here to be called Upstream Pathway Display (or Downstream Pathway Display), by cloning the subworkspace of Master-Up-Pathway (or Master-Down-Pathway), which contains a set of prebuilt auxiliary structures. The text of the title (3611) is changed to refer to such bioProcess. The x-pos and y-pos (3612) are two integer-parameters (Table 31) used to keep track of the most distant bioProcess added to the Display and which: i) are used by the program to compute the position of the next bioProcess to be added, after which their values are updated, ii) are used by the program to be compared to defined threshold values that, when reached as the display dynamically grows, trigger a reduction in the size of the display, and iii) may be used also by the user to read the size of the Display, which may in occasion get very large, by observing their value as displayed in digital form. The set of resize buttons (3615) allow the user to resize the Display at will, offering the options of full, three-quarter, half, and one-quarter scale (Table 19).

it creates a copy of such bioProcess, by cloning it and deleting its workspace, and then transfers the copy to the Pathway Display at a specified position (3614), and displays the as yet small Pathway Display on the window from which it was invoked; and calls the create-local-up-bp-proc (Table 191) (or the create-local-down-bp-proc, Table 193) with such original bioProcess and its copy among its arguments, which in turn for each bioReservoir that is an-up-bioReservoir-of (or a-down-bioReservoir-of) the original bioProcess finds each up (or down) bioProcess that is an-up-bioProcess-of (or a-down-bioProcess-of) such bioReservoir and then, for each such up (or down) bioProcess: i) if a copy of such up (or down) bioProcess already exists upon the Display then it proceeds to iv, otherwise it creates a copy of such up (or down) bioProcess, by cloning it and deleting its workspace, ii) it computes a new value for x-pos and y-pos, iii) it transfers the copy to the Pathway Display at the new specified position (3615), iv) it creates a connection between random locations at the icon of such new (or existing) copy and the icon of the copy that is an argument of this invocation of the procedure, and v) it calls itself (Table 191 or Table 193), but now with such up (or down) bioProcess and its copy among its arguments. Each of these procedures keeps looping and calling itself until all upstream (or downstream) bioProcesses have been processed, and their copies added to the Display and connected. The an-up-bioReservoir-of and a-down-bioProcess-of, as well as the a-down-bioReservoir-of and an-up-bioProcess-of, are inverse relations, as previously defined (Table 50), which were established during initialization (Table 122) between appropriate pairs of a bioReservoir and a bioProcess.

g) FIGS. 26 and 26 illustrate the feel and look of the so created Upstream Pathway Display (3610) and Downstream Pathway Display (3618). The connections are directional, with the directions of the connections above the bioProcesses indicating the direction of material flows, that is from the one that is upstream to the one that is downstream in relation to each other. The directions of the connections below the bioProcesses always show the right to left direction as a result of the next copy being one that already existed in the display, such as those connections that revert to 3619 from other posterior copies. Note also that those pathways are interactive, and selecting the "details" option (Table 140) of any of the icons, or changing to Navigation Mode and selecting the icons (3619, 3621), in this case displays the subworkspaces (3620, 3622) of the originals of those copies, which allow further access to any of the navigation (3623) and all other capabilities associated with their graphic components, as described throughout the description of this invention, and allowing further access to possibly distant parts of the application.

h) Pathways with only bioReservoirs (not shown), or pathways with alternating bioReservoirs and bioProcesses can be created with the same methods, using only minor modifications. In the current implementation of this invention the pathways with bioProcesses are the preferred ones because the provide the most information about the interactions within the space constrains. Mixed pathways may become very large, while the connected bioReservoirs can anyway be accessed by just clicking on two icons.

G. SIMULATION MODE

1. Menus and Access a) The Simulation Mode can be restricted to any desired set of individual users, by packaging the application accordingly. That mode may be selected from the Mode Selection Panel, or from the "Help & Mode Menus" menu head. Selecting Selection Mode causes a change to that mode of operation and displays the specific domain-menus associated with that user-mode, only for the window from which it is selected. When entering Simulation Mode from another mode causes (Table 18) the subworkspaces of all bioReservoirs and all bioProcesses to be deactivated, and during the processing involved in activating a submodel for simulation, the subworkspaces of only the bioReservoirs and bioProcesses selected to participate in such simulation will be activated. When leaving Simulation Mode to another mode causes (Table 18) the subworkspaces of all bioReservoirs and all bioProcesses to be activated again. The menu heads in this mode comprise in addition the options "Pathway Libraries" and "Panels", which are similar to those previously discussed in conjunction with FIGS. 12 and 20, respectively, with the difference that the Structure Query Panel is not available in this mode. The user can start from the "Pathway Libraries" to access the part of the application desired by selecting a desired pathway from the menu.

b) Before a simulation can be run, however, the application must be appropriately initialized for such purpose. This is accomplished by accessing the "Panels" menu and selecting the "Initialization Panel" option, which displays the Initialization Panel (2908) described earlier, and continuing as described below.

2. Initialization a) The following description of the simulation initialization procedures, as well as the simulation procedures and other complex processing that follow, only highlight the major tasks accomplished, and is not meant to substitute for the more detailed descriptions provided in the pseudo-code listings provided in the form of tables in the Appendix referred to. Initialization is necessary only if the application has been started or reset, or if additions or changes have been made in the part of the application to be simulated since the last Initialization. The "Add Simul" is to be selected only after the "Navig Init" was been successfully concluded. If changes to the database have been made by the modeler since the "Navig Init" was last concluded, or if the application has been restarted, then the "Simul Init" button should be selected, since it comprises the methods of the other two. The common purpose of both buttons is to scan the application for the availability of certain values of the bioReservoirs that define the initial conditions required by the simulation, and if those values have not been provided by the modeler, to infer those values from other values provided by the modeler, and if none of the alternative source of values are available, either default values will be used, including symbolic approximations, or, depending on the attribute which value is missing, to send messages to the user to provide any of the alternative values and also to provide messages to the to be used any time that the user request a predefined query that involves that kind of knowledge.

b) Selecting the "Add Simul" button calls the add-simul-callback, which in turn calls the simul-init-proc (Table 194), while selecting the "Simul Init" button calls the simul-init-callback (Table 126), which differs in that it first calls the navig-init-callback (Table 121), before calling the same simul-init-proc (Table 194), which in turn does the following:

it calls the send-no-input-messages-proc (Table 195) which scans the loaded application for every bioReservoir that has a name but that has no inputs, either in the form of bioProcesses connected to its biopool-p-posts, or as input model-blocks connected to its bioPool and it sends a message to the user for each of those bioReservoirs found with no inputs, as a warning for the user to take appropriated measures if those bioReservoirs are to be involved in a simulation. The simulation proceeds also without those values, since inputs can also be provided through the Simulation Panel as user inputs, or otherwise the quantity of such bioPool will initially be whatever value the modeler has set or the program will set for the basal-quantity parameter used, or its default value, and it may or may not be exhausted during the simulation run;

it creates a set of four lists, which are transferred to the Initialization Panel, and which are provided to inform the user about the source of the values for the Scaling-Density attribute of each bioPool, by adding the name of each bioReservoir to one of those lists, which elements that meet the following criteria: i) the list labeled UNList contains all bioReservoirs which initial-value of the Scaling-Density was provided by the modeler; ii) the list labeled ANList contains all bioReservoirs which initial-value of the Scaling-Density was set by the program to equal the value, provided by the modeler, of the if-scaling-amount of that bioReservoir; iii) the list labeled RNList contains all bioReservoirs which initial-value of the Scaling-Density was set by the program to equal the value of the if-scaling-amount of a bioReservoir which name was entered by the modeler in the "if-scaling-bioReservoir" attribute of the original bioReservoir; iv) the list labeled DNList contains all bioReservoirs which initial-value of the Scaling-Density was was set by the program to equal the default value of 100.0. To do so, for each bioReservoir it scans the value of its Scaling-Density and if it has a non-default value it enters the name of such bioReservoir to the first of those lists, otherwise it calls the set-scaling-density-proc (Table 196) which sorts and adds the bioReservoir to one of the other three lists, following the criteria mentioned above, after setting the value of the Scaling-Density of its bioPool accordingly.

c) The set-scaling-density-proc (Table 196) discussed above is the method used in the current implementation of this invention in conjunction with the scaled reasoning used as default. An alternative method for setting the values of the scaling-density attribute, to be used when more quantitative information is available for the system to be modeled, and in which case the modeler may prefer the mixed absolute/scaled type of reasoning, is listed in Table 197. This alternative method is much more complex but also more specific, and involves the known values of the kinetic-parameters of the participating bioReactants for each process. A mixed approach can also be developed where if those kinetic-parameters are known then the reasoning of this procedure is applied, and if they are not available, then the previous more generic procedure is called.

d) The "Icons Init" button (2914) calls the init-icons-callback (Table 138), which function is not essential for the functioning of this system, but which provides a very useful cosmetic function, by realigning the tracers in the subworkspaces of bioReservoirs and bioProcesses and making their connections invisible. Selection of this button is not necessary every time the application is started, and it can be selected any time thereafter, when problems are detected, in any mode other than Simulation Mode (where those subworkspaces may be deactivated). The same effect is achieved for individual bioReservoirs or bioProcesses by repositioning their bioPool or bioEngine, respectively, which triggers their respective icon-movement rules, as defined in Table 56, which also apply to repositioning the bioRole-posts any time a bioReactant or bioProduct is moved.

e) Selecting the "Init All" button (2915) calls all-init-callback (Table 139), which in turn calls the all the initialization procedures mentioned above, and selecting the "Hide" button (2916) calls the hide-workspace-callback, which hides this Panel.

3. Simulation Panel and Procedures a) As indicated earlier, a simulation can be initiated from any named and connected bioReservoir from any submodel, as can be found through the domain-menus, and it can also be started from the menu of the bioPool of such bioReservoirs, or from the bioReactants and bioProducts connected to such bioPool.

b) The "simul-panel" options are associated with the classes bioReservoir (3801), bioPool, and bioRole-Object (Table 198), and appear in the menus (3802) of each instance of those classes only when the user-mode is simulation (in addition to the user-modes administrator and developer). Upon selection of one of these options (3803) by the user, the create-input-type-callback (Table 198), creates one of two types of entry-panel by cloning one of the prebuilt masters and displays its subworkspace (3804), called here a Simulation Selection Panel, depending on the subclass of bioPool involved, which depend on whether it represents soluble or bound bioEntities (Concentrations or Density inputs, respectively). Either Panel prompts the user to select the type of input, and the choices offered are combinations of absolute or scaled values with one-time or periodic inputs. Upon selection of one of the radio-buttons (3805), the select-input-panel-callback (Table 199) is called, which: a) according to the user's selection it calls one of the specific procedures listed in Tables 200 and 201, such as in this example the create-relative-input-panel-proc (Table 200), which in turn creates and partially configure one entry-panel of the specified type by cloning one of the several prebuilt masters; and b) it completes that panel and displays its subworkspace (3806), called here a Simulation Panel. Each of the entry-panels is related to the bioReservoir, or the bioReservoir referred by the bioReactant, from which the request was originated, that is, the related-item attribute of the entry-panel newly created is a pointer to such bioReservoir. The master entry-panels are only partially build: a) the difference between the one-time or periodic inputs types of Simulation Panel is that the latter has two additional entry-boxes to allow the user to enter the time interval for subsequent entries and the number of subsequent entries at such intervals of the amount indicated by the entry value and starting at the indicated time; b) the difference between the absolute or scaled inputs types of Simulation Panel is that the entry value in the former is given in some units standardized throughout the application while the latter is a dimensionless value; and c) the prebuilt panels contain the overall layout with the common components, while other structures specific for each bioReservoir are added dynamically at run time.

c) The Simulation Panel can now be used by the user to interactively set-up and start simulations comprising a desired submodel (3807) which is transferred to the Simulation Panel. The variables and parameters that form part of the simulation model are all those encapsulated in any of the bioReservoirs and bioProcesses in the pathway contained in the subworkspace of such submodel that are further selected by the processing to be now discussed. In addition this Panel permits the user to enter the input value (3808) to be added to the Accumulation of such bioReservoir and the time (3809) of such input. Help buttons in each section of the Simulation Panel provides instructions for the user in how to proceed, such as the one (3810) which subworkspace is shown (3811). Following those instructions, the user next selects the "List" button (3812) which calls the list-simul-callback (Table 202), which creates three lists and then calls the fill-br-downstream-lists-proc (Table 203) to search the application for all bioReservoirs that are downstream of such reference bioReservoir, as defined by the relations established during the initial initialization as described earlier, and fill the list labeled DBRL (3813) with pointers to those bioReservoirs, and then do the same for the downstream bioProcesses to be added to the SDBPL list (3814), and finally finding other bioReservoirs that provide the inputs for such bioProcesses and which are not included in the first list, which are added to the UBRL list (3815).

d) As shown in FIG. 28, selecting one of the bioReservoir lists (3813) displays a workspace (3901) with pointers to each of the elements of that list, which allows to examine the bioReservoir that are to be included in the simulation. Selecting any of those pointers (3902) allows the user to either display the table of attributes (not shown) of that bioReservoir or to directly display the bioReservoir and from it, its subworkspace (3919). In a similar way, selecting the SDBPL list (3814) displays the pointers (3905) to the bioProcesses that are to be included in the simulation, which upon selection (3906) directly display the bioProcess and from it, its subworkspace (3925). The user can examine those lists to decide whether the selection made is appropriate before proceeding. If not satisfy the user can reset the panel, and transfer to the panel additional or different submodels, and press the "List" button again.

e) When a Simulation Panel is created, the "Activate" and "Start" buttons are disabled to prevent the user of taking such steps prematurely. When the processing associated with the "List" button is completed, the "Activate" button (3816) is enabled, and when selected by the user it calls its associated procedure, which is one of three listed (Table 204) that are specific for each type of Simulation Panel. That procedure checks that a value has been entered by the user and then calls a common activate-simulation-proc (Table 205), which in turn: a) looks on the Panel for the three lists created above and calls the activate-model-proc (Table 206) with those lists as arguments. As discussed in earlier sections, upon entering the Simulation Mode the subworkspace of all bioReservoirs and bioProcesses are deactivated, so that their variables become inaccessible to the simulator. The function of this procedure is now to scan the DBRL, SDBPL, and UBRL lists and activate the subworkspaces of each of their elements, which are the ones that will be now included in the simulation, after which returns back to the previous procedure, which scans for the Basal-Density attribute of the now accessible bioPool of each of the bioReservoirs on those DBRL and UBRL lists and if its value has been modified by the user then it adds the name of the bioReservoir to the User-BC list (3819) of the set described below, and if its value has a default value then it calls the basal-density-proc (Table 207) for such bioReservoir.

f) The basal-density-proc (Table 207) has an important inference role since the value of the Basal-Density (or the Basal-Concentration) is used when the simulation is started as the initial value for the state variable of the bioPool, the Accumulation. The task of this procedure is to obtain a value for that attribute, if the user has not specifically entered one, from other data and information contained in other attributes of that bioReservoir or its bioPool. It also uses a set of lists contained in the structure labeled BC (3817) upon the Simulation Panel to sort and list all the bioReservoirs to be included in the simulation, to indicate the source of those values used for the Basal-Density. The user can examine the results of that inference after the processing associated with the "Activate" button is completed, when the button becomes disabled and its appearance changes. By selecting (Table 208) the BC button (3817) its subworkspace is displayed (3818) with a set of lists filled by the program following the criteria discussed below. Those lists can now be examined, by selecting their icons as discussed elsewhere, to find out which of the bioReservoirs got the value from each of the alternative more or less precise sources.

g) Various alternative versions of this procedure are made available, which are disabled and the one preferred is enabled by the modeler to better match the particular application. Alternatively, each of the alternative versions could be made specific for particular subclasses or groups of bioReservoirs. This procedure initially scans the normal-basal-density value of the bioReservoir and if that value is different from the default value of 9.99e-99 then the Basal-Density is set equal to its value, and the name of the bioReservoir is added to the NBD-BC list (3820). If the subclass of bioReservoir is sol-mol-reservoir then the Basal-Concentration would be set equal to the value of the normal-basal-concentration if different from the default value. In the alternative implementation shown here, if the subclass of bioReservoir is sol-mol-reservoir this procedure scans the normal-basal-concentration value of the bioReservoir, if that value is different from the default value, 9.99e-99, then the Basal-Density is set equal to its value multiplied by the Avogadro's number, which states that each mol has 6.023e23 molecules, and the name of the bioReservoir is added to the NBC-BC list (3821). The conversion is made when modeling complex mixtures of bound and soluble molecules. For example, for many biochemical systems where the molecules form large localized active complexes molecules are not homogeneously distributed, and therefore it is more meaningful to integrate in a bioProcess the quantities of both types of bioPools representing bound and soluble molecules using the number of molecules rather that their concentrations. If the normal-basal-density (or normal-basal-concentration) has the default value, then this procedure scans for the Scaling-Density attribute of the bioPool and if it has the default value then the bioReservoir is added to the "NO BC" list (3824). Otherwise, this procedure scans for the Scaled-Basal-Amount of the bioPool, and if its value is not the default value, then the Basal-Density is set equal to the value resulting from multiplying the Scaling-Density by the Scaled-Basal-Amount values, and the name of the bioReservoir is added to the SBA-BC list (3822). Otherwise the Basal-Density is set equal to the value resulting from multiplying the Scaling-Density by a factor associated according to the symbolic value of the "abundance" attribute of the bioReservoir, which value is set by the modeler or otherwise the default value is used, and the name of the bioReservoir is added to the PAB-BC list (3823). The inference engine may proceeds the search for other sources of values, such as in an alternative method (not shown), where this procedure sets the value of the Basal-Density equal to a value proportional to the physiol-max-density (or physiol-max-concentration) of the bioReservoir if this value is different from default. If the user has not entered any of those values, then the inference engine sets the value of the Basal-Density equal to the average of any known thresholding parameters of any bioReactant connected as an output of this bioReservoir, such as the Km, Ks, Ki or 1/(2*Kp). This alternative method emulates the following reasoning: the value of Basal-Density represents physiological conditions and it is assumed that physiological concentrations approach the mid-range functional concentrations in the most relevant bioEngine in which the bioReservoir participates, as represented by constants such as the Km for a substrate, the Ki for an inhibitor or the Ks for a ligand or complex-subunit. If those values are not known, a message is displayed requesting the user to assumed some values, based on comparisons with similar systems. Under normal in vitro assay conditions, an enzyme is generally present in limiting or catalytic amounts, in a range between 10e-3 nM and 10e2 nM, while a substrate is generally in the range of 10e3 nM to 10e7 nM. This value can be adjusted at a later time as more is learned about the system. If none of the alternative means are provided the system's default values are set.

h) The parameters and optional capabilities used for the simulation at run-time are configured by using an structure upon the Simulation Panel specific for that purpose, the model-definition (3825). As shown in FIG. 28, its table of attributes (3909) allows the configuration of any desired attributes, which include: a) the items to be included in the simulation (3910), which is set by default to be any of the variables or parameters upon the workspace where the model-definition is located, in this case the submodel(s) upon Simulation Panel, but which could be one or more other specifically named workspaces or objects, such as submodels; b) the time interval between simulation cycles (3911); c) the type of integration algorithm desired for the state variables (3912); the configuration for any external simulator that can also be used to receive or provide values of the variables in this model (3913); the name of any main procedure that is invoked once every simulation cycle (3914), which in turn may start or call any other procedure, and which in this case calls the model-simulation-proc (Table 212); a choice to send all the values to external databases or simulators at the beginning of each cycle (3915); an indicator of whether the simulation is not-running, running or paused, or whether is nothing to simulate or is a simulation error (3916); and the configuration of the simulator clock to run either synchronously or as fast as possible, which is more appropriate for simulating models which actions take place over long time periods (3917).

i) Once the participants in the model have been activated and configured, the input values have been entered, and the model-definition has been configured, the simulation can be started by selecting the "Start" button (3926), which depending on the type of Simulation Panel will call one of the six procedures specific for each of the one-time Panels (Table 209) or for each of the periodic Panels (Table 210), which read the input values entered by the user and perform different types of processing depending on the types of variables involved. The concentration-entry-panel is used to input the absolute concentration value entered by the user in the input-value edit-box, in units such as molar, which is added as a concentration or is converted and added as a density (depending of the alternative options available in this implementation). In a similar way the density-entry-panel is used to input an absolute density value, such as units/compartment, while the relative-entry-panel is used to input the scaled dimensionless value. Those input values are used the values of the corresponding attributes in each type of bioPool, such as the density-entry or the scaled entry at the time of entry value entered by the user, where these values are then integrated by the formula of the Accumulation of such bioPool at the next simulation cycle, and the values of such attributes are reset to 0.0 after one simulation period has elapsed since the time the input values were set. The set of periodic type of Panel follow initially the same type of processing, but the setting of the values of the density-entry or the scaled entry attributes of the bioPool occurs then repeatedly as many times as entered by the user in the entry frequency edit-box at times intervals as entered by the user in the time-interval edit-box, beginning at the simulation time entered by the user in the input-time edit-box. Each of those procedures then call a common procedure, start-simulation-proc (Table 211) which requests the simulator to run the model as previously defined in the model-definition.

j) As mentioned before, while the simulation is running the model-simulation-proc (Table 212) is called once every simulation cycle, which sets the values of the attributes current-simulation-time and current-simulation-time-increment of the entry-panel. The user can select the "T" button (3827) to display its subworkspace (3918), which contains digital displays of those values as well as the values of other performance parameters. This procedure also calls the compute-graph-transform-proc (table 213) described below.

k) By selecting the "Pause" button (3828) or the "Resume" button (3829), which call their associated procedures (Table 214), the user can pause and resume the simulation at will. By selecting the "Reset" button (3830) the reset-simulation-proc (Table 215) resets all the buttons on the Panel and calls the reset-proc, which: a) first it scans the DBRL, UBRL, and SDBPL lists and resets each of the bioReservoirs and bioProducts listed, including their status attributes, their icons and deactivating their subworkspaces; and b) then delete those lists. Note than when a Simulation Panel is created, most of its buttons are disabled, and they are enabled as the previous step has been selected by the user and completed by the program, at which point the button of that previous step is disabled. Disabled and disabled buttons have different appearances, and this implementation both guides the user about which steps are available at each point in time, including "Reset" which is enabled at all times, and furthermore, prevents the user from taking steps ahead of time by mistake. Note also that the "Delete" button (3831) is disabled when the "Lists" button is selected and it is not enabled until the "Reset" is completed, preventing the user from deleting the panel before all the participants in the simulation that may have been modified are reset.

4. Digital and Graphic Displays of Dynamic Values a) Selecting the details option of any of the bioReservoirs or bioProcesses that take part in the simulation allows to follow up the quantitative simulation by providing access to the different structures in their subworkspaces. Only the icons upon subworkspaces (3919 and 3925) that are activated are active, or their associated tasks selectable. Therefore, when in Simulation Mode the capabilities now to be described, as well as the navigation capabilities, are restricted to only those structures that are selected participants for that simulation. The current values of the variables of each bioReservoir or bioProcess are displayed in digital form by default (3920). Other structures, called graph tracers, are specific for simulations and allow to dynamically display the time course of the values those variables for the time frame selected. The subworkspace of such graph tracers containing a graph and associated structures are not stored in the application, but are rather created when the user selects one of such buttons, and the subworkspace is deleted when the user unselects the button, and those methods are described below.

b) Any reference to a graph-tracer means a graphic programmed object (Table 24), to be located and connected to a bioPool or a bioEngine at a lateral position, where they play a support role as part of the interactive user-interface by controlling the dynamic creation and display at run-time of a graph which plots the values over time of key variables or parameters, scaled or absolute, respectively, of the bioReservoir or bioProcess upon which subworkspace the graph-tracer is located. As described above in the Buttons section, these classes inherit the user-menu-choice (Table 25) labeled "show-plot", which upon selection by the user starts the graph-tracer-handler-proc, and this procedure in turn calls, depending on the class of the graph-tracer from which this procedure was invoked, calls either the scaled-BR-graph-proc (Table 216), the absolute-BR-graph-proc (Table 217), or the scaled-BP-graph-proc (Table 218).

c) For the bioReservoirs, such graph displays can generated for either the scaled-valued or the scaled-valued sets of variables, by either: a) selection of the "show-s.graph" option (Table 216) of a bioReservoir, which appears in the menu only when the user-mode is simulation, as established by the class restrictions for the class bioReservoir, and when the subworkspace of the bioReservoir is activated and, to avoid duplication, when the graph does not currently exist, by the user, or b) by selecting the scaled-BR-graph-tracer (3921) connected to the bioPool upon the subworkspace of that bioReservoir, starts the scaled-BR-graph-proc (Table 216) which executes the processing described in more detail below. Similar options with the equivalent names are defined for absolute-BR-graph-tracer and its methods (Table 217), and for scaled-BP-graph-tracer (3926) and its methods (Table 218). Those procedures first create a subworkspace with all its contents for that tracer, by cloning the subworkspace of the corresponding prebuilt master structure, and then configure the labels of the graphs (3923 and 3928) and ref-bioreservoir or ref-bioprocess of each of the graph-tranfvars upon such new subworkspace to refer specifically to that bioReservoir (3924) or bioProcess (3929), respectively. The tables of attributes of the velocity-transf-factor and the graph upon the BP-Transf-Graph-Master, which are cloned to generate those shown in FIG. 28 (3928 and 3929), are listed in Table 219, while the table of attributes of the graph cloned to generate 3923 is listed in Table 220.

d) The design and implementation of domain-specific graphs and associated structures are a novel approach of this invention to deal with some of the current limitations of the graph structures available in the Shell. It is possible to preset a fixed scale for the y-axis of the graph, or by selecting the automatic option, the system automatically adjusts the scale to the current values of the time-series to be plotted. However, in order to be able to plot in one graph the time-series of several domain-specific variables, which values may be orders of magnitude apart, a system of intermediary variables have been devised to dynamically transform those disparate values into others that fit a common scale. This set of new variables are instances of subclasses of the class transf-factor-var (Table 40), which is itself a subclass of float-variable. Among the important attributes of transf-factor-var are: "transform", which value is given by an instance of the class graph-transf-var (Table 39); and "ref-variable", which makes reference to the particular attribute of a bioObject that provides the input value. The attributes "label" and "x" are merely tools to aid in their display. The instances of transf-factor-var, are displayed under the graph that plots their values, by showing their icon, an open rectangle, containing the value of three of its attributes, in that order: <label> <x> <last-recorded-value>, such as the several (3924) used for the bioReservoir and the one (3929) used for the bioProcess in the current implementation.

e) The role of the graph-transf-var is to hold a transformed value of the current value of the parameter or variable referred to by its "ref-variable". The transformed value is suitable for plotting within the scale of the related graph. The role of the transf-factor-var is to hold the value of the factor necessary to obtain the desired transformation, as inferred by the compute-graph-transforms-proc (Table 213). Each subclass of the class transf-factor-var corresponds to one of the bioObject's attributes to be transformed, which matches the value defined for the "label" attribute of each subclass. Computation of the value of those variables is executed by the compute-graph-transforms-proc (Table 213) only when a simulation-model is running. The different color-coded instances of the class transf-factor-var, displayed below each graph, have the additional graphic role to dynamically display the changing transformation factor by which the corresponding value plotted have to be multiplied if the user wants to grasp the actual value of the transformed variable. What is more important, the transf-factor-var provides by itself the order of magnitude of the variable it transforms.

f) Selection of the "hide-s.graph" option (Table 221) of the bioReservoir, which appears only when the graph upon the subworkspace of the scaled-BR-graph-tracer exists, or selecting the delete option directly from the subworkspace of the tracer deletes that subworkspace with its contents. The same applies for the other classes of graph tracers.

g) In addition, selection of the "show-sw" menu option of any existing model-box by the user to access (Table 146) the model-block upon that subworkspace, to view the value of its output-1 in digital form, as shown by the attribute display, or may also display the table of attributes of that model-block to modified the values of the model's parameters, if so desired. The user can also add a graph to that subworkspace, and configure it to display the time-variant values of the output-1 of such model-block, to visualized the so modeled inputs to that bioPool.

5. Scaled Computation Approach for the Variables of bioReservoirs and bioProcesses a) The formulas of the parameters and variables that dynamically characterize a bioPool, depend on other numeric variables or parameters that are either attributes of the bioPool or its bioReservoir, or that are attributes of the bioReactants and bioProducts that represent such bioReservoir in different bioProcesses. Table 56 lists a representative set of formulas, as examples of generic simulation formulas comprised in the current embodiment of this invention to simulate a set of scaled-valued variables and Table 57 lists a set of generic simulation formulas specific for the Contribution of different subclasses of bioReactants that incorporate the values of scaled-valued variables or parameters. Table 58 lists a set of generic simulation formulas that are alternatives to the formulas in the set shown in Table 57, and which can be used in the current embodiment of this invention to incorporate the values of absolute-valued variables or parameters into the Contribution of each bioReactant. These formulas for the Contribution do scale those absolute values using either a linear or sigmoid approach, depending the role in a bioProcess represented by each class of bioReactant. Therefore, since the output of the Contribution is dimensionless, whether the inputs are scaled (as in the case of using the formulas in Table 57) or absolute (as in the case of using the formulas in Table 58), it is now possible to integrate in a single bioProcess a mixture of bioReservoirs, where some of those bioReservoirs use only the scaled-valued variables while other bioReservoirs, called of mixed-type, use a mix of the scaled-valued variables, such as the Scaled-Amount, and absolute-valued variables, such as the Density. Those two values are interconvertible by using the value of the Scaling-Density, as computed by the formula for the Density in Table 58, so the user may be able to display the output of a simulation also as converted back into Density units in this case. The Contribution can be used in conjunction with either absolute-valued or scaled-valued variables, and therefore allows to integrate parts of the simulation where the absolute values of parameters and initial conditions are known, where other parts of the simulation where those values are unknown an have to be approximated, which is best done when using dimensionless values.

b) The Quantity of the bioPool is the only quantitative output value propagated from any component of a bioReservoir to any component of a bioProcess. That output quantity value of the bioPool is used to compute either: a) the value of the Velocity of each bioEngine connected to each bioReactant connected to such bioPool, which is the method normally used when using the absolute computation approach, to be discussed below; and b) the value of the Contribution of each bioReactant connected to such bioPool, which is an intermediary variable which in turn is used to compute the value of the Velocity of the bioEngine to which that bioReactant is connected, in combination with the Contributions of all bioReactants connected to such bioEngine, this being the preferred method used when the scaled reasoning mode of simulation is preferred by the modeler or user. The formulas for the variables that give the value for the Contribution are specific for different classes of bioReactants, as more specifically defined in Tables 57 and 58. The formulas for the classes that represent reactants that bind to specific sites other reactants, such as substrate.r, ligand.r, inhibitor.r or ion.r, are designed as to provide a sigmoid scaling around their characteristic kinetic parameters, which implicitly provides a smoothed thresholding of the Quantity of the bioPool for that particular bioProcess, as represented by the bioReactant. When using the scaled-valued set of variables, the Scaled-Amount is used in conjunction with the corresponding scaled kinetic parameter, as the examples given in Table 58 show. The formulas for the Contribution for other classes of bioReactant, such as receptor.r or enzyme.r, are designed as to provide a linear scaling from none to their maximum observed value, represented as 100 if such absolute value is unknown. In contrast with the absolute mode of computation, where there may be great variabilty in the formulas needed to provide the value for the Velocity, depending on the class of bioengine involved, in the scaled mode of computation the variability is introduced, to a much lesser extent in the simulation formulas that provide the value for the Contribution, while only one very generic simulation formula is required for the Velocity of all classes of bioEngines. As listed in Table 56, the very generic simulation formula for the Velocity included in the current implementation of this invention integrates various coefficients and a rate-constant to give the modeler or user the flexibility of by changing the values of those attributes of the bioEngine to modify the behavior of the system in different ways, without the need to write specific formulas for each situation, while the default values of those attributes do not affect the system.

c) The Velocity of each bioEngine in turn is used to compute: a) the Production-Rate any bioProduct connected to such bioEngine; and b) the Consumption-Rate any bioReactant connected to such bioEngine, which may be 0.0 if such bioReactant represents a reactant that is not consumed in such process, or may have a value that may be withdrawn from a bioPool as an output (like any standard Consumption-Rate), but then retained for a period of time and then returned back to the bioPool as an input (like any standard Production-Rate will do), as specified by methods specific for the variables of such particular pair of bioReactant and bioPool, or for a group of such pair which are identifiable by some specific common attribute, or which are defined as separate subclasses of their respective classes.

d) Several bioProcesses may contribute through their outputs to the Input-Rate of that bioPool, which values are then integrated when computing the value of the Accumulation of that bioPool. Users can also add (or remove) an absolute or scaled amount during a simulation to the selected bioPool, by having specific procedures setting the values of specific attributes of the bioPool, as discussed above, which are then integrated into the Accumulation by its simulation formula.

e) The Basal-Quantity (which may be either a Basal-Concentration, a Basal-Density, or a Scaled-Basal-Amount) represents the initial conditions, and provides the initial-value for the integration of Accumulation, which is a state variable that integrates all other dependent variables. When using the scaled-valued set of variables, the value of the Scaled-Amount is the value of the Accumulation constrained to a range within 0.0 and 1.0. The values of the Concentration or Density are constrained to not be less that 0.0.

f) In the current embodiment of this invention, the value of variables or parameters that are attributes of bioObjects upon the subworkspace of bioReservoirs and bioProcesses, can be simulated only if the subworkspace of the bioReservoir or bioProcess upon which it is located is activated. When the user selects simulation mode, the subworkspaces of all bioReservoirs and bioProcesses are deactivated, and only those that are to participate in a simulation run are activated. This is a mechanism to improve performance of what may become an extremely large system of parameters and variables. In the current implementation of this invention, each of the values is computed once each simulation cycle using the equations defined by simulation formulas.

g) The implementation of the intermediary variable, the Contribution, is a novel and very important teaching of this invention, particularly in applications when the knowledge of the quantitative parameters and initial conditions of the system are incomplete, or when a more abstract and generic system is desired, such as when providing a Shell to be used in different and unpredicted ways. This implementation is relevant in several different ways. It allows to treat each of the bioReactant of a bioProcess as a generic self-contained unit, which allows to model also participants in a bioProcess which are known to interact but which exact roles in such process are unknown, where the velocity is generically computed by simply multiplying the contributions of any participant that the modeler may want to model. These generic units become even more generic when used in combination with the set of scaled-valued variables, which allow the user to enter values based on expert knowledge, or quickly perform what-if analysis. Another important result of using the Contribution is that, as discussed above, allow to perform quantitative simulations that integrate into the Velocity of any bioProcess values originated from bioReservoirs with both types of absolute-valued and scaled-valued variables. This means that those parts of the complex model where the absolute values of their kinetic parameters and initial conditions are known can be integrated with other parts of the complex model where relative values are used because the absolute values may be unknown.

h) The abstraction provided by the Contribution also facilitates the use of bioProcesses as black-boxes, which are also be implemented in the current system of this invention without using the Contribution. Black-boxes are used to represent any type of participant that is known to cause something to change somewhere down the line, even if it is known that other intermediaries are involved, but where the details or identity or even the existence of those intermediaries is unknown. The bioReactants in a black-box represent the entities (of bioPool(s)) that cause some effect on some other distant entities or bioProducts (the input to other bioPool(s)), and like in other generic bioProcesses, either the kinetic-coefficient (scaled or absolute) that modifies each bioReactant, or the rate-constant that modifies the overall process, representing the proportionality factor between the quantity of cause(s) and the quantity of effects, can be used.

6. Absolute Computation Approach for the Variables of bioReservoirs and bioProcesses More standard ways of quantitative simulations using the known absolute values of the system parameters and initial conditions, can be performed by using only the set of absolute-valued variables or parameters, and by using a different set of generic simulation formulas, such as those shown in Table 59. From those variables, the one that offers more variability in the formulas needed for each class of bioEngine is the Velocity, which is in contrast with the scaled mode of computation where only one very generic simulation formula is required for the Velocity of all classes of bioEngines. It is also possible to write very complex simulation formulas to encompass a variety of different situations, such as that in Table 60 to be described below. The value of the Velocity of a bioEngine in this approach depends directly on the Quantities of the bioPools connected to each bioReactant connected to such bioEngine, which is the method normally used when the formulas that give the value of the Velocity are those that represent the equations that a biochemist will normally use to compute the velocity of a reaction, based on the quantities of the reactants and on some known kinetic parameters, such as the Michaelis constant (Km), inhibition constant (Ki) or the equilibrium dissociation constant, and which the preferred method used when the absolute reasoning mode of simulation is preferred by the modeler or user. The simulations formulas for the Velocity of absolute-valued enzymes, such as that listed in Table 59 (which is equivalent to the Briggs and Haldane approach where $V=n*kp*[E]*[S]/([S]+Km*X)$, where $X=1$ if no inhibitor.r is connected to the bioEngine, or $X=(1+[I]/Ki)$ if an inhibitor.r is also connected to the bioEngine), assume the instantaneous or initial velocity approach, since increases or decreases in the Concentration of the substrate are updated at small time intervals in the current embodiment of this invention.

7. Examples of how the common knowledge of chemists is implemented in the current invention:

a) For receptor-bioEngines or enzyme-bioEngines with multiple equal binding sites, the velocities can represent reactions of two major types: a) the generic simulation formula for non-cooperative-binding is equivalent to $V=n*Kp*[E]*[S]/(Ks+[S])$, and represents the situation where binding at one site has no effect on the intrinsic dissociation constants of the vacant sites, yielding hyperbolic velocity curves, and being impossible to tell from the kinetics whether there is 1 pmole with n identical sites or n pmoles of 1 site; and b) the generic simulation formula for cooperative-binding represents the simple sequential interaction model of an allosteric enzyme with 2 cooperative substrate sites. It is modeled as two substrate.r connected to the same bioPool, but each of those bioReactants have different dissociation constants, and the simulation formula is equivalent to $V=n*kp*[E]*([S]/K_{S1}+[S]^{\wedge 2}/K_{S2}^{\wedge 2})/(1+2*[S]/K_{S1}+[S]^{\wedge 2}/K_{S2}^{\wedge 2})$. Here, the binding of one substrate molecule increases the affinities of the vacant sites for the next substrate molecules, yielding sigmoid velocity curves.

Thus, the sigmoid response acts as a smooth "on-off" switch", and at intermediate specific velocities, this provides a much more sensitive control of the reaction rate by variations in the substrate Concentration. Allosteric enzymes generally result in sigmoid velocity curves due to cooperative binding, either positive or negative (binding one molecule facilitates binding of the next). The Hill Equation is used for an enzyme with n equivalent S binding sites, if the cooperativity is very marked, in which case the Km of the single substrate.r has to be set, not equal to the real Km but rather equal apparent Km to the n power. Under these conditions, dominated by $[S]^n$, the equation can be simplified to $V=kp*[E]*[S]^{\wedge}n/(Km'+[S]^{\wedge}n)$. For enzyme-bioEngines, the application in the current embodiment of this invention focus on regulatory pathways, which are controlled by enzymes which active form is only present in catalytic amounts and a steady-state is assumed. For receptor-bioEngines, which include processes for other specific binding proteins, the generic formula for the velocity represents the system at equilibrium, and is equivalent to $v\square[RL]=n[R]_t/(1+(Ks/[L]))$.

b) Inhibition can be modeled in different ways, and the modeler has to decide what best represents each situation. Table 60 lists a very generic formula that allows the modeler to connect to the bioEngine one inhibitor-reactant that can be of any one of the four common types represented by the four defined subclasses of inhibitor-reactant. This formula is capable of first detecting which subclass of inhibitor-reactant is connected to the bioEngine, and then applying the equation with one of the alternative modifiers included which apply to that particular type of inhibitor. However, some of those types of inhibitors may be better represented in the system of this invention as competing with the substrate from a separate bioProcess, which allows for a more intuitive representation and understanding of such competition and a higher level of manipulation by the user, which are in fact some of the advantages offered by the system of this invention when compared with other more global modeling approaches. Competitive inhibition may be modeled within the corresponding bioEngine, with the generic formula such as that in Table 59. Noncompetitive inhibition is best modeled as a separate complex-formation-process between the enzyme and the inhibitor that competes for the enzyme by being connected to the same bioPool. Feedback inhibition should always be modeled by a separate bioProcess. Any further velocity equations can be derived in the same manner, by using well established equations in the field of biochemical kinetics, and the reader is referred to Segel, I. H., 1976, Biochemical Calculations 2nd Edition, John Wiley & Sons, New York.

Figure 31:
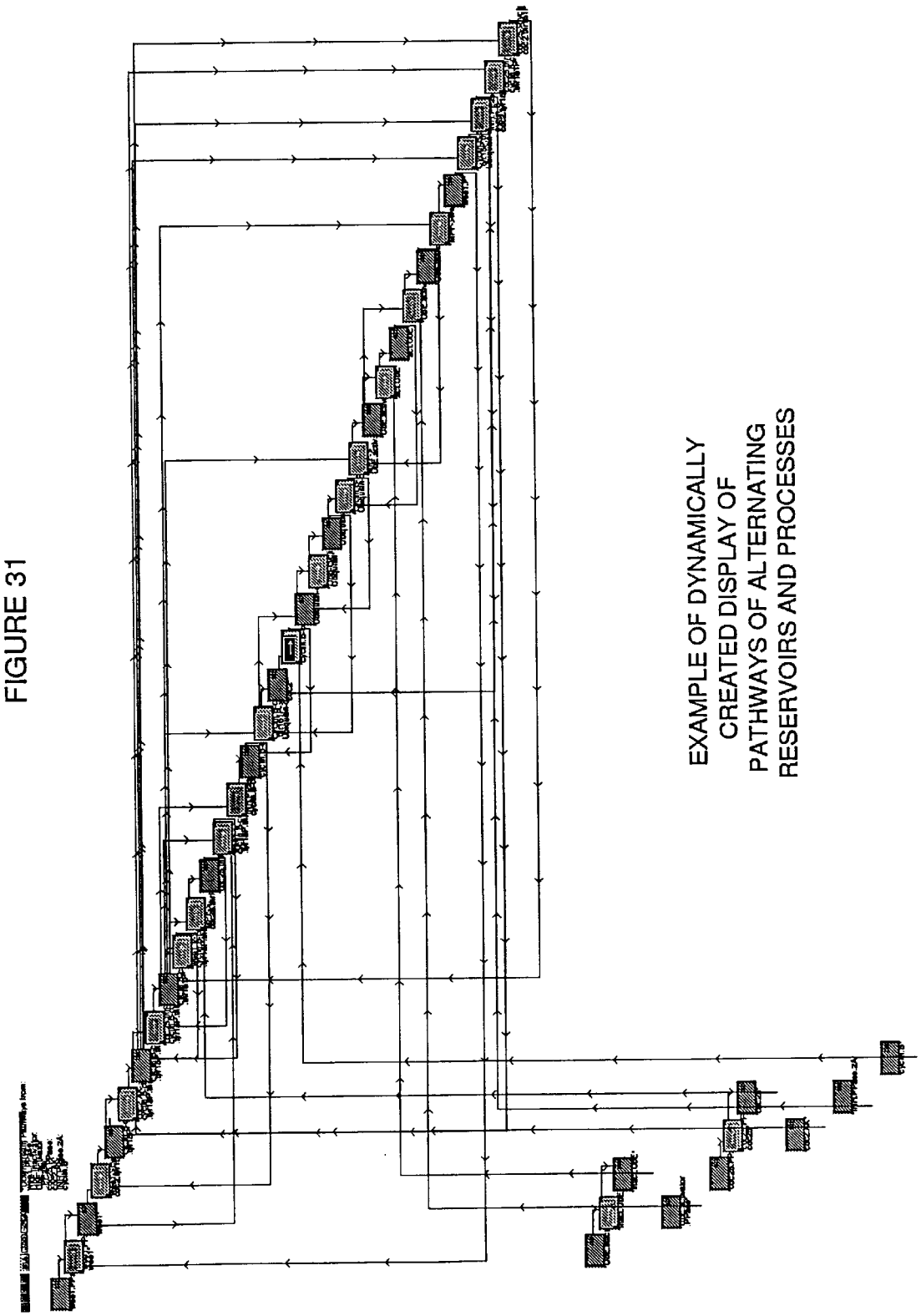

8. Experiment Panel and Procedures a) An Experiment Panel is a facility that allows to perform many of the capabilities previously discussed with one major difference: the generation of lists, creation of pathways, and simulations can be started with multiple points as points of reference or as the recipients of quantitative inputs. In contrast to the Simulation Panels, which are always requested from a bioReservoir the serves as point of reference, and are dynamically created and deleted, a variety of Experiment Panels can be created as permanent generic structures with different designs, that are then accessible through the domain-menus associated with the General Mode (2920) and with the Simulation Mode, as previously discussed. Each Experiment Panel is the subworkspace of an instance of entry-panel created by cloning the Master-Experiment-Setup-Panel.

b) As shown in FIG. 29, selecting one of those options from the domain-menu (4001) displays the subworkspace (4002) of the named entry-panel, which corresponds to one of those predesigned Experiment Panels. New designs are created by deleting of adding any number of the many button like structures organized in columns and rows which are instances of class experiment-selection (Table 28) that are auxiliary structures that allow to select the combination of bioReservoirs that are to serve as the points of reference in such experiments, and also to allow the user to enter the input values for quantitative simulations of such experiments.

c) Selecting one of those experiment-selections (4003) displays its table of attributes (4004) which allows to: a) enter a short name in its "label" attribute (4005), which is displayed on top of the icon, b) select a bioReservoir, as entered in its "ref-bioreservoir" slot (4006), and c) enter whether the "currently selected" (4007) is true or false. The values of those attributes are sufficient to perform any of the qualitative tasks associated with this panel. If a quantitative simulation is desired, any of the values for the other optional attributes may be entered, such as those for an absolute-valued input (4008), an scaled-valued input (4009), time of input (4010), time interval for periodic entries (4011), and entry frequency (4012), which meaning and use are the some as those previously discussed in conjunction with the Simulation Panels and will not be further discussed. The configurations of any or all those experiment-selections can be stored for later use, and the combinations of different experiment-selections may be quickly changed at will by changing the value of the "currently selected", since only those with such value set to true, which get also highlighted with a different color, are included in the processing when any of the tasks is requested. This allows the user to have a set of experiment designs for those types of experiments most frequently used The "BIORESERVOIRS" button (4013) is an structure that provides a graphic aid to facilitate the task of the user in selecting the appropriate name to enter in the "ref-bioreservoir" attribute of those experiment-selections. Selecting that button (Table 222) results in creating or displaying its subworkspace which contains an scroll area listing in alphabetical order all the bioReservoirs defined in the system, and which in addition to providing the specific nomenclature used for any particular bioReservoir, it also allows to directly access such bioReservoir to verify that it is the one wanted by displaying the details of such bioReservoir upon selection of the naming option, as described earlier for other scroll areas. For additional help about how to use the different sections of the panel, the user can select any of the Help buttons (4014), which result in the display of its subworkspace.

d) Upon entering the choices of "ref-bioreservoir" and setting the value true for the desired combination of experiment-selections, the user can proceed by selecting a number of buttons, most of which have similar or equal functions as those described for the Simulation Panel, and therefore here only the differences will be briefly highlighted. The reader is referred to the Tables 223 through 232 for a more detailed description of the processing involved. Selecting the "Lists" button (4015) calls the list-exper-callback (Table 223) which creates the "Exper. Selections" list (4016), and a set of SDBRL (4017), SDBPL (4018), and SUBRL (4019) lists, and transfers them to the Panel, then scans the Experiment Panel for any experiment-selection which value of "currently selected" is true and which "ref-bioreservoir" has a value, and for each such experiment-selection found, it adds the name of the bioReservoir named by such attribute to the list and it calls the same fill-br-downstream-lists-proc (Table 203) called from the Simulation Panel to fill the set of three lists. The only difference is that now, instead of once, that procedure is called as many times as experiment-selections meeting such criteria are found, and every time is called with the same set of three lists but with a different bioReservoir as arguments, pooling the elements downstream (or upstream) from the all of those bioReservoirs.

e) Selecting the "Pathway" button (4020) calls the draw-exper-pathway-callback (Table 224), which creates a navig-path-tracer (4021) together with its subworkspace by cloning the Master-Navig-Pathway and transfers it to the Panel, and then it scans the "Exper. Selections" list and for each bioReservoir listed calls the create-local-exper-BP-proc (Table 225), while setting the value of the x-pos to a value close to the initial position when changing from one bioReservoir to the next, which performs a processing very similar to that described earlier for the create-local-DBP-proc (Table 193). The difference is that now, instead of once, that procedure is called as many times as bioReservoirs are in the "Exper.Selections" list. One example of the display of one of those multi-origin pathways is shown in FIG. 30. The main difference between the pathways created for the path-tracers of bioProcesses and those for path-tracers of Experiment Panels, which can be observed by comparing the display 3610 on FIG. 25 with the display in FIG. 30, is that the latter are more complex because, unless the user selects only one experiment-selection, the pathways start from multiple initial bioReservoirs, and the pathways from latter initial points are connected, whenever the possibility arises, to the pathways from former initial points already on the Experiment Pathway Display. Alternative implementations of any of the types of pathways is to include in the drawing of the pathways not only the bioProcesses, but also the bioReservoirs that are intermediaries between those process in the chaining process. The procedures for those alternative implementations (not shown) apply the same methods and need only minor modifications to create, transfer and connect the intermediary bioReservoirs. An example of a display of such an implementation, is shown in FIG. 31.

f) This Experiment Panel can be used for just the purpose of generating those complex pathways, or they can be further used to perform quantitative simulations that apply to the variables and parameter of the components of those pathways. For that purpose, a submodel (4022) containing those bioReservoirs and bioProcesses to be simulated have to be transferred to the Panel. The remaining buttons and structures to be used in the subsequent steps have been described before, and the procedures called upon selection of the buttons (Tables 226 through 232) are only minor modifications of those described for the corresponding buttons of the Simulation Panel, to incorporate the fact that now there is not just one bioReservoir but the various bioReservoirs in the "Exper.Selections" list to consider.

9. Simulating Complex Models a) The modeler is provided with several methods to fine tune any specific parts of the complex model, including in the ability to write formulas specific for the individual instances of variables that are attributes of the bioReservoirs or bioProducts that model any such specific part of the complex model. Within those formulas, temporal reasoning is further achieved in the system of this invention in several ways, such as by specifying times or time intervals, using quantitative time constraints such as the expressions: during the last 30 seconds, as of 5 minutes ago, or between 3 hours ago and 4 hours ago. Fuzzy time intervals and time constraints may be specified if so desired to handle the uncertainty encountered in biochemical systems. The simulation can be synchronous or asynchronous, by setting different simulation time intervals for sets of variables of bioProcesses and bioReservoirs that represent different parts of the complex model.

b) The simulation can be continuous or time-constrained, and either way may be differentially applied to different parts of the complex model. To accomplish that, the simulation formulas can be complemented with rules that monitor those simulated variables to either set other values, particularly those that are further integrated into an state variable, or by controlling parts of the model. For example, a bioProcess or a bioReservoir can be programmed to be active only for certain time intervals during a simulation run, by means of rules or procedures that control the activation and deactivation of its subworkspace. Those time intervals may be either directly specified or dependent on the values of other parameters or variables or any of their combinations. Rules may be defined to monitor the simulated values of specific variables, such as the Quantity of a given bioPool or the Velocity of a given bioEngine, to be compared with a specified threshold, that when reached causes that rule to trigger some actions, such as setting the values of other parameters or variables, or activating and deactivating the subworkspace of one or more bioProcesses or bioReservoirs, or starting one or more procedures. Such rules in turn may be: a) if-type rules with their "scan-interval" attributes set to a specified time interval that preferably matches the time-interval used for the simulated variables, which means that such rules are invoked once every such interval; or b) whenever-type rules that are invoked whenever the specified variable receives a value and which trigger specified actions when such value fulfils any specified constraints; or c) initially-type rules, that may for example be hidden in the subworkspace of a bioEngine or bioPool, and which will be invoked once every time the subworkspace of their superior bioProcess or bioReservoir is activated, and which may trigger any of the actions described above which may apply to any bioProcess or bioReservoir in the complex model.

c) One of the several applications of this invention is that of a system for signal processing and signal integration. In such system, simulations can have three levels of control through:

the interactions explicitly modeled in the architecture of the graphic design of this invention, namely the network of connected bioReservoirs and bioProcesses, which represent and determines the specific interactions of the different components of the complex model;

the propagation through such network of the dynamic changes in the values of the variables of such components; and through the signals transmitted by the smoothed thresholding implicit in the design of the Contribution variables of the bioReactants which determine the output values of the Velocity of the bioEngines, and through the rates of consumption of the bioReactants and the rates of production of the bioProducts, that determine new changes in the values of the Concentrations, now amplified to a larger number of bioPools, which in turn initiate new waves of value propagation.

d) The simulation starts after a perturbation, such as a Concentration-Entry, Density-Entry or Scaled-Entry, has been introduced and integrated in the overall system's equation: $d[E](t)/dt=[E](t)+entry+\Sigma\ inputs(t)-\mu^*[E](t)-\Sigma\ outputs(t)$. In this system, the bioReservoirs and bioProcesses placed in a biological compartment-layer are activated successively in time and space, as the activation signal is propagating forwards based on various chaining relationships between those structures established during the initialization process according to the downstream or upstream positions of each of those structures respect to the others.

e) In summary, the system of this invention's bioObjects are connected in graphic schematics that represents the way in which scientists describe interactions; and operate as a network of parallel processors to approach the way biological entities operate. The system of this invention's graphic environment allows simulations to be followed in different ways, including:

animation of the activated parts of the schematics;
   display of the current values of desired variables in digital form;
   dynamic charts of a combinations of time series of desired variables;
   dynamic charts of a variable versus another variable; and
   through the drawing of dynamic networks of pathways on displays.

f) "When starting the knowledge base, the G2-s finds the initial values for all variables that receive values from simulation formulas, and then executes the main simulation procedure. For each simulation cycle, the G2-simulator evaluates in order: 1) simulated state variables and parameters, 2) dependent variables and parameters, and 3) the main simulation procedure. The G2-s only evaluates one, the most specific simulation formula for each variable"

H. ALTERNATIVE IMPLEMENTATIONS AND VARIATIONS

1. An equivalent system can be build with a less graphic interface by substituting each of the components represented in the current implementation as graphic bioObjects upon the subworkspace of bioReservoirs and bioProcesses, and representing them instead as attributes of the bioReservoirs and bioProcesses, respectively. The corresponding methods would need only minor modifications, such as for example, by substituting the current expression "the bioPool upon the subworkspace of bioReservoir X" with "the bioPool that is an attribute of bioReservoir X"; or substituting the current expression "the bioReactant-1 connected at port-1 of the bioEngine upon the subworkspace of bioProcess X" with "bioReactant-1 of bioReservoir X", where each of the specific bioReactants connected to each of the specific stubs of a specific type of bioEngine are now converted into specific attributes of the specific type of bioProcess, and where those attributes are not values but objects, and where those objects may have as attributes other objects. For example, the bioPosts now connected with each bioReactant and bioProduct can also be implemented as and attribute of such bioReactant or bioProduct, while the two sets of bioPosts connected to a bioPool can now become two sets of attributes objects of the bioReservoir, such as Input-1 or Output-3. By defining a specific attribute, such as "post" for these new classes of objects, the specific distant connections can now be established by giving the same unique value to the "post" attributes of one of the bioReactant attributes of a bioProcess and one of the Output attributes of a bioReservoir, or by giving the same unique value to the "post" attributes of one of the bioProduct attributes of a bioProcess and one of the Input attributes of a bioReservoir. The result of this alternative implementation is that the different levels of encapsulation currently provided through the workspace hierarchy would then be provided by an attribute hierarchy, and the current representation of those components by their icons would be then limited to their representation by their tables of attributes, which are also part of the current implementation. Many of the tasks associated with the menus of the icons of those components or other auxiliary icons can be associated in the alternative implementation as menu options of the superior bioReservoirs and bioProcesses, as many of those are already currently implemented. The advantage of using the approach described in the currently preferred embodiment of this invention is that the more graphic interface is more intuitive for the user, and easier to use. The disadvantage is the additional memory required to store the additional graphical structures.

2. Another alternative is to replace the complex knowledge-structures bioReservoir and bioProcess by the components encapsulated in their respective subworkspaces, after some modifications. One of the several possible alternatives is to bypass the bioReservoir and the bioProcess structures altogether, and to encode the pertinent information here defined within the bioReservoir's table of attributes in the bioPools table of attributes, and to encode the pertinent information here defined within the bioProcess's table of attributes in the bioEngine's table of attributes, and to construct the schematics now contained in the subworkspaces of the bioReservoirs and bioProcesses directly on the desired workspace. The advantage of using the approach described in the currently preferred embodiment of this invention is that the bioReservoir and bioProcess structures encapsulate the details and simplifies the schematics, and makes easy the cloning and transfer of the pre-constructed structures from one location to another, making the task of developing new models or modifying existing time much faster and keeping complex schematics simpler. The disadvantage is the additional memory required to store the additional graphical structures.

3. An alternative more compact implementation that would still allow developing multidimensional pathways, bypassing the need for bioReservoirs, is to directly connect all the bioReactant-post and bioproduct-post that in the current implementation are connected to the same bioPool, by giving them all the same name. In such implementation, the "ref-bioentity" attribute, as currently defined for the class bioReservoir could instead be defined for the classes bioReactant and bioProduct, allowing in that way access to the bioEntity corresponding to an instance of bioReactant or bioProduct that would provide the physical description of such bioReactant or bioProduct. This implementation would allow the user integrating the description of structure with function. In another related implementation, the variables and parameters, inputs and outputs, as well as other attributes, as currently implemented as attributes of the bioReservoir or its bioPool, or as separate icons within the bioReservoir, could be implemented as attributes of the currently corresponding bioEngine.

4. Other of the many alternatives include: storing the bioReservoir or equivalent structure within the subworkspace of the bioEntity; or storing the bioEntity within the subworkspace of the bioReservoir. However, note that in the current implementation, the bioEntities are stored independently of the bioReservoirs because in many cases, and particularly dealing with very large applications, it may not be necessary to store one bioEntity for each bioReservoir, and instead prototypic bioEntities can be used that are shared by many bioReservoirs. But even in such cases, another alternative is storing all the bioReservoirs that in the current implementation would refer to the same bioEntity in the subworkspace of such bioEntity.

5. The concepts and methods subject of this invention can be applied with each of the object-oriented expert system shells from various vendors, after those capabilities not provided by that particular shell are additionally encoded. An equivalent of those capabilities of the selected shell that are required to apply the concepts and methods of this invention may also be custom built from scratch or by combining a set of off-the-shelf components.

6. There are many sophisticated capabilities that can be further developed with this system, which a knowledgeable expert can derive from the teachings of this invention. Here, only a few important ones of which will be described in detail:

7. As an alternative, the methods here represented could in part be compiled using this Shell or other shells of the compiled type, including but not limited to RTworks and Activation Framework. The compilation may improve performance at runtime by eliminating graphical interpretation of the schematics. However, compilation does not facilitate frequent modifications of the design and information contained in the schematics, a feature which is of great importance when modeling biochemical systems, the knowledge of which is being continually updated and improved.

8. The same concepts described in this invention can be slightly modified by a person skilled in the art, to incorporate multiple inheritance capabilities, allowing the bioObjects to inherit attributes from two or more superior classes. Additional controls and code may be required in that case to resolve conflicts that may appear when more than one superior class have the same attributes but receiving values from different sources, or through different methods.

9. Many of the symbolic variables or parameters could be also represented as logical variables or parameters, with or without fuzzy-beliefs, by simply changing the language of the attribute name and its values. For instance, an attribute called status could have values: available, unknown and unavailable; or it could alternatively be called is-available and have values true, unknown or false, the unknown associated with fuzzy-beliefs, such as the range 0.2–0.8.

10. To further control the behavior of any component of a simulation, different types of filters could be applied to, for example, the Density (or Concentration) of bioPools or to the Velocity of bioEngines. These filters can be of any of the types of filters used in signal processing control systems, such as low-pass or ideal high-pass filters (such as $H(j\omega)= e^{-j\omega t_o}$ for $|\omega|>\omega_c$, else $H(j\omega)=0$), Gaussian filters ($H(\omega)=e^{-\alpha(\omega)^2} * e_{-j\omega t_o}$ and others). Such filters could be executed in either formulas or procedures, that could be generic for a whole class of variables, or more specific for certain instances or group of instances. The specific filters are more useful if fine control is required.

11. The Density (or Concentration) of a bioPool is the result of multiple interactions and is represented as a differential equation in the present embodiment. Alternatively, it could be represented as a discrete-time linear system or a continuous-time linear system of equations, or whenever the Shell is able to handle vectors, as their equivalent matrix system. Difference or differential equations can be converted to state form, and the state variables of the system are them described as a state vector, the coefficients of the variables are described as a system matrix and the forcing terms are described as the forcing vector, following standard procedures.

Appendix

TABLE 1

I. Group of schematicTools
  A. Class bioObject
    Class bioView-Object
    Class bioReservoir
    Class bioProcess
    Class bioModel
    Class bioRole-Object
      Class bioReactant
      Class bioProduct
    Class bioNode-Object
      Class bioPool
        Class sol-mol-pool
        Class bound-mol-pool
          Class membr-bound-mol-pool
      Class bioEngine
    Class bioEntity
      (see subclasses in TABLE 62)
  C. Class bioPost
    Class bioPool-Post
      Class bioPool-R-Post
      Class bioPool-P-Post
    Class bioRole-Post
      Class bioReactant-Post
      Class bioProduct-Post
  B. Class bioConnection
    Class P-connection
    Class R-connection
    Class Link
    Class Line
    Class Graph-Link
    Class Icon-Wire II. User Interface Tools
  A. Class Button
    Class Graph-Tracer
      Class scaled-BR-graphTracer
      Class absolute-BR-graphTracer
      Class scaled-BP-graphTracer
    Class Lists-Tracer
      Class BR-chaining-Tracer
      Class BP-chaining-Tracer
      Class Query-Tracer
      Class Basal-density-source-Tracer
      Class BR-scroll-Tracer
    Class Path-Tracer
      Class Down-path-Tracer
      Class Up-path-Tracer
      Class Complex-path-Tracer Class Action-Button
      Class go-to-sw-Button
      Class paletteButton
      Class go-to-ws-Button
      Class hide-ws-Button
      Class go-to-sup-obj-Button
      Class Change-Mode-Button
      Class Resize-Button
  B. Other bioTools
    Class bioReference
    Class Model-box
    Class Model-block
    Class Experiment-Selection
    Class bioEntity-Notes
    ...
  C. Group of Panels
    Selection-Panel
    Query-Panel
    Entry-Panel
    ...
  D. Group of User.Controls
    Class Toggle-Buttom
    Class Radio-Buttom
    Class Check-Box
    Class Type-in-Box
  E. Group of Displays
    Class Graph
    Class Scroll Area
    Class Message
    ...

III. Group of variableStructures
    Group of Parameters
    Group of Variables
    Class Lists
    Class Array IV. Group of Inference and
    Simulation Structures
    Class Relation
    Class Rule
    Class Tabular-Function
    Class Generic-Formula
    Class Generic-Simulation-Formula
    Class Specific-Formula
    Class Specific-Simulation-Formula
    Class Units-of-Measure-Declaration
    Class User-Menu-Choice
    Class Procedure

TABLE 2

| | |
|---|---|
| Class name | bio-object |
| Superior class | object |
| Attributes specific to class | label is "", with an index: description is "" |
| Class restrictions | unless in administrator, developer, or modeler mode: menu-choices exclude additionally: move-object, rotate-reflect |
| Menu option | not a final menu choice |
| Icon description | bio-object-pattern |
| | |
| Class name | bionode-object |
| Superior class | bio-object |
| Attributes specific to class | none |
| Menu option | not a final menu choice |
| Icon description | inherited |
| | |
| Class name | bioview-object |
| Superior class | bio-object |
| Attributes specific to class | references is ""; warnings is ""; toggle-state has values show or hide (default is HIDE), with an index |
| Menu option | not a final menu choice |
| Icon description | inherited |

TABLE 3 an user-menu-choice

| | |
|---|---|
| Label | details |
| Applicable class | bio-view-object |
| Condition | none |
| Action | start GO-TO-VIEW-PROC (the item, this window) |

GO-TO-VIEW-PROC (VO: class bioview-object,
  win: class window)

view = the SW of bVO;
  case the toggle-state of VO is
    hide:
      conclude that the toggle-state of bVO is show;
      change the size of view to minimum;
      show the SW of VO on win at the center of the screen;
    show:
      conclude that the toggle-state of VO is hide;
      hide the SW of VO on win

TABLE 4

CONNECTION DEFINITIONS

| | |
|---|---|
| Class name | icon-wire |
| Superior class | connection |
| Attributes specific to class | none |
| Inherited attributes | none |
| Cross section pattern | core = gray; 2 core |
| Stub length | 6 |

| | |
|---|---|
| Class name | link |
| Superior class | connection |
| Attributes specific to class | none |
| Inherited attributes | none |
| Cross section pattern | core = coral, cover = green; 1 cover, 1 core |
| Stub length | 6 |

| | |
|---|---|
| Class name | line |
| Superior class | connection |
| Attributes specific to class | none |
| Inherited attributes | none |
| Cross section pattern | core = medium-blue; 1 core |
| Stub length | 6 |

| | |
|---|---|
| Class name | graph-link |
| Superior class | connection |
| Attributes specific to class | none |
| Inherited attributes | none |
| Cross section pattern | core = gray; 1 core |
| Stub length | 6 |

| | |
|---|---|
| Class name | cycle-path |
| Superior class | connection |
| Attributes specific to class | none |
| Inherited attributes | none |
| Cross section pattern | core = violet-red, cover = forest-green; 2 cover, 2 core, 2 cover |
| Stub length | 6 |

| | |
|---|---|
| Class name | p-connection |
| Superior class | connection |
| Attributes specific to class | none |
| Inherited attributes | none |
| Cross section pattern | core = dim-gray, cover = green; 1 cover, 2 core, 1 cover |
| Stub length | 8 |

| | |
|---|---|
| Class name | r-connection |
| Superior class | connection |
| Attributes specific to class | none |
| Inherited attributes | none |
| Cross section pattern | core = red, cover = dim-gray; 2 cover, 2 core, 2 cover |
| Stub length | 8 |

| | |
|---|---|
| Class name | s-connection |
| Superior class | r-connection |
| Attributes specific to class | none |
| Inherited attributes | none |
| Cross section pattern | core = red, cover = blue; 2 cover, 2 core, 2 cover |
| Stub length | 8 |

| | |
|---|---|
| Class name | model-box-connection |
| Superior class | connection |
| Attributes specific to class | none |
| Inherited attributes | none |
| Cross section pattern | core = red, cover = green; 2 cover, 2 core |
| Stub length | 8 |

TABLE 5

| | |
|---|---|
| Class name | biopost |
| Superior class | connection-post |
| Attributes specific to class | toggle-state has values show or hide (default is HIDE), with an index |
| Class restrictions | unless in administrator or developer mode: attributes visible exclude additionally: superior-connection, toggle-state |
| Menu option | not a final menu choice |
| Inherited attributes | none |
| Stubs | inherited |
| Icon description | inherited |

TABLE 6

| | |
|---|---|
| Class name | biotool |
| Superior class | object |
| Attributes specific to class | none |
| Menu option | not a final menu choice |
| Inherited attributes | none |

TABLE 7

| | |
|---|---|
| Class name | button |
| Superior class | biotool |
| Attributes specific to class | toggle-state has values show or hide (default is HIDE) |
| Inherited attributes | none |
| Icon description | button-pattern (width 22; height 22; dark-color = dim-gray, light-color = light-gray) |

TABLE 8

| | |
|---|---|
| Class name | action-button |
| Superior class | button |
| Attributes specific to class | label; state has values enabled or disabled; action-proc-name; |
| Class restrictions | unless in administrator mode: selecting any action-button implies select; unless in administrator, developer, or modeler mode: non-menu choices exclude additionally: move-object |
| Inherited attributes | toggle-state has values show or hide (default is HIDE), with an index |
| Icon description | inherited |

TABLE 9

| | |
|---|---|
| | an user-menu-choice |
| Label | select |
| Applicable class | action-button |
| Condition | the state of the item is enabled |
| Action | start BUTTON-HANDLER-CALLBACK (the item, this window) |

BUTTON-HANDLER-CALLBACK (button: class action-button, win : class window)
    start the procedure named by the action-proc-name of button (button, win);
    change the color-pattern of button so that light-color is light-gray, dark-color is dim-gray ;
    conclude that the toggle-state of button is show;
    if button has a face-color FC then change FC to gray

TABLE 10

| | |
|---|---|
| Class name | go-to-SW-button |
| Superior class | action-button |
| Attributes specific to class | action-proc-name is GO-TO-SW-CALLBACK |
| Icon description | go-to-SW-button-pattern |

GO-TO-SW-CALLBACK (button: class action-button, win: class window)
    show the SW of button on win at the center of the screen;
    hide the workspace of button on win;

TABLE 11

| | |
|---|---|
| Class name | go-to-sup-obj-button |
| Superior class | action-button |
| Attributes specific to class | action-proc-name is GO-TO-SUP-OBJ-CALLBACK |
| Icon description | go-to-sup-obj-button-pattern |

GO-TO-SUP-OBJ-CALLBACK (button: class go-to-sup-obj-button, win: class window)
    show the WS of the object superior to the workspace of button on win at the center of the screen;

TABLE 12

---
Class name                     hide-sup-ws-button
Superior class                 action-button
Attributes specific to class   action-proc-name is HIDE-SUP-WS-
                                 CALLBACK
Icon description               hide-sup-ws-button-pattern
---

HIDE-SUP-WS-CALLBACK (button: class action-button, win: class window)
   WS = the workspace of button;
   OBJ = the object superior to WS;
   change the size of WS to minimum;
   hide WS on win;
   if the user-mode of win is not simulation then:
      if OBJ is a bioprocess then:
         change the status-color of OBJ to slate-blue
      else if OBJ is a bioreservoir then:
         change the status-color of OBJ to medium-aquamarine;
   if the toggle-state of OBJ is show then conclude that the
      toggle-state of OBJ is hide;

TABLE 13

---
Class name                     go-to-ws-button
Superior class                 action-button
Attributes specific to class   obj-w-sw-name;
                               action-proc-name is GO-TO-WS-CALLBACK
Icon description               go-to-ws-button-pattern
--- a go-to-ws-button

Names            none
Toggle state     hide
Label            none
State            enabled
Action proc name GO-TO-WS-CALLBACK
Obj w sw name    none ---
GO-TO-WS-CALLBACK (button: class go-to-ws-button, win: class window )
   OBJ = the object named by the obj-w-sw-name of button;
   if OBJ is a workspace then
      show OBJ on win;
   else
      show the subworkspace of OBJ on win
   hide the workspace of button on win;

TABLE 14

---
Class name                     go-to-and-activ-sw-buttom
Superior class                 action-button
Attributes specific to class   action-proc-name is GO-TO-AND-ACT-
                                 SW-CALLBACK
Capabilities and restrictions  activatable-subworkspace
Icon description               go-to-and-activ-sw-buttom-pattern
---

GO-TO-AND-ACT-SUBWS-CALLBACK (button: class action-button, win: class window)
   activate the SW of button;
   show the SW of button on win at the center of the screen

TABLE 15

| | |
|---|---|
| Class name | go-to-and-activate-ws-button |
| Superior class | go-to-ws-button |
| Attributes specific to class | action-proc-name is GO-TO-AND-ACTIVATE-WS-CALLBACK |
| Icon description | go-to-and-activate-ws-button-pattern |

GO-TO-AND-ACTIVATE-WS-CALLBACK (button: class button, win: class window)
  OBJ = the object named by the obj-w-sw-name of button;
  if OBJ is a workspace then
    activate the SW of the object superior to OBJ ;
    show OBJ on win;
  else
    activate the SW of OBJ;
    show the SW of OBJ on win

TABLE 16

| | |
|---|---|
| Class name | hide-and-deact-sup-ws-button |
| Superior class | action-button |
| Attributes specific to class | action-proc-name is HIDE-AND-DEACT-SUP-WS-CALLBACK |
| Icon description | hide-and-deact-sup-ws-button-pattern |

HIDE-AND-DEACT-SUP-WS-CALLBACK (button: class hide-and-deact-sup-ws-button, win: class window )

WS = the workspace of button;
  change the size of WS to minimum;
  hide WS on win;
  deactivate the subworkspace of the object superior to WS;

TABLE 17

| | |
|---|---|
| Class name | time-button |
| Superior class | action-button |
| Attributes specific to class | action-proc-name is SHOW-SW-CALLBACK |
| Icon description | time-button-pattern (width 30; height 30) |

DEACTIVATE-BUTTON-CALLBACK (button: class action-button)
  change the color-pattern of button so that light-color is light-gray, dark-color is light-gray;

TABLE 18

| | |
|---|---|
| Class name | change-mode-button |
| Superior class | action-button |
| Attributes specific to class | action-proc-name is CHANGE-MODE-CALLBACK; |
| | mode has values administrator, developer, modeler, explorer, simulation, default is MODELER |
| Icon description | change-mode-button-pattern |

```
CHANGE-MODE-CALLBACK (button: class change-mode-button, win
 : class window)
    mode = the mode of button;
    call CHANGE-MODE-PROC (mode, win);
    for each change-mode-button B upon the workspace of button do
        change the color-pattern of B so that face is forest-green;
    change the color-pattern of button so that face is green;
    return;

CHANGE-MODE-PROC (mode: symbol, win : class window)
    if the text of the g2-user-mode of win /= "simulation" and mode
            is simulation then
        inform the operator that "The subworkspaces of all
            bioReservoirs and all bioProcesses will be deactivated";
        for BR = each bioreservoir do
            allow other processing;
            if the subworkspace of BR exists then
                deactivate the subworkspace of BR;
                change the status-color icon-color of BR to aquamarine ;
        inform the operator that "The subworkspaces of all bioReservoirs
                have been deactivated";
        for BP = each bioprocess do
            allow other processing;
            if the subworkspace of BP exists then
                deactivate the subworkspace of BP;
                change the status-color icon-color of BP to aquamarine ;
        inform the operator that "The subworkspaces of all
            bioProcesses have been deactivated";
    else
    if the text of the g2-user-mode of win = "simulation" and mode
            is not simulation then
        inform the operator that "The subworkspaces of all
            bioReservoirs and all bioProcesses will be activated";
        for BR = each bioreservoir do
            allow other processing;
            if the subworkspace of BR exists then
                activate the subworkspace of BR;
        inform the operator that "The subworkspaces of all
            bioReservoirs have been activated";
        for BP = each bioprocess do
            allow other processing;
            if the subworkspace of BP exists then
                activate the subworkspace of BP;
        inform the operator that "The subworkspaces of all
            bioProcesses have been activated";
    case (mode) of
    administrator:
        change the text of the g2-user-mode of win to "administrator";
    developer:
        change the text of the g2-user-mode of win to "developer";
    modeler:
        change the text of the g2-user-mode of win to "modeler";
    general :
        change the text of the g2-user-mode of win to "general";
    navigation :
        change the text of the g2-user-mode of win to "navigation";
    simulation:
        change the text of the g2-user-mode of win to "simulation"
```

TABLE 19

---
| | |
|---|---|
| Class name | resize-button |
| Superior class | action-button |
| Attributes specific to class | action-proc-name is CRB-SCALE-WS-CALLBACK; |
| | scale has values one-quarter, half, three-quarter, or full (default is FULL) |
| Icon description | resize-button-pattern (width 25; heighth 25; dark-color = dim-gray; light-color = light-gray, face-color = forest-green) |

--- a resize-button

| | |
|---|---|
| Names | none |
| Toggle state | hide |
| Label | "full" |
| State | enabled |
| Action proc name | CRB-SCALE-WS-CALLBACK |
| Scale | full |

---

CRB-SCALE-WS-CALLBACK (button: class resize-button, win : class window)

case the scale of button is
        one-quarter: show the workspace of button at one-quarter scale with
            its bottom right corner at the bottom right corner of the screen;
        half: show the workspace of button at half scale with its bottom right
            corner at the bottom right corner of the screen;
        three-quarter: show the workspace of button at three-quarter scale with
            its bottom right corner at the bottom right corner of the screen ;
        full: show the workspace of button at full scale with its bottom right
            corner at the bottom right corner of the screen;
        otherwise : return;

TABLE 20

| | |
|---|---|
| Class name | lists-tracer |
| Superior class | button |
| Attributes specific to class | none |
| Class restrictions | unless in administrator or developer mode: selecting any lists-tracer implies show; non-menu choices exclude additionally: move-object; |
| Menu option | not a final menu choice |
| Stubs | inherited |
| Icon description | lists-tracer-pattern (width 14; height 21) |
| Class name | bp-chaininig-tracer |
| Superior class | lists-tracer |
| Attributes specific to class | none |
| Menu option | a final menu choice |
| Icon description | bp-chaininig-tracer-pattern |
| Class name | br-chaininig-tracer |
| Superior class | lists-tracer |
| Attributes specific to class | none |
| Menu option | a final menu choice |
| Icon description | br-chaininig-tracer-pattern (width 14; height 20) |
| Class name | basal-density-source-tracer |
| Superior class | lists-tracer |
| Attributes specific to class | none |
| Stubs | inherited |
| Icon description | basal-density-source-tracer-pattern (width 24; height 24) |
| Class name | br-scroll-tracer |
| Superior class | lists-tracer |
| Attributes specific to class | none |
| Menu option | a final menu choice |
| Icon description | br-chaininig-tracer-pattern (width 116; height 30) |
| Class name | query-tracer |
| Superior class | lists-tracer |
| Attributes specific to class | none |
| Class restrictions | unless in administrator or developer mode: selecting any query-tracer implies show; non-menu choices exclude additionally: move-object; |
| Menu option | not a final menu choice |
| Stubs | inherited |
| Icon description | lists-tracer-pattern (width 14; height 21) |

TABLE 21

```
                an user-menu-choice
Label           show
Applicable class lists-tracer
Condition       none
Action          start LIST-TRACER-HANDLER-PROC (the item,
                this window)
```

LIST-TRACER-HANDLER-PROC (tracer: class lists-tracer, win: class window)

```
if the toggle-state of tracer is hide then
   case the class of tracer is
      bp-chaininig-tracer:
         call BP-CHAINING-PROC (the bioprocess superior to the WS
            of tracer, win);
      br-chaininig-tracer :
         call BR-CHAINING-PROC (the bioreservoir superior to the WS
            of tracer, win);
      br-scroll-tracer:
         call BR-SCROLL-PROC (tracer, win);
   else if the toggle-state of tracer is show and the SW of tracer exists then
      delete the subworkspace of tracer;
call CONFIGURE-LISTS-TRACER-PROC (tracer, win);
return
```

CONFIGURE-LISTS-TRACER-PROC (tracer: class lists-tracer, win: class window )

```
case the toggle-state of tracer is
   hide:
      change the color-pattern of tracer so that light-color is dim-gray,
         dark-color is light-gray , white-color = the symbol black;
      conclude that the toggle-state of tracer is show;
   show:
      change the color-pattern of tracer so that light-color is light-gray,
         dark-color is dim-gray , white-color = the symbol white;
      conclude that the toggle-state of tracer is hide;
return
```

TABLE 22

| | |
|---|---|
| Class name | path-tracer |
| Superior class | button |
| Attributes specific to class | none |
| Class restrictions | unless in administrator or developer mode: selecting any c-path-tracer implies show |
| Menu option | not a final menu choice |
| Inherited attributes | toggle-state has values show or hide (default is HIDE), with an index |
| Attribute displays | inherited |
| Stubs | inherited |
| Icon description | path-tracer-pattern (width 14; height 21) |
| Class name | down-path-tracer |
| Superior class | path-tracer |
| Attributes specific to class | none |
| Menu option | a final menu choice |
| Inherited attributes | toggle-state has values show or hide (default is HIDE), with an index |
| Stubs | inherited |
| Icon description | down-path-tracer-pattern |
| Class name | up-path-tracer |
| Superior class | path-tracer |
| Attributes specific to class | none |
| Menu option | a final menu choice |
| Inherited attributes | toggle-state has values show or hide (default is HIDE), with an index |
| Stubs | inherited |
| Icon description | up-path-tracer-pattern (width 14; height 20) |
| Class name | navig-path-tracer |
| Superior class | path-tracer |
| Attributes specific to class | none |
| Menu option | a final menu choice |
| Inherited attributes | toggle-state has values show or hide (default is HIDE), with an index |
| Stubs | inherited |
| Icon description | up-path-tracer-pattern (width 14; height 20) |

TABLE 23

---
an user-menu-choice
Label             show
Applicable class  path-tracer
Condition         none
Action            start PATH-TRACER-HANDLER-PROC (the item,
                  this window )
---

PATH-TRACER-HANDLER-PROC (tracer: class path-tracer , win: class window)
  if the toggle-state of tracer is hide then
    if the subworkspace of tracer exists then
      case the class of tracer is
        up-path-tracer:
          call DRAW-UP-PATHWAY-PROC (tracer, win);
        down-path-tracer :
          call DRAW-DOWN-PATHWAY-PROC (tracer, win);
        complex-down-path-tracer :
          call DRAW-COMPLEX-DOWN-PATHWAY-PROC (tracer,
            win);
      return;
    call CONFIGURE-PATH-TRACER-PROC (tracer, win);
    return;
  if the toggle-state of tracer is show then
    if the SW of tracer exists then hide the SW of tracer;
    call CONFIGURE-PATH-TRACER-PROC (tracer, win);
  return

---

CONFIGURE-PATH-TRACER-PROC (tracer: class path-tracer, win: class window )
  case the toggle-state of tracer is
    hide:
      change the color-pattern of tracer so that light-color is dim-gray,
        dark-color is light-gray , white-color = the symbol black;
      conclude that the toggle-state of tracer is show;
    show:
      change the color-pattern of tracer so that light-color is light-gray,
        dark-color is dim-gray, white-color = the symbol white;
      conclude that the toggle-state of tracer is hide;
  return

---

TABLE 24

| | |
|---|---|
| Class name | graph-tracer |
| Superior class | button |
| Attributes specific to class | none |
| Class restrictions | when in simulation or developer mode: selecting any graph-tracer implies show-plot; |
| Menu option | not a final menu choice |
| Inherited attributes | toggle-state has values show or hide (default is HIDE), with an index |
| Icon description | graph-tracer-pattern (width 14; height 20) |
| Class name | scaled-br-graph-tracer |
| Superior class | graph-tracer |
| Attributes specific to class | none |
| Icon description | scaled-br-graph-tracer-pattern (width 14; height 20) |
| Class name | absolute-br-graph-tracer |
| Superior class | graph-tracer |
| Attributes specific to class | none |
| Icon description | absolute-br-graph-tracer-pattern (width 14; height 21) |
| Class name | scaled-bp-graph-tracer |
| Superior class | graph-tracer |
| Attributes specific to class | none |
| Icon description | scaled-bp-graph-tracer-pattern (width 14; height 20) |

TABLE 25

---
|  | an user-menu-choice |
| --- | --- |
| Label | show-plot |
| Applicable class | graph-tracer |
| Condition | the user-mode of this window is simulation or the user-mode of this window is developer |
| Action | start TRANSF-GRAPH-TRACER-HANDLER-PROC (the item, this window) |

---

TRANSF-GRAPH-TRACER-HANDLER-PROC (tracer: class graph-tracer, win: class window )

call CONFIGURE-GRAPH-TRACER-PROC (tracer, win):
   if the toggle-state of tracer is hide then:
     if the SW of tracer exists then
       make the SW of tracer transient;
       delete the SW of tracer;
     case the class of tracer is
       scaled-br-graph-tracer:
          call SCALED-BR-TRANSF-GRAPH-PROC (tracer, win):
       scaled-bp-graph-tracer:
          call SCALED-BP-TRANSF-GRAPH-PROC (tracer, win);
       absolute-br-graph-tracer:
          call ABSOLUTE-BR-TRANSF-GRAPH-PROC (tracer, win);
   else if the toggle-state of tracer is show then
     delete the SW of tracer;
   return

---

CONFIGURE-GRAPH-TRACER-PROC (tracer: class c-graph-tracer , win: class window )

case the toggle-state of tracer is
   show:
     change the color-pattern of tracer so that light-color is dim-gray ,
       dark-color is light-gray , white-color = the symbol black;
     conclude that the toggle-state of tracer is hide;
   hide:
     change the color-pattern of tracer so that light-color is light-gray,
       dark-color is dim-gray , white-color = the symbol white;
     conclude that the toggle-state of tracer is show;
   return

TABLE 26

| | |
|---|---|
| Class name | bioentity-notes |
| Superior class | biotool |
| Attributes specific to class | label is "", with an index;<br>toggle-state has values show or hide (default is HIDE) |
| Class restrictions | unless in administrator or developer mode: selecting any bioentity-notes implies details |
| Menu option | a final menu choice |
| Inherited attributes | none |
| Attribute displays | label offset by (-42, 20) |
| Icon description | bioentity-notes-pattern (width 74; height 48; dark-color = dim-gray, light-color = light-gray, white-color = white; |
| Class name | mol.sequence |
| Superior class | bioentity-notes |
| Attributes specific to class | label is "", with an index;<br>lenght is "";<br>description is "";<br>references is "";<br>id, with an index;<br>action-proc-name is crb-go-to-subws;<br>toggle-state has values show or hide (default is HIDE), with an index |
| Icon description | mol.sequence-pattern |
| Class name | function.notes |
| Superior class | bioentity-notes |
| Attributes specific to class | label is "", with an index;<br>references is "";<br>toggle-state has values show or hide (default is HIDE), with an index |
| Icon description | function.notes-pattern |
| Class name | reference.notes |
| Superior class | bioentity-notes |
| Attributes specific to class | none |
| Icon description | reference.notes-pattern |
| Class name | dendrogram |
| Superior class | bioentity-notes |
| Attributes specific to class | label is "Dendrogram";<br>references is "";<br>comments is "" |
| Icon description | dendrogram-pattern |

TABLE 27

| | |
|---|---|
| | an user-menu-choice |
| Label | details |
| Applicable class | bioentity-notes |
| Condition | none |
| Action | start BIOENTITY-NOTES-HANDLER (the item, this window) |

BIOENTITY-NOTES-HANDLER (BN: class bioentity-notes, W : class window)
SW = the subworkspace of BN;
if the toggle-state of BN is hide then
    conclude that the toggle-state of BN is show;
    show SW at the center of the screen;
else
if the toggle-state of BN is show then
    conclude that the toggle-state of BN is hide;
    hide the subworkspace of BN on W

TABLE 28

| | |
|---|---|
| Class name | bio-object-title |
| Superior class | biotool |
| Attributes specific to class | label is "long.name.of.biomodel" |
| Capabilities and restrictions | none |
| Class restrictions | unless in administrator or developer mode: menu choices exclude additionally: delete, transfer, name, disable, describe, create-subworkspace |
| Attribute displays | label offset by (-72, -7) |
| Icon description | bio-object-title-pattern (width 130; height 2) |
| Class name | experiment-selection |
| Superior class | biotool |
| Attributes specific to class | label is ""; ref-bioreservoir; amount-entry is 0.0; factor-entry is 0.0; time-entry is 0 seconds; currently-selected has values true or false (default is FALSE), with an index |
| Class restrictions | unless in administrator, developer, or modeler mode: selecting any experiment-selection implies table |
| Attribute displays | label offset by (-37, 12) |
| Icon description | experiment-selection-pattern (width 70; height 40; dark-color = dim-gray, light-color = light-gray, type-color = goldenrod, white-color = white |
| Class name | reference-block |
| Superior class | biotool |
| Attributes specific to class | id, with an index; short-ref is "", with an index; unique-identifier, with an index; author-s is "Smith AB. Morris AD. "; title is ""; institution is "Dept, Institution, Country"; journal is "Journal Full Name Ref"; abstract is "" |
| Capabilities and restrictions | none |
| Class restrictions | unless in administrator, developer, or modeler mode: menu choices exclude additionally: transfer, name, rotate-reflect, change-size, disable, describe; attributes visible for cabe-reference exclude additionally: user-restrictions, names, id; selecting any cabe-reference implies table |
| Attribute displays | short-ref offset by (8, 14) |
| Icon description | reference-pattern (width 27; height 35; yellow; dark-slate-blue) |

TABLE 29

| | |
|---|---|
| Class name | entry-panel |
| Superior class | uil-tailored-dialog |
| Attributes specific to class | id is "", with an index; related-item is none; current-simulation-time is given by an elapsed-simul-time-par; current-simulation-time-increment is given by an elapsed-simul-time-par |
| Capabilities and restrictions | none |
| Menu option | a final menu choice |
| Inherited attributes | several proprietary |
| Attribute displays | none |
| Stubs | none |
| Icon description | entry-panel (width 80; height 100; dark-color = dim-gray, light-color = light-gray, white-color = white) |
| Class name | query-panel |
| Superior class | uil-tailored-dialog |
| Attributes specific to class | id is "", with an index; related-item is none |
| Capabilities and restrictions | none |
| Menu option | a final menu choice |
| Inherited attributes | several proprietary |
| Attribute displays | none |
| Stubs | none |
| Icon description | entry-panel (width 80; height 100; dark-color = dim-gray, light-color = light-gray, white-color = white) |

TABLE 30

| | |
|---|---|
| | a message definition |
| Class name | cabe-reference-message |
| Superior class | message |
| Attributes specific to class | none |
| Inherited attributes | none |
| Default message properties | none |
| | a message definition |
| Class name | sequence-display |
| Superior class | message |
| Attributes specific to class | id, with an index; label is "" |
| Inherited attributes | none |
| Default message properties | minimum-with is 100; text-color is transparent; background color is foreground |

TABLE 31

| | |
|---|---|
| Class name | int-par |
| Superior class | integer-parameter |
| Attributes specific to class | none |
| Inherited attributes | none |
| Default settings | options for parameter: do forward chain |
| Icon description | width 40; height 40; |

| | |
|---|---|
| Class name | time-delay-par |
| Superior class | int-par |
| Attributes specific to class | none |
| Default settings | data type for quantitative-parameter: seconds; initial value for integer-parameter: 0 |

| | |
|---|---|
| Class name | elapsed-simul-time-par |
| Superior class | int-par |
| Attributes specific to class | none |
| Default settings | data type for quantitative-parameter: seconds |

| | |
|---|---|
| Class name | x-pos |
| Superior class | int-par |
| Attributes specific to class | none |
| Default settings | none |
| Attribute displays | last-recorded-value at standard position |
| Icon description | width 50; height 18; |

| | |
|---|---|
| Class name | y-pos |
| Superior class | int-par |
| Attributes specific to class | none |
| Default settings | none |
| Attribute displays | last-recorded-value at standard position |
| Icon description | width 50; height 18; |

| | |
|---|---|
| | a x-pos |
| Options | do forward chain |
| Names | none |
| Tracing and breakpoints | default |
| Data type | integer |
| Initial value | 0 |
| Last recorded value | 0 |
| History keeping spec | do not keep history |

TABLE 32

| | |
|---|---|
| Class name | float-par |
| Superior class | float-parameter |
| Attributes specific to class | none |
| Inherited attributes | none |
| Default settings | options for parameter: do forward chain; initial value for float-parameter: 0.0 |
| Icon description | width 40; height 40; |
| Class name | temperature-par |
| Superior class | float-par |
| Attributes specific to class | none |
| Default settings | initial value for float-parameter: 37.0; data type for quantitative-parameter: degrees |
| Class name | temp-factor-par |
| Superior class | float-par |
| Attributes specific to class | none |
| Default settings | initial value for float-parameter: 1.0 |
| Class name | pH-par |
| Superior class | float-par |
| Attributes specific to class | none |
| Default settings | initial value for float-parameter: 7.4 |
| Class name | pH-factor-par |
| Superior class | float-par |
| Attributes specific to class | none |
| Default settings | initial value for float-parameter: 1.0 |
| Class name | bias-par |
| Superior class | float-par |
| Attributes specific to class | none |
| Default settings | initial value for float-parameter: 0.0 |
| Class name | alpha-coeff-par |
| Superior class | float-par |
| Attributes specific to class | none |
| Default settings | initial value for float-parameter: 1.0 |
| Class name | tau-coeff-par |
| Superior class | float-par |
| Attributes specific to class | none |
| Default settings | initial value for float-parameter: 1.0 |

TABLE 33

| | |
|---|---|
| Class name | physiol-amount-par |
| Superior class | float-par |
| Attributes specific to class | none |
| Inherited attributes | none |
| Default settings | initial value for float-parameter: 9.9e-99 |

| | |
|---|---|
| Class name | physiol-conc-par |
| Superior class | physiol-amount-par |
| Attributes specific to class | none |
| Inherited attributes | none |
| Default settings | data type for quantitative-parameter: molar |

| | |
|---|---|
| Class name | physiol-quantity-par |
| Superior class | physiol-amount-par |
| Attributes specific to class | none |
| Default settings | none |

| | |
|---|---|
| Class name | basal-amount-par |
| Superior class | float-par |
| Attributes specific to class | none |
| Default settings | initial value for float-parameter: 9.9e-99 |

| | |
|---|---|
| Class name | basal-conc-par |
| Superior class | basal-amount-par |
| Attributes specific to class | none |
| Default settings | data type for quantitative-parameter: m |

| | |
|---|---|
| Class name | basal-quantity-par |
| Superior class | basal-amount-par |
| Attributes specific to class | none |
| Default settings | data type for quantitative-parameter: units |

| a physiol-conc-par | |
|---|---|
| Options | do forward chain |
| Names | none |
| Tracing and breakpoints | default |
| Data type | molar |
| Initial value | 9.9e-99 |
| Last recorded value | 9.9e-99 M |
| History keeping spec | do not keep history |

TABLE 34

| | |
|---|---|
| Class name | float-pvar |
| Superior class | float-parameter |
| Attributes specific to class | none |
| Inherited attributes | none |
| Default settings | options for parameter: do forward chain |
| Icon description | float-pvar-pattern (width 50; height 40) |

| | |
|---|---|
| Class name | entry-pvar |
| Superior class | float-pvar |
| Attributes specific to class | none |
| Inherited attributes | none |
| Default settings | history keeping spec: keep history with maximum number of data points = 4 |

| | |
|---|---|
| Class name | scaled-entry-pvar |
| Superior class | entry-pvar |
| Attributes specific to class | none |
| Default settings | initial value for quantitative-parameter: 0.0 |

| | |
|---|---|
| Class name | amount-entry-pvar |
| Superior class | entry-pvar |
| Attributes specific to class | none |
| Default settings | initial value for quantitative-parameter: 0.0 |

| | |
|---|---|
| Class name | conc-entry-pvar |
| Superior class | amount-entry-pvar |
| Attributes specific to class | none |
| Default settings | data type for quantitative-parameter: m |

| | |
|---|---|
| Class name | density-entry-pvar |
| Superior class | amount-entry-pvar |
| Attributes specific to class | none |
| Default settings | data type for quantitative-parameter: upcc |

| | |
|---|---|
| Class name | quantity-entry-pvar |
| Superior class | amount-entry-pvar |
| Attributes specific to class | none |
| Default settings | data type for quantitative-parameter: units |

| | |
|---|---|
| Class name | scaled-amount-pvar |
| Superior class | float-pvar |
| Attributes specific to class | none |
| Default settings | initial value for float-parameter: 9.9e-99; history keeping spec: keep history with maximum age of data points = 10 minutes |

TABLE 35

| | |
|---|---|
| Class name | amount-pvar |
| Superior class | float-pvar |
| Attributes specific to class | none |
| Default settings | initial value for float-parameter: 9.9e-99; history keeping spec: keep history with maximum age of data points = 10 minutes |
| Class name | accumulation-pvar |
| Superior class | amount-pvar |
| Attributes specific to class | none |
| Default settings | data type for quantitative-parameter: m |
| Class name | conc-pvar |
| Superior class | amount-pvar |
| Attributes specific to class | none |
| Default settings | data type for quantitative-parameter: m |
| Class name | density-pvar |
| Superior class | amount-pvar |
| Attributes specific to class | none |
| Default settings | data type for quantitative-parameter: upce |
| Class name | quantity-pvar |
| Superior class | amount-pvar |
| Attributes specific to class | none |
| Default settings | data type for quantitative-parameter: units |
| Class name | contribution-pvar |
| Superior class | float-pvar |
| Attributes specific to class | none |
| Default settings | initial value for float-parameter: 9.9e-99; history keeping spec: keep history with maximum age of data points = 10 minutes |

TABLE 36

| | |
|---|---|
| Class name | rate-pvar |
| Superior class | float-pvar |
| Attributes specific to class | none |
| Default settings | initial value for float-parameter: 9.9e-99; history keeping spec: keep history with maximum age of data points = 10 minutes |
| Class name | produc-rate-pvar |
| Superior class | rate-pvar |
| Attributes specific to class | none |
| Default settings | none |
| Class name | consum-rate-pvar |
| Superior class | rate-pvar |
| Attributes specific to class | none |
| Default settings | none |
| Class name | output-rate-pvar |
| Superior class | rate-pvar |
| Attributes specific to class | none |
| Default settings | none |
| Class name | input-rate-pvar |
| Superior class | rate-pvar |
| Attributes specific to class | none |
| Default settings | none |

TABLE 37

| | |
|---|---|
| Class name | velocity-pvar |
| Superior class | float-pvar |
| Attributes specific to class | none |
| Menu option | not a final menu choice |
| Default settings | none |

| | |
|---|---|
| Class name | enzyme-velocity |
| Superior class | velocity-pvar |
| Attributes specific to class | none |
| Inherited attributes | none |
| Menu option | not a final menu choice |
| Default settings | none |

| | |
|---|---|
| Class name | receptor-velocity |
| Superior class | velocity-var |
| Attributes specific to class | none |
| Menu option | not a final menu choice |

| | |
|---|---|
| Class name | complex-formation-velocity |
| Superior class | velocity-pvar |
| Attributes specific to class | none |
| Menu option | not a final menu choice |

| | |
|---|---|
| Class name | complex-dissoc-velocity |
| Superior class | velocity-pvar |
| Attributes specific to class | none |
| Menu option | not a final menu choice |

| | |
|---|---|
| Class name | ion-transport-velocity |
| Superior class | velocity-pvar |
| Attributes specific to class | none |
| Menu option | not a final menu choice |

| | |
|---|---|
| Class name | conform-change-velocity |
| Superior class | velocity-pvar |
| Attributes specific to class | none |
| Menu option | not a final menu choice |

| | |
|---|---|
| Class name | translocation-velocity |
| Superior class | velocity-pvar |
| Attributes specific to class | none |
| Menu option | not a final menu choice |

TABLE 38

---

| | |
|---|---|
| Class name | float-var |
| Superior class | float-variable |
| Attributes specific to class | none |
| Inherited attributes | none |
| Default settings | options for variable: do forward chain, do not backward chain; data server: G2 simulator; validity interval: indefinite; supply simulation-subtable |
| Stubs | inherited |
| Class name | velocity-var |
| Superior class | float-var |
| Attributes specific to class | none |
| Menu option | not a final menu choice |
| Default settings | none |

---

| | |
|---|---|
| Class name | kinetic-parameter-var |
| Superior class | float-var |
| Attributes specific to class | none |
| Menu option | not a final menu choice |
| Default settings | initial value for float-variable: 9.9e-99 |

---

The kinetic-parameter-vars are for use when user-defined specific-simulation-formulas are needed, such as when the kinetic parameter vary at run time as a result of changes in concentration or other factors

---

| | |
|---|---|
| Class name | michaelis-constant-var |
| Superior class | kinetic-parameter-var |
| Attributes specific to class | none |
| Default settings | none |

---

| | |
|---|---|
| Class name | equilibrium-dissociation-constant-var |
| Superior class | kinetic-parameter-var |
| Attributes specific to class | none |
| Default settings | none |

---

| | |
|---|---|
| Class name | equilibrium-association-constant-var |
| Superior class | kinetic-parameter-var |
| Attributes specific to class | none |
| Default settings | none |

---

| | |
|---|---|
| Class name | inhibition-constant-var |
| Superior class | kinetic-parameter-var |
| Attributes specific to class | none |
| Default settings | none |

---

TABLE 39

| | |
|---|---|
| Class name | model-block-var |
| Superior class | float-var |
| Attributes specific to class | none |
| Menu option | a final menu choice |
| Default settings | default update interval: 3 seconds supply simulation subtable: |
| Icon description | inherited |
| Class name | model-block-output-var |
| Superior class | float-var |
| Attributes specific to class | none |
| Default settings | validity interval: indefinite; history keeping spec: keep history with maximum age of data points = 20 minutes; initial value for float-variable: 1.0e-19; default update interval: 3 seconds |
| Attribute displays | inherited |
| Icon description | inherited |
| Class name | graph-transf-var |
| Superior class | float-var |
| Attributes specific to class | none |
| Menu option | a final menu choice |
| Inherited attributes | none |
| Default settings | initial value for float-variable: 0.0; default update interval: 3 seconds; history keeping spec: keep history with maximum age of data points = 10 minutes |
| Attribute displays | inherited |

TABLE 40

| | |
|---|---|
| Class name | transf-factor-var |
| Superior class | float-variable |
| Attributes specific to class | transform is given by a graph-transf-var; ref-variable; label; x is x |
| Inherited attributes | none |
| Default settings | initial value for float-variable: 0.0; default update interval: 3 seconds; history keeping spec: keep history with maximum number of data points = 3 |
| Attribute displays | label offset by (-148, 7); x offset by (-20, 7) last-recorded-value offset by (-10, 6); |
| Icon description | transf-factor-var-pattern (width 320; height 24; edge-color = foreground) |

| | |
|---|---|
| Class name | velocity-transf-factor |
| Superior class | transf-factor-var |
| Attributes specific to class | label is scaled-velocity |
| Icon description | velocity-transf-factor-pattern |

| | |
|---|---|
| Class name | input-transf-factor |
| Superior class | transf-factor-var |
| Attributes specific to class | label is input-rate |
| Icon description | input-transf-factor-pattern |

| | |
|---|---|
| Class name | output-transf-factor |
| Superior class | transf-factor-var |
| Attributes specific to class | label is output-rate |
| Icon description | output-transf-factor-pattern |

| | |
|---|---|
| Class name | accum-transf-factor |
| Superior class | transf-factor-var |
| Attributes specific to class | label is accumulation-rate |
| Icon description | taccum-transf-factor-pattern |

| | |
|---|---|
| Class name | scaled-amount-transf-factor |
| Superior class | transf-factor-var |
| Attributes specific to class | label is scaled-conc |
| Icon description | inherited |

| | |
|---|---|
| Class name | density-transf-factor |
| Superior class | transf-factor-var |
| Attributes specific to class | label is density |
| Icon description | density-transf-factor-pattern |

| | |
|---|---|
| Class name | conc-transf-factor |
| Superior class | transf-factor-var |
| Attributes specific to class | label is concentration |
| Icon description | conc-transf-factor-pattern |

TABLE 41

| | |
|---|---|
| Class name | query-array |
| Superior class | symbol-array |
| Attributes specific to class | major-class; ref-component-class |
| Capabilities and restrictions | none |
| Class restrictions | none |
| Menu option | a final menu choice |
| Inherited attributes | none |
| Default settings | initial values for symbol-array: none |
| Attribute displays | ref-component-class at (-10, -15) |
| Icon description | query-array-pattern (width 38; height 38; medium-orchid, cyan) | a query-array

| | |
|---|---|
| Names | none |
| Array length | 0 |
| Element type | symbol |
| Initial values | none |
| Major class | none |
| Ref component class | none |

TABLE 42

| | |
|---|---|
| Class name | references-array |
| Superior class | text-array |
| Attributes specific to class | none |
| Capabilities and restrictions | none |
| Class restrictions | none |
| Menu option | a final menu choice |
| Inherited attributes | none |
| Default settings | initial values for symbol-array: none |
| Attribute displays | ref-component-class at (-10, -15) |
| Icon description | references-array-pattern (width 38; height 38; violet, cyan) | a query-array

| | |
|---|---|
| Names | none |
| Array length | 0 |
| Element type | text |
| Initial values | "" |

TABLE 43 a float-array

| | |
|---|---|
| Names | none |
| Array length | 0 |
| Element type | float |
| Initial values | 0.0 |

TABLE 44

| | |
|---|---|
| Class name | query-list |
| Superior class | symbol-list |
| Attributes specific to class | lenght is 0; ref-array |
| Capabilities and restrictions | none |
| Class restrictions | none |
| Menu option | a final menu choice |
| Inherited attributes | none |
| Default settings | allow duplicate elements for g2-list: no |
| Attribute displays | ref-array at (-10, -15) |
| Icon description | query-list-pattern (width 36; height 40; salmon; medium-blue) | a query-list

| | |
|---|---|
| Names | none |
| Element type | symbol |
| Allow duplicate elements? | no |
| Lenght | 0 |
| Ref array | none |

TABLE 45

| | |
|---|---|
| Class name | scroll-text-list |
| Superior class | text-list |
| Attributes specific to class | label is scroll-list |
| Class restrictions | unless in administrator or developer mode: selecting any c-scroll-text-list implies describe |
| Default settings | allow duplicate elements for g2-list: no |
| Attribute displays | label offset by (-32, -25) |
| Icon description | inherited | a scroll-text-list

| | |
|---|---|
| Names | none |
| Element type | text |
| Allow duplicate elements? | no |
| Label | scroll-list |

TABLE 46

| | |
|---|---|
| Class name | bioitem-list |
| Superior class | item-list |
| Attributes specific to class | none |
| Class restrictions | unless in administrator or developer mode: selecting any c-item-list implies describe |
| Inherited attributes | none |
| Default settings | none |
| Icon description | bioitem-list-pattern (width 36; height 40; aquamarine, slate-blue) |

| | |
|---|---|
| Class name | experiment-selections-list |
| Superior class | bioitem-list |
| Attributes specific to class | label is "Exper. Selections" |
| Default settings | allow duplicate elements for g2-list: no; element type for item-list: experiment-selection |
| Attribute displays | label offset by (-65, -26) |
| Icon description | experiment-selections-list-pattern (width 36; height 40; goldenrod, slate-blue) | an experiment-selections-list

| | |
|---|---|
| Names | none |
| Element type | experiment-selection |
| Allow duplicate elements? | no |
| Label | "Exper. Selections" |

TABLE 47

| | |
|---|---|
| Class name | bioreservoirs-list |
| Superior class | bioitem-list |
| Attributes specific to class | list-is-completed has values true or false (default is FALSE); label |
| Inherited attributes | none |
| Default settings | element type for item-list: bioreservoir; allow duplicate elements for g2-list: no |
| Icon description | c-item-list-pattern (width 36; height 40; pale-green, medium-aquamarine) |

| | |
|---|---|
| Class name | downstream-bioreservoirs-list |
| Superior class | bioreservoirs-list |
| Attributes specific to class | label is "DBRL" |
| Default settings | none |
| Attribute displays | label offset by (-26, -25) |

| | |
|---|---|
| Class name | upstream-bioreservoirs-list |
| Superior class | bioreservoirs-list |
| Attributes specific to class | label is "UBRL" |
| Default settings | none |
| Attribute displays | label offset by (-26, -25) |

| | |
|---|---|
| Class name | down-br-simulation-list |
| Superior class | bioreservoirs-list |
| Attributes specific to class | label is "DBRL" |
| Default settings | none |
| Attribute displays | label offset by (-26, -26) |

| | |
|---|---|
| Class name | up-br-simulation-list |
| Superior class | bioreservoirs-list |
| Attributes specific to class | label is "UBRL" |
| Default settings | none |
| Attribute displays | label offset by (-26, -26) |

| | |
|---|---|
| Class name | downstream-br-simulation-list |
| Superior class | bioreservoirs-list |
| Attributes specific to class | label is "SDBRL" |
| Default settings | none |
| Attribute displays | label offset by (-30, -25) |

| | |
|---|---|
| Class name | bm-downstream-br-simulation-list |
| Superior class | downstream-br-simulation-list |
| Attributes specific to class | none |
| Default settings | none |

| | |
|---|---|
| Class name | upstream-br-simulation-list |
| Superior class | bioreservoirs-list |
| Attributes specific to class | label is "SUBRL" |
| Default settings | none |
| Attribute displays | label offset by (-30, -25) |

| | |
|---|---|
| Class name | bm-upstream-br-simulation-list |
| Superior class | upstream-br-simulation-list |
| Attributes specific to class | none |
| Default settings | none | a bm-upstream-br-simulation-list

| | |
|---|---|
| Names | none |
| Element type | bioreservoir |
| Allow duplicate elements? | no |
| Label | "SUBRL" |
| List is completed | false |

TABLE 48

| | |
|---|---|
| Class name | user-bc-br-list |
| Superior class | bioreservoirs-list |
| Attributes specific to class | label is "User-BC" |
| Default settings | none |
| Attribute displays | label offset by (-26, -24) |

| | |
|---|---|
| Class name | nbc-bc-br-list |
| Superior class | bioreservoirs-list |
| Attributes specific to class | label is "NBC-BC" |
| Default settings | none |
| Attribute displays | label offset by (-26, -24) |

| | |
|---|---|
| Class name | nbd-bc-br-list |
| Superior class | bioreservoirs-list |
| Attributes specific to class | label is "NBD-BC" |
| Default settings | none |
| Attribute displays | label offset by (-26, -24) |

| | |
|---|---|
| Class name | pab-bc-br-list |
| Superior class | bioreservoirs-list |
| Attributes specific to class | label is "PAB-BC" |
| Default settings | none |

| | |
|---|---|
| Class name | sba-bc-br-list |
| Superior class | bioreservoirs-list |
| Attributes specific to class | label is "SBA-BC" |
| Default settings | none |
| Attribute displays | label offset by (-26, -24) |

| | |
|---|---|
| Class name | no-bc-br-list |
| Superior class | bioreservoirs-list |
| Attributes specific to class | label is "NO-BC" |
| Default settings | none |
| Attribute displays | label at standard position |

| | |
|---|---|
| Class name | no-sd-br-list |
| Superior class | bioreservoirs-list |
| Attributes specific to class | label is "List of bioReservoirs with default scaling-density" |
| Class restrictions | unless in administrator or developer mode: menu choices include: describe, transfer, delete |
| Default settings | none |
| Attribute displays | label offset by (-45, -25) |

TABLE 19

| | |
|---|---|
| Class name | bioprocesses-list |
| Superior class | bioitem-list |
| Attributes specific to class | list-is-completed has values true or false (default is FALSE); label |
| Default settings | element type for item-list: bioprocess; allow duplicate elements for g2-list: no |
| Icon description | inherited |

| | |
|---|---|
| Class name | downstream-bioprocesses-list |
| Superior class | bioprocesses-list |
| Attributes specific to class | label is "DBPL" |
| Attribute displays | label offset by (-26, -25) |

| | |
|---|---|
| Class name | upstream-bioprocesses-list |
| Superior class | bioprocesses-list |
| Attributes specific to class | label is "UBPL" |
| Attribute displays | label offset by (-26, -25) |

| | |
|---|---|
| Class name | downstream-bp-simulation-list |
| Superior class | bioprocesses-list |
| Attributes specific to class | label is "SDBPL" |
| Attribute displays | label offset by (-30, -25) |

| | |
|---|---|
| Class name | bm-downstream-bp-simulation-list |
| Superior class | downstream-bp-simulation-list |
| Attributes specific to class | ref-biomodel |
| Inherited attributes | label is "SDBPL" |
| Attribute displays | inherited |

| | |
|---|---|
| Class name | upstream-bp-simulation-list |
| Superior class | bioprocesses-list |
| Attributes specific to class | label is "SUBPL" |
| Attribute displays | label offset by (-30, -25) |

| | |
|---|---|
| Class name | bm-upstream-bp-simulation-list |
| Superior class | upstream-bp-simulation-list |
| Attributes specific to class | ref-biomodel |
| Inherited attributes | label is "SUBPL" |
| Default settings | none |

| a bm-upstream-bp-simulation-list | |
|---|---|
| Names | none |
| Element type | bioprocess |
| Allow duplicate elements? | no |
| Label | "SUBPL" |
| List is completed | false |
| Ref biomodel | none |

TABLE 50

---

A-DOWN-BIORESERVOIR-OF, a relation
First class                bioreservoir
Second class               bioprocess
Relation name              a-down-bioreservoir-of
Inverse of relation        an-up-bioprocess-of
Type of relation           many-to-many
Relation is symmetric?     no
a bioreservoir may be a-down-bioreservoir-of more
  than one bioprocess;
a bioprocess may be an-up-bioprocess-of more than
  one bioreservoir

---

A-DOWN-BIOPROCESS-OF, a relation
First class                bioprocess
Second class               bioreservoir
Relation name              a-down-bioprocess-of
Inverse of relation        an-up-bioreservoir-of
Type of relation           many-to-many
Relation is symmetric?     no
a bioprocess may be a-down-bioprocess-of more than
  one bioreservoir;
a bioreservoir may be an-up-bioreservoir-of more
  than one bioprocess

---

A-DOWNSTREAM-BIOPROCESS-OF, a relation
First class                bioprocess
Second class               bioprocess
Relation name              a-downstream-bioprocess-of
Inverse of relation        an-upstream-bioprocess-of
Type of relation           many-to-many
Relation is symmetric?     no
a bioprocess may be a-downstream-bioprocess-of more
  than one bioprocess;
a bioprocess may be an-upstream-bioprocess-of more than
  one bioprocess

---

A-DOWNSTREAM-BIORESERVOIR-OF, a relation
First class                bioreservoir
Second class               bioreservoir
Relation name              a-downstream-bioreservoir-of
Inverse of relation        an-upstream-bioreservoir-of
Type of relation           many-to-many
Relation is symmetric?     no
a bioreservoir may be a-downstream-bioreservoir-of more
  than one bioreservoir;
a bioreservoir may be an-upstream-bioreservoir-of more
  than one bioreservoir

---

TABLE 51

---

THE-UPSTREAM-BIORESERVOIRS-LIST-OF
First class           upstream-bioreservoirs-list
Second class          bioreservoir
Relation name         the-upstream-bioreservoirs-list-of
Inverse of relation   none
Type of relation      one-to-one
Relation is symmetric? no

---

THE-DOWNSTREAM-BIORESERVOIRS-LIST-OF
First class           downstream-bioreservoirs-list
Second class          bioreservoir
Relation name         the-downstream-bioreservoirs-list-of
Inverse of relation   none
Type of relation      one-to-one
Relation is symmetric? no

---

THE-UPSTREAM-BIOPROCESSES-LIST-OF
First class           bioprocesses-list
Second class          bioreservoir
Relation name         the-upstream-bioprocesses-list-of
Inverse of relation   none
Type of relation      one-to-one
Relation is symmetric? no

---

THE-DOWNSTREAM-BIOPROCESSES-LIST-OF
First class           bioprocesses-list
Second class          bioreservoir
Relation name         the-downstream-bioprocesses-list-of
Inverse of relation   none
Type of relation      one-to-one
Relation is symmetric? no

---

THE-UP-BIORESERVOIRS-LIST-OF
First class           up-bioreservoirs-list
Second class          bioreservoir
Relation name         the-up-bioreservoirs-list-of
Inverse of relation   none
Type of relation      one-to-one
Relation is symmetric? no

---

THE-UP-BIOPROCESSES-LIST-OF
First class           bioprocesses-list
Second class          bioreservoir
Relation name         the-up-bioprocesses-list-of
Inverse of relation   none
Type of relation      one-to-one
Relation is symmetric? no

---

THE-DOWN-BIOPROCESSES-LIST-OF
First class           bioprocesses-list
Second class          bioreservoir
Relation name         the-down-bioprocesses-list-of
Inverse of relation   none
Type of relation      one-to-one
Relation is symmetric? no

---

TABLE 52

Chaining Rules

Options for all whenever rules:  not invocable via backward chaining,
 not invocable via forward chaining,
 may cause data seeking,
 may cause forward chaining for any bioprocess BP
 for any bioprocess BP1 that is *an-upstream-bioprocess-of* BP
  for any bioprocess BP2 that is *an-upstream-bioprocess-of* BP
 whenever BP1 ceases to be *an-upstream-bioprocess-of* BP and when not
 (there exists a bioprocess BP3 such that (BP2 is *an-upstream-bioprocess-of* BP3 and BP3 is *an-upstream-bioprocess-of BP*)) then
  conclude that BP2 is not A-*DOWNSTREAM-BIOPROCESS-OF* BP for any bioprocess BP
 for any bioprocess BP1 that is *an-upstream-bioprocess-of* BP
 whenever any bioprocess BP2 becomes *an-upstream-bioprocess-of* BP1
 and when BP2 is not *an-upstream-bioprocess-of* BP then
  conclude that BP2 is AN-*UPSTREAM-BIOPROCESS-OF* BP for any bioprocess BP
 for any bioprocess BP1 that is *a-downstream-bioprocess-of* BP
  for any bioprocess BP2 that is *a-downstream-bioprocess-of* BP
 whenever BP1 ceases to be *a-downstream-bioprocess-of* BP and when not
 (there exists a bioprocess BP3 such that (BP2 is *a-downstream-bioprocess-of* BP3 and BP3 is *a-downstream-bioprocess-of* BP)) then
  conclude that BP2 is not A-*DOWNSTREAM-BIOPROCESS-OF* BP for any bioprocess BP
 for any bioprocess BP1 that is *a-downstream-bioprocess-of* BP
 whenever any bioprocess BP2 becomes *a-downstream-bioprocess-of* BP1
 and when BP2 is not *a-downstream-bioprocess-of* BP then
 conclude that BP2 is A-*DOWNSTREAM-BIOPROCESS-OF* BP

TABLE 54

Labeling Rules for any bioentity BET
whenever BET is moved by the user and when BET has a name then
 conclude that the master-bioentity of BET = the name of BET for any bioentity BET
 for any bio-object-title T upon the subworkspace of BET
whenever BET is moved by the user then
 conclude that the label of T = "[the label of BET]"

for any bioentity-notes FN upon the SW of any bioentity BET
whenever FN is moved by the user then
 conclude that the label of the bio-object-title upon the subworkspace of
FN = the label of BET

TABLE 53

BR-CONTAINED-IN, a relation
First class         bioreservoir
Second class        biomodel
Relation name       br-contained-in
Inverse of relation the-container-of-br
Type of relation    many-to-many
Relation is symmetric? no
a bioreservoir may be br-contained-in more than
  one biomodel;
a biomodel may be the-container-of-br more than
  one bioreservoir BP-CONTAINED-IN, a relation
First class         bioprocess
Second class        biomodel
Relation name       bp-contained-in
Inverse of relation the-container-of-bp
Type of relation    many-to-many
Relation is symmetric? no
a bioprocess may be bp-contained-in more than one
  biomodel;
a biomodel may be the-container-of-bp more than
  one bioprocess BM-CONTAINED-IN, a relation
First class         biomodel
Second class        biomodel
Relation name       bm-contained-in
Inverse of relation the-container-of-bm
Type of relation    many-to-many
Relation is symmetric? no
a biomodel may be bm-contained-in more than one
  biomodel;
a biomodel may be the-container-of-bm more than
  one biomodel AN-ABOVE-BIORESERVOIR-OF, a relation
First class         bioreservoir
Second class        bioreservoir
Relation name       an-above-bioreservoir-of
Inverse of relation a-below-bioreservoir-of
Type of relation    many-to-many
Relation is symmetric? no
a bioreservoir may be an-above-bioreservoir-of more
  than one bioreservoir;
a bioreservoir may be a-below-bioreservoir-of more
  than one bioreservoir AN-ABOVE-BIOPROCESS-OF, a relation
First class        bioprocess
Second class       bioprocess
Relation name      an-above-bioprocess-of
Inverse of relation a-below-bioprocess-of
Type of relation   many-to-many
Relation is symmetric? no
a bioprocess may be an-above-bioprocess-of more
  than one bioprocess;
a bioprocess may be a-below-bioprocess-of more than
  one bioprocess A-NU-BIOPROCESS-OF, a relation
First class        bioprocess
Second class       bioprocess
Relation name      a-nu-bioprocess-of
Inverse of relation a-nd-bioprocess-of
Type of relation   many-to-many
Relation is symmetric? no
a bioprocess may be a-nu-bioprocess-of more than
  one bioprocess;
a bioprocess may be a-nd-bioprocess-of more than
  one bioprocess

TABLE 54

Icon Color Rules for any bioview-object O
whenever the toggle-state T of O receives a value and when T is hide then
   change the color-pattern of O so that light-color is light-gray, dark-color
   is dim-gray, white-color is white for any bioprocess P
  for any bioengine E
whenever the type-color of E receives a value then
   change the color-pattern of P so that type-color = the type-color of E for any bioprocess BP
whenever BP is moved by the user and when the subworkspace SW of BP
exists and there exists a bioengine E upon SW and not (the type-color of
BP = the type-color of E) then
   conclude that the type-color of BP = the type-color of E for any bionode-object O
whenever the toggle-state T of O receives a value and when T is hide then
   change the color-pattern of O so that light-color is light-gray, dark-color
   is dim-gray, white-color is white for any complex-bioentity O
whenever the toggle-state T of O receives a value and when T is show
then
   change the color-pattern of O so that light-color is dim-gray, dark-color
   is light-gray, white-color is black for any bioentity-notes N
whenever the toggle-state T of N receives a value and when T is hide then
   change the color-pattern of N so that light-color is light-gray, dark-color
   is dim-gray, white-color is white for any bioentity-notes N
whenever the toggle-state T of N receives a value and when T is show
then
   change the color-pattern of N so that light-color is dim-gray, dark-color
   is light-gray, white-color is black for the subworkspace SW of any bioreservoir-bin BRB
  for any bioreservoir BR upon SW
whenever BR is moved by the user and when not (there exists a
bioreservoir upon SW) then
   change the type-color of BRB to gray for the subworkspace SW of any bioreservoir-bin BRB
  for any bioreservoir BR upon SW
whenever BR is moved by the user and
  when there exists a bioreservoir upon SW then
   change the type-color icon-color of BRB to purple for any experiment-selection ES
whenever ES is moved by the user and when the currently-selected of ES
is false then
   change the type-color icon-color of ES to goldenrod for any experiment-selection ES
whenever ES is moved by the user and when the currently-selected of ES
is true then
   change the type-color icon-color of ES to gold

TABLE 55

Icon Movement Rules for any biopool P connected to any graph-tracer
whenever P is moved by the user then
    move the scaled-br-graph-tracer connected to P to (left-edge(P) - 8,
        middle-y(P) + 11) and
    move the absolute-br-graph-tracer connected to P to (left-edge(P) - 8,
        middle-y(P) - 10) and
    move the br-chaininig-tracer connected to P to (right-edge(P) + 6,
        middle-y(P) + 11) and
    move the query-tracer connected to P to (right-edge(P) - 6, middle-y(P) -
        10) and
    change the core stripe-color of every graph-link connected to P to
        transparent for any bioengine E connected to any graph-tracer
whenever E is moved by the user then
    move the scaled-bp-graph-tracer connected to E to (left-edge(E) - 8,
        middle-y(E) + 11) and
    move the bp-chaininig-tracer connected to E to (left-edge(E) - 8,
        middle-y(E) - 10) and
    move the up-path-tracer connected to E to (right-edge(E) + 8,
        middle-y(E) + 11) and
    move the down-path-tracer connected to E to (right-edge(E) + 8,
        middle-y(E) - 10) and
    change the core stripe-color of every graph-link connected to E to
        transparent for any bioproduct P connected to any bioproduct-post PP
whenever P is moved by the user then
    move PP to (right-edge(P) + 4, middle-y(P))
    change the core stripe-color of the icon-wire connected to R to
        transparent and
    change the core stripe-color of the icon-wire connected to P to
        transparent for any bioreactant R connected to any bioreactant-post RP
whenever R is moved by the user then
    move RP to (left-edge(R) - 3, middle-y(R)) and
    change the core stripe-color of the icon-wire connected to R to
        transparent

TABLE 56

---

GENERIC-SIMULATION-FORMULAS for Scaled-Valued Variables

--- the SCALED-AMOUNT C of any BIOPOOL PO = ( max ( 9.9e-9, the accumulation of PO))

--- state variable : d / dt (the ACCUMULATION C of any BIOPOOL PO) = the input-rate of PO - the output-rate of PO + the scaled-entry of PO - the decay-rate-factor of the bioreservoir superior to the workspace of PO * the scaled-amount of PO, with initial value the scaled-basal-amount of the bioreservoir superior to he workspace of PO

--- the INPUT-RATE of any BIOPOOL PO = the first of the following expressions that has a value ( (max ( 0.0, the sum over each bioproduct P connected to PO of ( the production-rate of P ) + the first of the following expressions that has a value (the output-1 of the model-block M upon the subworkspace of the scaled-input-model-box connected to PO, 0.0 ))) , 9.9e-9)

--- the OUTPUT-RATE of any BIOPOOL PO = the first of the following expressions that has a value ( max (0.0, the sum over each bioreactant R connected to PO of (the consumption-rate of R ) + the first of the following expressions that has a value (the output-1 of the model-block M upon the subworkspace of the output-model-box connected to PO, 0.0 ) ) , 9.9e-9)

--- the CONSUMPTION-RATE of any BIOREACTANT R = the first of the following expressions that has a value ( max (0.0, the velocity of the bioengine connected to R / the stoichiometric-coeff of R ), 9.9e-9)

--- the CONSUMPTION-RATE of any AMPLIFIER-BIOREACTANT R = 0.0

--- the PRODUCTION-RATE of any BIOPRODUCT P = the first of the following expressions that has a value (max ( 0.0, the velocity of the bioengine connected to P * the stoichiometric-coeff of P ), 9.9e-9)

--- the VELOCITY of any BIOENGINE E = the first of the following expressions that has a value ( max ( 0.0, the product over each bioreactant R connected to E of (the alpha-coeff of R * the contribution of R) * the rate-constant-sec of E * the tau-coeff of E + the bias of E ), 9.9e-9 )

TABLE 57

GENERIC-SIMULATION-FORMULAS FOR THE CONTRIBUTION
Based on Scaled-Valued Variables and Parameters the CONTRIBUTION of any AMPLIFIER-BIOREACTANT R = the first of the
following expressions that has a value ( min (1.0, max (0.0, the effective-
binding-sites of R * the scaled-amount of the biopool connected to R )),
0.5 )

the CONTRIBUTION of any SUBSTRATE.R  R = the first of the following
expressions that has a value ( min (1.0, max (0.0, the scaled-amount Q of
the biopool PO connected to R / ( the scaled-michaelis.k of R + Q ))) ,
0.5)

the CONTRIBUTION of any INHIBITOR.BIOREACTANT R = the first of the
following expressions that has a value ( min (1.0, max (0.0, the scaled-
amount Q of the biopool PO connected to R / ( the scaled-inhibition.k of
R + Q ))) , 0.5 )

the CONTRIBUTION of any LEADING-BIOREACTANT R = the first of the
following expressions that has a value ( min (1.0, max (0.0, the effective-
   binding-sites of R * the scaled-amount of the biopool connected to R )) ^
the stoichiometric-coeff of R, 0.5 )

the CONTRIBUTION of any BINDING-BIOREACTANT R = the first of the
following expressions that has a value ( min (1.0, max (0.0, the scaled-
amount Q of the biopool PO connected to R / ( the scaled-equil.dissoc.k
of R + Q ))) ^ the stoichiometric-coeff of R , 0.5 )

the CONTRIBUTION of any ION.R R = the first of the following expressions
that has a value ( min (1.0, max (0.0, the scaled-amount Q of the biopool
PO connected to R / ( the scaled-equilibrium.k of R + Q ))) , 0.5 )

the CONTRIBUTION of any SINGLE-BIOREACTANT R = the first of the
following expressions that has a value ( min (1.0, max (0.0, the scaled-
amount of the biopool connected to R )), 0.5 )

TABLE 58

GENERIC SIMULATION FORMULAS FOR MIXED-TYPE SIMULATIONS state variable : d / dt (the ACCUMULATION of any BIOPOOL PO) = the input-rate of PO - the output-rate of PO + the density-entry of PO - the decay-rate-factor of the bioreservoir superior to the workspace of PO * the density of PO, with initial value the basal-density of PO the DENSITY of any BIOPOOL PO = the first of the following expressions that has a value ( max ( 1.0e-9, ( the scaled-amount of PO * the scaling-density of PO ) ), 9.9e-99 )

the CONCENTRATION C of any BIOPOOL PO = the first of the following expressions that has a value ( max ( 1.0e-9, ( the density of PO / ( 6.023e23 * top-volume-po(PO)))) , 9.9e-99 )

the CONTRIBUTION of any AMPLIFIER-BIOREACTANT R = the first of the following expressions that has a value ( min (1.0, max (0.0, the effective-binding-sites of R * the density of the biopool PO connected to R / the scaling-density of PO)), 0.5 )

the CONTRIBUTION of any SUBSTRATE.R R = the first of the following expressions that has a value ( min (1.0, max (0.0, the concentration Q of the biopool PO connected to R / ( the michaelis-constant of R + Q ))) , 0.5 )

the CONTRIBUTION of any INHIBITOR.BIOREACTANT R =
 the first of the following expressions that has a value ( min (1.0, max (0.0, the concentration Q of the biopool PO connected to R / ( the inhibition-constant of R + Q ))) , 0.5 )

the CONTRIBUTION of any LEADING-BIOREACTANT R = the first of the following expressions that has a value ( min (1.0, max (0.0, the effective-binding-sites of R * the density of the biopool PO connected to R / the scaling-density of PO)) ^ the stoichiometric-coeff of R, 0.5 )

the CONTRIBUTION of any BINDING-BIOREACTANT R = the first of the following expressions that has a value ( min (1.0, max (0.0, the density Q of the biopool PO connected to R / ( the equilibrium-dissociation-constant of R + Q ))) ^ the stoichiometric-coeff of R , 0.5 )

the CONTRIBUTION of any ION.R R = the first of the following expressions that has a value ( min (1.0, max (0.0, the concentration Q of the biopool PO connected to R / ( the equilibrium-constant of R + Q ))) , 0.5 )

the CONTRIBUTION of any SINGLE-BIOREACTANT R = the first of the following expressions that has a value ( min (1.0, max (0.0, the density of the biopool PO connected to R / the scaling-density of PO)), 0.5 )

TABLE 59

GENERIC SIMULATION FORMULAS FOR ABSOLUTE-VALUED VARIABLES the CONCENTRATION of any SOLUBLE-MOL-POOL PO = (max (0.0, the accumulation of PO))

the DENSITY of any COMPLEXED-MOL-POOL PO = (max (0.0, the accumulation of PO))

state variable : d / dt (the ACCUMULATION of any SOL-MOL-POOL PO) = the input-rate of PO - the output-rate of PO + the concentration-entry of PO - the decay-rate-factor of the sol-mol-reservoir superior to the workspace of PO * the concentration of PO, with initial value the basal-concentration of PO state variable : d / dt (the ACCUMULATION of any COMPLEXED-MOL-POOL PO) = the input-rate of PO - the output-rate of PO + the density-entry of PO - the decay-rate-factor of the bound-mol-reservoir superior to the workspace of PO * the density of PO, with initial value the basal-density of PO the INPUT-RATE of any BIOPOOL PO = the first of the following expressions that has a value (max ( 0.0, the sum over each bioproduct P connected to PO of ( the production-rate of P ) + the first of the following expressions that has a value (the output-1 of the model-block M upon the subworkspace of the input-model-box connected to PO, 0.0 )), 0.0)

the OUTPUT-RATE of any BIOPOOL PO = the first of the following expressions that has a value ( max (0.0, the sum over each bioreactant R connected to PO of (the consumption-rate of R ) + the first of the following expressions that has a value (the output-1 of the model-block M upon the subworkspace of the output-model-box connected to PO, 0.0 ) ) , 0.0)

the PRODUCTION-RATE of any BIOPRODUCT P = the first of the following expressions that has a value (max ( 0.0, the velocity of the bioengine connected to P * the stoichiometric-coeff of P ), 0.0)

the CONSUMPTION-RATE of any BIOREACTANT R = the first of the following expressions that has a value ( max (0.0, the velocity of the bioengine connected to R / the stoichiometric-coeff of R ), 0.0)

the CONSUMPTION-RATE of any AMPLIFIER-BIOREACTANT R = 0.0 the VELOCITY of any BIOENGINE.E1.S1.I1 E = the first of the following expressions that has a value (the effective-binding-sites of the enzyme.r Z connected at the port-1 of E * the catalytic-rate-constant of Z * (the concentration of the sol-mol-pool connected to Z * the concentration SQ of the sol-mol-pool connected to the substrate.r S connected at the s1 of E / SQ + the michaelis-constant of S * (if there exists a comp-inhibitor.r I connected at the i1 of E then ( 1 + the concentration of the sol-mol-pool conneceted to I / the Inhibition-constant of I ) else 1)), 1.0e-99)

TABLE 60 the VELOCITY of any BIOENGINE.E1.S1.I1 E = the first of the
following expressions that has a value (the effective-binding-sites of the
enzyme.r Z connected at the port-1 of E * the catalytic-rate-constant of Z *
(the concentration of the soluble-mol-pool connected to Z * the
concentration SQ of the soluble-mol-pool connected to the substrate.r S
connected at the s1 of E /
(if not (there exists an inhibitor.bioreactant connected at the i1 of E)
 then SQ + the michaelis-constant of S else
(if there exists a comp-inhibitor.r CI connected at the i1 of E then SQ +
 the michaelis-constant of S * (1 + the concentration of the sol-mol-pool
conneceted to I / the Inhibition-constant of I / the inhibition-constant of CI )
else
(if there exists a noncomp-inhibitor.r NI connected at the i1 of E then
 SQ * (1 + the concentration of the sol-mol-pool conneceted to I / the
Inhibition-constant of I / the inhibition-constant of NI + the michaelis-
constant of S) * (1 + the concentration of the sol-mol-pool conneceted to I /
the Inhibition-constant of I / the Inhibition-constant of NI) else
(if there exists an uncomp-inhibitor.r UI connected at the i1 of E then
 SQ * (1 + the concentration of the sol-mol-pool conneceted to I / the
Inhibition-constant of I / the inhibition-constant of UI + the michaelis-
constant of S) else
(if there exists a mixed-inhibitor.r MI connected at the i1 of E then
 SQ * (1 + the concentration of the sol-mol-pool conneceted to I / the
Inhibition-constant of I / the inhibition-constant of MI + the michaelis-
constant
 of S ) * (1 + the concentration of the sol-mol-pool conneceted to I / the
Inhibition-constant of I / the inhibition-constant of MI )))))), 0.0)

TABLE 61 a tabular function of 1 argument

Table of values

| [Substrate1] | [Product1]([Substrate1]) |
|---|---|
| 0 | 112 |
| 3.13 | 757 |
| 6.25 | 1,305 |
| 12.50 | 1,932 |
| 25.00 | 3,045 |
| 50.00 | 3,356 |
| 100.00 | 3,478 |

TABLE 62

+ BioEntity
I. Simple-bioEntity
  A. Protein-site
    Ligand.site
    ...
    Catalytic.site
    ...
    Tyr.site
    Ser.site
    Thr.site
    Cys.site
    ...
    Isoprenylation-site
    Myristoylation-site
    ...
    Protein-loss-of-function-mutation
    Protein-gain-of-function-mutation
    ...
  B. Protein-modified-group
    Tyr.P-group
    Ser.P-group
    Thr.P-group
    Disulphide-bridge
    Isoprenylated-group
    Myristoylated-group
    ...
  C. ...
  D. DNA-binding-site
    Transcription-element
    ...
    Enhancer-element
    ...
    Promoter-proximal-element
    ...
    Response-element
    ...
    Activator-site
    ...
    ...
  E. DNA-modification-site
    Methylation.site
    ...
  F. RNA-binding-site
    ...
  G. ...
II. Complex-bioEntity
  A. BioEntity-Component
    1. Protein-Component
      a. Protein-domain
        Cytoplasmic-domain
        Transmembrane-domain
        Extracellular-domain
        COOH-terminal-domain
        NH2-terminal-domain
        Protein-spacer
        SH2-domain
        SH3-domain
        HSP-domain
        Alpha-β-domain
        β-sheet-domain
        Helix-turn-helix-domain
        Ig-fold-domain
          Ig-CH1-domain
          ...
        Collagen-domain
        Fibronectin-type-III-domain
        Superbarrel-domain
        8-stranded-barrel-domain
        ...
      b. Protein-motif
        Leucin-zipper-motif
        Zinc-finger-motif
        Alpha-helix-motif
        Helix-turn-motif
        β-strand-motif
        EF-hand-motif
        Trefoil-motif
        Greek-key-motif
        Loop-region-motif
        Signal-peptide-motif
        ...
      c. ...
    2. DNA-Component
      a. DNA-domain
        Operator
        ...
        Promoter
        ...
      b. DNA-motif
        TATA-box
        ...
      c. RNA-domain
        ...
      d. RNA-motif
        ...
    3. Membrane
      Plasma.Membrane
      Nuclear.Membrane
      ...
      ...
  B. Molecule
    1. Protein
      a. Active.polypeptide
        Cytokine
          EPO.like
          ...
          IL2.like
          ...
          IL4.like
          ...
          IL6.like
          ...
          IL7.like
          ...
          LIF.like
          ...
          ...
        Growth-factor
          EGF.like
          ...
          PDGF.like
          ...
        Peptide.hormone
          GH.like
          ...
          Insulin.like
          ...
        ...
      b. Receptor
        PTK.Rcp
          EGF.R.like
            EGF.R
            HER-2/neu
            erbB3
          ...
          PDGF.R.like
          ...
          Insulin.R.like
          ...
          FGF.R.like
          ...
          ...
        PSTK.Rcp
        ...
        PPase.Rcp
        ...
        Hematopoietin.R.like
          ...
          Ig.R.like
          IL1.R.like
          ...
        G.coupled.R.like
          IL8.R.like
          ...
        Steroid-receptors
          ...
          ...
        ...
      Receptor -complex
        PTK.Rcp.complex
          EGF.R.like.complex
            EGF-EGF.R
            EGF-HER-2/neu
            EGF-erbB3
          ...
          PDGF.R.like.complex
            PDGF-PDGF.R
            CSF1-CSF1.R/fms
          ...
          Insulin.R.likecomplex
            Insulin-Insulin.R
            IGF-IGF1.I
          ...

TABLE 62-continuation

FGF.R.like.complex
    FGF-FGF.R
    ...
Hematop.R.like.complex
    Di.hematop.R.complex
    GP130.complex
    IL2.Rg.complex
    KH97.complex
    ...
Ig.R.like.complex
IL1.R.like.complex
    ...
G.coupled.R.like.complex
IL8.R.like.complex
    ...
...

c. Enzyme
  P.tyr.kinase
    ...
  P.ser.Thr.kinase
    p85 Rsk S6-kinase
    p70 S6-kinase
    ...
  P.tyr.P.ase
  P.ser.Thr.P.ase
    ...
  Phosphorilase
    ...
  Synthetase
    ...
  RNA.Polymerase.II
    ...
  Topoisomerase-II
    ...
  ...
  Enzyme-complex
    ...

d. Transcription-factor
  Jun.like
    c.Jun
    Fos
    ...
  NF.kB.like
    ...
  NF.IL2A.like
    ...
  SP1.like
    ...
  TFIID.like
    ...
  TFIIB.like
    ...
  TFIIE.like
    ...
  ...

Complex.transcrip-factor
  AP.1.like
    ...
  NF.AT.like
    ...
  ...

e. Repressor.factor
  ...

f. Histone
  H1
  H2A
  H2B
  ...

g. Ribosonal.protein
  6S
  40S
  70S
  ...

h. Cytoskeleton.protein
  Actin
  Myosin
  Tubulin
  Keratin
  ...

i. Ion.channel
  Voltage-gated-channel
    Volt-gated-Ca++-channel
  LigandGatedChannel
    Ca++-gated-K+-channel
  ...

j. Transplantation.antigen
  MHC.I
  ...
  MHC.II
  ...

k. Adhesion.protein
  Integrin
  ...
  Cadherin
  ...
  Selectin
  ...
  ...

l. Immunoglobulin
  IgG
  ...
  IgM
  ...
  IgA
  ...

m. ECM.protein
  Fibronectin
  ...
  Collagen
  ...
  Adhesin
  ...
  ...

2. Nucleic.acid
  a. DNA
    Gene
    ...
    cDNA
    ...
  b. mRNA
    ...
  c. rRNA
    ...
  d. tRNA
    ...
  e. Oligonucleotide
    ...

3. Carbohydrate
  a. Polysacharide
    ...

4. Lipid
  a. Steroid.hormone
    Estrogen
    ...
  b. Prostaglandin
    ...
  c. Leukotrienes
    ...
  d. Phospholipid
    ...
  e. Isoprene
    ...
  f. Fatty.acid
    ...
  ...

5. Small.molecule
  a. Nucleotide
    ATP
    GTP
    cAMP
    ...
  b. Aminoacid
    ...
  c. Vitamin
    ...
  d. Retinoid
    ...
  e. Sugar
    ...
  f. Ion
    Cation
    ...

III. Heter-Mol-Complex
  A. TF-DNA.Complex
    E2F-RB-DNA.complex
    ...
  B. Nucleosome
    ...
  ...

TABLE 63

| | |
|---|---|
| Class name | bioentity |
| Superior class | bioobject |
| Attributes specific to class | id is ""; <br> references is ""; |
| Class restrictions | unless in administrator, or developer mode: menu choices for bioentity exclude additionally: go-to-subworkspace, disable, describe, name, move; <br> when in simulation, navigation, or general mode: <br>     menu choices for bioentity exclude additionally: transfer, clone, change-size, color, create-local, delete; <br>     non-menu choices for item exclude additionally: move-object, move-connection, click-to-edit |
| Menu option | not a final menu choice |
| Inherited attributes | label is "", with an index; <br> description is "" |
| Attribute displays | inherited |
| Stubs | none |
| Icon description | bioentity-pattern (width 100; height 80; dark-color = dim-gray, light-color = light-gray, white-color = white, type-color = purple, status-color = medium-aquamarine) |

TABLE 64

| | |
|---|---|
| Class name | simple-bioentity |
| Superior class | bioentity |
| Attributes specific to class | position is ""; <br> superior-bioentity, with an index; |
| Capabilities and restrictions | none |
| Class restrictions | when in developer or modeler mode: menu choices for simple-bioentity include additionally: rotate-reflect |
| Menu option | not a final menu choice |
| Stubs | inherited |
| Icon description | inherited |

TABLE 65

| | |
|---|---|
| Class name | protein-site |
| Superior class | simple-bioentity |
| Attributes specific to class | none |
| Capabilities and restrictions | none |
| Menu option | not a final menu choice |
| Attribute displays | position at standard position; label offset by (-30, 35) |
| Stubs | a link located at bottom 14 |
| Icon description | width 28; height 40; |

| | |
|---|---|
| Class name | ligand.site |
| Superior class | protein-site |
| Attributes specific to class | none |
| Stubs | inherited |
| Icon description | ligand.site-pattern (width 36; height 26; lime-green) |

| | |
|---|---|
| Class name | tyr.site |
| Superior class | protein-site |
| Attributes specific to class | none |
| Stubs | inherited |
| Icon description | tyr.site-pattern (width 28; height 40; green) |

TABLE 66

| | |
|---|---|
| Class name | protein-modified-group |
| Superior class | simple-bioentity |
| Attributes specific to class | modifiers is "" |
| Capabilities and restrictions | none |
| Menu option | not a final menu choice |
| Attribute displays | position at standard position; label offset by (-30, 35) |
| Stubs | a link located at bottom 15 |
| Icon description | protein-modified-group-pattern (width 30; height 32) |

| | |
|---|---|
| Class name | gly.isoprenyl.linker |
| Superior class | protein-modified-group |
| Attributes specific to class | none |
| Stubs | a link located at right 20 |
| Icon description | gly.isoprenyl.linker-pattern (width 66; height 36; violet) |

| | |
|---|---|
| Class name | disulphide-bridge |
| Superior class | protein-modified-group |
| Attributes specific to class | none |
| Stubs | a link located at bottom 18; a link located at top 18 |
| Icon description | disulphide-bridge-pattern (width 36; height 32; gold) |

| | |
|---|---|
| Class name | tyr.p-group |
| Superior class | protein-modified-group |
| Attributes specific to class | none |
| Stubs | inherited |
| Icon description | tyr.p-group-pattern (width 30; height 32; green) |

| a tyr.p-group | |
|---|---|
| Names | none |
| Label | "" |
| Description | "" |
| Toggle state | hide |
| References | "" |
| Superior bioentity | none |
| Master bioentity | none |

TABLE 67

| | |
|---|---|
| Class name | complex-bioentity |
| Superior class | bioentity |
| Attributes specific to class | toggle-state has values show or hide (default is HIDE), with an index; warnings is ""; master-bioentity, with an index |
| Menu option | not a final menu choice |
| Stubs | none |
| Icon description | inherited |

TABLE 68

| | |
|---|---|
| Class name | bioentity-component |
| Superior class | complex-bioentity |
| Attributes specific to class | superior-bioentity; position is "" |
| Class restrictions | when in developer or modeler mode: menu choices for bioentity-component include additionally: rotate-reflect |
| Menu option | not a final menu choice |
| Inherited attributes | references is ""; master-bioentity, with an index; label is "", with an index; description is "" |
| Stubs | none |
| Icon description | inherited |
| | |
| Class name | membrane |
| Superior class | bioentity-component |
| Attributes specific to class | none |
| Capabilities and restrictions | none |
| Menu option | not a final menu choice |
| Stubs | none |
| Icon description | membrane-pattern (width 20; height 130; |
| | |
| Class name | plasma-membrane |
| Superior class | membrane |
| Attributes specific to class | none |
| Stubs | none |
| Icon description | plasma-membrane-pattern |

TABLE 69

| | |
|---|---|
| Class name | dna-component |
| Superior class | bioentity.component |
| Attributes specific to class | size is 0 BASE-PAIRS |
| Menu option | not a final menu choice |
| Icon description | inherited |
| | |
| Class name | dna-domain |
| Superior class | dna-component |
| Attributes specific to class | position is "" |
| Menu option | a final menu choice |
| Icon description | dna-domain-pattern |
| | |
| Class name | operator |
| Superior class | dna-domain |
| Attributes specific to class | position is "" |
| Icon description | operator-pattern |
| | |
| Class name | promoter |
| Superior class | dna-domain |
| Attributes specific to class | position is "" |
| Icon description | promoter-pattern |

TABLE 70

| | |
|---|---|
| Class name | protein-component |
| Superior class | bioentity-component |
| Attributes specific to class | none |
| Menu option | not a final menu choice |
| Attribute displays | label offset by (-45, -45) |
| Stubs | inherited |
| Icon description | inherited |

| | |
|---|---|
| Class name | protein-domain |
| Superior class | protein-component |
| Attributes specific to class | none |
| Menu option | a final menu choice |
| Attribute displays | label offset by (-42, 16); position offset by (-47, -25) |
| Stubs | a link located at top 40; a link located at right 23; a link located at bottom 40; a link located at left 23 |
| Icon description | protein-domain-pattern (width 80; height 46) |

| | |
|---|---|
| Class name | protein-motif |
| Superior class | protein-component |
| Attributes specific to class | none |
| Attribute displays | label offset by (-40, 18) |
| Stubs | a link located at top 40; a link located at right 23; a link located at bottom 40; a link located at left 23 |
| Icon description | protein-motif-pattern (width 80; height 46) |

| | |
|---|---|
| Class name | leucin-zipper-motif |
| Superior class | protein-motif |
| Attributes specific to class | none |
| Stubs | inherited |
| Icon description | leucin-zipper-motif |

TABLE 71

| | |
|---|---|
| Class name | molecule |
| Superior class | complex-bioentity |
| Attributes specific to class | synonims is ""; |
| | in-species is " "; |
| | in-tissues is " "; |
| | in-cells is " "; |
| | in-organelles is " " |
| Menu option | a final menu choice |
| Inherited attributes | references is ""; |
| | master-bioentity, with an index; |
| | label is "", with an index; |
| | description is "" |
| Stubs | a link located at top 50; |
| | a link located at right 40; |
| | a link located at bottom 50; |
| | a link located at left 40 |
| Icon description | inherited |

TABLE 72

| | |
|---|---|
| Class name | protein |
| Superior class | molecule |
| Attributes specific to class | cas-number is 00000-00-0, with an index; |
| | number-amino-acids |
| | sequence is " "; |
| | mol-weight is 0 DALTONS, with an index; |
| | isoelectric-point is 0.0; |
| Menu option | a final menu choice |
| Stubs | none |
| Icon description | protein-pattern (width 100; height 80; |
| | dark-color = dim-gray, light-color = |
| | light-gray, white-color = white, type- |
| | color = yellow, status-color = medium- |
| | aquamarine; |

| | |
|---|---|
| Class name | catalytic-subunit |
| Superior class | protein |
| Attributes specific to class | none |
| Stubs | inherited |
| Icon description | catalytic-subunit-pattern (width 100; height 80) |

| | |
|---|---|
| Class name | protein-complex |
| Superior class | protein |
| Attributes specific to class | none |
| Stubs | inherited |
| Icon description | protein-complex-pattern |

| | |
|---|---|
| Class name | immunoglobulin |
| Superior class | protein |
| Attributes specific to class | none |
| Stubs | inherited |
| Icon description | immunoglobulin-pattern |

TABLE 73

| | |
|---|---|
| Class name | enzyme |
| Superior class | protein |
| Attributes specific to class | cas-number is "EC 0-0-0-000", with an index: <br> substrates-info is ""; <br> inhibitors-info is ""; <br> ligand-info is "" |
| Menu option | not a final menu choice |
| Inherited attributes | synonims is ""; <br> mol-weight is 0 DALTONS, with an index; <br> isoelectric-point is 0.0; <br> formula-or-sequence is " "; <br> in-species is " "; <br> in-tissues is " "; <br> in-cells is " "; <br> in-organelles is " "; <br> references is ""; <br> icon-configuration is an instance of a view-icon-configuration; <br> label is "", with an index; <br> description is ""; <br> code is xxx.00000, with an index |
| Stubs | inherited |
| Icon description | enzyme-pattern (width 100; height 80; dark-color = dim-gray, light-color = light-gray, type-color = red, status-color = dark-gray; |

| | |
|---|---|
| Class name | p.tyr.kinase |
| Superior class | enzyme |
| Attributes specific to class | none |
| Icon description | protein.kinase-pattern ( type-color = coral) |

| a p.tyr.kinase | |
|---|---|
| Names | none |
| Label | "" |
| Description | "" |
| Id | "" |
| Toggle state | hide |
| References | "" |
| Master bioentity | none |
| Synonims | "" |
| In species | "" |
| In tissues | "" |
| In cells | "" |
| In organelles | "" |
| Cas number | "EC 0-0-0-000" |
| Mol weight | 0 DALTONS |
| Isoelectric point | 0.0 |
| Sequence | "" |
| Substrates info | "" |
| Inhibitors info | "" |
| Ligands info | "" |

TABLE 74

| | |
|---|---|
| Class name | receptor |
| Superior class | protein |
| Attributes specific to class | ligands-info is "" |
| Stubs | none |
| Icon description | receptor-pattern (width 100; height 80; type-color = medium-aquamarine) |

| | |
|---|---|
| Class name | receptor.complex |
| Superior class | receptor |
| Attributes specific to class | none |
| Menu option | a final menu choice |
| Stubs | none |
| Icon description | receptor.complex-pattern (width 100; height 80; dark-color = dim-gray, light-color = light-gray, type-color = coral, status-color = medium-aquamarine; |

| | |
|---|---|
| Class name | ptk.rcp.complex |
| Superior class | receptor |
| Attributes specific to class | none |
| Stubs | inherited |
| Icon description | ptk.rcp-pattern (width 260; height 56; type-color = medium-aquamarine) |

| | |
|---|---|
| Class name | pdgf.r.like.complex |
| Superior class | ptk.rcp.complex |
| Attributes specific to class | none |
| Stubs | inherited |
| Icon description | inherited | a pdgf.r.like.complex

| | |
|---|---|
| Names | none |
| Label | "" |
| Description | "" |
| Id | "" |
| Toggle state | hide |
| References | "" |
| Master bioentity | none |
| Synonims | "" |
| In species | "" |
| In tissues | "" |
| In cells | "" |
| In organelles | "" |
| Cas number | 00000-00-0 |
| Number amino acids | "" |
| Sequence | "" |
| Mol weight | 0 |
| Isoelectric point | 0.0 |
| Ligands info | "" |

TABLE 75

| | |
|---|---|
| Class name | nucleic-acid |
| Superior class | molecule |
| Attributes specific to class | reg-number is 00000000, with an index; size is 0 KILOBASES, with an index; sequence is ""; |
| Capabilities and restrictions | none |
| Class restrictions | none |
| Change | none |
| Menu option | not a final menu choice |
| Inherited attributes | synonims is ""; in-species is ""; in-tissues is ""; in-cells is ""; in-organelles is ""; toggle-state has values show or hide (default is HIDE), with an index; references is ""; master-bioentity; label is "", with an index; description is "" |
| Stubs | inherited |
| Icon description | nucleic-acid-pattern (width 100; height 80; dark-color = dim-gray, light-color = light-gray, white-color = white; |

| | |
|---|---|
| Class name | dna |
| Superior class | nucleic-acid |
| Attributes specific to class | none |
| Menu option | a final menu choice |
| Stubs | inherited |
| Icon description | dna-pattern (width 100; height 80) |

| | |
|---|---|
| Class name | gene |
| Superior class | dna |
| Attributes specific to class | chromosomal-location is "" |
| Menu option | a final menu choice |
| Stubs | inherited |
| Icon description | gene-pattern (width 100; height 80) |

| a gene | |
|---|---|
| Names | none |
| Label | "" |
| Description | "" |
| Id | "" |
| Toggle state | hide |
| References | "" |
| Master bioentity | none |
| Synonims | "" |
| In species | "" |
| In tissues | "" |
| In cells | "" |
| In organelles | "" |
| Reg number | 00000000 |
| Size | 0 KILOBASES |
| Sequence | "" |
| Chromosomal location | "" |

TABLE 76

| | |
|---|---|
| Class name | heter-mol-complex |
| Superior class | complex-bioentity |
| Attributes specific to class | synonims is ""; <br> in-species is " "; <br> in-tissues is " "; <br> in-cells is " "; <br> in-organelles is " " <br> mol-weight is 0 DALTONS, with an index |
| Menu option | not a final menu choice |
| Inherited attributes | references is ""; <br> master-bioentity, with an index; <br> label is "", with an index; <br> description is "" |
| Stubs | none |
| Icon description | heter.mol.complex-pattern (width 100; height 80; type-color = purple) |
| Class name | nucleosome |
| Superior class | heter.mol.complex |
| Attributes specific to class | none |
| Stubs | none |
| Icon description | nucleosome-pattern |
| Class name | tf-dna.complex |
| Superior class | heter.mol.complex |
| Attributes specific to class | none |
| Stubs | none |
| Icon description | tf-dna.complex -pattern |

TABLE 77

| | |
|---|---|
| Class name | biomodel |
| Superior class | bioview-object |
| Attributes specific to class | none |
| Class restrictions | unless in administrator, uil-build, or developer mode:<br>  menu choices for biomodel exclude additionally: change-size;<br>  attributes visible for biomodel exclude additionally: toggle-state;<br>when in simulation, navigation, or explorer mode: selecting any biomodel implies details |
| Menu option | not a final menu choice |
| Inherited attributes | references is "";<br>warnings is "";<br>toggle-state has values show or hide (default is HIDE), with an index;<br>label is "", with an index;<br>description is "" |
| Attribute displays | inherited |
| Stubs | inherited |
| Icon description | biomodel-pattern (width 100; height 100; dark-color = dim-gray, light-color = light-gray, white-color = white) |
| Class name | sub-model |
| Superior class | biomodel |
| Attributes specific to class | none |
| Menu option | a final menu choice |
| Inherited attributes | references is "";<br>warnings is "";<br>toggle-state has values show or hide (default is HIDE), with an index;<br>label is "", with an index;<br>description is "" |
| Attribute displays | label offset by (-73, 15) |
| Stubs | inherited |
| Icon description | sub-model-pattern (width 160; height 60; dark-color = dim-gray, light-color = light-gray, white-color = white, status-color = medium-aquamarine, flag-color = medium-aquamarine; |
| Class name | bioreservoir-bin |
| Superior class | biomodel |
| Attributes specific to class | none |
| Menu option | a final menu choice |
| Icon description | bioreservoir-bin-pattern (width 100; height 60; dark-color = dim-gray, light-color = light-gray, white-color = white, type-color = gray, status-color = cadet-blue; |
| Class name | on-hold-bin |
| Superior class | biomodel |
| Attributes specific to class | none |
| Capabilities and restrictions | activatable-subworkspace |
| Menu option | a final menu choice |
| Icon description | on-hold-bin-pattern (width 50; height 60; dark-color = dim-gray, light-color = light-gray, white-color = white, status-color = green-yellow; |

TABLE 77b

```
                 an user-menu-choice
Label            deactivate-sw
Applicable class on-hold-bin
Condition        the thide-and-deact-sup-ws-button upon the
                     subworkspace of the item exists
Action           in order
                 start go-to-biomodel-subws-proc (the item,
                     this window) and deactivate the subworkspace of the
                     item and change the status-color icon-color of the
                     item to green-yellow
```

```
                 an user-menu-choice
Label            activate-sw
Applicable class on-hold-bin
Condition        the toggle-state of the item is hide
Action           in order
                 activate the subworkspace of the item and
                     change the status-color icon-color of the item
                     to coral and start go-to-biomodel-subws-proc (the
                     item, this window)
```

TABLE 78

| | |
|---|---|
| Class name | bioreservoir |
| Superior class | bioview-object |
| Attributes specific to class | references is given by a references-array; compartment is ""; ref-bioentity is none; master-bioreservoir is none; status has values available, selected, selected-for-input, selected-for-output, down-selected, up-selected, forw-activated, back-activated, downstream-activated, upstream-activated, or deactivated (default is AVAILABLE), decay-rate-factor is 2.0e-4; if-scaling-bioreservoir is none; if-scaling-amount is 100; scaled-basal-amount is 9.9e-9; physiol-abundance has values highest, abundant, steady-state, low-induced, or only-induced (default is ONLY-INDUCED) |
| Capabilities and restrictions | activatable-subworkspace |
| Class restrictions | unless in administrator or developer mode: menu choices exclude additionally: go-to-subworkspace, rotate-reflect, clone; attributes visible exclude additionally: status; toggle-state, master-bioreservoir; when in simulation, navigation or general mode: menu choices exclude additionally: move, name, color, delete, disable, change-size, create-subworkspace, transfer, describe, clean-clone; non-menu choices exclude additionally: move-object; when in general mode: menu choices exclude additionally: simul-panel, show-s.graph, hide-s.graph; attributes visible exclude additionally: decay-rate-factor, if-scaling-bioreservoir, if-scaling-amount, scaled-basal-amount; when in navigation mode: selection of any bioreservoir implies details |
| Menu option | not a final menu choice |
| Attribute displays | label offset by (-57, -30) |
| Icon description | bioreservoir-pattern (width 96; height 56; dark-color = dim-gray, light-color = light-gray, white-color = white, type-color = pale-green, status-color = medium-aquamarine, flag-color = medium-aquamarine |

| | |
|---|---|
| Class name | sol-mol-reservoir |
| Superior class | bioreservoir |
| Attributes specific to class | normal-basal-concentration is 9.9e-99; physiol-max-concentration is 9.9e-99 |
| Icon description | inherited |

| | |
|---|---|
| Class name | bound-mol-reservoir |
| Superior class | bioreservoir |
| Attributes specific to class | normal-basal-density is 9.9e-99; physiol-max-density is 9.9e-99 |
| Icon description | inherited |

TABLE 79

| | |
|---|---|
| Class name | biopool |
| Superior class | bionode-object |
| Attributes specific to class | basal-density is given by a basal-density-par; scaling-density is given by a scaling-density-par; density-entry is given by a density-entry-pvar; scaled-entry is given by a scaled-entry-pvar; input-rate is given by an input-rate-pvar; output-rate is given by an output-rate-pvar; accumulation is given by an accum-pvar; density is given by a density-pvar; scaled-amount is given by a scaled-amount-pvar; |
| Class restrictions | unless in administrator or developer mode: menu choices exclude additionally: describe, rotate-reflect, move, transfer when in simulation or explorer mode: menu choices exclude additionally: add-scaled-input, add-input, add-output, add-top-post, add-bottom-post; when in explorer mode: menu choices exclude additionally: simul-panel; attributes visible exclude additionally: basal-density, density-entry, density |
| Inherited attributes | label is "", with an index; description is "" |
| Attribute displays | input-rate, output-rate, accumulation-rate, scaled-amount offset by (105, 20) |
| Stubs | an input-box-connection inp located at top 8; a scaled-input-box-connection sip located at top 17; an output-box-connection oup located at bottom 15; a p-connection p01 located at top 37; a p-connection p02 located at top 50; a p-connection p03 located at top 62; a p-connection p04 located at top 75; a p-connection p05 located at top 87; a p-connection p06 located at top 100; a p-connection p07 located at top 112; a p-connection p08 located at top 125; a p-connection p09 located at top 137; a p-connection p10 located at top 150; a p-connection p11 located at top 162; a p-connection p12 located at top 175; a r-connection r01 located at bottom 37; a r-connection r02 located at bottom 50; a r-connection r03 located at bottom 62; a r-connection r04 located at bottom 75; a r-connection r05 located at bottom 87; a r-connection r06 located at bottom 100; a r-connection r07 located at bottom 112; a r-connection r08 located at bottom 125; a r-connection r09 located at bottom 137; a r-connection r10 located at bottom 150; a r-connection r11 located at bottom 162; a r-connection r12 located at bottom 175 a graph-link s-plot located at left 11; a graph-link a-plot located at left 31; a graph-link lists located at right 11; a graph-link query located at right 31; |
| Icon description | biopool-pattern (width 180; height 42; dark-color = dim-gray, light-color = light-gray, white-color = white, type-color = green-yellow |

TABLE 80

| | |
|---|---|
| Class name | sol-mol-pool |
| Superior class | biopool |
| Attributes specific to class | basal-concentration is given by a basal-conc-par; concentration is given by a conc-pvar |
| Attribute displays | basal-concentration, concentration offset by (80, 60); input-rate, output-rate, accumulation-rate, scaled-amount offset by (105, 20) |
| Stubs | inherited |
| Icon description | inherited |
| Class name | bound-mol-pool |
| Superior class | biopool |
| Attributes specific to class | none |
| Attribute displays | inherited |
| Stubs | inherited |
| Icon description | biopool-pattern (width 180; height 42; dark-color = dim-gray, light-color = light-gray, white-color = white, status-color = forest-green, type-color = medium-goldenrod) |

TABLE 81

| | |
|---|---|
| Class name | biopool-post |
| Superior class | biopost |
| Attributes specific to class | id is ""; |
| | ref-bioprocess is none |
| Capabilities and restrictions | none |
| Class restrictions | when in navigation or simulation mode: |
| |   selecting any biopost implies show-bp; |
| | when in explorer mode: |
| |   selecting any biopost implies activate-bp; |
| | when in developer or modeler mode: |
| |   menu choices for biopost exclude |
| |     additionally: name, move, rotate-reflect, |
| |     change-size, color, delete, describe, |
| |     create-subworkspace, show-bp |
| Menu option | a final menu choice |
| Stubs | inherited |
| Icon description | biopool-post-pattern (width 17; height 17) |
| Class name | biopool-r-post |
| Superior class | biopool-post |
| Attributes specific to class | none |
| Menu option | a final menu choice |
| Stubs | inherited |
| Icon description | biopool-r-post-pattern (width 17; height 17) |
| Class name | biopool-p-post |
| Superior class | biopool-post |
| Attributes specific to class | none |
| Menu option | a final menu choice |
| Stubs | inherited |
| Icon description | inherited |

| a biopool-p-post | |
|---|---|
| Names | none |
| Toggle state | hide |
| Id | "" |
| Ref bioprocess | none |

TABLE 82

| | |
|---|---|
| Class name | model-box |
| Superior class | biotool |
| Attributes specific to class | toggle-state has values show or hide (default is HIDE), with an index |
| Class restrictions | unless in administrator or developer mode: menu choices exclude additionally: move, name, change-size, color, describe, go-to-subworkspace; selecting any model-box implies show-sw |
| Menu option | not a final menu choice |
| Icon description | model-box-pattern |
| Class name | input-model-box |
| Superior class | model-box |
| Attributes specific to class | none |
| Stubs | a p-connection located at right 10 |
| Icon description | input-model-box-pattern |
| Class name | scaled-input-model-box |
| Superior class | model-box |
| Attributes specific to class | none |
| Stubs | a p-connection located at right 10 |
| Icon description | scaled-input-model-box-pattern |
| Class name | output-model-box |
| Superior class | model-box |
| Attributes specific to class | none |
| Stubs | a r-connection located at right 10 |
| Icon description | output-model-box-pattern |
| an output model-box | |
| Names none | |
| Toggle state hide | |

TABLE 83

| | |
|---|---|
| Class name | model-block |
| Superior class | biotool |
| Attributes specific to class | output-1 is given by a model-block-output-var |
| Class restrictions | unless in administrator or developer mode: menu choices exclude additionally: move, name, change-size, color, describe, create-subworkspace; when in simulation, navigation, or general mode: menu choices exclude additionally: clone, delete; attributes visible for model-block exclude additionally: notes, names |
| Menu option | not a final menu choice |
| Stubs | none |
| Icon description | model-block-pattern |

---

| | |
|---|---|
| Class name | constant.f |
| Superior class | model-block |
| Attributes specific to class | constant is 0.0 |
| Icon description | constant.f-pattern (omitted) | a generic-simulation-formula
the output-1 of any CONSTANT.F CF = the constant of CF

---

| | |
|---|---|
| Class name | increasing.f |
| Superior class | model-block |
| Attributes specific to class | input-1; gain is 1.5; bias is 0.0 |
| Icon description | increasing.f-pattern | a generic-simulation-formula
Tracing and breakpoints default the output-1 of any INCREASING.F = the current time * 1e-5

---

| | |
|---|---|
| Class name | proportional.f |
| Superior class | model-block |
| Attributes specific to class | input-1 is given by a model-block-var; gain is 1.0; bias is 0.0 |
| Icon description | proportional.f-pattern | a generic-simulation-formula
the output-1 of any PROPORTIONAL.F PF = the input-1 of PF * the gain of PF + the bias of PF

---

| | |
|---|---|
| Class name | sigmoid.f |
| Superior class | model-block |
| Attributes specific to class | input-1; gain is 1.5; bias is 0.0 |
| Icon description | sigmoid.f-pattern | a generic-simulation-formula
the output-1 of any SIGMOID.F SF = 1.0 / ( 1.0 + exp ( - the gain of SF * ( 10 * the input-1 of SF ) - the bias of SF ) )

TABLE 84

| | |
|---|---|
| Class name | exp.c.pdf |
| Superior class | model-block |
| Attributes specific to class | mean is 0.0;<br>x-val is given by a model-block-var |
| Icon description | exp.c.pdf-pattern (omitted) | a generic-simulation-formula
the output-1 of any EXP.C.PDF C = 1.0 - exp (- the x-val of E / the mean of E)

| | |
|---|---|
| Class name | exp.i.pdf |
| Superior class | model-block |
| Attributes specific to class | mean is 0.0;<br>x-val |
| Icon description | exp.i.pdf-pattern (omitted) | a generic-simulation-formula
the output-1 of any EXP.I.PDF E = exp (- the x-val X of E / the mean M of E) / M

| | |
|---|---|
| Class name | unif.c.pdf |
| Superior class | model-block |
| Attributes specific to class | min-val is 1.0e-5;<br>max-val is 1.0;<br>x-val is given by a model-block-var |
| Icon description | unif.c.pdf-pattern (omitted) | the output-1 of any UNIF.C.PDF UC = ( if the x-val X of UC < the min-val MI of UC then MI else (if X > the max-val MA of UC then MA else ( ( X - MI ) / ( MA - MI ))) )

| | |
|---|---|
| Class name | unif.rn.f |
| Superior class | model-block |
| Attributes specific to class | min-val is 1.0e-5;<br>max-val is 1.0 |
| Icon description | unif.rn.f-pattern (omitted) | a generic-simulation-formula
the output-1 of any UNIF.RN.F UR = random ( the min-val of UR, the max-val of UR )

| | |
|---|---|
| Class name | normal.rn.pdf |
| Superior class | model-block |
| Attributes specific to class | mean is 0.0;<br>min-val is 1.0e-5;<br>max-val is 1.0 |
| Icon description | normal.rn.pdf-pattern (omitted) | a generic-simulation-formula
the output-1 of any NORMAL.RN.PDF NR = the mean of NR + ( ( the max-val of NR + the min-val of NR) / 6 ) * sqrt ( -2.0 * ln ( random ( 0.0, 1.0) ) ) * sin ( 2.0 * pi () * random ( 0.0, 1.0) ) * ln ( random ( 0.0, 1.0) )

| | |
|---|---|
| Class name | normal.i.pdf |
| Superior class | model-block |
| Attributes specific to class | mean is 0.0;<br>min-val is 1.0e-5;<br>max-val is 1.0;<br>x-val |
| Icon description | normal.i.pdf-pattern (omitted) | a generic-simulation-formula
the output-1 of any NORMAL.I.PDF NI = exp ((expt ((the x-val of NI - the mean of NI ), 2)) / (2.0 * ( the max-val MA of NI + the min-val MI of NI) / 6 )) * (1.0 / (sqrt ( 2.0 * pi () * ( MA + MI) / 6 )))

Note: As in PERT/CPM, the variance is substituted based on the notion that a standard deviation is approximately 1/6th of the difference between extreme values of the distribution --> variance = $sigma^2 = ((b - a) / 6)^2$

TABLE 85

| | |
|---|---|
| Class name | sin.time.f |
| Superior class | model-block |
| Attributes specific to class | min-val is 1.0e-5; |
| | max-val is 1.0; |
| | frequency is 25; |
| | gain is 2; |
| | bias is 1.0 |
| Icon description | sin.time.f-pattern | a generic-simulation-formula
the output-1 of any SIN.TIME.F ST = max ( the min-val of ST, min ( the max-val of ST, the bias of ST + the gain of ST * sin ( the current time / the frequency of ST ) ) )

| | |
|---|---|
| Class name | cos.time.f |
| Superior class | model-block |
| Attributes specific to class | min-val is 1.0e-5; |
| | max-val is 1.0; |
| | frequency is 25; |
| | gain is 2; |
| | bias is 1.0 |
| Icon description | cos.time.f-pattern (omitted) | a generic-simulation-formula
the output-1 of any COS.TIME.F CT = max ( the min-val of CT, min ( the max-val of CT, cos ( the current time / the frequency of CT ) / the gain of CT ) )

| | |
|---|---|
| Class name | exp.rn.pdf |
| Superior class | model-block |
| Attributes specific to class | mean is 0.0; |
| | min-val is 1.0e-5; |
| | max-val is 1.0 |
| Icon description | exp.rn.pdf-pattern (omitted) | a generic-simulation-formula
the output-1 of any EXP.RN.PDF E = max ( the min-val of E, min ( the max-val of E, - ln ( random (0.0, 1.0) ) * the mean of E ))

| | |
|---|---|
| Class name | generic.model.block |
| Superior class | model-block |
| Attributes specific to class | p.1; p.2; p.3; p.4; p.5; p.6; p.7; p.8; p.9; |
| | v.1; v.2; v.3; v.4; v.5; v.6; v.7; v.8; v.9 |
| Icon description | generic.model.block-pattern (omitted) |

TABLE 86

| | |
|---|---|
| Class name | bioprocess |
| Superior class | bioview-object |
| Attributes specific to class | compartment is "";<br>status has values available, selected, selected-for-input, down-selected, up-selected, forw-activated, back-activated, downstream-activated, upstream-activated, or deactivated (default is AVAILABLE);<br>deactivation-hold-interval is given by a time-delay-par;<br>master-bioprocess is none |
| Capabilities and restrictions | activatable-subworkspace |
| Class restrictions | unless in administrator or developer mode:<br>  menu choices exclude additionally:<br>    go-to-subworkspace, rotate-reflect, change-size, clone;<br>  attributes visible exclude additionally:<br>    toggle-state; master-bioprocess;<br>when in general, navigation, or simulation mode:<br>  menu choices exclude additionally:transfer, move, name, color, delete, disable, describe, create-subworkspace, clone, labeled-clone, clean-clone;<br>  attributes visible exclude additionally:<br>    notes, label;<br>when in general or navigation mode:<br>  attributes visible exclude additionally:<br>    activation-hold-interval, deactivation-hold-interval;<br>when in navigation mode:<br>  selecting any bioprocess implies details<br>when in simulation mode:<br>  menu choices exclude additionally:<br>    up-pathway, down-pathway |
| Menu option | not a final menu choice |
| Inherited attributes | references is "";<br>warnings is "";<br>toggle-state has values show or hide (default is HIDE), with an index;<br>label is "", with an index;<br>description is "" |
| Attribute displays | label offset by (-57, -30) |
| Stubs | none |
| Icon description | bioprocess-pattern (width 96; height 56; dark-color = dim-gray, light-color = light-gray, white-color = white, status-color = slate-blue, type-color = slate-blue, flag-color = medium-aquamarine |

TABLE 87

| | |
|---|---|
| Class name | bioengine |
| Superior class | bionode-object |
| Attributes specific to class | velocity;<br>rate-constant-sec is 1.0;<br>tau-coeff is given by a tau-coeff-par;<br>bias is given by a bias-par;<br>time-lag is given by a time-delay-par;<br>ph is given by a ~@ph-par;<br>ph-deviation-factor is given by a ~@ph-factor-par;<br>temperature is given by a temperature-par;<br>temp-deviation-factor is given by a temp-factor-par;<br>toggle-state has values show or hide (default is HIDE), with an index;<br>type-color |
| Capabilities and restrictions | none |
| Class restrictions | unless in administrator, developer, or modeler mode: menu choices exclude additionally: move, name, clone, change-size, color, delete, disable, enable, create-subworkspace, describe, go-to-subworkspace, create-sw;<br>when in modeler mode: menu choices exclude additionally: move, name, disable, enable, create-subworkspace, describe, go-to-subworkspace;<br>unless in administrator or developer mode: attributes visible for bioengine exclude additionally: toggle-state, type-color<br>when in simulation or explorer, mode: attributes visible for bioengine exclude additionally: notes, label; |
| Menu option | not a final menu choice |
| Inherited attributes | label is "", with an index;<br>description is "" |
| Attribute displays | velocity offset by (58, 5) |
| Stubs | a r-connection port-1 located at top 25;<br>a r-connection port-2 located at top 50;<br>a r-connection port-3 located at top 75;<br>a p-connection p1 located at bottom 25;<br>a p-connection p2 located at bottom 50;<br>a p-connection p3 located at bottom 75;<br>a c-graph-link gr located at left 11;<br>a c-graph-link ls located at left 31;<br>a c-graph-link up located at right 11;<br>a c-graph-link dn located at right 31 |
| Icon description | bioengine-pattern (width 86; height 42;<br>dark-color = dim-gray, light-color = light-gray, white-color = white, type-color = forest-green |

TABLE 88

Class bioEngine
    Class Binding-bioEngine
        Class Receptor-bioEngine
            Class bioengine.R1.L1
            Class bioengine.R2.L1
            Class bioengine.R1.L1.AC1
            Class bioengine.R1.L1.AN1
            Class bioengine.R2.L1.AC2
            Class bioengine.R2.L2.AN1
        ...

Class Complex-Formation-bioEngine
            Class bioengine.U3
            Class bioengine.U5
            Class bioengine.U7
            Class bioengine.KU3
            Class bioengine.M1C3
            Class bioengine.C3
        ...

Class DNA-Complex-Formation-bioEngine
            Class bioengine.DNA.U2
            Class bioengine.DNA.U5
        ...

Class Conform-Change-bioEngine
            Class bioengine.CA1.T2
        ...

Class Transport-bioEngine
            Class bioengine.EX1.L2
            Class bioengine.M2.EF1
        ...
    ...

Class Amplifier-bioEngine
        Class Enzyme-bioEngine
            Class bioengine.E1.S1
                Class bioengine.PK1.S1
                Class bioengine.PP1.S1
                Class bioengine.Pase1.S1
                Class bioengine.LK1.S1
            ...
            Class bioengine.E1.S2
            Class bioengine.E1.S1.I1
            Class bioengine.E1.S2.I1
            Class bioengine.E1.S2.I2
            Class bioengine.E3.S1.I1
        ...

Class Channel-bioEngine
            Class bioengine.CH1.IO1
            Class bioengine.CH1.IO1.L1
        ...

Class IonPump-bioEngine
            Class bioengine.PU1.IO1
        ...

Class Lumped-bioEngine
        Class Complex-Dissoc-bioEngine
        Class Translocation-bioEngine
        Class Auto-Catalitic-bioEngine

TABLE 89

| | |
|---|---|
| Class name | amplifier-bioengine |
| Superior class | bioengine |
| Attributes specific to class | none |
| Menu option | not a final menu choice |
| Stubs | inherited |
| Icon description | inherited |

| | |
|---|---|
| Class name | enzyme-bioengine |
| Superior class | amplifier-bioengine |
| Attributes specific to class | velocity is given by a catalytic-rate-pvar |
| Menu option | not a final menu choice |
| Stubs | an e-connection port-1 located at top 25; |
| | a s-connection s1 located at top 50; |
| | a s-connection s2 located at top 75; |
| | a p-connection p1 located at bottom 25; |
| | a p-connection p2 located at bottom 50; |
| | a p-connection p3 located at bottom 75; |
| | a c-graph-link gr located at left 11; |
| | a c-graph-link ls located at left 31; |
| | a c-graph-link up located at right 11; |
| | a c-graph-link dn located at right 31 |
| Icon description | bioengine-pattern (width 86; height 42; dark-color = dim-gray, light-color = light-gray, white-color = white, type-color = red) |

| | |
|---|---|
| Class name | bioengine.e1.s2 |
| Superior class | enzyme-bioengine |
| Attributes specific to class | none |
| Stubs | inherited |
| Icon description | inherited |

| | |
|---|---|
| Class name | bioengine.pk1.s2 |
| Superior class | bioengine.e1.s2 |
| Attributes specific to class | none |
| Stubs | inherited |
| Icon description | bioengine-pattern (width 86; height 42; dark-color = dim-gray, light-color = light-gray, white-color = white, type-color = coral) |

TABLE 90

| | |
|---|---|
| Class name | binding-bioengine |
| Superior class | bioengine |
| Attributes specific to class | velocity is given by a binding-rate-pvar |
| Menu option | not a final menu choice |
| Stubs | inherited |
| Icon description | inherited |

| | |
|---|---|
| Class name | receptor-bioengine |
| Superior class | binding-bioengine |
| Attributes specific to class | none |
| Menu option | not a final menu choice |
| Icon description | bioengine-pattern (width 86; height 42; dark-color = dim-gray, light-color = light-gray, white-color = white, type-color = medium-aquamarine; |

| | |
|---|---|
| Class name | bioengine.r1.l1 |
| Superior class | receptor-bioengine |
| Attributes specific to class | none |
| Stubs | a rc-connection port-1 located at top 25; a l-connection l1 located at top 50; a p-connection p1 located at bottom 50; a c-graph-link gr located at left 11; a c-graph-link ls located at left 31; a c-graph-link up located at right 11; a c-graph-link dn located at right 31 |
| Icon description | inherited |

| | |
|---|---|
| Class name | bioengine.r2.l1.ac2 |
| Superior class | receptor-bioengine |
| Attributes specific to class | none |
| Stubs | a rc-connection port-1 located at top 25; a rc-connection r2 located at top 50; a l-connection l2 located at top 75; an ac-connection ac1 located at top 100; an ac-connection ac2 located at top 125; a p-connection p1 located at bottom 50; a p-connection p2 located at bottom 100; a c-graph-link gr located at left 11; a c-graph-link ls located at left 31; a c-graph-link up located at right 11; a c-graph-link dn located at right 31 |
| Icon description | medium-bioengine-pattern (width 136; height 42; dark-color = dim-gray, light-color = light-gray, white-color = white, type-color = medium-aquamarine; |

TABLE 91

| | |
|---|---|
| Class name | lumped-bioengine |
| Superior class | bioengine |
| Attributes specific to class | none |
| Menu option | a final menu choice |
| Default settings | none |
| Attribute displays | inherited |
| Stubs | a co-connection c1 located at top 25; a p-connection p1 located at bottom 25; a p-connection p2 located at bottom 50; a p-connection p3 located at bottom 75; a c-graph-link gr located at left 11; a c-graph-link ls located at left 31; a c-graph-link up located at right 11; a c-graph-link dn located at right 31 |
| Color | inherited |
| Icon description | inherited |
| Class name | complex-dissoc-bioengine |
| Superior class | lumped-bioengine |
| Attributes specific to class | velocity is given by a dissociation-rate-pvar |
| Menu option | a final menu choice |
| Inherited attributes | as above (less velocity) |
| Attribute displays | inherited |
| Stubs | inherited |
| Icon description | bioengine-pattern (width 86; height 42; dark-color = dim-gray, light-color = light-gray, white-color = white, type-color = plum; |
| Class name | translocation-bioengine |
| Superior class | lumped-bioengine |
| Attributes specific to class | velocity is given by a tranlocation-rate-pvar |
| Menu option | a final menu choice |
| Inherited attributes | as above |
| Attribute displays | inherited |
| Stubs | a t-connection t1 located at top 25; a p-connection p2 located at bottom 25; a c-graph-link gr located at left 11; a c-graph-link ls located at left 31; a c-graph-link up located at right 11; a c-graph-link dn located at right 31 |
| Icon description | bioengine-pattern (width 86; height 42; dark-color = dim-gray, light-color = light-gray, white-color = white, type-color = medium-goldenrod) |
| Class name | auto-catal-bioengine |
| Superior class | lumped-bioengine |
| Attributes specific to class | none |
| Stubs | inherited |
| Icon description | bioengine-pattern (width 86; height 42; dark-color = dim-gray, light-color = light-gray, white-color = white, type-color = magenta) |

In COMPLEX-DISSOC-BIOENGINE and TRANSLOCATION-BIOENGINE the unique bioreactant is like a leading unit, there is only that

TABLE 92

| | |
|---|---|
| Class name | biorole-object |
| Superior class | bio-object |
| Attributes specific to class | stoichiometric-coeff is 1.0 |
| Capabilities and restrictions | none |
| Class restrictions | unless in administrator, or developer mode: menu choices for biorole-object exclude additionally: move, change-size, describe, create-subworkspace, go-to-subworkspace, rotate-reflect, clone, name; when in simulation, navigation, or general mode: menu choices for biorole-object exclude additionally: transfer, move, name, clone, change-size, color, create-subworkspace, delete, disable, describe, go-to-subworkspace; attributes visible for biorole-object exclude additionally: notes, label; when in simulation mode: menu choices for biorole-object exclude additionally: details, navig-panel; when in navigation or general mode: menu choices for biorole-object exclude additionally: input-panel; |
| Menu option | a final menu choice |
| Inherited attributes | label is "", with an index; description is "" |
| Attribute displays | inherited |
| Stubs | none |
| Icon description | biorole-object-pattern (width 100; height 40; dark-color = dim-gray, light-color = light-gray, type-color = sky-blue, white-color = white) |

TABLE 93

| | |
|---|---|
| Class name | bioreactant |
| Superior class | biorole-object |
| Attributes specific to class | description is ""; alpha-coeff is given by an alpha-coeff-par; contribution is given by a contribution-pvar; consumption-rate is given by a consum-rate-pvar |
| Capabilities and restrictions | none |
| Class restrictions | none |
| Menu option | not a final menu choice |
| Inherited attributes | stoichiometric-coeff is 1; label is "", with an index |
| Attribute displays | label offset by (-62, 35); contribution offset by (-42, 14); consumption-rate offset by (-42, 0) |
| Stubs | none |
| Icon description | inherited |

TABLE 95

| | |
|---|---|
| Class name | amplifier-bioreactant |
| Superior class | bioreactant |
| Attributes specific to class | effective-binding-sites is 1.0 |
| Menu option | not a final menu choice |
| Attribute displays | inherited |
| Stubs | inherited |
| Icon description | inherited |
| Class name | enzyme.r |
| Superior class | amplifier-bioreactant |
| Attributes specific to class | catalytic-rate-constant is 1.0; scaled-cat-rate.k is 1.0; |
| Stubs | an e-connection located at bottom 30 |
| Icon description | bioreactant-pattern (width 100; height 40; dark-color = dim-gray, light-color = light-gray, type-color = red, white-color = white) |
| Class name | prot.kinase.r |
| Superior class | enzyme.r |
| Attributes specific to class | none |
| Stubs | inherited |
| Icon description | bioreactant-pattern (width 100; height 40; dark-color = dim-gray, light-color = light-gray, type-color = coral, white-color = white) |

| | a prot.kinase.r |
|---|---|
| Names | none |
| Label | "prot.kinase" |
| Description | "" |
| Stoichiometric coeff | 1.0 |
| Alpha coeff | 1.0 |
| Contribution | 9.9e-99 |
| Consumption rate | 9.9e-99 |
| Effective binding sites | 1.0 |
| catalytic-rate-constant | 1.0 |
| scaled-cat-rate.k | 1.0 |

H73

TABLE 96

| | |
|---|---|
| Class name | source-bioreactant |
| Superior class | bioreactant |
| Attributes specific to class | none |
| Menu option | not a final menu choice |
| Inherited attributes | description is ""; alpha-coeff is given by an alpha-coeff-par; contribution is given by a contribution-pvar; consumption-rate is given by a consum-rate-pvar; stoichiometric-coeff is 1; label is "", with an index |
| Attribute displays | inherited |
| Stubs | inherited |
| Icon description | inherited |
| Class name | substrate.r |
| Superior class | source-bioreactant |
| Attributes specific to class | michaelis-constant is 9.9e-99 |
| Stubs | a s-connection s1 located at bottom 30 |
| Icon description | bioreactant-pattern (width 100; height 40; dark-color = dim-gray, light-color = light-gray, type-color = wheat, white-color = white; | a substrate.r

| | |
|---|---|
| Names | none |
| Label | "substrate" |
| Description | "" |
| Stoichiometric coeff | 1 |
| Alpha coeff | 1.0 |
| Contribution | 9.9e-99 |
| Consumption rate | 9.9e-99 |
| Michaelis constant | 9.9e-99 |

TABLE 97

| | |
|---|---|
| Class name | leading-bioreactant |
| Superior class | bioreactant |
| Attributes specific to class | effective-binding-sites is 1 |
| Menu option | a final menu choice |
| Inherited attributes | description is ""; alpha-coeff is given by an alpha-coeff-par; contribution is given by a contribution-pvar; consumption-rate is given by a consum-rate-pvar; stoichiometric-coeff is 1; label is "", with an index |
| Attribute displays | inherited |
| Stubs | inherited |
| Icon description | inherited |

TABLE 98

| | |
|---|---|
| Class name | binding-bioreactant |
| Superior class | bioreactant |
| Attributes specific to class | equilibrium-dissociation-constant is 9.9e-99 scaled-equil.dissoc.k is 1.0 |
| Menu option | not a final menu choice |
| Attribute displays | inherited |
| Stubs | inherited |
| Icon description | inherited |

| | |
|---|---|
| Class name | ligand.r |
| Superior class | binding-bioreactant |
| Attributes specific to class | none |
| Stubs | a 1-connection 11 located at bottom 30 |
| Icon description | bioreactant-pattern (width 100; height 40; dark-color = dim-gray, light-color = light-gray, type-color = pale-green, white-color = white) | a ligand.r

| | |
|---|---|
| Names | none |
| Label | "ligand" |
| Description | "" |
| Stoichiometric coeff | 1 |
| Alpha coeff | 1.0 |
| Contribution | 9.9e-99 |
| Consumption rate | 9.9e-99 |
| Equilibrium dissociation constant | 9.9e-99 |
| Scaled equil.dissoc.k | 1.0 |

TABLE 99

| | |
|---|---|
| Class name | inhibitor.bioreactant |
| Superior class | bioreactant |
| Attributes specific to class | inhibition-constant is 9.9e-99; scaled-inhibitor.k is 1.0 |
| Menu option | not a final menu choice |
| Attribute displays | inherited |
| Stubs | an i-connection i1 located at bottom 30 |
| Icon description | bioreactant-pattern (width 100; height 40; dark-color = dim-gray, light-color = light-gray, type-color = light-gray, white-color = white) |
| Class name | comp-inhibitor.r |
| Superior class | inhibitor.bioreactant |
| Attributes specific to class | none |
| Stubs | inherited |
| Icon description | inherited | a comp-inhibitor.r

| | |
|---|---|
| Names | none |
| Label | "comp-inh" |
| Description | "" |
| Stoichiometric coeff | 1.0 |
| Alpha coeff | 1.0 |
| Contribution | 9.9e-99 |
| Consumption rate | 9.9e-99 |
| Inhibition constant | 9.9e-99 |
| Scaled inhibitor.k | 1.0 |

| | |
|---|---|
| Class name | antagonist.r |
| Superior class | inhibitor.bioreactant |
| Attributes specific to class | none |
| Stubs | an an-connection an1 located at bottom 30 |
| Icon description | antagonist-pattern (width 100; height 40; dark-color = dim-gray, light-color = light-gray, type-color = light-gray, white-color = white) |

TABLE 100

| | |
|---|---|
| Class name | single-bioreactant |
| Superior class | bioreactant |
| Attributes specific to class | none |
| Menu option | not a final menu choice |
| Attribute displays | inherited |
| Stubs | inherited |
| Icon description | inherited |

| | |
|---|---|
| Class name | translocated.r |
| Superior class | single-bioreactant |
| Attributes specific to class | none |
| Stubs | a t-connection located at bottom 30 |
| Icon description | bioreactant-pattern (width 100; height 40; dark-color = dim-gray, light-color = light-gray, type-color = medium-goldenrod, white-color = white) |

| | |
|---|---|
| Class name | complex.r |
| Superior class | single-bioreactant |
| Attributes specific to class | none |
| Stubs | a co-connection u1 located at bottom 30 |
| Icon description | bioreactant-pattern (width 100; height 40; dark-color = dim-gray, light-color = light-gray, type-color = plum, white-color = white) | a translocated.r

| | |
|---|---|
| Names | none |
| Label | "translocated" |
| Description | "" |
| Stoichiometric coeff | 1 |
| Alpha coeff | 1.0 |
| Contribution | 9.9e-99 |
| Consumption rate | 9.9e-99 |

TABLE 101

| | |
|---|---|
| Class name | bioproduct |
| Superior class | biorole-object |
| Attributes specific to class | production-rate is given by a produc-rate-pvar; scaling-precursors is an instance of a symbol-array, with an index |
| Menu option | a final menu choice |
| Inherited attributes | stoichiometric-coeff is 1; label is "", with an index; description is "" |
| Attribute displays | label offset by (-55, -22); production-rate offset by (-42, 1) |
| Stubs | a p-connection located at top 30 |
| Icon description | bioproduct-pattern (width 100; height 40; dark-color = dim-gray, light-color = light-gray, type-color = khaki, white-color = white) |

TABLE 102

| | |
|---|---|
| Class name | biorole-post |
| Superior class | biopost |
| Attributes specific to class | ref-bioreservoir is none |
| Capabilities and restrictions | none |
| Class restrictions | unless in administrator or developer mode: menu choices for biorole-post exclude additionally: move, clone, rotate-reflect, change-size, color, delete, describe, create-subworkspace; when in modeler mode: menu choices for biorole-post include additionally: delete; menu choices for biorole-post exclude additionally: show-br; when in navigation or simulation mode: selecting any biopost implies show-br; when in explorer mode: selecting any biopost implies activate-br |
| Menu option | a final menu choice |
| Inherited attributes | toggle-state has values show or hide (default is HIDE), with an index |
| Stubs | a icon-wire located at right 7 with style diagonal |
| Icon description | biorole-post-pattern (width 8; height 16) |

| | |
|---|---|
| Class name | bioreactant-post |
| Superior class | biorole-post |
| Attributes specific to class | none |
| Capabilities and restrictions | none |
| Class restrictions | none |
| Menu option | a final menu choice |
| Inherited attributes | ref-bioreservoir is none; toggle-state has values show or hide (default is HIDE), with an index |
| Stubs | a icon-wire located at right 7 |
| Icon description | bioreactant-post-pattern (width 8; height 16) |

| | |
|---|---|
| Class name | bioproduct-post |
| Superior class | biorole-post |
| Attributes specific to class | none |
| Capabilities and restrictions | none |
| Class restrictions | none |
| Menu option | a final menu choice |
| Inherited attributes | ref-bioreservoir is none; toggle-state has values show or hide (default is HIDE), with an index |
| Stubs | a icon-wire located at left 7 |
| Icon description | bioproduct-post-pattern (width 8; height 16) |

TABLE 103 an user-menu-choice
Label                create-local
Applicable class     complex-bioentity
Condition            the item has a name
Action               start ET-CREATE-LOCAL-PROC (the item, this
window)

ET-CREATE-LOCAL-PROC (EN: class complex-bioentity, W: class window)
   create a complex-bioentity LO by cloning EN;
   transfer LO to the WS of EN at (the item-x-position of EN +
     10, the item-y-position of EN - 30);
   for each bioentity CO upon the SW of LO do
     make CO transient and delete CO;
   for each bioentity-notes BN upon the SW of LO do
     make BN transient and delete BN;
   make LO permanent;

TABLE 104 an user-menu-choice
Label                clean-clone
Applicable class     bioreservoir
Condition            none
Action               start BR-CLEAN-CLONE-PROC (the item, this
                     window)

BR-CLEAN-CLONE-PROC (BR: class bioreservoir, W: class window)
   create a bioreservoir CO by cloning BR;
   conclude that the label of CO = "";
   conclude that the description of CO = "";
   conclude that the references of CO = "";
   conclude that the warnings of CO = "";
   conclude that the status of CO is available;
   conclude that the compartment of CO = "";
   change the text of the if-scaling-bioreservoir of CO to "none";
   conclude that the if-scaling-amount of CO = 100;
   change the text of the ref-bioentity of CO to "none";
   change the text of the master-bioreservoir of CO to "none";
   conclude that the decay-rate-factor of CO = 2.0e-4 ;
   conclude that the scaled-basal-amount of CO = 9.9e-99 ;
   change the text of the physiol-abundance of CO to "only-induced";
   if CO has normal-basal-density then
     conclude that the normal-basal-density of CO = 9.9e-99;
   if CO has normal-basal-concentration then
     conclude that the normal-basal-concentration of CO = 9.9e-99;
   if CO has physiol-max-density then
     conclude that the physiol-max-density of CO = 9.9e-99;
   if CO has physiol-max-concentration then
     conclude that the physiol-max-concentration of CO = 9.9e-99;
   SW = the subworkspace of CO;
   activate SW;
   for each biopool-post PP upon SW do;
     delete PP;
   for each model-box MB upon SW do
     delete MB;
   transfer CO to the WS of BR at (the item-x-position of BR + 30,
     the item-y-position of BR - 30);
   conclude that the toggle-state of CO is hide;
   change the status-color icon-color of CO to medium-aquamarine;
   make CO permanent;

TABLE 105

|  |  |
|---|---|
|  | an user-menu-choice |
| Label | add-scaled-input |
| Applicable class | biopool |
| Condition | the scaled-input-model-box connected to the item does not exist |
| Action | start CREATE-SCALED-INPUT-MODEL-BOX-PROC (the item, this window) |

CREATE-SCALED-INPUT-MODEL-BOX-PROC (BP: class biopool, Win: class window)
create a scaled-input-model-box B by cloning MASTER-SCALED-INPUT-MODEL-BOX;
transfer B to the workspace of BP at (left-edge(BP) -7, middle-y(BP)+56);
make B permanent;
show the subworkspace of B on Win with its center 340 units above the center of the screen;

TABLE 106

|  |  |
|---|---|
|  | an user-menu-choice |
| Label | add-input |
| Applicable class | biopool |
| Condition | the input-model-box connected to the item does not exist |
| Action | start CREATE-INPUT-MODEL-BOX-PROC (the item, this window) |

CREATE-INPUT-MODEL-BOX-PROC (BP: class biopool, Win: class window)
create an input-model-box B by cloning MASTER-INPUT-MODEL-BOX;
transfer B to the workspace of BP at (left-edge(BP) -7, middle-y(BP)+38);
make B permanent;
show the subworkspace of B on Win with its center 320 units above the center of the screen;

TABLE 107

|  |  |
|---|---|
|  | an user-menu-choice |
| Label | add-output |
| Applicable class | biopool |
| Condition | the output-model-box connected to the item does not exist |
| Action | start CREATE-OUTPUT-MODEL-BOX-PROC (the item, this window) |

CREATE-OUTPUT-MODEL-BOX-PROC (BP: class biopool, Win: class window)
create an output-model-box B by cloning MASTER-OUTPUT-MODEL-BOX;
transfer B to the workspace of BP at (left-edge(BP) -7, middle-y(BP)-40);
make B permanent;
show the subworkspace of B on Win with its center 300 units above the center of the screen;

TABLE 108

| | |
|---|---|
| | an user-menu-choice |
| Label | activate-sw |
| Applicable class | bioprocess |
| Condition | the bioengine upon the subworkspace of the item does not exist |
| Action | activate the subworkspace of the item |

TABLE 109

| | |
|---|---|
| | an user-menu-choice |
| Label | clean-clone |
| Applicable class | bioprocess |
| Condition | the subworkspace of the item exists |
| Action | start BP-CLEAN-CLONE-PROC (the item, this window) |

BP-CLEAN-CLONE-PROC (BP: class bioprocess, win: class window)

```
CO = call BP-LABELED-CLONE-PROC (BP, win)
conclude that the label of CO = "";
SW = the subworkspace of CO;
for each bioreactant RO upon SW do
    conclude that the label of RO = "";
for each bioproduct PO upon SW do
    conclude that the label of PO = "";
```

TABLE 110

```
                an user-menu-choice
Label           labeled-clone
Applicable class bioprocess
Condition       the subworkspace of the item exists
Action          start BP-LABELED-CLONE-PROC (the item, this
                window)
```

BP-LABELED-CLONE-PROC (BP: class bioprocess, win: class window)

```
create a bioprocess CO by cloning BP;
conclude that the description of CO = "";
conclude that the references of CO = "";
conclude that the warnings of CO = "";
conclude that the status of CO is available;
conclude that the activation-hold-interval of CO = 0 seconds;
conclude that the deactivation-hold-interval of CO = 0 seconds;
conclude that the master-bioprocess of CO is none;
view = the subworkspace of CO;
activate view;
for each bioreactant RO upon view do
    conclude that the description of RO = "";
    conclude that the stoichiometric-coeff of RO = 1;
    conclude that the alpha-coeff of RO = 1.0;
    conclude that the contribution of RO = 9.9e-99;
    conclude that the consumption-rate of RO = 9.9e-99;
    if RO has effective-binding-sites then
        conclude that the effective-binding-sites of RO = 1.0;
    if RO has equilibrium-dissociation-constant then
        conclude that the equilibrium-dissociation-constant of RO =
            9.9e-99;
    if RO has scaled-equil.dissoc.k then
        conclude that the scaled-equil.dissoc.k of RO = 1.0;
    if RO has michaelis-constant then
        conclude that the michaelis-constant of RO = 9.9e-99;
    if RO has scaled-michaelis.k then
        conclude that the scaled-michaelis.k of RO = 1.0;
    if RO has equilibrium-constant then
        conclude that the equilibrium-constant of RO = 9.9e-99;
    if RO has scaled-equilibrium.k then
        conclude that the scaled-equilibrium.k of RO = 1.0;
    if RO has inhibition-constant then
        conclude that the inhibition-constant of RO = 9.9e-99;
    if RO has scaled-inhibition.k then
        conclude that the scaled-inhibition.k of RO = 1.0;
for each bioproduct PO upon view do
    conclude that the description of PO = "";
    conclude that the stoichiometric-coeff of PO = 1.0;
    conclude that the production-rate of PO = 9.9e-99;
    change the array-length of the scaling-precursors of PO to 0;
    change the text of the initial-values of the scaling-precursors
        of PO to "not-computed";
for each biorole-post RP upon view do
    conclude that the ref-bioreservoir of RP is none;
conclude that the toggle-state of CO is hide;
change the status-color of CO to slate-blue;
transfer CO to the workspace of BP at (the item-x-position of BP
    + 30, the item-y-position of BP - 30);
make CO permanent;
```

TABLE 111

|  |  |
|---|---|
|  | an user-menu-choice |
| Label | create-sw |
| Applicable class | bioengine |
| Condition | not (there exists a subworkspace of the item) and the toggle-state of the item is hide |
| Action | start CREATE-SW-FOR-BIOENGINE (the item, this window) |

CREATE-SW-FOR-BIOENGINE (E: class bioengine, win: class window)

create a workspace box by cloning the SW of BIOENGINE-SW-MASTER;
show box on win at the center of the screen;
make box the subworkspace of E;
make box permanent;

TABLE 112a

|  |  |
|---|---|
|  | an user-menu-choice |
| Label | add-top-post |
| Applicable class | biopool |
| Condition | none |
| Action | start CREATE-BIOPOOL-P-POST-PROC (the item, this window) |

TABLE 112b

|  |  |
|---|---|
|  | an user-menu-choice |
| Label | add-bottom-post |
| Applicable class | biopool |
| Condition | none |
| Action | start CREATE-BIOPOOL-R-POST-PROC (the item, this window) |

TABLE 112b
```
CREATE-BIOPOOL-P-POST-PROC (BP: class biopool, Win: class
window)
  create a biopool-p-post P;
  if the biopool-p-post connected at the p02 of BP does not exist then
      next-label = "pp02";
      x = - 50; else
  if the biopool-p-post connected at the p04 of BP does not exist then
      next-label = "pp04";
      x = - 25; else
  if the biopool-p-post connected at the p06 of BP does not exist then
      next-label = "pp06";
      x = 0; else
  if the biopool-p-post connected at the p08 of BP does not exist then
      next-label = "pp08";
      x = 25; else
  if the biopool-p-post connected at the p10 of BP does not exist then
      next-label = "pp10";
      x = 50; else
  if the biopool-p-post connected at the p12 of BP does not exist then
      next-label = "pp12";
      x = 75; else
  go to part-2-routine;
  transfer P to the workspace of BP at (middle-x (BP) + x, middle-y(BP) +
      40);
  change the text of the label of P to "[next-label]";
  call POOLPOST-NAME-IT-PROC (P, Win);
  make P permanent;
  return;
part-2-routine:
  if not (there exists a biopool-p-post connected at the p01 of BP) then
      next-label = "pp01";
      x = - 63; else
  if the biopool-p-post connected at the p03 of BP does not exist then
      next-label = "pp03";
      x = - 38; else
  if the biopool-p-post connected at the p05 of BP does not exist then
      next-label = "pp05";
      x = - 13; else
  if the biopool-p-post connected at the p07 of BP does not exist then
      next-label = "pp07";
      x = 12; else
  if the biopool-p-post connected at the p09 of BP does not exist then
      next-label = "pp09";
      x = 37; else
  if the biopool-p-post connected at the p11 of BP does not exist then
      next-label = "pp11";
      x = 62; else
  go to exit-routine;
  transfer P to the workspace of BP at (middle-x (BP) + x, middle-y(BP) +
      60);
  change the text of the label of P to "[next-label]";
  call POOLPOST-NAME-IT-PROC (P, Win);
  make P permanent;
  return;
exit-routine:
  md = call uil-create-message-dialog ("md", "Change the label of the new
      post to the next consecutive number, such as pp13, place it in next
      position, and connect it to the connection of the last raised post, and
      select name-it from its menu", win, the symbol none, 0, 0);
  transfer P to the workspace of BP at (middle-x (BP) + 100, middle-
      y(BP) + 100);
  make P permanent;
  if the biopool-p-post connected at the p01 of BP exists then
      move the biopool-p-post connected at the p01 of BP to (middle-x (BP)
      - 63, middle-y(BP) + 100);
```

A84

TABLE 113b

```
CREATE-BIOPOOL-R-POST-PROC (BP: class biopool, Win: class
window)
  create a biopool-r-post P;
  if the biopool-r-post connected at the r02 of BP does not exist then
      next-label = "rp02";
      x = - 50; else
  if the biopool-r-post connected at the r04 of BP does not exist then
      next-label = "rp04";
      x = - 25; else
  if the biopool-r-post connected at the r06 of BP does not exist then
      next-label = "rp06";
      x = 0; else
  if the biopool-r-post connected at the r08 of BP does not exist then
      next-label = "rp08";
      x = 25; else
  if the biopool-r-post connected at the r10 of BP does not exist then
      next-label = "rp10";
      x = 50; else
  if the biopool-r-post connected at the r12 of BP does not exist then
      next-label = "rp12";
      x = 75; else
  go to part-2-routine;
  transfer P to the workspace of BP at (middle-x (BP) + x, middle-y(BP) -
      42);
  change the text of the label of P to "[next-label]";
  call POOLPOST-NAME-IT-PROC (P, Win);
  make P permanent;
  return;
part-2-routine:
  if not (there exists a biopool-r-post connected at the r01 of BP) then
      next-label = "rp01";
      x = - 63; else
  if the biopool-r-post connected at the r03 of BP does not exist then
      next-label = "rp03";
      x = - 38; else
  if the biopool-p-post connected at the r05 of BP does not exist then
      next-label = "rp05";
      x = - 13; else
  if the biopool-r-post connected at the r07 of BP does not exist then
      next-label = "rp07";
      x = 12; else
  if the biopool-r-post connected at the r09 of BP does not exist then
      next-label = "rp09";
      x = 37; else
  if the biopool-r-post connected at the r11 of BP does not exist then
      next-label = "rp11";
      x = 62; else
  go to exit-routine;
  transfer P to the workspace of BP at (middle-x (BP) + x, middle-y(BP) -
      64);
  change the text of the label of P to "[next-label]";
  call POOLPOST-NAME-IT-PROC (P, Win);
  make P permanent;
  return;
exit-routine:
  md = call uil-create-message-dialog ("md", "Change the label of the new
      post to the next consecutive number, such as rp13, place it in next
      position, and connect it to the connection of the last raised post", win,
      0, 0);
  transfer P to the workspace of BP at (middle-x (BP) + 100, middle-
      y(BP) - 100);
  make P permanent;
  if the biopool-p-post connected at the r01 of BP exists then
      move the biopool-r-post connected at the r01 of BP to (middle-x (BP)
          - 63, middle-y(BP) - 100);
```

TABLE 114

|  |  |
|---|---|
|  | an user-menu-choice |
| Label | name-it |
| Applicable class | biopool-post |
| Condition | the item has no name |
| Action | start POOLPOST-NAME-IT-PROC (the item, this window) |

POOLPOST-NAME-IT-PROC (post: class biopool-post, win: class window)

BR = the bioreservoir superior to the workspace of post;
  br-name = "[the name of BR]";
  length = length-of-text (br-name );
  base-name = omit-from-text (br-name, length - 1, length);
  L = "[the label of post]";
  post-name = insert-in-text ( L, base-name, length - 1 );
  change the name of post to symbol ("[post-name]");
  change the text of the label of post to "[post-name]";
  change the face-color icon-color of post to green;
  make post permanent;

TABLE 115

|  |  |
|---|---|
|  | an user-menu-choice |
| Label | unname-it |
| Applicable class | biopool-post |
| Condition | the item has a name |
| Action | start POOLPOST-REMOVE-NAME-PROC (the item, this window) |

POOLPOST-REMOVE-NAME-PROC (post: class biopool-post, W: class window)

change the text of the names of post to "none";
change the text of the ref-bioprocess of post to "none";
post-label = the label of post;
length = length-of-text (post-label);
base-label = omit-from-text (post-label, 1, length - 4);
change the text of the label of post to "[base-label]";
change the face-color icon-color of post to light-gray;
make post permanent;

TABLE 117
---
                        an user-menu-choice
Label                   unname-it
Applicable class        biorole-post
Condition               the item has a name
Action                  start ROLEPOST-REMOVE-NAME-PROC (the item,
                        this window)
---
ROLEPOST-REMOVE-NAME-PROC (post: class biorole-post, win:
 class window)

if there exists a biopool connected to post then
    BR = the bioreservoir superior to the workspace of the biopool
        connected to post;
    PPN = the name of post;
    if the biopool-post named by PPN exists then
        PP = the biopool-post named by PPN;
        change the text of the ref-bioprocess of PP to "none";
        make PP permanent;
change the text of the ref-bioreservoir of post to "none";
change the text of the names of post to "none";
change the text of the label of post to "none";
make post permanent;
---

TABLE ___
---
                        an user-menu-choice
Label                   set-refs
Applicable class        biorole-post
Condition               the item has a name
Action                  start ROLEPOST-SET-REFS-PROC (the item, this
                        window)
---
ROLEPOST-SET-REFS-PROC (post: class biorole-post, W: class
 window)

BP = the bioprocess superior to the workspace of post;
if there exists a biopool PO connected to post then
    BR = the bioreservoir superior to the workspace of PO;
    PPN = the name of post;
    PP = the biopost named by PPN;
    if post is a bioreactant-post and PP is not a biopool-r-post then
        inform the operator that "You are trying to establish the wrong
            connection. Only a biopool-r-post should be given the same
            name as a bioreactant-post" else
    if post is a bioproduct-post and PP is not a biopool-p-post then
        inform the operator that "You are trying to establish the wrong
            connection. Only a biopool-p-post should be given the same
            name as a bioproduct-post"
    else
        conclude that the ref-bioprocess of PP = the name of BP;
        make PP permanent;
        conclude that the ref-bioreservoir of post = the name of BR;
        make post permanent;
---

TABLE 118
---
a rule initially
    show the subworkspace of INITIALIZATION-PANEL at the center of
    the screen
---

TABLE 119
---
BASIS-MENU-HEAD-CALLBACK (button: class button, win: class
window, dlg-or-wksp: class item)

if the user-mode of win is developer then
        start gdm-init-and-show-menu-system (developer -menu-head, win) else
    if the user-mode of win is modeler then
        start gdm-init-and-show-menu-system (modeler -menu-head, win) else
    if the user-mode of win is general or the user-mode of win is navigation
            then
        start gdm-init-and-show-menu-system (general -menu-head, win) else
    if the user-mode of win is simulation then
        start gdm-init-and-show-menu-system (simulation-menu-head, win);
    return
---

TABLE 121
---
NAVIG-INIT-CALLBACK (button: class uil-button, win: class window,
panel: class selection-panel)

call NAVIG-INIT-PROC (win);
return
---
NAVIG-INIT-PROC (win: class window)

inform the operator that "Initialization started";
    for BP = each bioprocess do
        allow other processing;
        if the subworkspace of BP exists then activate the subworkspace of BP;
    for BR = each bioreservoir do
        allow other processing;
        if the subworkspace of BR exists then activate the subworkspace of BR;
    call BR-INITIALIZATION-PROC ();
    inform the operator that "The bioReservoirs have been initialized";
    for BP = each bioprocess do
        if BP has a name then
            call BP-INITIALIZATION-PROC (BP);
            call DOWNSTREAM-CHAINING-PROC (BP);
            call UPSTREAM-CHAINING-PROC (BP);
    inform the operator that "The bioProcesses have been initialized and
        chaining is completed"
---

TABLE 120 a gd-menu-head-template

| | |
|---|---|
| Names | none |
| Label | "Receptor Library" |
| Action procedure name | gdm-run-action-and-wrapup-procedures-for-submenus |
| State | enabled |
| Wrapup procedure name | gdm-hide-this-menu-and-dehighlight-previous-menu-option |
| Menu class name | gd-wide-menu-head |
| Initial position | up |
| No of pixels down | 0 |
| No of pixels right | 0 | a gd-go-to-submenu-option-template

| | |
|---|---|
| Names | none |
| Label | "Receptor Library" |
| Action procedure name | show-sub-menu |
| State | enabled |
| Wrapup procedure name | do-nothing |
| Menu class name | gd-wide-menu-option |
| Leave highlighted | true | a gd-go-to-ws-menu-option-template

| | |
|---|---|
| Names | none |
| Label | "References Scroll" |
| Action procedure name | gdm-go-to-workspace |
| State | enabled |
| Wrapup procedure name | roll-up |
| Menu class name | gd-wide-menu-option |
| Leave highlighted | false |
| Object w subworkspace name | master-reference-panel | a gd-go-to-ws-menu-option-template

| | |
|---|---|
| Names | none |
| Label | "Experiment Setup 1" |
| Action procedure name | gdm-go-to-workspace |
| State | enabled |
| Wrapup procedure name | roll-up |
| Menu class name | gd-wide-menu-option |
| Leave highlighted | false |
| Object w subworkspace name | experiment-setup-panel-1 | a gd-plain-menu-option-template

| | |
|---|---|
| Names | none |
| Label | "Structure Queries" |
| Action procedure name | create-general-structure-selection-panel-callback |
| State | enabled |
| Wrapup procedure name | roll-up |
| Menu class name | gd-wide-menu-option |
| Leave highlighted | false | a gd-go-to-named-menu-system

| | |
|---|---|
| Names | none |
| Label | "Simulation Mode" |
| Action procedure name | change-mode-and-show-named-menu-system |
| State | enabled |
| Wrapup procedure name | do-nothing |
| Menu class name | gd-wide-menu-option |
| Leave highlighted | false |
| Next menu system name | simulation-mode-menu |

TABLE 122

```
BR-INITIALIZATION-PROC ()

for BR = each bioreservoir do
  if BR has a name then
    allow other processing;
    conclude that the status of BR is available;
    SW = the subworkspace of BR;
    PO = the biopool upon SW;
    conclude that the label of PO = the label of BR;
    change the text of the master-bioreservoir of BR to"[the name of BR]";
    WS = the workspace of BR;
    if the warnings of BR /= "" then change the flag-color icon-
        color of BR to yellow else change the flag-color icon-color
        of BR to the status-color icon-color of BR;
    if there exists a biopool-r-post connected to PO then
      for PRP = each biopool-r-post connected to PO do
        if PRP has a name then
          allow other processing;
          if there exists a bioreactant-post RP such that (RP has
              a name and the name of RP = the name of PRP) then
            DBP = the bioprocess superior to the workspace of RP;
            conclude that the ref-bioprocess of PRP = the name of DBP;
            conclude that DBP is a-down-bioprocess-of BR;
    if there exists a biopool-p-post connected to PO then
      for PPP = each biopool-p-post connected to PO do
        if PPP has a name then
          allow other processing;
          if there exists a bioproduct-post PP such that (PP has
              a name and the name of PP = the name of PPP) then
            UBP = the bioprocess superior to the workspace of PP;
            conclude that the ref-bioprocess of PPP = the name of UBP;
            conclude that UBP is an-up-bioprocess-of BR;
  make BR permanent;
  return
```

TABLE 123

BP-INITIALIZATION-PROC (BP: class bioprocess)

SW: class kb-workspace = the subworkspace of BP;
WS: class kb-workspace = the workspace of BP;
allow other processing;
conclude that the status of BP is available;
if there exists a bioengine E upon SW then
  change the type-color icon-color of BP to the type-color icon-color
    of the bioengine upon SW;
  conclude that the label of E = the label of BP;
change the text of the master-bioprocess of BP to "[the name of BP]";
if the warnings of BP /= "" then change the flag-color icon-color
  of BP to yellow else change the flag-color icon-color of BP to
  the type-color icon-color of BP;
if there exists a bioreactant upon SW then
  for R = each bioreactant upon SW do
  allow other processing;
  RP = the bioreactant-post connected to R;
  if RP has a name then
    if there exists a biopost PRP such that (PRP has a name and
      the name of PRP = the name of RP and PRP is not a biopool-
      r-post) then inform the operator that "A wrong connection
      has been establised. A bioreactant-post named [the name
      of RP] has been given the same name as a biopost that is
      not a biopool-r-post" else
    if there exists a biopool-r-post PRP such
      that (PRP has a name and the name of PRP = the name of RP) then
    UBR = the bioreservoir superior to the workspace of PRP;
    conclude that the ref-bioreservoir of RP = the name of UBR;
    if there exists a bioprocess that is an-up-bioprocess-of UBR then
      for USBP = each bioprocess that is an-up-bioprocess-of UBR do
        conclude that USBP is an-upstream-bioprocess-of BP;
        if there exists a bioreservoir that is an-up-bioreservoir-of USBP
          then
          for USBR = each bioreservoir that is an-up-bioreservoir-of
            USBP do
            conclude that USBR is an-upstream-bioreservoir-of UBR;
if there exists a bioproduct upon SW then
  for P = each bioproduct upon SW do
  allow other processing;
  PP = the bioproduct-post connected to P;
  if PP has a name then
    if there exists a biopost PPP such that (PPP has a name and
      the name of PPP = the name of PP and PPP is not a biopool-
      p-post) then inform the operator that "A wrong connection
      has been establised. A bioproduct-post named [the name of
      PP] has been given the same name as a biopost that is not
      a biopool-p-post" else
    if there exists a biopool-p-post PPP such
      that (PPP has a name and the name of PPP = the name of PP) then
    DBR = the bioreservoir superior to the workspace of PPP;
    conclude that the ref-bioreservoir of PP = the name of DBR;
    if there exists a bioprocess that is a-down-bioprocess-of DBR then
      for DSBP = each bioprocess that is a-down-bioprocess-of
        DBR do
      allow other processing;
      conclude that DSBP is a-downstream-bioprocess-of BP;
      if there exists a bioreservoir that is a-down-bioreservoir-of
        DSBP then
        for DSBR = each bioreservoir that is a-down-bioreservoir-of
          DSBP do
          conclude that DSBR is a-downstream-bioreservoir-of DBR;
make BP permanent;
return;

TABLE 124

DOWNSTREAM-CHAINING-PROC (BP: class bioprocess)

```
if there exists a bioprocess that is a-downstream-bioprocess-of BP then
  for BP1 = each bioprocess that is a-downstream-bioprocess-of BP do
    allow other processing;
    if there exists a bioprocess that is a-downstream-bioprocess-of BP1 then
      for DBP = each bioprocess that is a-downstream-bioprocess-of BP1 do
        if DBP is not a-downstream-bioprocess-of BP then
          allow other processing;
          conclude that DBP is a-downstream-bioprocess-of BP;
          call DOWNSTREAM-CHAINING-PROC (DBP);
if there exists a bioreservoir that is a-down-bioreservoir-of BP then
  for BR1 =each bioreservoir that is a-down-bioreservoir-of BP do
    allow other processing;
    if there exists a bioreservoir that is a-downstream-bioreservoir-of
        BR1 then
      for BR2 =each bioreservoir that is a-downstream-bioreservoir-of
          BR1 do
        if there exists a bioreservoir that is a-downstream-bioreservoir-of
            BR2 then
          for DBR = each bioreservoir that is a-downstream-bioreservoir-of
              BR2 do
            if DBR is not a-downstream-bioreservoir-of BR1 then
              allow other processing;
              conclude that DBR is a-downstream-bioreservoir-of BR1;
```

TABLE 125

UPSTREAM-CHAINING-PROC (BP: class bioprocess)

```
if there exists a bioprocess that is an-upstream-bioprocess-of BP then
  for BP1 = each bioprocess that is an-upstream-bioprocess-of BP do
    allow other processing;
    if there exists a bioprocess that is an-upstream-bioprocess-of BP1 then
      for UBP = each bioprocess that is an-upstream-bioprocess-of BP1 do
        if UBP is not an-upstream-bioprocess-of BP then
          allow other processing;
          conclude that UBP is an-upstream-bioprocess-of BP;
          call UPSTREAM-CHAINING-PROC (UBP);
if there exists a bioreservoir that is an-up-bioreservoir-of BP then
  for BR1 =each bioreservoir that is an-up-bioreservoir-of BP do
    allow other processing;
    if there exists a bioreservoir that is an-upstream-bioreservoir-of BR1 then
      for BR2 =each bioreservoir that is an-upstream-bioreservoir-of BR1 do
        if there exists a bioreservoir that is an-upstream-bioreservoir-of BR2
            then
          for UBR = each bioreservoir that is an-upstream-bioreservoir-of
              BR2 do
            if UBR is not an-upstream-bioreservoir-of BR1 then
              allow other processing;
              conclude that UBR is an-upstream-bioreservoir-of BR1;
```

TABLE 126

ADD-QUERY-CALLBACK (button: class uil-button, win: class window, panel: class selection-panel)

call ET-INITIALIZATION-PROC ();
call INIT-QUERY-TABLES-PROC (win);
return

TABLE 127

QUERY-INIT-CALLBACK (button: class button, win: class window, panel: class selection-panel)

call NAVIG-INIT-PROC (win);
call ET-INITIALIZATION-PROC ();
call INIT-QUERY-TABLES-PROC (win);
return

TABLE 128

ET-INITIALIZATION-PROC ()

n: integer = 0;
  for ET = each complex-bioentity do
    if ET has a name then
      EN = the name of ET;
      CL = the class of ET;
      n = 0;
      conclude that the id of ET = "[EN]-0";
      for CE = each complex-bioentity that is of the class named by CL do
        if the master-bioentity of CE = EN then
          n = n + 1;
          conclude that the id of CE = "[EN]-[n]";
return ;

TABLE 129

INIT-QUERY-TABLES-PROC (win: class g2-window)

activate the subworkspace of QUERY-ARRAYS-BIN;
ASW = the subworkspace of QUERY-ARRAYS-BIN;
LSW = the subworkspace of QUERY-LISTS-BIN;
if there exists a query-array upon ASW then
  for QA = each query-array upon ASW do
    make QA transient;
    delete QA;
if there exists a query-list upon LSW then
  for QL = each query-list upon LSW do
    delete QL;
call FIND-BIOENTITY-DEFINITIONS-PROC ();
call CREATE-QUERY-LISTS-PROC ();
for QL = each query-list upon LSW do
  CL = the ref-component-class of QL;
  if there exists a bioentity EC that is of the class named by CL then
    for EC = each bioentity that is of the class named by CL do
      allow other processing;
      call FIND-NAMED-BIOENTITIES-WITH-COMPONENT-PROC
(EC, QL, win);
    conclude that the lenght of QL = the number of elements in QL;
call COMPLETE-QUERY-TABLE-PROC (win);
call CREATE-AUXILIARY-QUERY-ARRAYS-PROC (win);
deactivate the subworkspace of QUERY-ARRAYS-BIN;
activate the subworkspace of QUERY-ARRAYS-BIN;
inform the operator that "The master query lists have been completed"

TABLE 130

FIND-BIOENTITY-DEFINITIONS-PROC ()

for B = each uil-goto-workspace-button upon the subworkspace of
BIOENTITIES do
  for B1 = each uil-goto-workspace-button upon the subworkspace of B do
    SW1 = the subworkspace of B1;
    if there exists an object-definition upon SW1 then
      for OD = each object-definition upon SW1 do
        allow other processing;
        call CREATE-QUERY-ARRAY-PROC (OD)
    else
      for B2 = each uil-goto-workspace-button upon the subworkspace of
B1 do
        SW2 = the subworkspace of B2;
        if there exists an object-definition upon SW2 then
          for OD = each object-definition upon SW2 do
            allow other processing;
            call CREATE-QUERY-ARRAY-PROC (OD)
        else
          for B3 = each uil-goto-workspace-button upon the subworkspace of
B2 do
            SW3 = the subworkspace of B3;
            if there exists an object-definition upon SW3 then
              for OD = each object-definition upon SW3 do
                allow other processing;
                call CREATE-QUERY-ARRAY-PROC (OD)

TABLE 131

CREATE-QUERY-ARRAY-PROC (MC: class object-definition)

SC = symbol (the text of the superior-class of MC);
SW = the subworkspace of query-arrays-bin
   case (SC) of
      protein-site :
         create a query-array MA;
         transfer MA to SW at (-160, -265);
         CL = the text of the class-name of MC;
         change the text of the major-class of MA to "protein-site";
         change the text of the ref-component-class of MA to "[CL]";
         change the name of MA to symbol ("[CL]-query-array");
      protein-modified-group :
         create a query-array MA;
         transfer MA to SW at (-160, -265);
         CL = the text of the class-name of MC;
         change the text of the major-class of MA to "protein-
            modified-group";
         change the text of the ref-component-class of MA to "[CL]";
         change the name of MA to symbol ("[CL]-query-array");
      protein-motif:
         create a query-array MA;
         transfer MA to SW at (-160, -140);
         CL = the text of the class-name of MC;
         change the text of the major-class of MA to "protein-motif";
         change the text of the ref-component-class of MA to "[CL]";
         change the name of MA to symbol ("[CL]-query-array");
      protein-domain:
         create a query-array MA;
         transfer MA to SW at (-160, -10);
         CL = the text of the class-name of MC;
         change the text of the major-class of MA to "protein-domain";
         change the text of the ref-component-class of MA to "[CL]";
         change the name of MA to symbol ("[CL]-query-array");
      protein:
         create a query-array MA;
         transfer MA to SW at (-160, 120);
         CL = the text of the class-name of MC;
         change the text of the major-class of MA to "protein";
         change the text of the ref-component-class of MA to "[CL]";
         change the name of MA to symbol ("[CL]-query-array");
      heter.mol.complex:
         create a query-array MA;
         transfer MA to SW at (-160, 245);
         CL = the text of the class-name of MC;
         change the text of the major-class of MA to "heter.mol.complex";
         change the text of the ref-component-class of MA to "[CL]";
         change the name of MA to symbol ("[CL]-query-array");
      dna-component :
         create a query-array MA;
         transfer MA to SW at (-160, 370);
         CL = the text of the class-name of MC;
         change the text of the major-class of MA to "dna-component";
         change the text of the ref-component-class of MA to "[CL]";
         change the name of MA to symbol ("[CL]-query-array");
      nucleic-acid:
         create a query-array MA;
         transfer MA to SW at (-160, 370);
         CL = the text of the class-name of MC;
         change the text of the major-class of MA to "nucleic-acid";
         change the text of the ref-component-class of MA to "[CL]";
         change the name of MA to symbol ("[CL]-query-array");
      otherwise:
         allow other processing;

TABLE 132
---
CREATE-QUERY-LISTS-PROC ()

SW = the subworkspace of QUERY-ARRAYS-BIN ;

for QA = each query-array upon SW do
  allow other processing;
  QAN = the name of QA;
  create a query-list QL;
  transfer QL to SW at (middle-x(QA), middle-y (QA));
  change the text of the ref-array of QL to "[QAN]";
  change the text of the ref-component-class of QL to "[the ref-
    component-class of QA]";
---

TABLE 133
---
FIND-NAMED-BIOENTITIES-WITH-COMPONENT-PROC (EC: class
bioentity , QL: class query-list, win: class window)

if EC has a name then
  call SEEK-BIOENTITY-COPIES-PROC (EC, QL, win)
else
  allow other processing;
  SECN = call FIND-NAMED-BIOENTITY (EC, win);
  if SECN is not none then
    allow other processing;
    SEC = the bioentity named by SECN;
    call SEEK-BIOENTITY-COPIES-PROC (SEC, QL, win);
return;
---

TABLE 134
---
FIND-NAMED-BIOENTITY (E: class bioentity, win: class window) =
(symbol )

SE1 = the object superior to the workspace of E;
if SE1 is not a bioentity then return the symbol none else
if SE1 has a name then return the name of SE1 else
  SE2 = the object superior to the workspace of SE1;
  if SE2 is not a bioentity then return the symbol none else
  if SE2 has a name then return the name of SE2 else
    SE3 = the object superior to the workspace of SE2;
    if SE3 is not a bioentity then return the symbol none else
    if SE3 has a name then return the name of SE3 else
      SE4 = the object superior to the workspace of SE3;
      if SE4 is not a bioentity then return the symbol none else
      if SE4 has a name then return the name of SE4 else
        SE5 = the object superior to the workspace of SE4;
        if SE5 is not a bioentity then return the symbol none else
        if SE5 has a name then return the name of SE5 else
          SE6 = the object superior to the workspace of SE5;
          if SE6 is not a bioentity then return the symbol none else
          if SE6 has a name then return the name of SE6;
---

TABLE 135

---

SEEK-BIOENTITY-COPIES-PROC (SE: class bioentity, SEL: class query-list, win: class window)

EN: symbol = the name of SE;

insert EN at the end of the symbol list SEL;
    CL = the class of SE;
    if SE is a PROTEIN-MOTIF then
        if there exists a protein-motif CSE that is of the class named by CL
            such that (the text of the master-bioentity of CSE = "[EN]") then
        for CSE = each protein-motif that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
    else
    if SE is a PROTEIN-DOMAIN then
        if there exists a protein-domain CSE that is of the class named by CL
            such that (the text of the master-bioentity of CSE = "[EN]") then
        for CSE = each protein-domain that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
    else
    if SE is a SMALL-COMPONENT then
        if there exists a small-component CSE that is of the class named by
            CL such that (the text of the master-bioentity of CSE = "[EN]") then
        for CSE = each small-component that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
    else
    if SE is a DNA-COMPONENT then
        if there exists a dna-component CSE that is of the class named by CL
            such that (the text of the master-bioentity of CSE = "[EN]") then
        for CSE = each dna-component that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
    else
    if SE is a HETER.MOL.COMPLEX then
        if there exists a heter.mol.complex CSE that is of the class named by
            CL such that (the text of the master-bioentity of CSE = "[EN]") then
        for CSE = each heter.mol.complex that is of the class named by CL do
        allow other processing;
        if the text of the master-bioentity of CSE = "[EN]" then
            call FIND-NAMED-BIOENTITIES-WITH-COMPONENT-PROC
        (CSE, SEL, win);
    else

```
if SE is a PROTEIN then
    if there exists a protein CSE that is of the class named by CL such
            that (the text of the master-bioentity of CSE = "[EN]" ) then
        for CSE = each protein that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
else
if SE is a NUCLEIC-ACID then
    if there exists a nucleic-acid CSE that is of the class named by CL
            such that (the text of the master-bioentity of CSE = "[EN]") then
        for CSE = each nucleic-acid that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
else
if SE is a MEMBRANE then
    if there exists a membrane CSE that is of the class named by CL such
            that (the text of the master-bioentity of CSE = "[EN]" ) then
        for CSE = each membrane that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
else
if SE is a BIOENTITY then
    if there exists a bioentity CSE that is of the class named by CL such
            that ( the text of the master-bioentity of CSE = "[EN]" ) then
        for CSE = each bioentity that is of the class named by CL do
        allow other processing;
        if the text of the master-bioentity of CSE = "[EN]" then
            call FIND-NAMED-BIOENTITIES-WITH-COMPONENT-PROC
                (CSE, SEL, win);
return;
```

TABLE 136

COMPLETE-QUERY-TABLE-PROC (win: class g2-window)

ASW = the subworkspace of QUERY-ARRAYS-BIN;
LSW = the subworkspace of QUERY-LISTS-BIN;
if there exists a query-list upon LSW then
  for QL = each query-list upon LSW do
    if the lenght of QL > 0 then
      if there exists a query-array QA upon ASW such that (QA is the same
          object as the query-array named by the ref-array of QL) then
        allow other processing;
        change the array-length of QA to the lenght of QL;
        for S = each symbol in QL do
          IV = the text of the initial-values of QA;
          change the text of the initial-values of QA to "[IV], [S]";
        IV = omit-from-text (the text of the initial-values of QA, 1, 6);
        change the text of the initial-values of QA to "[IV]";
        make QA permanent;

TABLE 136b

|  | a sup-et-array |
|---|---|
| Names | A-HELIX-MOTIF-QUERY-ARRAY |
| Array length | 28 |
| Element type | symbol |
| Initial values | a.helix.domain.mc, gh.ma, prolactin.ma, f.somatolactin.ma, m.cpo.ma, il2.ma, m.il6.ma, m.g.csf.ma, c.mgf.ma, il6.ma, g.csf.ma, m.lif.ma, osm.ma, r.entf.ma, lif.ma, m.il4.ma, m.il3.ma, m.gm.csf.ma, m.il5.ma, il3.ma, m.il4.ma, il5.ma, il3.ma, gm.csf.ma, m.il7.ma, m.il9.ma, il7.ma, il9.ma, a.helix.motif.mc |
| Ref component class | a-helix-motif |
| Major class | protein-motif |

|  | a query-list |
|---|---|
| Names | A-HELIX-MOTIF-QUERY-LIST |
| Element type | symbol |
| Allow duplicate elements? | no |
| Ref component class | a-helix-motif |
| Ref array | a-helix-motif-query-array |
| Lenght | 28 |

TABLE 137

CREATE-AUXILIARY-QUERY-ARRAYS-PROC (win: class window)

SW = the subworkspace of QUERY-ARRAYS-BIN
create a query-array MA;
transfer MA to SW at (-160, -390);
change the name of MA to the symbol no-group-selection-query-array;
make MA permanent;
create a query-array MA;
transfer MA to SW at (-160, -390);
change the name of MA to the symbol no-motif-selection-query-array;
make MA permanent;
create a query-array MA;
transfer MA to SW at (-160, -390);
change the name of MA to the symbol no-domain-selection-query-array;
make MA permanent;
create a query-array MA;
transfer MA to SW at (-160, -390);
change the name of MA to the symbol no-subunit-selection-query-array;
make MA permanent;

TABLE 138

```
INIT-ICONS-CALLBACK (button: class button, win: class window,
panel : class selection-panel )

call INIT-BR-ICONS-PROC ();
  call INIT-BP-ICONS-PROC ();
  return

INIT-BR-ICONS-PROC ()
  for BR = each bioreservoir do
    if the subworkspace of BR exists then
      allow other processing;
      WS = the subworkspace of BR;
      P = the biopool upon WS;
      for GL = each c-graph-link connected to P do
        change the core stripe-color of GL to transparent;
      if there exists a c-graph-tracer upon WS then
        SG = the c-scaled-br-graph-tracer connected to P;
        move SG to (left-edge(P) - 8, middle-y(P) + 11);
        AG = the c-absolute-br-graph-tracer connected to P;
        move AG to (left-edge(P) - 8, middle-y(P) - 10);
        CH = the c-br-chaininig-tracer connected to P;
        move CH to (right-edge(P) + 7, middle-y(P));
      change the size of WS to minimum;
      make WS permanent;

INIT-BP-ICONS-PROC ()
  for BP = each bioprocess do
    if the subworkspace of BP exists then
      allow other processing;
      WS = the subworkspace of BP;
      E = the bioengine upon WS;
      for GL = each c-graph-link connected to E do
        change the core stripe-color of GL to transparent;
      ST = the c-scaled-bp-graph-tracer connected to E;
      move ST to (left-edge(E) - 9, middle-y(E) + 11);
      CH = the c-bp-chaininig-tracer connected to E;
      move CH to (left-edge(E) - 9, middle-y(E) - 11);
      UP = the c-up-path-tracer connected to E;
      move UP to (right-edge(E) + 9, middle-y(E) + 11);
      DN = the c-down-path-tracer connected to E;
      move DN to (right-edge(E) + 9, middle-y(E) - 11);
      if there exists a bioreactant-post upon WS then
        for RP = each bioreactant-post upon WS do
          R = the bioreactant connected to RP;
          move RP to (left-edge(R) - 3, middle-y(R));
      if there exists a bioproduct-post upon WS then
        for PP = each bioproduct-post upon WS do
          P = the bioproduct connected to PP;
          move PP to (right-edge(P) + 4, middle-y(P));
      change the size of WS to minimum;
      make WS permanent;
```

TABLE 139

```
NAVIG-INIT-CALLBACK (button: class button, win: class window,
panel: class selection-panel)
  call NAVIG-INIT-PROC (win);
  call SIMUL-INIT-PROC (win);
  call INIT-BR-ICONS-PROC ();
  call INIT-BP-ICONS-PROC ();
  return
```

TABLE 140

|  |  |
|---|---|
|  | an user-menu-choice |
| Label | details |
| Applicable class | bioprocess |
| Condition | the subworkspace of the item exists |
| Action | start DETAILS-BP-PROC (the item, this window) |

DETAILS-BP-PROC (BP: class bioprocess, WIN: class window)
if the subworkspace of BP exists then
  SW = the subworkspace of BP;
  if the toggle-state of BP is hide then:
    if the status of bP is available then
      conclude that the status of bP is selected;
      activate SW;
      change the status-color of BP to brown;
      conclude that the toggle-state of BP is show;
    E = the bioengine upon SW ;
    move the scaled-bp-graph-tracer connected to E to (left-edge(E) - 9,
      middle-y(E) + 11);
    move the bp-chaininig-tracer connected to E to (right-edge(E) - 9,
      middle-y(E) - 10);
    move the up-path-tracer connected to E to (right-edge(E) + 9,
      middle-y(E) + 11);
    move the down-path-tracer connected to E to (right-edge(E) + 9,
      middle-y(E) - 10);
    for each bioreactant R upon view do
      move the bioreactant-post connected to R to (left-edge(R) - 3,
        middle-y(R));
    for P = each bioproduct upon view do
      move the bioproduct-post connected to P to (right-edge(P) + 4,
        middle-y(P));
    change the size of SW to minimum;
    show SW on Win at the center of the screen;
  else if the toggle-state of BP is show then:
    conclude that the toggle-state of BP is hide;
    change the status-color of BP to slate-blue;
    if the status of bP is selected then
      conclude that the status of bP is available;
    deactivate SW ;
    hide SW on Win
else if the master-bioprocess of BP has a value then
  call BP-MASTER-DETAILS-PROC (BP, win)
else return BP-MASTER-DETAILS-PROC (BP: class bioprocess, win: class window)
  MA = the bioprocess named by the master-bioprocess of BP;
  if the toggle-state of BP is hide then
    conclude that the toggle-state of BP is show;
    if the subworkspace of the item named by the master-bioprocess of
      BP exists then
      SW = the subworkspace of MA;
      change the size of SW to minimum;
      show SW at full scale with its center at the center of the screen;
      conclude that the toggle-state of MA is show;
  else
  if the toggle-state of BP is show then
    conclude that the toggle-state of BP is hide;
    conclude that the toggle-state of MA is hide;
    hide the subworkspace of MA on win;

TABLE 141

```
                    an user-menu-choice
Label               details
Applicable class    bioreservoir
Condition           none
Action              start DETAILS-BR-PROC (the item, this window)
```

DETAILS-BR-PROC (BR: class bioreservoir, win: class window)
if the subworkspace of Br exists then
  SW = the subworkspace of BR;
  if the toggle-state of BR is hide then
    change the status-color icon-color of BR to brown;
    conclude that the toggle-state of BR is show;
    P = the biopool upon SW;
    CL = the br-chaininig-tracer connected to P;
    SG = the scaled-br-graph-tracer connected to P;
    AG = the absolute-br-graph-tracer connected to P;
    move CL to (right-edge(P) + 6, middle-y(P));
    move SG to (left-edge(P) - 8, middle-y(P) + 11);
    move AG to (left-edge(P) - 8, middle-y(P) - 10);
    change the size of SW to minimum;
    show the subworkspace of BR on win at full scale with its bottom
      left corner 200 units to the right of the center of the screen;
  else
    conclude that the toggle-state of BR is hide;
    change the status-color icon-color of BR to medium-aquamarine;
    hide the subworkspace of BR on win;
else if the master-bioprocess of BP has a value then
  call BR-MASTER-DETAILS-PROC (BP, win)
else return BR-MASTER-DETAILS-PROC (BR: class bioreservoir, win: class
window)

MA = the bioreservoir named by the master-bioreservoir of BR;
  if the toggle-state of BR is hide then
    conclude that the toggle-state of BR is show;
    if the subworkspace of the item named by the master-bioreservoir of
        BR exists then
      SW = the subworkspace of MA;
      change the size of SW to minimum;
      show SW at full scale with its center at the center of the screen;
      conclude that the toggle-state of MA is show;
      if the text of the user-mode of win /= "simulation" then
        change the status-color icon-color of MA to brown;
  else
    conclude that the toggle-state of BR is hide;
    conclude that the toggle-state of MA is hide;
    hide the subworkspace of MA on win;
    if the text of the user-mode of win /= "simulation" then
      change the status-color icon-color of MA to slate-blue;

TABLE 142

---

|  | an user-menu-choice |
|---|---|
| Label | create-sw |
| Applicable class | bioengine |
| Condition | not (there exists a subworkspace of the item) and the toggle-state of the item is hide |
| Action | start CREATE-SW-FOR-BIOENGINE (the item, this window) |

---

CREATE-SW-FOR-BIOENGINE (E: class bioengine, win: class window)

create a workspace box by cloning the SW of BIOENGINE-SW-MASTER;
show box on win at the center of the screen;
make box the subworkspace of E;
make box permanent;

---

|  | an user-menu-choice |
|---|---|
| Label | show-sw |
| Applicable class | bioengine |
| Condition | there exists a subworkspace of the item and the toggle-state of the item is hide |
| Action | start SHOW-BIOENGINE-PROC (the item, this window) |

---

SHOW-BIOENGINE-PROC (E: class bioengine , win: class window)

box = the subworkspace of E;
if the toggle-state of E is hide then:
   conclude that the toggle-state of E is show;
   change the size of box to minimum;
   show box on win at the center of the screen;
else if the toggle-state of E is show then:
   conclude that the toggle-state of E is hide;
   hide the subworkspace of E on W

---

TABLE 143

```
                    an user-menu-choice
Label               details
Applicable class    complex-bioentity
Condition           none
Action              start ET-DETAILS-PROC (the item, this window)
```

ET-DETAILS-PROC (EN: class complex-bioentity, W: class window)

```
if the subworkspace of EN exists then
  view = the subworkspace of EN
if the toggle-state of EN is hide then
  conclude that the toggle-state of EN is show;
  show view at the center of the screen
  if the master-bioentity of the item has a value then
    if the bioentity named by the master-bioentity of EN has a SW then
      master-view = the subworkspace of the bioentity named by the
          master-bioentity of EN;
      change the size of master-view to minimum;
      show master-view at the center of the screen;
  return;
else
if the toggle-state of EN is show then
  conclude that the toggle-state of EN is hide;
  hide view on W;
  hide master-view on W
  return;
```

TABLE 144

---
an user-menu-choice
Label              show-br
Applicable class   biorole-post
Condition          the item has a name
Action             start ROLEPOST-SHOW-BR-PROC (the item, this
                   window)

---

ROLEPOST-SHOW-BR-PROC (post: class biorole-post , W: class window)

BP = the bioprocess superior to the workspace of post;
if post has a name then
  BR = the bioreservoir named by the ref-bioreservoir of post
else
if there exists a bioreservoir ABR such that (ABR has no name and
    the master-bioreservoir of ABR has a current value and the
    master-bioreservoir of ABR = the ref-bioreservoir of post) then
  BR = ABR;
change the size of the subworkspace of BP to minimum;
case (the toggle-state of post ) of
  show:
    change the color-pattern of post so that light-color is dim-
      gray , dark-color is light-gray ;
    conclude that the toggle-state of post is hide;
    case (the class of post) of
      bioreactant-post :
        show the subworkspace of BR on W at full scale with its
          center 400 units to the left of the center of the screen;
        change the color-pattern of post so that white-color =
          the symbol black;
      bioproduct-post:
        show the subworkspace of BR on W at full scale with its
          center 400 units to the right of the center of the screen;
  hide:
    change the color-pattern of post so that light-color is light-gray ,
      dark-color is dim-gray ;
    conclude that the toggle-state of post is show;
    hide the subworkspace of BR on W;
    if the class of post is bioreactant-post then
      change the color-pattern of post so that white-color = the
        symbol white;

---

TABLE 145
---
an user-menu-choice
Label            show-bp
Applicable class biopool-post
Condition        the item has a name and the ref-bioprocess of the
                 item has a value
Action           start POOLPOST-SHOW-BP-PROC (the item, this
                 window)
---

POOLPOST-SHOW-BP-PROC (post: class biopool-post, win: class
  window)

BP = the bioprocess named by the ref-bioprocess of post
change the size of the subworkspace of BP to minimum;
case (the toggle-state of post ) of
  show :
    change the color-pattern of post so that light-color is dim-
      gray , dark-color is light-gray , white-color = the symbol
      black;
    conclude that the toggle-state of post is hide;
    case (the class of post) of
      biopool-p-post:
        show the subworkspace of BP on W at full scale with its
          center 280 units above the center of the screen;
      biopool-r-post:
        show the subworkspace of BP on W at full scale with its
          center 280 units below the center of the screen;
  hide:
    change the color-pattern of post so that light-color is light-
      gray , dark-color is dim-gray , white-color = the symbol
      white;
    conclude that the toggle-state of post is show;
    hide the subworkspace of BP on W;
---

TABLE 146

---
an user-menu-choice
Label             show-sw
Applicable class  model-box
Condition         there is a SW of the item
Action            start SHOW-MODEL-BOX-SW-PROC (the item, this
                  window)

---

SHOW-MODEL-BOX-SW-PROC (box: class model-box, win: class window)

case the toggle-state of box is
  show :
    change the color-pattern of box so that light-color is dim-gray,
      dark-color is light-gray , white-color = the symbol black;
    conclude that the toggle-state of box is hide;
    show the subworkspace of box on win 200 units above the center of
      the screen;
  hide:
    change the color-pattern of box so that light-color is light- gray ,
      dark-color is dim-gray , white-color = the symbol white;
    conclude that the toggle-state of box is show;
    hide the subworkspace of box on win;

---

TABLE 147

---
an user-menu-choice
Label             bioentity
Applicable class  bioreservoir
Condition         the ref-bioentity of the item has a value
Action            change the size of the subworkspace SW of the
                  bioentity named by the ref-bioentity of the item to
                  minimum and show SW on win at the center of
                  the screen;

---
an user-menu-choice
Label             bioentity
Applicable class  biopool
Condition         the ref-bioentity of the bioreservoir superior to
                  the workspace of the item has a value
Action            change the size of the subworkspace SW of the ref-
                  bioentity of the bioreservoir superior to the
                  workspace of the item to minimum and
                  show SW on this window at the center of the screen ---
an user-menu-choice
Label             bioentity
Applicable class  biorole-object
Condition         the ref-bioentity of the bioreservoir superior to
                  the biopool connected to the item has a value
Action            change the size of the subworkspace SW of the ref-
                  bioentity of the bioreservoir superior to the
                  biopool connected to the item to minimum and
                  show SW on this window at the center of the screen

---

TABLE 148

```
                an user-menu-choice
Names           none
Label           show-references
Applicable class bioreservoir
Condition       none
Action          start SHOW-REFERENCES-OF-ARRAY-PROC (the
                item, this window)
```

SHOW-REFERENCES-OF-ARRAY-PROC (BR: class bioreservoir, win: class window)

```
array = the references-array that gives the references of BR;
BIN = the subworkspace of REFERENCES-BIN;
x = 0;
y = 0;
if the array-length of array /= 0 then
  create a workspace WS by cloning the subworkspace of REFERENCE-
    WS;
  for ref-button = each go-to-subws-button upon BIN do
    SW = the subworkspace of ref-button;
    for R = each cabe-reference upon SW do
      for T = each text in array do
        if T /= "" and the short-ref of R = T then
          create a cabe-reference R1 by cloning R;
          transfer R1 to WS at (x, y);
          y = y - 50;
          if y < -900 then
            x = x + 300;
            y = 0;
  change the size of WS to minimum;
  show WS on win at the center of the screen;
```

TABLE 149

PRINT-THIS-WS-CALLBACK (button: class action-button,
   W : class window)

print the workspace of button;

---

DELETE-SUP-OBJ-CALLBACK (button: class action-button,
   W : class window)

delete the object superior to the workspace of button;

TABLE 150
---
a scroll-area
Names                                MASTER-LIST-OF-REFERENCES
Id                                   ""
Configuration                        scroll-configuration
User data                            none
Ordering method                      alphabetic
Maximum allowed messages             100
Uil message selection method         REF-SEARCH-PROC
Uil message unselection method       REF-RESET-SCROLLER-PROC
Allow multiple simultaneous selections false
Allow unselect on selected message   true
---
a relation
First class       g2-stream
Second class      scroll-area
Relation name     THE-REF-STREAM-FOR
Inverse of relation  none
Type of relation  one-to-one
Relation is symmetric? no
a g2-stream may be the-ref-stream-for at most one scroll-area;
at most one g2-stream may be the-ref-stream-for an scroll-area
---
a log-par
Options                  do forward chain
Names                    REF-SEARCH-COMPLETE
Tracing and breakpoints  default
Data type                truth value
Initial value            false
Last recorded value      true
History keeping spec     do not keep history
---
a log-par
Options                  do forward chain
Names                    REF-ALLOW-SEARCH-TO-PROCEED
Tracing and breakpoints  default
Data type                truth value
Initial value            false
Last recorded value      true
History keeping spec     do not keep history
---

TABLE 151

REF-SEARCH-PROC (MO: class message-object, SA: class scroll-area,
W: class window)

ML = the message-list of SA;
WS = the workspace of SA;
SA2 = REF-TEXT-SCROLLER;
S: item-or-value;
en: symbol;
indx: integer;
T, et, end-text, error: text;
if there exists a g2-stream that is THE-REF-STREAM-FOR SA then
   for S = each g2-stream that is THE-REF-STREAM-FOR SA do
     if S exists then call g2-close-file (S);
if ML [the message-display-priority of MO + 1] exists then
  end-text = the text of ML[the message-display-priority of MO + 1]
else end-text = "!!!!!!!!!!";
call uil-enable-button (REF-CANCEL-BUTTON);
call uil-clear-messages (SA2);
call uil-reset-scroll-area (SA2);
conclude that REF-SEARCH-COMPLETE is false;
change the text of REF-PROGRESS-TEXT-1 to "Opening file.";
start REF-SEARCH-PROGRESS-INDICATOR-PROC ();
S, error = call REF-GET-FILE-PROC ();
if error /= "" or S is not a g2-stream then
  change the text of REF-PROGRESS-TEXT-1 to "[error]";
  go to error-exit;
conclude that S is now the-ref-stream-for SA;
change the text of REF-PROGRESS-TEXT-1 to "Searching";
conclude that REF-ALLOW-SEARCH-TO-PROCEED is true;
repeat
  if not (REF-ALLOW-SEARCH-TO-PROCEED) then begin
    change the text of REF-PROGRESS-TEXT-1 to "Cancelled.";
    go to error-exit;
  allow other processing;
  if not (S exists) then go to error-exit;
  T = call g2-read-line (S);
  if the g2-stream-status of S = symbol("end-of-file-reached") then
    change the text of REF-PROGRESS-TEXT-1 to "Not found.";
    call g2-close-file (S);
    go to error-exit;
  if T = the text of MO then
    call uil-disable-button (REF-CANCEL-BUTTON);
    change the text of REF-PROGRESS-TEXT-1 to "Formatting.";
    repeat
      allow other processing;
      T = call g2-read-line (S);
      if T = "" or the g2-stream-status of S = symbol ("end-of-file-
        reached") or T = end-text then
        call g2-close-file (S);
        go to exit-processing;
      else call REF-TEXT-FORMATTER-PROC (T, SA2);
exit-processing:
  change the text of REF-PROGRESS-TEXT-1 to "Done.";
  conclude that REF-SEARCH-COMPLETE;
  change the size of WS to minimum;
  call uil-display-message-list (SA2, 0);
  call uil-enable-button (REF-PRINT-BUTTON);
  if S exists then call g2-close-file (S);
  go to get-next-record;

get-next-record:
error-exit:
conclude that REF-SEARCH-COMPLETE;
call uil-disable-button (REF-CANCEL-BUTTON);

TABLE 152
---

REF-SEARCH-PROGRESS-INDICATOR-PROC ()

repeat
 change the text of REF-PROGRESS-TEXT-1 to "[the text of REF-PROGRESS-TEXT-1].";
 wait for 1 second;
 exit if REF-SEARCH-COMPLETE;

---

TABLE 153
---

REF-GET-FILE-PROC () = (item-or-value, text)
S: class g2-stream;
file-exists: truth-value;
error: text = "";
operation-error, error-text: text;
error-name: symbol;
HF: class uil-help-system-location = REF-FILE-LOCATION;
file-string: text = "[the uil-help-system-directory of HF][the uil-help-system-file-name of HF]";

{verify sys-proc is loaded}
 operation-error = "sys-proc or sys-mod not loaded.";
 file-exists = (if g2-open-file-for-read exists then true else false);
 if not (file-exists) then
  signal the symbol file-not-found, "File error";
{locate help file}
 operation-error = "The references file ~@"[file-string]~@" could not
  be located.";
 file-exists = call g2-file-exists ("[file-string]");
 if not (file-exists) then
  signal the symbol file-not-found, "File error";
{open help file}
 operation-error = "References file could not be opened.";
 S = call g2-open-file-for-read ("[file-string]");
return S, error;
on error (error-name, error-text)
return "none", "Error - [error-name] [operation-error]";

---

TABLE 154
---

REF-SYSTEM-CANCEL-SEARCH-PROC (B: class text-button, W: class window, WS: class workspace)

conclude that cabe-ref-allow-search-to-proceed is false;

---

TABLE 155
---

REF-TEXT-FORMATTER-PROC (T: text, SA: class scroll-area)
MO: class message-object;
title-message: truth-value = false ;

if T = "Unique identifier  " or
   T = "Authors      " or
   T = "Title     " or
   T = "Institution  " or
   T = "Journal    " or
   T = "Abstract   " then
   title-message = true;
if title-message is false then T = " [T]";
MO = call uil-create-message (SA, T, 1);
if title-message is true then
   conclude that the configuration of MO = the symbol ref-title-
      message-configuration
else
   conclude that the configuration of MO = the symbol ref-
      message-configuration;
call uil-configure-scroll-message (MO);
if T = "" then
   go to exit-routine;
exit-routine:
---

TABLE 156
---

REF-PRINT-CALLBACK (B: class text-button, W: class window, WS: class workspace)

print WS;
---

REF-RESET-SCROLLER-PROC (MO: class message-object, SA: class scroll-area, W: class window)

call uil-clear-messages (REF-TEXT-SCROLLER);
change the text of REF-PROGRESS-TEXT-1 to "Reset.";
change the size of the workspace of SA to minimum;
---

TABLE 157

CREATE-GENERAL-STRUCTURE-SELECTION-PANEL-CALLBACK
(menu: class menu-option, win: class window)

md = call create-message-dialog ("md", "Processing . . . . .    ", the
    symbol extra-large, win, 0, 0);
panel = call clone-panel (MASTER-GENERAL-STRUCTURE-QUERY-
    PANEL);
SW = the subworkspace of panel;
call SET-RADIO-BOX-ID-PROC ("general-structure-panel","GENERAL-
    STRUCTURE-QUERY-PANEL-radio-box", SW, win);
if there exists a uil-medium-text-pushbutton de upon SW such that (the id
        of de = "de") then
    change the text of the callback of de to "DELETE-QUERY-PANEL-
        CALLBACK";
show SW on win at the center of the screen;
delete md;
return;

TABLE 158

SET-RADIO-BOX-ID-PROC (r-id: text, rb-id: text, SW: class workspace,
win: class window)

if there exists a radio-button r upon SW such that (the id of r = r-id) then
    rb = the radio-box that is the-group-master-of r;
    urb-id = call unique-id ("[rb-id]");
    conclude that the id of rb = "[urb-id]";
return;

GET-RADIO-BOX-ID-PROC (r-id: text, SW: class workspace, win: class
window) = (value )

if there exists a radio-button r upon SW such that (the id of r = r-id) then
    rb = the adio-box that is the-group-master-of r;
return "[the id of rb]";

TABLE 159

```
SELECT-GENERAL-STRUCTURE-QUERY-PANEL-CALLBACK
(button: class button, win: class window, dlg: class query-panel)

SW = the subworkspace of dlg;
  md = call create-message-dialog ("md", "Processing . . . . .   ", the
      symbol extra-large, win, 0, 0);
  rb-id = call GET-RADIO-BOX-ID-PROC ("general-structure-panel",
      SW, win);
  type = call get-radio-box-value (dlg, rb-id);
  case (type) of
    subunits:
      MP = MASTER-SUBUNITS-QUERY-PANEL;
    domains:
      MP = MASTER-DOMAINS-QUERY-PANEL;
    motifs:
      MP = MASTER-MOTIFS-QUERY-PANEL;
    groups:
      MP = MASTER-GROUPS-QUERY-PANEL;
    subunits-subunits:
      MP = MASTER-SUBUNITS-SUBUNITS-QUERY-PANEL;
    domains-domains:
      MP = MASTER-DOMAINS-DOMAINS-QUERY-PANEL;
    domains-motifs:
      MP = MASTER-DOMAINS-MOTIFS-QUERY-PANEL;
    domains-groups:
      MP = MASTER-DOMAINS-GROUPS-QUERY-PANEL;
    motifs-motifs:
      MP = MASTER-MOTIFS-MOTIFS-QUERY-PANEL;
    motifs-groups:
      MP = MASTER-MOTIFS-GROUPS-QUERY-PANEL;
    groups-groups:
      MP = MASTER-GROUPS-GROUPS-QUERY-PANEL;
  panel = call clone-panel (MP);
  call CREATE-GENERAL-QUERY-PANEL-PROC (type, panel, win);
  show the subworkspace of dlg with its bottom right corner at the bottom
      right corner of the screen;
  show the subworkspace of panel at the center of the screen;
  delete md;
  return;
```

TABLE 160
---
CREATE-GENERAL-QUERY-PANEL-PROC (type: symbol, panel: class query-panel, win : class window)

SW = the subworkspace of panel;
if there exists a radio-button B upon SW such that (the id of B = "subunits") then
   call SET-RADIO-BOX-ID-PROC ("subunits", "3-BR-["type"]-QUERY-
     radio-box", SW, win);
if there exists a radio-button B upon SW such that (the id of B = "domains") then
   call SET-RADIO-BOX-ID-PROC ("domains", "4-BR-[type]-QUERY-
     radio-box", SW, win);
if there exists a radio-button B upon SW such that (the id of B = "motifs") then
   call SET-RADIO-BOX-ID-PROC ("motifs", "5-BR-[type]-QUERY-
     radio-box", SW, win);
if there exists a radio-button B upon SW such that (the id of B = "groups") then
   call SET-RADIO-BOX-ID-PROC ("groups", "6-BR-[type]-QUERY-
     radio-box", SW, win);
if there exists a radio-button B upon SW such that (the id of B = "subunits-2") then
   call SET-RADIO-BOX-ID-PROC ("subunits", "3-BR-[type]-QUERY-
     radio-box", SW, win);
if there exists a radio-button B upon SW such that (the id of B = "domains-2") then
   call SET-RADIO-BOX-ID-PROC ("domains", "4-BR-[type]-QUERY-
     radio-box", SW, win);
if there exists a radio-button B upon SW such that (the id of B = "motifs-2") then
   call SET-RADIO-BOX-ID-PROC ("motifs", "5-BR-[type]- QUERY-radio-box", SW, win);
if there exists a radio-button B upon SW such that (the id of B = "groups-2") then
   call SET-RADIO-BOX-ID-PROC ("groups", "6-BR-[type]-QUERY-
     radio-box", SW, win);
if there exists a text-pushbutton de upon SW such that (the id of de = "de") then
   change the text of the callback of de to "DELETE-QUERY-PANEL-
     CALLBACK";
show SW on win at the center of the screen;
return;

---

TABLE 161
---
QUERY-GENERAL-STRUCTURE-CALLBACK (button: class button, win : class window, panel: class query-panel)
  md = call uil-create-message-dialog ("md", "Processing . . . . . ", the
    symbol extra-large, win, 0, 0);
ETL, TX2 = call QUERY-GENERAL-STRUCTURE-PROC (panel, win);
create a free-text FT2;
change the text of FT2 to "[TX2]";
conclude that the scroll-title of ETL = TX2;
conclude that FT2 is THE-TEST-ITEM-LIST-OF ETL;
call CREATE-GENERAL-QUERY-OUTPUT-PANEL-PROC (ETL, FT2, panel, win);
delete md;
return;
---

TABLE 162

```
QUERY-GENERAL-STRUCTURE-PROC (panel: class query-panel, win
: class window) = (class scroll-text-list, text)

PN = the name of panel;
  SW = the subworkspace of panel;
  if there exists a radio-button B upon SW such that (the id of B =
      "subunits") then
    type1, PSA = call FIND-SPECIFIC-ARRAY-PROC ("subunits", panel,
        win);
  if there exists a radio-button B upon SW such that (the id of B =
      "subunits-2") then
    type2, PSA-2 = call FIND-SPECIFIC-ARRAY-PROC ("subunits-2",
        panel, win);
  if there exists a radio-button B upon SW such that (the id of B =
      "domains") then
    type3, PDA = call FIND-SPECIFIC-ARRAY-PROC ("domains", panel,
        win);
  if there exists a radio-button B upon SW such that (the id of B =
      "domains-2") then
    type4, PDA-2 = call FIND-SPECIFIC-ARRAY-PROC ("domains-2",
        panel, win);
  if there exists a radio-button B upon SW such that (the id of B =
      "motifs") then
    type5, PMA = call FIND-SPECIFIC-ARRAY-PROC ("motifs", panel,
        win);
  if there exists a radio-button B upon SW such that (the id of B =
      "motifs-2") then
    type6, PMA-2 = call FIND-SPECIFIC-ARRAY-PROC ("motifs-2",
        panel, win);
  if there exists a radio-button B upon SW such that (the id of B =
      "groups") then
    type7, PGA = call FIND-SPECIFIC-ARRAY-PROC ("groups", panel,
        win);
  if there exists a radio-button B upon SW such that (the id of B =
      "groups-2") then
    type8, PGA-2 = call FIND-SPECIFIC-ARRAY-PROC ("groups-2",
        panel, win);
  if PSA exists then
    if PSA-2 exists then
      if there exists a scroll-text-list ETL such that (the label of ETL =
          "[PN]-type1-type2-ETL") then
        go to final-routine
      else
        ETL, TX2 = call MERGE-TWO-STRUCTURE-LISTS-PROC (the
            symbol subunit, the symbol subunit, type1, type2, PSA,
            PSA-2, panel, win);
    else
      TX2 = capitalize-words ("proteins with structures defined in this
          module that contain [type1]");
      for T1 = each symbol in PSA do
        insert T1 at the end of the text list ETL;
  else
  if PDA exists then
    if PDA-2 exists then
      if there exists a scroll-text-list ETL such that (the label of ETL =
          "[PN]-type3-type4-ETL") then
        go to final-routine
      else
        ETL, TX2 = call MERGE-TWO-STRUCTURE-LISTS-PROC (the
            symbol domain, the symbol domain, type3, type4, PDA, PDA-2,
            panel, win)
    else
    if PMA exists then
```

```
       if there exists a scroll-text-list ETL such that (the label of ETL =
           "[PN]-type3-type5-ETL") then
         go to final-routine
       else
         ETL, TX2 = call MERGE-TWO-STRUCTURE-LISTS-PROC (the
             symbol domain, the symbol motif, type3, type5, PDA, PMA,
             panel, win)
     else
     if PGA exists then
       if there exists a scroll-text-list ETL such that (the label of ETL =
           "[PN]-type3-type7-ETL") then
         go to final-routine
       else
         ETL, TX2 = call C-MERGE-TWO-STRUCTURE-LISTS-PROC
             (the symbol domain, the symbol group, type3, type7, PDA,
             PGA, panel, win)
     else
       TX2 = capitalize-words ("proteins with structures defined in this
           module that contain [type3]");
       for T1 = each symbol in PDA do
         insert T1 at the end of the text list ETL;
 else
 if PMA exists then
   if PMA-2 exists then
     if there exists a c-scroll-text-list ETL such that (the label of
         ETL = "[PN]-type5-type6-ETL") then
       go to final-routine
     else
       ETL, TX2 = call MERGE-TWO-STRUCTURE-LISTS-PROC
           (the symbol motif, the symbol motif, type5, type6, PMA,
           PMA-2, panel, win)
   else
   if PGA exists then
     if there exists a scroll-text-list ETL such that (the label of ETL =
         "[PN]-type5-type7-ETL") then
       go to final-routine
     else
       ETL, TX2 = call MERGE-TWO-STRUCTURE-LISTS-PROC (the
           symbol motif, the symbol group, type5, type7, PMA, PGA,
           panel, win)
   else
     TX2 = capitalize-words ("proteins with structures defined in this
         module that contain [type5]");
     for T1 = each symbol in PMA do
       insert T1 at the end of the text list ETL;
 else
 if PGA exists then
   if PGA-2 exists then
     if there exists a scroll-text-list ETL such that (the label of ETL =
         "[PN]-type7-type8-ETL") then
       go to final-routine
     else
       ETL, TX2 = call MERGE-TWO-STRUCTURE-LISTS-PROC (the
           symbol group, the symbol group, type7, type8, PGA, PGA-2,
           panel, win)
   else
     TX2 = capitalize-words ("proteins with structures defined in this
         module that contain [type7]");
     for T1 = each symbol in PGA do
       insert T1 at the end of the text list ETL;
 return ETL, TX2;
final-routine:
 TX2 = the scroll-title of ETL.
 return ETL, TX2;
```

TABLE 163

FIND-SPECIFIC-ARRAY-PROC (r-id: text, panel: class query-panel, win
: class window) = (symbol, class query-array)

SW = the subworkspace of panel;
rb-id = call C-GET-UIL-RADIO-BOX-ID-PROC (r-id, SW, win);
type = call uil-get-radio-box-value (panel, rb-id);
array-name = symbol("[type]-QUERY-ARRAY");
if the c-query-array named by array-name exists then
  QA = the c-query-array named by array-name
else inform the operator that "[array-name] does not exist";
move QA to (middle-x (QA) + 50, middle-y (QA));
return type, QA;

TABLE 164

MERGE-TWO-STRUCTURE-LISTS-PROC (tag1: symbol, tag2: symbol,
type4: symbol, type5: symbol, QA1: class query-array, QA2: class query-
array, panel: class query-panel, win : class window) = (class scroll-text-list,
text)

PN = the name of panel;
if there exists a c-scroll-text-list ETL such that (the label of ETL =
  "[PN]-[type4]-[type5]-ETL") then
  go to exit-routine
else
  create a scroll-text-list ETL;
  conclude that the label of ETL = "[PN]-[type4]-[type5]-ETL";
  conclude that ETL is a-list-associated-to-dlg panel;
  transfer ETL to the subworkspace of safe-home-for-lists at (50, -245);
  TX2 = the scroll-title of ETL;
  if the array-length of QA1 = 0 then
    if the array-length of QA2 = 0 then
      if type5 = symbol ("no-[tag2]-selection") and type4 = symbol
        ("no-[tag1]-selection") then
        TX2 = capitalize-words ("no selection has been made")
      else
        if type5 = symbol ("no-[tag2]-selection") then
          TX2 = capitalize-words ("there are no structures defined
            in this module that contain [type4]")
        else
          if type4 = symbol ("no-[tag1]-selection") then
            TX2 = capitalize-words ("there are no structures defined
              in this module that contain [type5]")
          else
            TX2 = capitalize-words ("there are no structures defined
              in this module that contain [type4] or [type5]");
    else
      if type4 = symbol ("no-[tag1]-selection") then
        TX2 = capitalize-words ("proteins with structures defined
          in this module that contain [type5]")
      else
        TX2 = capitalize-words ("proteins with structures defined in this
          module that contain [type5]. None was found also containing
          [type4]");

```
        for T2 = each symbol in QA2 do
            insert "[T2]" at the end of the text list ETL;
    else
        if the array-length of QA2 = 0 then
            if type5 = symbol ("no-[tag2]-selection") then
                TX2 = capitalize-words ("proteins with structures defined
                    in this module that contain [type4]")
            else
                TX2 = capitalize-words ("proteins with structures defined in this
                    module that contain [type4]. None was found also containing

[type5]");
            for T1 = each symbol in QA1 do
                insert "[T1]" at the end of the text list ETL;
        else
            TX2 = capitalize-words ("proteins with structures defined in this
                module that contain [type4] and [type5]");
            for T1 = each symbol in QA1 do
                for T2 = each symbol in QA2 do
                    if T1 = T2 then
                        insert "[T1]" at the end of the text list ETL;
    return ETL, TX2;
exit-routine:
    TX2 = the scroll-title of ETL;
    return ETL, TX2;
```

TABLE 165
---

CREATE-GENERAL-QUERY-OUTPUT-PANEL-PROC (ETL: class
scroll-text-list, FT: class free-text, dlg: class query-panel, win : class
window) = (class query-panel)

if there exists a query-panel panel such that (the text of the id of panel =
        "[the label of ETL]-QUERY-OUTPUT-PANEL") then
    go to final-routine
else
    create a query-panel panel by cloning MASTER-MOLECULAR-
        QUERY-OUTPUT-PANEL;
    transfer panel to the subworkspace of UIL-dialog-bin at (0,0);
    SW = the subworkspace of panel;
    change the text of the id of panel to "[the label of ETL]-QUERY-
        OUTPUT-PANEL";
    transfer FT to SW at (0, 90);
    make panel permanent;
    sa = call create-scroll-area-from-list ("query-general-scroll", 5, ETL);
    conclude that the allow-unselect-on-selected-message of sa is true;
    conclude that the allow-multiple-simultaneous-selections of sa is true;
    call add-obj-to-dialog (panel, sa, 0, -30);
    change the text of the uil-message-selection-method of sa to "query-
        message-selection";
    change the text of the uil-message-unselection-method of sa to
        "query-message-unselection";
    change the text of the ordering-method of sa to "alphabetic";

de = call create-pushbutton ("de", the symbol DELETE-QUERY-
        PANEL-CALLBACK, "DELETE", panel, 0, -145);
    go to final-routine;
final-routine :
    change the size of the subworkspace of panel to minimum;
    show the subworkspace of dlg with its top right corner 40 units below the
        top right corner of the screen;
    show the subworkspace of panel on win with its center 300 units to the left
        of the center of the screen;
    return panel;

TABLE 166
---

QUERY-MESSAGE-SELECTION-PROC (MO: class message-object, SA: class scroll-area, win: class window)

BON = symbol (the text of MO);
BO = the bio-object named by BON;
 change the size of the subworkspace of BO to minimum;
 show the subworkspace of BO on win with its center 300 units to the
  right of the center of the screen ;

---

TABLE 167
---

QUERY-MESSAGE-UNSELECTION-PROC (MO: class message-object, SA: class scroll-area, win: class window)

BON = symbol (the text of MO);
hide the subworkspace of the bio-object named by BON on win;

---

TABLE 168
---

DELETE-QUERY-PANEL-CALLBACK (button: class button, win : class window, panel: class dialog)

SW = the subworkspace of DIALOG-BIN;
md = call create-message-dialog ("md", the symbol DELETE-MD-
  CALLBACK, "Processing . . . . . ", the symbol extra-large, win, 0, 0);
if there exists a scroll-text-list that is a-list-associated-to-dlg panel then
 for L = each scroll-text-list that is a-list-associated-to-dlg panel do
  delete L;
call delete-dialog (panel);
if there exists a message-dialog ME upon SW then
for md = each message-dialog upon SW do
 delete md;

---

TABLE 169

|  |  |
|---|---|
|  | an user-menu-choice |
| Label | query-panels |
| Applicable class | bioreservoir |
| Condition | the subworkspace of the item exists |
| Action | start CREATE-BR-RELATED-SELECTION-PANEL-CALLBACK (the item, this window) |

|  |  |
|---|---|
|  | an user-menu-choice |
| Label | show |
| Applicable class | query-tracer |
| Condition | none |
| Action | start CREATE-BR-RELATED-SELECTION-PANEL-CALLBACK (the bioreservoir superior to the workspace of the item, this window) |

CREATE-BR-RELATED-SELECTION-PANEL-CALLBACK (BR: class bioreservoir, win: class window)

BRN = the name of BR;
   if not (there exists a bioreservoir DBR such that (DBR is a-downstream-
       bioreservoir-of BR or DBR is an-upstream-bioreservoir-of BR)) then
      go to exit-routine
   else
      create a message-dialog md, set the text of the message upon the SW of
         md to "Processing . . . . . " and show the SW of md on the
         current window;
      panel = call uil-clone-grobj (MASTER-BR-MOLECULAR-QUERY-
         PANEL);
      SW = the subworkspace of panel;
      create a borderless-free-text FT;
      change the text of FT to "[BRN]";
      transfer FT to SW at (60, 115);
      make panel permanent;
      call SET-RADIO-BOX-ID-PROC ("br-panel", "BR-RELATED-
         QUERY-PANEL-radio-box", SW, win);
      if there exists a text-pushbutton de upon SW such that (the id of
         de = "de") then
         change the text of the callback of de to "DELETE-QUERY-PANEL-
            CALLBACK";
      show the SW of panel on win at (0, 0);
      change the text of the related-item of panel to "[BRN]";
   delete md;
   return;

exit-routine:
   create a message-dialog md, set the text of the message upon the SW of
   md to "There is no downstream bioreservoir of [the name of BR]", the
   symbol extra-large);
      return;

TABLE 170
---
SELECT-BR-RELATED-QUERY-PANEL-CALLBACK (button: class button, win
: class window, dlg: class query-panel)

BRN: symbol = the related-item of dlg;
SW: class kb-workspace = the subworkspace of dlg;

create a message-dialog md, set the text of the message upon the SW of
  md to "Processing . . . . . " and show the SW of md on the current
  window at (0, 0);

rb-id = call GET-RADIO-BOX-ID-PROC ("br-panel", SW, win);
type = call get-radio-box-value (dlg, rb-id);

case (type) of
  function:
    MP = MASTER-BR-FUNCTION-QUERY-PANEL;
  function-subunits:
    MP = MASTER-BR-FUNCTION-SUBUNIT-QUERY-PANEL;
  function-domains:
    MP = MASTER-BR-FUNCTION-DOMAIN-QUERY-PANEL;
  function-motifs:
    MP = MASTER-BR-FUNCTION-MOTIF-QUERY-PANEL;
  function-groups:
    MP = MASTER-BR-FUNCTION-GROUP-QUERY-PANEL;
  function-domains-motifs:
    MP = MASTER-BR-FUNCTION-DOMAIN-MOTIF-QUERY-PANEL;
  function-location:
    MP = MASTER-BR-FUNCTION-LOCATION-QUERY-PANEL;
  function-location-subunits:
    MP = MASTER-BR-FUNCTION-LOCATION-SUBUNIT-QUERY-PANEL;
  function-location-domains:
    MP = MASTER-BR-FUNCTION-LOCATION-DOMAIN-QUERY-PANEL;
  function-location-motifs:
    MP = MASTER-BR-FUNCTION-LOCATION-MOTIF-QUERY-PANEL;
  function-location-groups:
    MP = MASTER-BR-FUNCTION-LOCATION-GROUP-QUERY-PANEL;
  function-location-domains-motifs:
    MP = MASTER-BR-FUNCTION-LOCATION-DOMAIN-MOTIF-QUERY-
      PANEL;

panel = call clone-grobj (MP);
change the text of the related-item of panel to "[BRN]";
call SET-BR-RELATED-QUERY-PANEL-PROC (type, panel, win);

show the subworkspace of dlg with its bottom right corner at the bottom right
  corner of the screen;
show the subworkspace of panel at the center of the screen;
delete md TABLE 171
---
SET-BR-RELATED-QUERY-PANEL-PROC (type: symbol, panel: class query-panel, win : class window)

BRN: symbol = the related-item of panel;
SW: class kb-workspace = the subworkspace of panel;

create a borderless-free-text FT;
change the text of FT to "[BRN]";
transfer FT to SW at (175, 110);
make panel permanent;
if there exists a radio-button B upon SW such that (the id of B = "direction") then
   call SET-RADIO-BOX-ID-PROC ("direction", "1-BR-[type]-QUERY-radio-box", SW, win);
if there exists a radio-button B upon SW such that (the id of B = "function") then
   call C-SET-RADIO-BOX-ID-PROC ("function", "2-BR-[type]-QUERY-radio-box", SW, win);
if there exists a radio-button B upon SW such that (the id of B = "subunits") then
   call SET-RADIO-BOX-ID-PROC ("subunits", "3-BR-[type]-QUERY-radio-box", SW, win);
if there exists a radio-button B upon SW such that (the id of B = "domains") then
   call SET-RADIO-BOX-ID-PROC ("domains", "4-BR-[type]-QUERY-radio-box", SW, win);
if there exists a radio-button B upon SW such that (the id of B = "motifs") then
   call SET-RADIO-BOX-ID-PROC ("motifs", "5-BR-[type]-QUERY-radio-box", SW, win);
if there exists a radio-button B upon SW such that (the id of B = "groups") then
   call SET-RADIO-BOX-ID-PROC ("groups", "6-BR-[type]-QUERY-radio-box", SW, win);

if there exists a text-pushbutton de upon SW such that (the id of de = "de") then
   change the text of the callback of de to "DELETE-QUERY-PANEL-CALLBACK";
show panel on win at (0, 0);
return;
---

TABLE 172
---
DOWNSTREAM-QUERY-LISTS-CALLBACK (button: class button, win
: class window, panel: class query-panel)

BR: class bioreservoir = the bioreservoir named by the related-item of panel;

create a message-dialog md, set the text of the message upon the SW of
      md to "Processing . . . . .   " and show the SW of md on the current
      window;
   call DOWNSTREAM-FUNCTION-QUERY-LISTS-PROC (BR, panel,
win);
   delete md;
   return
---
UPSTREAM-QUERY-LISTS-CALLBACK, (button: class button, win :
class window, panel: class query-panel)

BR: class bioreservoir = the bioreservoir named by the related-item of panel;
md: class uil-message-dialog;

create a message-dialog md, set the text of the message upon the SW of
      md to "Processing . . . . .   " and show the SW of md on the current
      window;
   call UPSTREAM-FUNCTION-QUERY-LISTS-PROC (BR, panel, win);
   delete md;
   return
---

TABLE 173

DOWNSTREAM-FUNCTION-QUERY-LISTS-PROC (BR: class bioreservoir, panel: class c-query-panel, win : class window)

BRN: symbol = the name of BR;
DAPL = call CREATE-BR-QUERY-LIST-PROC ("DAPL", panel, win);
DAPBRL = call CREATE-BR-QUERY-LIST-PROC ("DAPBRL", panel, win);
DEFL = call CREATE-BR-QUERY-LIST-PROC ("DEFL", panel, win);
DEFBRL = call CREATE-BR-QUERY-LIST-PROC ("DEFBRL", panel, win);
DCRL = call CREATE-BR-QUERY-LIST-PROC ("DCRL", panel, win);
DCRBRL = call CREATE-BR-QUERY-LIST-PROC ("DCRBRL", panel, win);
DPKL = call CREATE-BR-QUERY-LIST-PROC ("DPKL", panel, win);
DPKBRL = call C-CREATE-BR-QUERY-LIST-PROC ("DPKBRL", panel, win);
DPPL = call CREATE-BR-QUERY-LIST-PROC ("DPPL", panel, win);
DPPBRL = call CREATE-BR-QUERY-LIST-PROC ("DPPBRL", panel, win);
DTFL = call CREATE-BR-QUERY-LIST-PROC ("DTFL", panel, win);
DTFBRL = call CREATE-BR-QUERY-LIST-PROC ("DTFBRL", panel, win);
DGL = call CREATE-BR-QUERY-LIST-PROC ("DGL", panel, win);
DGBRL = call C-CREATE-BR-QUERY-LIST-PROC ("DGBRL", panel, win);

for DBR = each bioreservoir that is a-downstream-bioreservoir-of BR do
  if the biopool upon the subworkspace of DBR exists then
    insert "[the name of DBR]" at the end of the text list DAPBRL;
    PO = the biopool upon the subworkspace of DBR;
    if there exists a bioreactant connected to PO then
      for R = each bioreactant connected to PO do
        if R is a extracell-ligand.r or R is a extracell-antagonist.r
          or R is a ligand.r or R is a antagonist.r then insert "[the
          name of DBR]" at the end of the text list DEFBRL;
        if R is a cell-receptor.r or R is a receptor.r then insert
          "[the name of DBR]" at the end of the text list DCRBRL;
        if R is a prot.kinase.r then insert "[the name of DBR]" at the
          end of the text list DPKBRL;
        if R is a prot-phosphatase.r then insert "[the name of DBR]" at
          the end of the text list DPPBRL;
        if R is a transcription-factor.r then insert "[the name of
          DBR]" at the end of the text list DTFBRL;
        if R is a gene.r then insert "[the name of DBR]" at the end of
          the text list DGBRL;
        {if R is a mRNA.r then insert "[the name of DBR]" at the end of
          the text list DMRBRL;}
call FILL-BR.ET-LIST-PROC (DAPBRL, DAPL, panel, win);
call FILL-BR.ET-LIST-PROC (DEFBRL, DEFL, panel, win);
call FILL-BR.ET-LIST-PROC (DCRBRL, DCRL, panel, win);
call FILL-BR.ET-LIST-PROC (DPKBRL, DPKL, panel, win);
call FILL-BR.ET-LIST-PROC (DPPBRL, DPPL, panel, win);
call FILL-BR.ET-LIST-PROC (DTFBRL, DTFL, panel, win);
call FILL-BR.ET-LIST-PROC (DGBRL, DGL, panel, win);
return

TABLE 174

UPSTREAM-FUNCTION-QUERY-LISTS-PROC (BR: class bioreservoir, panel: class query-panel, win : class window)

BRN: symbol = the name of BR;

UAPL = call CREATE-BR-QUERY-LIST-PROC ("UAPL", panel, win);
  UAPBRL = call CREATE-BR-QUERY-LIST-PROC ("UAPBRL", panel, win);
  UEFL = call CREATE-BR-QUERY-LIST-PROC ("UEFL", panel, win);
  UEFBRL = call CREATE-BR-QUERY-LIST-PROC ("UEFBRL", panel, win);
  UCRL = call CREATE-BR-QUERY-LIST-PROC ("UCRL", panel, win);
  UCRBRL = call CREATE-BR-QUERY-LIST-PROC ("UCRBRL", panel, win);
  UPKL = call CREATE-BR-QUERY-LIST-PROC ("UPKL", panel, win);
  UPKBRL = call CREATE-BR-QUERY-LIST-PROC ("UPKBRL", panel, win);
  UPPL = call CREATE-BR-QUERY-LIST-PROC ("UPPL", panel, win);
  UPPBRL = call CREATE-BR-QUERY-LIST-PROC ("UPPBRL", panel, win);
  UTFL = call CREATE-BR-QUERY-LIST-PROC ("UTFL", panel, win);
  UTFBRL = call C-CREATE-BR-QUERY-LIST-PROC ("UTFBRL", panel, win);
  UGL = call CREATE-BR-QUERY-LIST-PROC ("UGL", panel, win);
  UGBRL = call CREATE-BR-QUERY-LIST-PROC ("UGBRL", panel, win);

for UBR = each bioreservoir that is an-upstream-bioreservoir-of BR do
  if the biopool upon the subworkspace of UBR exists then
    insert "[the name of UBR]" at the end of the text list UAPBRL;
    PO = the biopool upon the subworkspace of UBR;
    if there exists a bioreactant connected to PO then
      for R = each bioreactant connected to PO do
        if R is an extracell-ligand.r or R is a extracell-antagonist.r then
          insert "[the name of UBR]" at the end of the text list UEFBRL else
        if R is a cell-receptor.r then insert "[the name of UBR]" at the end of
          the text list UCRBRL else
        if R is a prot.kinase.r then insert "[the name of UBR]" at the end of
          the text list UPKBRL else
        if R is a prot-phosphatase.r then insert "[the name of UBR]" at the
          end of the text list UPPBRL;
        if R is a transcription-factor.r then insert "[the name of UBR]" at the
          end of the text list UTFBRL;
        if R is a gene.r then insert "[the name of UBR]" at the end of the text
          list UGBRL;

call FILL-BR.ET-LIST-PROC (UAPBRL, UAPL, panel, win);
call FILL-BR.ET-LIST-PROC (UEFBRL, UEFL, panel, win);
call FILL-BR.ET-LIST-PROC (UCRBRL, UCRL, panel, win);
call FILL-BR.ET-LIST-PROC (UPKBRL, UPKL, panel, win);
call FILL-BR.ET-LIST-PROC (UPPBRL, UPPL, panel, win);
call FILL-BR.ET-LIST-PROC (UTFBRL, UTFL, panel, win);
call FILL-BR.ET-LIST-PROC (UGBRL, UGL, panel, win);
return

TABLE 175
---

CREATE-BR-QUERY-LIST-PROC (lbl: text, panel: class query-panel,
win: class window) = (class scroll-text-list)

PN: symbol = the name of panel;
BRN: symbol = symbol (the related-item of panel);

if BRN is not none then
  if not (there exists a scroll-text-list L such that (the label of
    L = "[PN]-[lbl]-[BRN]")) then
    create a scroll-text-list L;
    conclude that the label of L = "[PN]-[lbl]-[BRN]";
    transfer L to the subworkspace of safe-home-for-lists at (-105, 25);
    conclude that L is a-list-associated-to-dlg panel;}
    return L;
  else
    return L

TABLE 176
---

FILL-BR.ET-LIST-PROC (BRL: class scroll-text-list, L: class scroll-text-
list, panel: class query-panel, win : class window)

move BRL to (135, 10);
if the number of elements in BRL >= 0 then
  for T = each text in BRL do
    BRN = symbol (T);
    BR = the bioreservoir named by BRN;
    if the ref-bioentity of BR has a current value then
      EN = the bioentity named by the ref-bioentity of BR;
      insert "[the name of EN]" at the end of the text list L;
return

TABLE 177

QUERY-BR-RELATED-CALLBACK (button: class button, win : class window, panel: class query-panel)

BRN: symbol = symbol (the related-item of panel);
PN: symbol = the name of panel;
SW: class kb-workspace = the subworkspace of panel;

```
if not (there exists a scroll-text-list L such that (the label of L =
     "[PN]-DPKL-[BRN]" or the label of L = "[PN]-UPKL-[BRN]" )) then
   create a message-dialog md, set the text of the message upon the SW of
       md to "Required information is not available. Click on Downstream
       or Upstream and try to query again" and show the SW of md on the
       current window at (0, 0);
else
   create a message-dialog md, set the text of the message upon the SW of
       md to "Processing . . . . .    " and show the SW of md on the
       current window at (0, 0);
rb-id0 = call GET-RADIO-BOX-ID-PROC ("direction", SW, win);
type0 = call get-radio-box-value (panel, rb-id0);
if there exists a radio-button B upon SW such that (the id of B =
     "function") then
   rb-id2 = call GET-RADIO-BOX-ID-PROC ("function", SW, win);
   type2 = call get-radio-box-value (panel, rb-id2);
   FL, FBRL = call GET-BR-FUNCTION-LIST-PROC (type0, type2,
       panel, win);
if FBRL exists then
   create a panel-text FT1;
   TX1 = capitalize-words ("bioReservoirs [type0] of [BRN] that contain
[type2]");
change the text of FT1 to TX1;
create a panel-text FT2;
if FL exists then
   if not (there exists a radio-button B upon SW such that (the id of B =
       "subunits" or the id of B = "domains" or the id of B = "motifs"
       or the id of B = "groups")) then
       if there exists a scroll-text-list EL such that (the label of EL =
           "[PN]-[type0]-[type2]-ETL") then
         ETL = EL
       else
         create a c-scroll-text-list ETL;
         conclude that the label of ETL = "[PN]-[type0]-[type2]-ETL";
         conclude that ETL is a-list-associated-to-dlg panel;
         transfer ETL to the subworkspace of safe-home-for-lists at (50,-245);
         TX2 = capitalize-words ("[type2] with structures defined in this
       module that are [type0] of [BRN]");
         for T1 = each text in FL do
             insert T1 at the end of the text list ETL;
   else
       ETL, TX2 = call QUERY-BR-STRUCTURE-LISTS-PROC (type0, type2,
           FL, panel, win);
change the text of FT2 to "[TX2]";
call CREATE-DOUBLE-QUERY-OUTPUT-PANEL-PROC (FBRL, ETL,
     FT1, FT2, panel, win);
delete md;
return
```

TABLE 178

```
GET-BR-FUNCTION-LIST-PROC (type2: symbol, type3: symbol, panel: class query-
panel, win : class window) = (class scroll-text-list, class scroll-text-list)

PN: symbol = the name of panel;
BRN: symbol = the related-item of panel;
  if type2 is downstream then
    case (type3) of
      extracellular-factors:
        lbl = "[PN]-DEFL-[BRN]";
        lblbr = "[PN]-DEFBRL-[BRN]";
      cell-receptors:
        lbl = "[PN]-DCRL-[BRN]";
        lblbr = "[PN]-DCRBRL-[BRN]";
      protein-kinases:
        lbl = "[PN]-DPKL-[BRN]";
        lblbr = "[PN]-DPKBRL-[BRN]";
      protein-phosphatases:
        lbl = "[PN]-DPPL-[BRN]";
        lblbr = "[PN]-DPPBRL-[BRN]";
      transcription-factors:
        lbl = "[PN]-DTFL-[BRN]";
        lblbr = "[PN]-DTFBRL-[BRN]";
      genes:
        lbl = "[PN]-DGL-[BRN]";
        lblbr = "[PN]-DGBRL-[BRN]";
      any-protein:
        lbl = "[PN]-DAPL-[BRN]";
        lblbr = "[PN]-DAPBRL-[BRN]";
      no-function-selection:
        lbl = "[PN]-DNL-[BRN]";
        lblbr = "[PN]-DNBRL-[BRN]";  else
  if type2 is upstream then
    case (type3) of
      extracellular-factors:
        lbl = "[PN]-UEFL-[BRN]";
        lblbr = "[PN]-UEFBRL-[BRN]";
      cell-receptors:
        lbl = "[PN]-UCRL-[BRN]";
        lblbr = "[PN]-UCRBRL-[BRN]";
      protein-kinases:
        lbl = "[PN]-UPKL-[BRN]";
        lblbr = "[PN]-UPKBRL-[BRN]";
      protein-phosphatases:
        lbl = "[PN]-UPPL-[BRN]";
        lblbr = "[PN]-UPPBRL-[BRN]";
      transcription-factors:
        lbl = "[PN]-UTFL-[BRN]";
        lblbr = "[PN]-UTFBRL-[BRN]";
      genes:
        lbl = "[PN]-UGL-[BRN]";
        lblbr = "[PN]-UGBRL-[BRN]";
      any-protein:
        lbl = "[PN]-UAPL-[BRN]";
        lblbr = "[PN]-UAPBRL-[BRN]";
      no-function-selection:
        lbl = "[PN]-UNL-[BRN]";
        lblbr = "[PN]-UNBRL-[BRN]";
  if there exists a c-scroll-text-list FL such that (the label of FL = lbl) then move FL to
    (-110, -280);
  if there exists a c-scroll-text-list FBRL such that (the label of FBRL = lblbr) then move
    FL to (-30, -280) ;
  return FL, FBRL;
```

TABLE 179

QUERY-BR-STRUCTURE-LISTS-PROC (type0: symbol, type2: symbol, FL: class
scroll-text-list, panel: class query-panel, win : class window) = (class scroll-text-list, text)

PN: symbol = the name of panel;
   SW: class kb-workspace = the subworkspace of panel;
   if there exists a radio-button B upon SW such that (the id of B = "subunits") then
     type3, PSA = call FIND-SPECIFIC-ARRAY-PROC ("subunits", panel, win);
   if there exists a radio-button B upon SW such that (the id of B = "subunits-2") then
     type4, PSA-2 = call FIND-SPECIFIC-ARRAY-PROC ("subunits-2", panel, win);
   if there exists a radio-button B upon SW such that (the id of B = "domains") then
     type5, PDA = call FIND-SPECIFIC-ARRAY-PROC ("domains", panel, win);
   if there exists a radio-button B upon SW such that (the id of B = "domains-2") then
     type6, PDA-2 = call FIND-SPECIFIC-ARRAY-PROC ("domains-2", panel, win);
   if there exists a radio-button B upon SW such that (the id of B = "motifs") then
     type7, PMA = call FIND-SPECIFIC-ARRAY-PROC ("motifs", panel, win);
   if there exists a radio-button B upon SW such that (the id of B = "motifs-2") then
     type8, PMA-2 = call FIND-SPECIFIC-ARRAY-PROC ("motifs-2", panel, win);
   if there exists a radio-button B upon SW such that (the id of B = "groups") then
     type9, PGA = call FIND-SPECIFIC-ARRAY-PROC ("groups", panel, win);
   if there exists a radio-button B upon SW such that (the id of B = "groups-2") then
     type10, PGA-2 = call FIND-SPECIFIC-ARRAY-PROC ("groups-2", panel, win);

if PSA exists then
     if PSA-2 exists then
       if there exists a scroll-text-list ETL such that (the label of ETL
          = "[PN]-[type0]-[type2]-[type3]-[type4]-ETL") then
         go to final-routine
       else
         ETL, TX2 = call MERGE-BR-FUNCTION-STRUCTURE-STRUCTURE-PROC
           (the symbol subunit, the symbol subunit, type0, type2, type3, type4, FL,
           PSA, PSA-2, panel, win);
     else
       if there exists a c-scroll-text-list ETL such that (the label of ETL
          = "[PN]-[type0]-[type2]-[type3]-ETL") then
         go to final-routine
       else
        ETL, TX2 = call MERGE-BR-FUNCTION-STRUCTURE-PROC (the symbol
          subunit, type0, type2, type3, FL, PSA, panel, win);
   else
   if PDA exists then
     if PDA-2 exists then
       if there exists a c-scroll-text-list ETL such that (the label of ETL
          = "[PN]-[type0]-[type2]-[type5]-[type6]-ETL") then
         go to final-routine
       else
         ETL, TX2 = call MERGE-BR-FUNCTION-STRUCTURE-STRUCTURE-PROC
           (the symbol domain, the symbol domain, type0, type2, type5, type6, FL, PDA,
           PDA-2, panel, win)
     else
     if PMA exists then
       if there exists a c-scroll-text-list ETL such that (the label of ETL
          = "[PN]-[type5]-[type7]-ETL") then
         go to final-routine
       else
         ETL, TX2 = call MERGE-BR-FUNCTION-STRUCTURE-STRUCTURE-PROC
           (the symbol domain, the symbol motif, type0, type2, type5, type7, FL, PDA,
           PMA, panel, win)
     else
     if PGA exists then
       if there exists a scroll-text-list ETL such that (the label of ETL
          = "[PN]-[type0]-[type2]-[type5]-[type9]-ETL") then

```
            go to final-routine
        else
            ETL, TX2 = call MERGE-BR-FUNCTION-STRUCTURE-STRUCTURE-PROC
                (the symbol domain, the symbol group, type0, type2, type5, type9, FL, PDA,
                PGA, panel, win)
    else
        if there exists a c-scroll-text-list ETL such that (the label of ETL =
            "[PN]-[type0]-[type2]-[type5]-ETL") then
            go to final-routine
        else
        ETL, TX2 = call MERGE-BR-FUNCTION-STRUCTURE-PROC (the symbol
            domain, type0, type2, type5, FL, PDA, panel, win);
else
if PMA exists then
    if PMA-2 exists then
        if there exists a scroll-text-list ETL such that (the label of ETL
            = "[PN]-[type0]-[type2]-[type7]-[type8]-ETL") then
            go to final-routine
        else
            ETL, TX2 = call MERGE-BR-FUNCTION-STRUCTURE-STRUCTURE-PROC
                (the symbol motif, the symbol motif, type0, type2, type7, type8, FL, PMA,
                PMA-2, panel, win)
    else
        if there exists a scroll-text-list ETL such that (the label of ETL
            = "[PN]-[type0]-[type2]-[type7]-ETL") then
            go to final-routine
        else
        if PGA exists then
            if there exists a scroll-text-list ETL such that (the label of ETL
                = "[PN]-[type0]-[type2]-[type7]-[type9]-ETL") then
                go to final-routine
            else
                ETL, TX2 = call MERGE-BR-FUNCTION-STRUCTURE-STRUCTURE-PROC
                    (the symbol motif, the symbol group, type0, type2, type7, type9, FL, PMA,
                    PGA, panel, win)
        else
            if there exists a scroll-text-list ETL such that (the label of ETL
                = "[PN]-[type0]-[type2]-ETL") then
                go to final-routine
            else
            ETL, TX2 = call MERGE-BR-FUNCTION-STRUCTURE-PROC (the symbol
                motif, type0, type2, type7, FL, PMA, panel, win);
else
if PGA exists then
    if PGA-2 exists then
        if there exists a scroll-text-list ETL such that (the label of ETL
            = "[PN]-[type0]-[type2]-[type9]-[type10]-ETL") then
            go to final-routine
        else
            ETL, TX2 = call MERGE-BR-FUNCTION-STRUCTURE-STRUCTURE-PROC
                (the symbol group, the symbol group, type0, type2, type9, type10, FL, PGA,
                PGA-2, panel, win)
    else
        if there exists a scroll-text-list ETL such that (the label of ETL
            = "[PN]-[type0]-[type2]-[type9]-ETL") then
            go to final-routine
        else
        ETL, TX2 = call MERGE-BR-FUNCTION-STRUCTURE-PROC (the symbol
            group, type0, type2, type9, FL, PGA, panel, win);
return ETL, TX2;

final-routine:
    return ETL, TX2;
```

TABLE 180

MERGE-BR-FUNCTION-STRUCTURE-PROC (tag1: symbol, type0:
symbol, type2: symbol, type3: symbol, FL: class scroll-text-list, QA: class
query-array, panel: class query-panel, win : class window) = (class scroll-
text-list, text)

PN: symbol = the name of panel;
BRN: symbol = the related-item of panel;

if there exists a scroll-text-list ETL such that (the label of ETL =
    "[PN]-[type0]-[type2]-[type3]-ETL") then
    go to exit-routine
  else
    create a scroll-text-list ETL;
    conclude that the label of ETL = "[PN]-[type0]-[type2]-[type3]-ETL";
    conclude that ETL is a-list-associated-to-dlg panel;
    transfer ETL to the subworkspace of safe-home-for-lists at (50, -245);
    TX2 = the scroll-title of ETL;

if the number of elements in FL = 0 then
      TX2 = capitalize-words ("There are no structures defined in this
        module of [type2] that are [type0] of [BRN]") ;
  else
    call BR-FILL-ETL-LIST-PROC (FL, QA, ETL, panel, win);
    if the number of elements in ETL >= 0 then
      TX2 = capitalize-words ("[type2] that are [type0] of [BRN] and contain
        [type3]");
    else
      if the number of elements in ETL = 0 then
        if type3 = symbol ("no-[tag1]-selection") then
          TX2 = capitalize-words ("[type2] with structures defined in this
            module that are [type0] of [BRN]")
        else
          TX2 = capitalize-words ("[type2] with structures defined in this
            module that are [type0] of [BRN]. None of those contain
            [type3]");
    for T1 = each text in FL do
      insert T1 at the end of the text list ETL;
  return ETL, TX2;

exit-routine:
  TX2 = the scroll-title of ETL;
  return ETL, TX2;

TABLE 181

```
MERGE-BR-FUNCTION-STRUCTURE-STRUCTURE-PROC (tag1:
symbol, tag2: symbol, type0: symbol, type2: symbol, type4: symbol,
type5: symbol, FL: class scroll-text-list, DQA: class query-array, MQA:
class query-array, panel: class query-panel, win : class window) = (class
scroll-text-list, text)

PN: symbol = the name of panel;
BRN: symbol = symbol (the related-item of panel);

if there exists a scroll-text-list ETL such that (the label of ETL =
    "[PN]-[type0]-[type2]-[type4]-[type5]-ETL") then
        go to exit-routine
else
    create a scroll-text-list ETL;
    conclude that the label of ETL = "[PN]-[type0]-[type2]-[type4]-[type5]-
        ETL";
    conclude that ETL is a-list-associated-to-dlg panel;
    transfer ETL to the subworkspace of safe-home-for-lists at (50, -245);
    TX2 = the scroll-title of ETL;
    if the number of elements in FL = 0 then
        TX2 = capitalize-words ("There are no structures defined in this
            module of [type2] that are [type0] of [BRN]") ;
    else
        if the array-length of DQA = 0 then
            if the array-length of MQA = 0 then
                if type5 = symbol ("no-[tag2]-selection") then
                    TX2 = capitalize-words ("[type2] with structures defined
                        in this module that are [type0] of [BRN]. None of those
                        contain [type4]")
                else
                    if type4 = symbol ("no-[tag1]-selection") then
                        TX2 = capitalize-words ("[type2] with structures defined
                            in this module that are [type0] of [BRN]. None of those
                            contain [type5]")
                    else
                        if type5 = symbol ("no-[tag2]-selection") and type4 =
                            symbol ("no-[tag1]-selection") then
                            TX2 = capitalize-words ("[type2] with structures defined
                                in this module that are [type0] of [BRN]")
                        else
                            TX2 = capitalize-words ("[type2] with structures defined
                                in this module that are [type0] of [BRN]. None of
                                those contain [type4] or [type5]");
                for T1 = each text in FL do
                    insert T1 at the end of the text list ETL;

else
            if type4 = symbol ("no-[tag1]-selection") then
                TX2 = capitalize-words ("[type2] with structures defined in this
                    module that are [type0] of [BRN] and contain [type5]")
            else
                TX2 = capitalize-words ("[type2] with structures defined
                    in this module that are [type0] of [BRN] and contain [type5].
                    None of those contain [type4]");
            call BR-FILL-ETL-LIST-PROC (FL, MQA, ETL, panel, win);
```

```
else
  if the array-length of MQA = 0 then
    if type5 = symbol ("no-[tag2]-selection") then
      TX2 = capitalize-words ("[type2] with structures defined
            in this module that are [type0] of [BRN] and contain [type4]")
    else
      TX2 = capitalize-words ("[type2] with structures defined in this
            module that are [type0] of [BRN] and contain [type4]. None of
            those contain [type5]");
    call BR-FILL-ETL-LIST-PROC (FL, DQA, ETL, panel, win);
  else
    TX2 = capitalize-words ("[type2] with structures defined in this
          module that are [type0] of [BRN] and contain [type4] and
          [type5]");
    call BR-FILL-DOUBLE-ETL-LIST-PROC (FL, DQA, MQA, ETL,
      panel, win);

return ETL, TX2;

exit-routine:
  TX2 = the scroll-title of ETL;
  return ETL, TX2;
```

TABLE 182

BR-FILL-ETL-LIST-PROC (FL: class scroll-text-list, QA: class query-array, ETL: class scroll-text-list, panel: class query-panel, win : class window)

```
if the number of elements in FL >= 0 and the array-length of QA >= 0
  then
  for T = each text in FL do
    for AE = each symbol in QA do
      if T = "[AE]" then
        insert T at the end of the text list ETL;
return
```

BR-FILL-DOUBLE-ETL-LIST-PROC (FL: class scroll-text-list, DQA: class query-array, MQA: class query-array, ETL: class scroll-text-list, panel: class query-panel, win : class window)

```
for T = each text in FL do
  for DAE = each symbol in DQA do
    if T = "[DAE]" then
      for MAE = each symbol in MQA do
        if T = "[MAE]" then
          insert T at the end of the text list ETL;
return
```

TABLE 183

CREATE-DOUBLE-QUERY-OUTPUT-PANEL-PROC (BRL: class scroll-text-list, ETL:class scroll-text-list, FT1: class free-text, FT2: class free-text, dlg: class query-panel, win : class window)

d-id: text= the id of dlg:
  create a query-panel panel by cloning MASTER-MOLECULAR-
      QUERY-OUTPUT- PANEL;
  transfer panel to the subworkspace of dialog-bin at (0,0);
  SW = the subworkspace of panel;
  uid = call unique-id (d-id);
  change the text of the id of panel to uid;
  transfer FT1 to SW at (0, 110);
  transfer FT2 to SW at (0, -180);
  make panel permanent;
  sa1 = call create-scroll-area-from-list ("query-BR-scroll", 6, BRL);
  call C-COMPLETE-BR-PANEL-PROC (sa1, panel, win);
  sa2 = call create-scroll-area-from-list ("query-BR-scroll", 6, ETL);
  call C-COMPLETE-BE-PANEL-PROC (sa2, panel, win);
  change the size of the subworkspace of panel to minimum;
  show the subworkspace of dlg with its top right corner 40 units below the
      top right corner of the screen;
  show the subworkspace of panel on win with its center 300 units to the
      left of the center of the screen;
  return :

TABLE 184

COMPLETE-BE-PANEL-PROC (sa: class scroll-area, panel: class query-panel, win : class window)

de: class uil-button;
  conclude that the allow-unselect-on-selected-message of sa is true;
  conclude that the allow-multiple-simultaneous-selections of sa is true;
  call add-grobj-to-dialog(panel, sa, 0, -320);
  call scroll-area-reflect (sa);
  call set-attribute(SA, the symbol message-selection-method, the
      symbol query-message-selection);
  call set-attribute(SA, the symbol message-unselection-method, the
      symbol query-message-unselection);
  de = call create-pushbutton ("de", the symbol text, the symbol DELETE-QUERY-
          PANEL-CALLBACK, the symbol medium, "DELETE");
  call add-grobj-to-dialog(panel, de, 0, -440);
  return;

COMPLETE-BR-PANEL-PROC (sa: class scroll-area, panel: class
  query-panel, win : class window)

conclude that the allow-unselect-on-selected-message of sa is true;
  conclude that the allow-multiple-simultaneous-selections of sa is true;
  call uil-add-grobj-to-dialog(panel, sa, 0, -30);
  call uil-scroll-area-reflect (sa);
  call uil-set-attribute(SA, the symbol message-selection-method, the
      symbol c-query-message-selection);
  call uil-set-attribute(SA, the symbol message-unselection-method, the
      symbol query-message-unselection);
  change the text of the ordering-method of sa to "alphabetic";
  return;

TABLE 185

|  |  |
|---|---|
|  | an user-menu-choice |
| Label | list-copies |
| Applicable class | complex-bioentity |
| Condition | the item has a name |
| Action | start ET-LIST-COPIES-CALLBACK (the item, this window) |

ET-LIST-LOCAL-COPIES-CALLBACK (ET: class complex-bioentity, win
: class window)

EN: symbol = the name of ET;
  n: integer = 0;
  create a message-dialog md, set the text of the message upon the SW of
    md to "Processing . . . . . " and show the SW of md on the current
    window at (0, 0);
  if there exists a scroll-text-list that is the-copies-list-of ET then
    for CEL = each scroll-text-list that is the-copies-list-of ET do
      delete CEL;
  create a scroll-text-list CEL;
  conclude that CEL is THE-COPIES-LIST-OF ET;
  transfer CEL to the subworkspace of safe-home-for-lists at (55, 15);
  call LIST-LOCAL-BIOENTITY-COPIES-PROC (ET, CEL, win);
  if the number of elements in CEL = 0 then
    go to exit--routine
  else
    create a query-panel panel by cloning MASTER-LOCAL-BIOENTITY-
      COPIES-PANEL;
    transfer panel to the subworkspace of dialog-bin at (0, 0);
    SW = the subworkspace of panel;
    make panel permanent;
    create a panel-text FT;
    change the text of FT to "COPIES OF: [EN]";
    transfer FT to SW at (0, 80);
    sa = call create-scroll-area-from-list ("ET-copies-scroll", 5, CEL);
    conclude that the allow-unselect-on-selected-message of sa is true;
    conclude that the allow-multiple-simultaneous-selections of sa is true;
    call add-grobj-to-dialog(panel, sa, 0, -30);
    call scroll-area-reflect (sa);
    call set-attribute(SA, the symbol uil-message-selection-method, the
      symbol ET-COPIES-MESSAGE-SELECTION-CALLBACK );
    call uil-set-attribute(SA, the symbol uil-message-unselection-method,
      the symbol ET-COPIES-MESSAGE-UNSELECTION-
      CALLBACK );
    de = call create-pushbutton ("de", the symbol text, the symbol
      DELETE-QUERY-PANEL-CALLBACK, the symbol medium,
      "DELETE");
    call add-grobj-to-dialog(panel, de, 0, -145);
    change the size of the subworkspace of panel to minimum;
    show the subworkspace of panel on win with its center 200 units to the
      left of the center of the screen;
  delete md;
  return;
exit--routine:
  delete md;
  create a message-dialog md, set the text of the message upon the SW of
    md to "There are no copies of: [EN]" and show the SW of md on the
    current window at (0, 0);
  return;

TABLE 186

```
LIST-LOCAL-BIOENTITY-COPIES-PROC (ET: class bioentity, CEL:
class scroll-text-list, win: class window)

EN: symbol = the name of ET;
  CL = the class of ET;
  if ET is a PROTEIN then
      if there exists a protein CE that is of the class named by CL such that
          (the text of the master-bioentity of CE = "[EN]") then
          for CE = each protein that is of the class named by CL do
              if the text of the master-bioentity of CE = "[EN]" then
                  insert "[the id of CE]" at the end of the text list CEL; else
  if ET is a PROTEIN-MOTIF then
      if there exists a protein-motif CE that is of the class named by CL such
          that (the text of the master-bioentity of CE = "[EN]" ) then
          for CE = each protein-motif that is of the class named by CL do
              if the text of the master-bioentity of CE = "[EN]" then
                  insert "[the id of CE]" at the end of the text list CEL; else
  if ET is a PROTEIN-DOMAIN then
      if there exists a protein-domain CE that is of the class named by CL such
          that (the text of the master-bioentity of CE = "[EN]" ) then
          for CE = each protein-domain that is of the class named by CL do
              if the text of the master-bioentity of CE = "[EN]" then
                  insert "[the id of CE]" at the end of the text list CEL; else
  if ET is a PROTEIN-COMPONENT then
      if there exists a protein-component CE that is of the class named by CL
          such that (the text of the master-bioentity of CE = "[EN]" ) then
          for CE = each protein-component that is of the class named by CL do
              if the text of the master-bioentity of CE = "[EN]" then
                  insert "[the id of CE]" at the end of the text list CEL;  else
  if ET is a DNA-COMPONENT then
      if there exists a dna-component CE that is of the class named by CL such
          that (the text of the master-bioentity of CE = "[EN]" ) then
          for CE = each dna-component that is of the class named by CL do
              if the text of the master-bioentity of CE = "[EN]" then
                  insert "[the id of CE]" at the end of the text list CEL; else
  if ET is a HETER.MOL.COMPLEX then
      if there exists a heter.mol.complex CE that is of the class named by CL
          such that (the text of the master-bioentity of CE = "[EN]" ) then
          for CE = each heter.mol.complex that is of the class named by CL do
              if the text of the master-bioentity of CE = "[EN]" then
                  insert "[the id of CE]" at the end of the text list CEL; else
  if ET is a NUCLEIC-ACID then
      if there exists a nucleic-acid CE that is of the class named by CL such
          that (the text of the master-bioentity of CE = "[EN]" ) then
          for CE = each nucleic-acid that is of the class named by CL do
              if the text of the master-bioentity of CE = "[EN]" then
                  insert "[the id of CE]" at the end of the text list CEL; else
  if ET is a MEMBRANE then
      if there exists a membrane CE that is of the class named by CL such that
          (the text of the master-bioentity of CE = "[EN]" ) then
          for CE = each membrane that is of the class named by CL do
              if the text of the master-bioentity of CE = "[EN]" then
                  insert "[the id of CE]" at the end of the text list CEL; else
  if ET is a BIOENTITY then
      if there exists a bioentity CE that is of the class named by CL such that
          (the text of the master-bioentity of CE = "[EN]" ) then
          for CE = each bioentity that is of the class named by CL do
              if the text of the master-bioentity of CE = "[EN]" then
                  insert "[the id of CE]" at the end of the text list CEL;
  return;
```

TABLE 187

---
ET-COPIES-MESSAGE-SELECTION-CALLBACK (MO: class message-object, SA: class scroll-area, win: class window)

BRN: symbol;
T: text = the text of MO;

if there exists a bioentity EN such that (the id of EN = T) then
      show EN on win with its center 300 units to the right of the center of
        the screen ;

---
ET-COPIES-MESSAGE-UNSELECTION-CALLBACK (MO: class message-object, SA: class scroll-area, win: class window)

T: text = the text of MO;
if there exists a bioentity EN such that (the id of EN = T) then
hide the workspace of EN on win;

---

TABLE 188
```
                     an user-menu-choice
Label            show-lists
Applicable class bioreservoir
Condition        the br-chaining-tracer upon the subworkspace of the
                    item exits
Action           start BR-CHAINING-PROC (the item, this window)
```
---
BR-CHAINING-PROC (BR: class bioreservoir, win: class window)

```
tracer: = the br-chaining-tracer upon the subworkspace of BR;
if the subworkspace of tracer exists then
   show the subworkspace of tracer on Win with its center 400
      units to the right of the center of the screen
else
   if BR has a name then go to chaining-routine
   else if the master-bioreservoir of BR is not none then
      BR = the bioreservoir named by the master-bioreservoir of BR;
      go to chaining-routine;
   else return;

chaining-routine:
   create a workspace SW by cloning the subworkspace of
      BR-CHAINING-LISTS ;
   make SW the subworkspace of tracer;
   change the text of the panel-text upon SW to "Lists of bioReservoirs and
         bioProcesses Downstream and Upstream of: [the name of BR]";
   DBPL = the downstream-bioprocesses-list upon SW ;
   DBRL = the downstream-bioreservoirs-list upon SW ;
   for DBP = each bioprocess that is a-down-bioprocess-of BR do
      allow other processing;
      insert DBP at the end of the bioprocess list DBPL;
      for DDBP = each bioprocess that is a-downstream-bioprocess-of DBP
            do
         insert DDBP at the end of the bioprocess list DBPL;
   for LDDBP = each bioprocess in DBPL do
      for DDBR = each bioreservoir that is a-down-bioreservoir-of
            LDDBP do
         insert DDBR at the end of the bioreservoir list DBRL;
   UBPL = the upstream-bioprocesses-list upon SW ;
   UBRL = the upstream-bioreservoirs-list upon SW ;
   for UBP = each bioprocess that is an-up-bioprocess-of BR do
      allow other processing;
      insert UBP at the end of the bioprocess list UBPL;
      for UUBP=each bioprocess that is an-upstream-bioprocess-of UBP do
         insert UUBP at the end of the bioprocess list UBPL;
   for LUUBP = each bioprocess in UBPL do
      for UUBR =each bioreservoir that is an-up-bioreservoir-of LUUBP do
         insert UUBR at the end of the bioreservoir list UBRL;
   change the size of SW to minimum;
   show SW on win with its center 400 units to the right of the center of
      the screen;
return;
```

TABLE 189

|  |  |
|---|---|
|  | an user-menu-choice |
| Label | show-lists |
| Applicable class | bioprocess |
| Condition | tthe bp-chaining-tracer upon the subworkspace of the item exits |
| Action | start BP-CHAINING-PROC (the item, this window ) |

BP-CHAINING-PROC (BP: class bioprocess, win: class window )

```
tracer= the bp-chaining-tracer upon the subworkspace of BP;
if the subworkspace of tracer exists then
   show the subworkspace of tracer on win with its center 400
      units to the right of the center of the screen
else
  if BP has a name then go to chaining-routine
  else if the master-bioprocessof BP is not none then
     BP = the bioprocess named by the master-bioprocess of BP;
     go to chaining-routine:
  else return;

chaining-routine:
     create a workspace SW by cloning the subworkspace of BP-
        CHAINING-LISTS;
     make SW the subworkspace of tracer;
     change the text of the panel-text upon SW to "[the name of BP]";
     DBPL = the downstream-bioprocesses-list upon SW ;
     SDBPL = the downstream-bp-simulation-list upon SW ;
     DBRL = the downstream-bioreservoirs-list upon SW ;
     SDBRL = the downstream-br-simulation-list upon SW ;
     for DBP = each bioprocess that is a-downstream-bioprocess-
           of BP do
        allow other processing;
        insert DBP at the end of the bioprocess list DBPL;
        if the status of DBP is downstream-activated or the
              status of DBP is forw-activated then
           insert DBP at the end of the bioprocess list SDBPL;
        for DBR = each bioreservoir that is a-down-bioreservoir- of DBP do
           insert DBR at the end of the bioreservoir list DBRL;
     UBPL = the upstream-bioprocesses-list upon SW ;
     SUBPL = the upstream-bp-simulation-list upon SW ;
     UBRL = the upstream-bioreservoirs-list upon SW ;
     SUBRL = the upstream-br-simulation-list upon SW ;
     for UBP = each bioprocess that is an-upstream-bioprocess-of BP do
        allow other processing;
        insert UBP at the end of the bioprocess list UBPL;
        if the status of UBP is upstream-activated or the status of UBP is
              back-activated then
           insert UBP at the end of the bioprocess list SUBPL;
        for UBR = each bioreservoir that is an-up-bioreservoir-of UBP do
           insert UBR at the end of the bioreservoir list UBRL;
     change the size of SW to minimum;
     show SW on win with its center 400 units to the right of the center of
           the screen:
     return;
```

TABLE 190
---
an user-menu-choice
Label            up-pathway
Applicable class bioprocess
Condition        the subworkspace of the
                 item has been activated and the subworkspace of
                 the up-path-tracer upon the subworkspace of
                 the item does not exist
Action           start DRAW-UP-PATHWAY-PROC (the up-path-tracer
                 upon the subworkspace of the item, this window )
---
DRAW-UP-PATHWAY-PROC (PT: class up-path-tracer, win: class window)

BP = the bioprocess superior to the workspace of PT;
if BP has a name and there exists a bioreservoir that is an-up-
    bioreservoir-of BP then
  create a workspace SW by cloning the subworkspace of MASTER-
      UP-PATHWAY;
  make SW the subworkspace of PT;
  T = the biomodel-title upon SW;
  conclude that the label of T = "[the label of T] [the label of BP]";
  change the status-color icon-color of BP to brown;
  create a bioprocess LBP by cloning BP;
  make the subworkspace of LBP transient;
  delete the subworkspace of LBP;
  x = the x-pos upon SW;
  y = the y-pos upon SW;
  conclude that x = -305;
  conclude that y = -240;
  transfer LBP to SW at (x, y);
  show SW at three-quarter scale with its bottom left corner 50 units to the
      right of the bottom left corner of the screen;
  for UBP = each bioprocess that is an-upstream-bioprocess-of BP do
    allow other processing;
    change the status-color icon-color of UBP to brown;
    conclude that y = y + 30;
    call CREATE-LOCAL-UP-BP-PROC (BP, LBP, SW, win);
  change the size of SW to minimum;
return;
---

TABLE 191
---
CREATE-LOCAL-UP-BP-PROC (BP: class bioprocess, LBP: class
bioprocess, SW: class workspace, win: class window)

x = the x-pos upon SW;
  y = the y-pos upon SW;
  if there exists a bioreservoir that is an-up-bioreservoir-of BP then
    for UBR = each bioreservoir that is an-up-bioreservoir-of BP do
      allow other processing;
      if there exists a bioprocess that is an-up-bioprocess-of UBR then
        for UBP = each bioprocess that is an-up-bioprocess-of UBR do
          if there exists a bioprocess MBP upon SW such that (the master-
              bioprocess of MBP = the master-bioprocess of UBP) then
            LUBP = MBP;
          go to connect-routine;
        else
          allow other processing;
          conclude that x = x + 110;
          if x > 2600 then show SW at one-quarter scale with its top left corner
              50 units below the top left corner of the screen else
          if x > 1800 then show SW at half scale with its top left corner 50
              units below the top left corner of the screen;
          create a bioprocess LUBP by cloning UBP;
          make the subworkspace of LUBP transient;
          delete the subworkspace of LUBP;
          transfer LUBP to SW at (x, y);
          t = random (20, 76);
          l = random (5, 25);
          create a connection connected between LBP newly locating it at
              top at the position given by t and LUBP newly locating it at left at
              the position given by l with direction input;
          conclude that y = y + 30;
          call CREATE-LOCAL-UP-BP-PROC (UBP, LUBP, SW, win);
  return;

connect-routine:
  for C = each connection connected to LBP do
    if there exists a connection UC connected to LUBP such that (UC is
        the same object as C) then return;
  b = random (20, 76);
  r = random (40, 51);
  p = x-rel-position (LBP, LUBP);
  if p > 0 then
    create a connection of class c-line connected between LBP newly
        locating it at bottom at the position given by b and LUBP newly
        locating it at right at the position given by r with direction
        input, with vertices 10 else
  if p < 0 then
    create a connection of class c-line connected between LBP newly
        locating it at right at the position given by r and LUBP newly
        locating it at bottom at the position given by b with direction
        input ;
---

TABLE 192

---
|  | an user-menu-choice |
|---|---|
| Label | down-pathway |
| Applicable class | bioprocess |
| Condition | the item has a name and the subworkspace of the item has been activated and the subworkspace of the down-path-tracer upon the subworkspace of the item does not exist |
| Action | start DRAW-DOWN-PATHWAY-PROC (the down-path-tracer upon the subworkspace of the item, this window ) |

---

DRAW-DOWN-PATHWAY-PROC (PT: class down-path-tracer, win: class window)

BP = the bioprocess superior to the workspace of PT;
if BP has a name and there exists a bioreservoir that is a-down-bioreservoir-of BP then
   create a workspace SW by cloning the subworkspace of MASTER-DOWN-PATHWAY;
   make SW the subworkspace of PT;
   T = the biomodel-title upon SW;
   conclude that the label of T = "[the label of T] [the label of BP]";
   change the status-color icon-color of BP to brown;
   create a bioprocess LBP by cloning BP;
   make the subworkspace of LBP transient;
   delete the subworkspace of LBP;
   x = the x-pos upon SW;
   y = the y-pos upon SW;
   conclude that x = -305;
   conclude that y = 50;
   transfer LBP to SW at (x, y);
   show SW at three-quarter scale with its top left corner 50 units
      below the top left corner of the screen;
   for DBP = each bioprocess that is a-downstream-bioprocess-of BP do
     allow other processing;
     change the status-color icon-color of DBP to brown;
   conclude that y = y - 40;
   call CREATE-LOCAL-DOWN-BP-PROC (BP, LBP, SW, win);
   change the size of SW to minimum;
return;

TABLE 193

```
CREATE-LOCAL-DOWN-BP-PROC (BP: class bioprocess, LBP: class
bioprocess, SW: class workspace, win: class window)

x = the x-pos upon SW;
  y = the y-pos upon SW;
  if there exists a bioreservoir that is a-down-bioreservoir-of BP then
  for DBR = each bioreservoir that is a-down-bioreservoir-of BP do
    allow other processing;
    if there exists a bioprocess that is a-down-bioprocess-of DBR then
     for DBP = each bioprocess that is a-down-bioprocess-of DBR do
       allow other processing;
       if there exists a bioprocess MBP upon SW such that (the master-
          bioprocess of MBP = the master-bioprocess of DBP ) then
          LDBP = MBP;
          call CONNECT-EXISTING-LOCAL-DBP-PROC (LBP, LDBP,
             win);
       else
         allow other processing;
         conclude that x = x + 110;
         if x > 2600 then show SW at one-quarter scale with its top left corner
            50 units below the top left corner of the screen
         else
            if x > 1800 then show SW at half scale with its top left corner 50
               units below the top left corner of the screen;
         create a bioprocess LDBP by cloning DBP;
         make the subworkspace of LDBP transient;
         delete the subworkspace of LDBP;
         transfer LDBP to SW at (x, y);
         r = random (3, 35);
         t = random (20, 76);
         create a connection connected between LBP newly locating it at
             right at the position given by r and LDBP newly locating it
             at top at the position given by t with direction output;
         conclude that y = y - 40;
         call CREATE-LOCAL-DOWN-BP-PROC (DBP, LDBP, SW, win)
  return:
```

TABLE 194

---
SIMUL-INIT-CALLBACK (button: class button, win: class window, panel: class selection-panel)

call GENERAL-INIT-PROC (win);
call SIMUL-INIT-PROC (win);
return;

---
ADD-SIMUL-CALLBACK (button: class uil-button, win: class window, panel: class selection-panel)

call SIMUL-INIT-PROC (win);
return;

---
SIMUL-INIT-PROC (win: class g2-window)

SW = the subworkspace of INITIALIZATION-PANEL;

call SEND-NO-INPUT-MESSAGES (win);
if there exists a sd-br-list upon SW then
 for NL = each sd-br-list upon SW do
  delete NL;
create a sd-br-list UNL;
conclude that the label of UNL = "UNList";
create a sd-br-list ANL;
conclude that the label of ANL = "ANList";
create a sd-br-list RNL;
conclude that the label of RNL = "RNList";
create a sd-br-list DNL;
conclude that the label of DNL = "DNList";
for BR = each bioreservoir do
 if BR has a name then
  allow other processing;
  SD = the scaling-density of the biopool upon the subworkspace of BR;
  if the set-by-user of SD is true then
   insert BR at the end of the bioreservoir list UNL
  else
   call SET-SCALING-DENSITY-PROC (BR, ANL, RNL, DNL)
transfer UNL to SW at (-130, -235);
transfer ANL to SW at (-80, -235);
transfer RNL to SW at (60, -235);
transfer DNL to SW at (110, -235);
inform the operator that "The setting of the scaling-density of all bioPools has been concluded";
change the size of SW to minimum;
return;

---

TABLE 195
---

SEND-NO-INPUT-MESSAGES (win: class item)

for BR = each bioreservoir do
exit if BR has no name;
PO = the biopool upon the subworkspace of BR;
if not (there exists a bioproduct connected to PO) and not (there
        exists a model-block M connected to PO) then
    create a message-dialog md, change the text of the message upon the
SW of md to "The bioPool of [the name of BR] has no input !!!
        To model an input source:
            1. Select 'create sw' from the menu of the scaled-input-model-box
        or the input-model-box of this bioPool, as desired.
            2. Add / connect / configure an appropriate model-block" and show
        the SW of md on the current window at (0, 0);
    change the text of the callback of the text-pushbutton upon the
subworkspace of md to "C-DELETE-DIALOG-CALLBACK";

TABLE 196
---

SET-SCALING-DENSITY-PROC (BR: class bioreservoir, ANL: class sd-br-list, RNL: class sd-br-list, DNL: class sd-br-list)

PO = the biopool upon the subworkspace of BR;
SDE = the scaling-density of PO;

if the if-scaling-amount of BR /=100 then
    insert BR at the end of the bioreservoir list ANL;
    sa = the if-scaling-amount of BR;
    change the text of the initial-value of the scaling-density of PO to "[sa]";
    make the scaling-density of PO permanent;
    if the if-scaling-bioreservoir of BR is not none then go to
        conflict-routine;
else
if the if-scaling-bioreservoir of BR is not none then
    insert BR at the end of the bioreservoir list RNL;
    sr = the if-scaling-amount of the bioreservoir named by the if-
        scaling-bioreservoir of BR;
    change the text of the initial-value of the scaling-density of PO to "[sr]";
    make the scaling-density of PO permanent;
else
if the if-scaling-amount of BR =100 then
    insert BR at the end of the bioreservoir list DNL;
    change the text of the initial-value of the scaling-density of PO to
    "100.0";
    make the scaling-density of PO permanent;
return;
conflict-routine:
sr = the if-scaling-amount of the bioreservoir named by the if-scaling-
    bioreservoir of BR;
if sa /= sr then
    inform the operator that "The attributes if-scaling-amount and if-
        scaling-bioreservoir of [the name of BR] have both values, which
        provide two conflicting scaling-density values for its bioPool:
        [sa] and [sr], respectively. The initial value of scaling-density
        has been set to [sa], but it is recommended that the conflict is
        resolved, and this value changed if desired.";
    return;

TABLE 198

|  |  |
|---|---|
|  | an user-menu-choice |
| Label | simul-panel |
| Applicable class | bioreservoir |
| Condition | the item has a name and the subworkspace of the item exists |
| Action | start CREATE-INPUT-TYPE-CALLBACK (the item, this window) |

|  |  |
|---|---|
|  | an user-menu-choice |
| Label | simul-panel |
| Applicable class | biopool |
| Condition | the bioreservoir superior to the workspace of the item has a name |
| Action | start CREATE-INPUT-TYPE-CALLBACK (the bioreservoir superior to the workspace of the item, this window) |

|  |  |
|---|---|
|  | an user-menu-choice |
| Label | simul-panel |
| Applicable class | biorole-object |
| Condition | the biopost connected to the item has a name |
| Action | start CREATE-INPUT-TYPE-CALLBACK (the bioreservoir named by the ref-bioreservoir of the biopost connected to the item, this window) |

CREATE-INPUT-TYPE-CALLBACK (BR: class bioreservoir, win: class window)

```
WS = the subworkspace of BR;
BRN: symbol = the name of BR;
if not (there exists a bioprocess that is a-down-bioprocess-of BR) then
   go to exit-routine;
activate the subworkspace of BR;
PO = the biopool upon WS;
if PO is a sol-mol-pool then
   panel = call clone-panel (SIMUL-CONCENTRATION-INPUT-TYPE-
      PANEL);
   SW = the subworkspace of panel;
   call SET-RADIO-BOX-ID-PROC ("simul-conc", "[BRN]-INPUT-
      TYPE-radio-box", SW, win);
else
   panel = call clone-panel (SIMUL-DENSITY-INPUT-TYPE-PANEL);
   SW = the subworkspace of panel;
   call SET-RADIO-BOX-ID-PROC ("simul-density", "[BRN]-INPUT-
      TYPE-radio-box", SW, win);
create a panel-text FT;
change the text of FT to "INPUT TYPE FOR: [BRN]";
transfer FT to SW at (0, 110);
change the size of SW to minimum
change the text of the related-item of panel to "[BRN]";
show SW on win at the center of the screen;
return;
exit-routine:
   md = call create-message-dialog ("md", "There is no down-bioprocess-of
      [the name of BR]", the symbol extra-large, win, 0, 0);
   return;
```

TABLE 199

---
SELECT-INPUT-PANEL-CALLBACK (button: class button, win : class window, dlg: class dialog)

BRN = the related-item of dlg;
BR = the bioreservoir named by BRN;
WS = the subworkspace of dlg;
rb-id = call GET-RADIO-BOX-ID-PROC ("simul-selection", WS, win);
type = call get-radio-box-value (dlg, rb-id);
call delete-dialog (dlg);
md = call create-message-dialog ("md", "Processing . . . . .     ", the symbol extra-large, win, 0, 0);
case (type) of
  "one-time-concentration":
    panel = call CREATE-CONC-INPUT-PANEL-PROC (BR, win);
  "one-time-density":
    panel = call CREATE-DENSITY-INPUT-PANEL-PROC (BR, win);
  "one-time-relative":
    panel = call CREATE-RELATIVE-INPUT-PANEL-PROC (BR, win);
  "periodic-concentration":
    panel = call CREATE-PERIODIC-CONC-INPUT-PANEL-PROC (BR, win);
  "periodic-density":
    panel = call CREATE-PERIODIC-DENSITY-INPUT-PANEL-PROC (BR, win);
  "periodic-relative":
    panel = call CREATE-PERIODIC-RELATIVE-INPUT-PANEL-PROC (BR, win);
make panel permanent;
change the text of the related-item of panel to "[BRN]";
SW = the subworkspace of panel;
if there exists a text-pushbutton de upon SW such that (the id of de = "de") then
  change the text of the callback of de to "DELETE-ENTRY-PANEL-CALLBACK";
change the size of SW to minimum
show SW on win at the center of the screen;
return panel;
delete md;

TABLE 200

---

CREATE-CONC-INPUT-PANEL-PROC (BR: class bioreservoir, win : class window) = (class entry-panel )

BRN = the name of BR;
panel = call clone-panel (MASTER-CONCENTRATION-ENTRY-PANEL);
SW = the subworkspace of panel;
create a panel-text FT and transfer FT to SW at (-20, 300);
change the text of the id of panel to "[BRN]-conc-entry-panel";
change the text of FT to "1. CONCENTRATION INPUT FOR: [BRN]";
ac = call create-pushbutton ("ac", the symbol ACTIVATE-CONC-INPUT-CALLBACK, "ACTIVATE", panel, 490, 60);
disable ac;
st = call create-pushbutton ("st", the symbol text, the symbol START-CONC-INPUT-CALLBACK, "START", panel, 138, 60);
disable st;
return panel;

---

CREATE-DENSITY-INPUT-PANEL-PROC (BR: class bioreservoir, win : class window) = (class entry-panel )

BRN = the name of BR;
panel = call clone-panel (MASTER-DENSITY-ENTRY-PANEL);
SW = the subworkspace of panel;
create a panel-text FT and transfer FT to SW at (-20, 300);
change the text of the id of panel to "[BRN]-density-entry-panel";
change the text of FT to "1. DENSITY INPUT FOR: [BRN]";
ac = call create-pushbutton ("ac", the symbol ACTIVATE-DENSITY-INPUT-CALLBACK, the symbol medium, "ACTIVATE", panel, 490, 60);
disable ac;
st = call uil-create-pushbutton ("st", the symbol START-DENSITY-INPUT-CALLBACK, "START", panel, 138, 60);
disable st;
return panel;

---

CREATE-RELATIVE-INPUT-PANEL-PROC (BR: class bioreservoir, win : class window) = (class entry-panel )

BRN = the name of BR;
panel = call uil-clone-grobj (MASTER-RELATIVE-ENTRY-PANEL) ;
SW = the subworkspace of panel;
create a panel-text FT and transfer FT to SW at (-20, 300);
change the text of the id of panel to "[BRN]-relative-entry-panel";
change the text of FT to "1. RELATIVE INPUT FOR: [BRN]";
ac = call create-pushbutton ("ac", the symbol ACTIVATE-RELATIVE-INPUT-CALLBACK, "ACTIVATE", panel, 490, 60);
disable ac;
st = call create-pushbutton ("st", the symbol START-RELATIVE-INPUT-CALLBACK, "START", panel, 138, 60);
disable st;
return panel;

---

TABLE 201

---

CREATE-PERIODIC-CONC-INPUT-PANEL-PROC (BR: class bioreservoir, win : class window) = (class entry-panel )

BRN = the name of BR;
panel = call clone-panel (MASTER-PERIODIC-CONC-ENTRY-PANEL);
SW = the subworkspace of panel;
create a panel-text FT and transfer FT to SW at (-30, 380);
change the text of the id of panel to "[BRN]-periodic-conc-entry-panel";
change the text of FT to "1. PERIODIC CONCENTRATION INPUT FOR: [BRN]";
ac = call create-pushbutton ("ac", the symbol ACTIVATE-CONC-INPUT-CALLBACK, "ACTIVATE"), panel, 490, 65);
call uil-disable-button (ac);
call uil-configure-grobj (ac);
st = call uil-create-pushbutton ("st", the symbol text, the symbol START-PERIODIC-CONC-INPUT-CALLBACK, "START", panel, 140, 65);
disable st;
return panel;

---

CREATE-PERIODIC-DENSITY-INPUT-PANEL-PROC (BR: class bioreservoir, win : class window) = (class entry-panel )

BRN = the name of BR;
panel = call clone-panel (MASTER-PERIODIC-DENSITY-ENTRY-PANEL) ;
SW = the subworkspace of panel;
create a panel-text FT and transfer FT to SW at (-30, 380);
change the text of the id of panel to "[BRN]-periodic-density-entry-panel";
change the text of FT to "1. PERIODIC DENSITY INPUT FOR: [BRN]";
ac = call create-pushbutton ("ac", the symbol ACTIVATE-DENSITY-INPUT-CALLBACK, "ACTIVATE", panel, 490, 65);
disable ac;
st = call create-pushbutton ("st", the symbol START-PERIODIC-DENSITY-INPUT-CALLBACK, "START", panel, 142, 65);
disable st;
return panel;

---

CREATE-PERIODIC-RELATIVE-INPUT-PANEL-PROC (BR: class bioreservoir, win : class window) = (class entry-panel )

BRN = the name of BR;
panel = call clone-panel (MASTER-PERIODIC-RELATIVE-ENTRY-PANEL) ;
SW = the subworkspace of panel;
create a panel-text FT and transfer FT to SW at (-20, 380);
change the text of the id of panel to "[BRN]-periodic-relative-entry-panel";
change the text of FT to "1 PERIODIC RELATIVE INPUT FOR: [BRN]";
ac = call create-pushbutton ("ac", the symbol ACTIVATE-RELATIVE-INPUT-CALLBACK, "ACTIVATE", panel, 490, 65);
disable ac;
st = call create-pushbutton ("st", the symbol START-PERIODIC-RELATIVE-INPUT-CALLBACK, "START", panel, 140, 65);
disable st;
return panel;

TABLE 202

LIST-SIMUL-CALLBACK (button: class button, win: class window, dlg: class dialog)

SW = the subworkspace of dlg;
BRN = the related-item of dlg;
BR = the bioreservoir named by BRN;
M = the model-definition upon SW;
SM = the name of the item superior to the workspace of BR;
change the text of the items-belonging-to-this-model of M to "[SM]";
allow other processing;
create a bm-downstream-bp-simulation-list DBPL;
create a down-br-simulation-list DBRL;
create an up-br-simulation-list UBRL;
call FILL-BR-DOWNSTREAM-LISTS-PROC (BR, DBRL, DBPL, UBRL, win);
conclude that the lenght of DBRL = the number of elements in DBRL;
transfer DBRL to SW at (-35, 69);
conclude that the lenght of DBPL = the number of elements in DBPL;
transfer DBPL to SW at (395, 70);
conclude that the lenght of UBRL = the number of elements in UBRL;
transfer UBRL to SW at (53, 69);
if there exists a text-pushbutton ac upon SW such that (the id of ac = "ac ") then enable ac;
if there exists a text-pushbutton de upon SW such that (the id of de = "de") then disable de;
disable button;
return;

TABLE 203

FILL-BR-DOWNSTREAM-LISTS-PROC (BR: class bioreservoir, DBRL: class downstream-bioreservoirs-list, DBPL: class downstream-bioprocesses-list, UBRL: class up-bioreservoirs-list, win: class window)

insert BR at the end of the bioreservoir list DBRL;
if there exists a bioreservoir DBR such that (DBR is a-downstream-bioreservoir-of BR) then
  for DBR = each bioreservoir that is a-downstream-bioreservoir-of BR do
    insert DBR at the end of the bioreservoir list DBRL;
if there exists a bioprocess DBP such that (DBP is a-down-bioprocess-of BR) then
  for DBP = each bioprocess that is a-down-bioprocess-of BR do
    insert DBP at the end of the bioprocess list DBPL;
    if there exists a bioprocess DSBP such that (DSBP is a-downstream-bioprocess-of DBP) then
      for DSBP = each bioprocess that is a-downstream-bioprocess-of DBP do
        insert DSBP at the end of the bioprocess list DBPL;
for FDBP = each bioprocess in DBPL do
  allow other processing;
  if there exists a bioreservoir that is an-up-bioreservoir-of FDBP then
    for UBR = each bioreservoir that is an-up-bioreservoir-of FDBP do
      if not (there exists a bioreservoir DBR in DBRL such that
          (DBR is the same object as UBR)) then
        insert UBR at the end of the bioreservoir list UBRL;
return;

TABLE 204

---

ACTIVATE-CONC-INPUT-CALLBACK (button: class button, Win: class window, dlg: class dialog)

define three local text values, EVtext, ETtext, SBMT, and val;
    define a local float value, EV;
    panel = the SW of dlg;
    set EV equal to the quantity extracted from the value of the edit-box
       upon panel which id is "conc-entry-value";
    if EV = 0.0e-0 then go to no-value-routine else go to main-routine;

no-value-routine:
    create a query-dialog fd and add a message "No value for the
       concentration of <the related-item of dlg> has been entered.  If you
       want to run the simulation with no external input then enter YES in
       the box below and press OK.  Otherwise, press NO, enter the desired
       Value in the simulation dialog, and press ACTIVATE again.";
    display fd at the center of the screen;
    set val equal to the value of the query-dialog fd;
    if val = "YES" then go to main-routine else return main-routine:
    call ACTIVATE-SIMULATION-PROC (win, dlg);
    disable button;
    return

---

ACTIVATE-DENSITY-INPUT-CALLBACK (button: class button, Win: class window, dlg: class dialog)

This procedure is the same as above, substituting :
    set EV equal to the quantity extracted from the value of the edit-box
       upon panel which id is "density-entry-value";
    create a query-dialog fd and add a message "No value for the density of
       ........."

---

ACTIVATE-RELATIVE-INPUT-CALLBACK (button: class button, win: class window, dlg: class dialog)
This procedure is the same as above, substituting :
    set EV equal to the quantity extracted from the value of the edit-box
       upon panel which id is "factor-entry-value";
    create a query-dialog fd and add a message "No value for the entry-
       factor ........."

---

TABLE 205

ACTIVATE-SIMULATION-PROC (win: class window, panel: class entry-panel)

SW = the subworkspace of panel;
DBPL = the bm-downstream-bp-simulation-list upon SW;
DBRL = the down-br-simulation-list upon SW;
UBRL = the up-br-simulation-list upon SW;
M = the model-definition upon SW;
BCB = the subworkspace of the c-basal-density-source-tracer upon SW;
User-BC = the user-bc-br-list upon BCB;
call ACTIVATE-MODEL-PROC (DBPL, DBRL, UBRL);
change the text of the free-text upon BCB to "Sources of values for Basal
   Concentration within: [the text of the items-belonging-to-this-model of
   M]";
for DBR = each bioreservoir in DBRL do
   allow other processing;
   PO = the biopool upon the subworkspace of DBR;
   if the basal-density of PO /= 9.9e-99 then
     insert DBR at the end of the bioreservoir list User-BC
   else
     call BASAL-DENSITY-PROC (DBR, panel);
for UBR = each bioreservoir in UBRL do
   allow other processing;
   PO = the biopool upon the subworkspace of UBR;
   if the basal-density of PO /= 9.9e-99 then
     insert UBR at the end of the bioreservoir list User-BC
   else
     call BASAL-DENSITY-PROC (UBR, panel);
if there exists a text-pushbutton st upon SW such that (the id of st =
   "st ") then
   disable st ;
return;

TABLE 206

ACTIVATE-MODEL-PROC (DBPL: class downstream-bp-simulation-list,
DBRL: class down-br-simulation-list, UBRL: class up-br-simulation-list)

for DBP = each bioprocess in DBPL do
   allow other processing;
   activate the subworkspace of DBP;
   change the status-color icon-color of DBP to brown;
   conclude that the status of DBP is downstream-activated;
for DBR = each bioreservoir in DBRL do
   allow other processing;
   activate the subworkspace of DBR;
   change the status-color icon-color of DBR to brown;
   conclude that the status of DBR is downstream-activated;
for UBR = each bioreservoir in UBRL do
   allow other processing;
   exit if the status of UBR is downstream-activated;
   activate the subworkspace of UBR;
   change the status-color icon-color of UBR to brown;
   conclude that the status of UBR is back-activated;
return;

TABLE 207

BASAL-DENSITY-PROC (BR: class bioreservoir, dlg: class item)
  PO = the biopool upon the SW of BR;
  BC = the basal-density of PO;
  top = the top-container that is *the-container-of-br* BR;
  conclude that the volume of top = the volume of top;
  BCB = the SW of the basal-density-source-tracer upon the SW of dlg;
  if BR is a sol-mol-reservoir then:
    NBC = the normal-basal-concentration of BR;
    if NBC /= 9.9e-99 then
      conclude that the basal-density of PO = NBC * 6.023e23 * the
      volume of top;
      insert BR at the end of the NBC-bc-br-list upon BCB;
      return;
    else go to main-routine;
  else:
    NBD = the normal-basal-density of BR;
    if NBD /= 9.9e-99 then
      conclude that BC = NBD;
      insert BR at the end of the NBD-bc-br-list upon BCB;
      return;
    else go to main-routine;
  main-routine:
  if the scaling-density of PO = 99.999 then:
    insert BR at the end of the no-bc-br-list upon BCB;
    return;
  else:
    AK = the scaling-density of PO;
    if the scaled-basal-amount of BR /= 9.9e-99 then:
      conclude that BC = SBA * AK;
      insert BR at the end of the SBA-bc-br-list upon BCB;
      return;
    else:
      case the physiol-abundance of BR is
        highest: conclude that BC = 1.0 * AK;
        abundant: conclude that BC = 0.9 * AK;
        steady-state: conclude that BC = 0.5 * AK;
        low-induced: conclude that BC = 0.1 * AK;
        only-induced: conclude that BC = 1.0e-9 * AK;
      insert BR at the end of the pab-bc-br-list upon BCB;
  return

TABLE 208 an user-menu-choice

| | |
|---|---|
| Label | show |
| Applicable class | basal-density-source-tracer |
| Condition | none |
| Action | start BASAL-DENSITY-SOURCE-TRACER-PROC (the item, this window) |

BASAL-DENSITY-SOURCE-TRACER-PROC (tracer: class lists-tracer, win: class window)
  if the toggle-state of tracer is hide then
    show the SW of tracer at the top right corner of the screen;
    start CONFIGURE-LISTS-TRACER-PROC (tracer, win)
  else if the toggle-state of tracer is show then
    hide the SW of tracer on win;
    start CONFIGURE-LISTS-TRACER-PROC (tracer, win)

TABLE 209

```
START-CONC-INPUT-CALLBACK (button: class button, win: class
window, dlg: class dialog)
  BR = the bioreservoir named by the related-item of dlg;
  PO = the biopool upon the subworkspace of BR;
  top = the top-container that is the-container-of-br BR;
  define two local float values V and EV, two quantity values t and
  incr, and one integer value ET;
  set t = the current-simulation-time of dlg;
  set incr = the current-simulation-time-increment of dlg;
  set V equal to the quantity extracted from the value of the edit-box
     upon dlg which id is "conc-entry-value";
  set EV = V {molar} * 6.023e23 {molecules/liter} * the volume
  {liters per top-container} of top;
  disable button;
  set ET equal to the quantity extracted from the value of the edit-
  box upon dlg which id is "entry-time";
  call START-SIMULATION-PROC (win, dlg);
  wait until t >= ET checking every 1 second;
  conclude that the density-entry of PO = EV;
  wait until t >= ET + incr checking every 1 second;
  conclude that the density-entry of PO = 0.0;
  if t > ET + incr then return
---------------------------------------------------------------------------------
START-DENSITY-INPUT-CALLBACK (button: class button, win:
  class window, dlg: class dialog)
  BR = the bioreservoir named by the related-item of dlg;
  PO = the biopool upon the subworkspace of BR;
  top = the top-container that is the-container-of-br BR;
  define a local float value EV, two quantity values t and incr, and an
     integer value ET;
  set t = the current-simulation-time of dlg;
  set incr = the current-simulation-time-increment of dlg;
  set EV equal to the quantity extracted from the value of the edit-
  box upon dlg which id is "density-entry-value";
  disable button;
  set ET equal to the quantity extracted from the value of the edit-
  box upon dlg which id is "entry-time";
  call START-SIMULATION-PROC (win, dlg);
  wait until t >= ET checking every 1 second;
  conclude that the density-entry of PO = EV;
  wait until t >= ET + incr checking every 1 second;
  conclude that the density-entry of PO = 0.0;
  if t > ET + incr then return
---------------------------------------------------------------------------------
START-RELATIVE-INPUT-CALLBACK (button: class button, win:
  class window, dlg: class dialog)
  BR: = the bioreservoir named by the related-item of dlg;
  PO = the biopool upon the subworkspace of BR;
  top = the top-container that is the-container-of-br BR;
  define a local float EV, two quantities t and incr, and an integer ET;
  set t = the current-simulation-time of dlg;
  set incr = the current-simulation-time-increment of dlg;
  set EV equal to the quantity extracted from the value of the edit-box
     upon dlg which id is "factor-entry-value";
  disable button;
  set ET equal to the quantity extracted from the value of the edit-box
     upon dlg which id is "entry-time";
  call START-SIMULATION-PROC (win, dlg);
  wait until t >= ET checking every 1 second;
  conclude that the scaled-entry of PO = EV;
  wait until t >= ET + incr checking every 1 second;
  conclude that the scaled-entry of PO = 0.0;
  if t > ET + incr then return
```

TABLE 210

---

START-PERIODIC-CONC-INPUT-CALLBACK (button: class button, win: class window, dlg: class dialog)
  BR: = the bioreservoir named by the related-item of dlg;
  PO = the biopool upon the subworkspace of BR;
  top = the top-container that is *the-container-of-br* BR;
  define two local float s V and EV, two quantities t and incr, and four
  integers ET, EI, EF, and n;
  set t = the current-simulation-time of dlg;
  set incr = the current-simulation-time-increment of dlg;
  set V equal to the quantity extracted from the value of the edit-box upon
  dlg which id is "conc-entry-value";
  set EV = V {molar} * 6.023e23 {molecules/liter} * the volume {liters per top-
    container} of top;
  disable button;
  set ET equal to the quantity extracted from the value of the edit-box
  upon dlg which id is "entry-time";
  set EF equal to the quantity extracted from the value of the edit-box
  upon dlg which id is "entry-frequency";
  set EI equal to the quantity extracted from the value of the edit-box
  upon dlg which id is "entry-interval";
  call START-SIMULATION-PROC (win, dlg);
  wait until t >= ET checking every 1 second;
  conclude that the density-entry of PO = EV;
  wait until t >= ET + incr checking every 1 second;
  conclude that the density-entry of PO = 0.0;
  for n = 1 to EF - 1 do
  wait until t >= ET + EI * n checking every 1 second;
  conclude that the density-entry of PO = EV;
  wait until t >= ET + EI * n + incr checking every 1 second;
  conclude that the density-entry of PO = 0.0;
  if t > ET + EI * n + incr then return;

---

START-PERIODIC-DENSITY-INPUT-CALLBACK (button: class button, win: class window, panel: class entry-panel)
  BR: = the bioreservoir named by the related-item of dlg;
  PO = the biopool upon the subworkspace of BR;
  top = the top-container that is *the-container-of-br* BR;
  define two local float values V and EV, two quantity values t and incr, and
    four integer values ET, EI, EF, and n;
  set t = the current-simulation-time of dlg;
  set incr = the current-simulation-time-increment of dlg;
  set EV equal to the quantity extracted from the value of the edit-box
  upon dlg which id is "density-entry-value";
  disable button;
  set ET equal to the quantity extracted from the value of the edit-box
  upon dlg which id is "entry-time";
  set EF equal to the quantity extracted from the value of the edit-box
    upon dlg which id is "entry-frequency";
  set EI equal to the quantity extracted from the value of the edit-box
    upon dlg which id is "entry-interval";
  call START-SIMULATION-PROC (win, dlg);
  wait until t >= ET checking every 1 second;
  conclude that the density-entry of PO = EV;
  wait until t >= ET + incr checking every 1 second;
  conclude that the density-entry of PO = 0.0;
  for n = 1 to EF - 1 do
  wait until t >= ET + EI * n checking every 1 second;
  conclude that the density-entry of PO = EV;
  wait until t >= ET + EI * n + incr checking every 1 second;
  conclude that the density-entry of PO = 0.0;
  if t > ET + EI * n + incr then return;

TABLE 211

START-SIMULATION-PROC (win: class window, panel: class entry-panel)

M = the model-definition upon the subworkspace of panel;
BRN: symbol = the related-item of panel;
if there exists a text-pushbutton pa upon SW such that (the id of pa = "pa ") then enable pa ;
call start-model (M);
if the model-simulation-status of M is running then
    sd = call uil-create-message-dialog ("sd", "The simulation starting from [BRN] and within [the text of the items-belonging-to-this-model of M] has started at [the current time as a time stamp]", win, 0, 0);

TABLE 212

MODEL-SIMULATION-PROC ()
M = call get-current-model-definition ();
if the item superior to the workspace of M is a entry-panel then
    EP = the entry-panel superior to the workspace of M;
    conclude that the current-simulation-time of EP is equal to the model-simulation-time of M;
    conclude that the current-simulation-time-increment of EP is equal to the model-simulation-time-increment of M;
start COMPUTE-GRAPH-TRANSFORMS-PROC ();

TABLE 214

PAUSE-SIMULATION-CALLBACK (button: class uil-button, win: class window, panel: class entry-panel)

SW = the workspace of button;
M = the model-definition upon SW;
call g2-pause-model (M);
if there exists a text-pushbutton rm upon SW such that (the id of rm = "rm") then
    enable rm ;
disable button ;

RESUME-SIMULATION-CALLBACK (button: class uil-button, win: class window, panel: class entry-panel)

SW = the workspace of button;
M = the model-definition upon SW;
call g2-resume-model (M);
if there exists a text-pushbutton pa upon SW such that (the id of pa = "pa ") then
    enable pa ;
disable button ;

TABLE 213

COMPUTE-GRAPH-TRANSFORMS-PROC ()

GT: class c-graph-tracer;
SW: class kb-workspace;
TF: class transf-factor-var;
T: class graph-transf-var;
C: class variable-or-parameter;

for each c-graph-tracer GT do
  if there is a bionode-object BO connected to GT and GT has a SW
  then
  for each transf-factor-var TF upon SW do
    if BO is a biopool then
      case the class of TF of
        scaled-conc-transf-factor:   C = the scaled-amount of BO;
        input-transf-factor :   C = the input-rate of BO;
        output-transf-factor :   C = the output-rate of BO;
        accum-transf-factor :   C = the accumulation-rate of BO;
        density-transf-factor :   C = the density of BO;
    else if BO is a bioengine and the transf-factor-var upon SW is a
      velocity-transf-factor then    C = the velocity of BO;
  conclude that the transform of TF =
    (if C <= 1.0e-9 then C * 1.0e9 else (if C <= 1.0e-8 then C * 1.0e8 else
    (if C <= 1.0e-7 then C * 1.0e7 else (if C <= 1.0e-6 then C * 1.0e6 else
    (if C <= 1.0e-5 then C * 1.0e5 else (if C <= 1.0e-4 then C * 1.0e4 else
    (if C <= 1.0e-3 then C * 1.0e3 else (if C <= 1.0e-2 then C * 1.0e2 else
    (if C <= 1.0e-1 then C * 1.0e1 else (if C <= 1.0 then C * 1.0 else
    (if C <= 1.0e1 then C * 1.0e-1 else (if C <= 1.0e2 then C * 1.0e-2 else
    (if C <= 1.0e3 then C * 1.0e-3 else (if C <= 1.0e4 then C * 1.0e-4 else
    (if C <= 1.0e5 then C * 1.0e-5 else (if C <= 1.0e6 then C * 1.0e-6 else
    (if C <= 1.0e7 then C * 1.0e-7 else (if C <= 1.0e8 then C * 1.0e-8 else
    (if C <= 1.0e9 then C * 1.0e-9 else (if C <= 1.0e10 then C*1.0e-10else
    (if C <= 1.0e11then C*1.0e-11 else (if C<=1.0e12 then C*1.0e-12 else
    (if C<=1.0e13 then C*1.0e-13 else (if C<=1.0e14 then C*1.0e-14 else
    (if C<=1.0e15 then C*1.0e-15 else (if C<= 1.0e16 then C*1.0e-16 else
    (if C<=1.0e17 then C*1.0e-17 else (if C<=1.0e18 then C*1.0e-18 else
    (if C <= 1.0e19 then C * 1.0e-19 else 1.0e20)))))))))))))))))))))))))))));
  conclude that TF =
    (if C <= 1.0e-9 then 1.0e9 else (if C <= 1.0e-8 then 1.0e8 else
    (if C <= 1.0e-7 then 1.0e7 else (if C <= 1.0e-6 then 1.0e6 else
    (if C <= 1.0e-5 then 1.0e5 else (if C <= 1.0e-4 then 1.0e4 else
    (if C <= 1.0e-3 then 1.0e3 else (if C <= 1.0e-2 then 1.0e2 else
    (if C <= 1.0e-1 then 1.0e1 else (if C <= 1.0 then 1.0 else
    (if C <= 1.0e1 then 1.0e-1 else (if C <= 1.0e2 then 1.0e-2 else
    (if C <= 1.0e3 then 1.0e-3 else (if C <= 1.0e4 then 1.0e-4 else
    (if C <= 1.0e5 then 1.0e-5 else (if C <= 1.0e6 then 1.0e-6 else
    (if C <= 1.0e7 then 1.0e-7 else (if C <= 1.0e8 then 1.0e-8 else
    (if C <= 1.0e9 then 1.0e-9 else (if C <= 1.0e10 then 1.0e-10 else
    (if C <= 1.0e11 then 1.0e-11 else (if C <= 1.0e12 then 1.0e-12 else
    (if C <= 1.0e13 then 1.0e-13 else (if C <= 1.0e14 then 1.0e-14 else
    (if C <= 1.0e15 then 1.0e-15 else (if C <= 1.0e16 then 1.0e-16 else
    (if C <= 1.0e17 then 1.0e-17 else (if C <= 1.0e18 then 1.0e-18 else
    (if C <= 1.0e19 then 1.0e-19 else 1.0e20))))))))))))))))))))))))))))

TABLE 215

RESET-SIMULATION-CALLBACK (button: class uil-button, win: class window, panel: class entry-panel)

M = the model-definition upon the workspace of button;
call g2-reset-model (M);
conclude that the current-simulation-time of dlg = 0.0;
conclude that the current-simulation-time-increment of dlg = 0.0;
call RESET-PROC (M, dlg);
allow other processing;
if there exists a text-pushbutton st upon SW such that (the id of st = "st ") then disable st ;
if there exists a text-pushbutton pa upon SW such that (the id of pa = "pa") then disable pa;
if there exists a text-pushbutton rm upon SW such that (the id of rm = "rm") then disable rm;
if there exists a text-pushbutton de upon SW such that (the id of de = "de") then disable de;

RESET-PROC (M: class model-definition, panel: class entry-panel)

SW = the subworkspace of panel;
if there exists a bm-downstream-bp-simulation-list CDBPL upon SW then
    for DBP = each bioprocess in CDBPL do
        allow other processing;
        change the status-color icon-color of DBP to slate-blue;
        conclude that the status of DBP is available;
        deactivate the subworkspace of DBP;
    delete DBPL;
if there exists a down-br-simulation-list CDBRL upon SW then
    for DBR = each bioreservoir in CDBRL do
        allow other processing;
        deactivate the subworkspace of DBR;
        change the status-color icon-color of DBR to medium-aquamarine;
        conclude that the status of DBR is available;
    delete CDBRL;
if there exists a up-br-simulation-list UBRL upon SW then
    for UBR = each bioreservoir in UBRL do
        allow other processing;
        deactivate the subworkspace of UBR;
        change the status-color icon-color of UBR to medium-aquamarine;
        conclude that the status of UBR is available;
    delete UBRL;
allow other processing;
if there exists a text-pushbutton ls upon SW such that (the id of ls = "ls") then enable ls;
if there exists a text-pushbutton ac upon SW such that (the id of ac = "ac") then disable ac;
return

TABLE 216

```
                    an user-menu-choice
Label               show-s.graph
Applicable class    bioreservoir
Condition           the subworkspace of the scaled-br-graph-tracer
                      upon the subworkspace of the item does not exist
Action              in order
                    start SCALED-BR-TRANSF-GRAPH-PROC (the
                      scaled-br-graph-tracer upon the subworkspace of the
                      item, this window) and
                    create a min-rev-display T and
                    change the text of T to "G" and
                    transfer T to the workspace of the item at (middle-x
                      (the item) - 29, middle-y (the item) + 6)
```

SCALED-BR-GRAPH-PROC (tracer: class scaled-br-graph-tracer, win: class window )
  BR = the bioreservoir superior to the workspace of tracer;
  if the subworkspace of tracer exists then
    show the subworkspace of tracer on Win with its top right corner 35
      units below the top right corner of the screen
  else
    create a workspace SW by cloning the subworkspace of SCALED-
      BR-TRANSF-GRAPH-MASTER;
    G = the graph upon SW;
    change the text of the label-to-display of G to "[the name of BR]";
    change the size of SW to minimum;
    show SW on Win with its top right corner 35 units below the top right
      corner of the screen;
    make SW the subworkspace of tracer;
    for TF = each transf-factor-var upon SW do
      change the text of the ref-variable of TF to "[the name of BR]";

TABLE 217

```
                    an user-menu-choice
Label               show-a.graph
Applicable class    bioreservoir
Condition           the subworkspace of the absolute-br-graph-tracer
                      upon the subworkspace of the item does not exist
Action              in order
                    start ABSOLUTE-BR-TRANSF-GRAPH-PROC (the
                      absolute-br-graph-tracer upon the subworkspace of
                    the item, this window) and
                    create a min-rev-display T and
                    change the text of T to "G" and
                    transfer T to the workspace of the item at (middle-x
                      (the item) - 29, middle-y (the item) + 6)
```

ABSOLUTE-BR-TRANSF-GRAPH-PROC (tracer: class graph-tracer, win: class window )
  BR = the bioreservoir superior to the workspace of tracer;
  if the subworkspace of tracer exists then
    show the subworkspace of tracer on Win with its top left corner 35 units
      below the top left corner of the screen
  else
    create a kb-workspace SW by cloning the subworkspace of
      DENSITY-BR-TRANSF-GRAPH-MASTER;
    G = the graph upon SW;
    change the text of the label-to-display of G to "[the name of BR]";
    change the size of SW to minimum;
    show SW on Win with its top left corner 35 units below the top left
      corner of the screen;
    make SW the subworkspace of tracer;
    for TF = each transf-factor-var upon SW do
      change the text of the ref-variable of TF to "[the name of BR]";

TABLE 218

```
                   an user-menu-choice
Label              show-graph
Applicable class   bioprocess
Condition          the subworkspace of the scaled-br-graph-tracer
                     upon the subworkspace of the item does not exist
Action             in order
                   start BP-TRANSF-GRAPH-PROC (the
                     scaled-bp-graph-tracer upon the subworkspace of the
                     item, this window) and
                   create a min-rev-display T and
                   change the text of T to "G" and
                   transfer T to the workspace of the item at (middle-x
                     (the item) - 29, middle-y (the item) + 6)
```

BP-TRANSF-GRAPH-PROC (tracer: class scaled-bp-graph-tracer, win: class window )

```
BP = the bioprocess superior to the workspace of tracer;
E = the bioengine connected to tracer;
if the subworkspace of tracer exists then
  show the subworkspace of tracer on Win with its bottom right corner at
    the bottom right corner of the screen
else
  create a workspace SW by cloning the subworkspace of BP-TRANSF-
    GRAPH-MASTER;
  G = the graph upon SW;
  change the text of the label-to-display of G to "[the name of BP]";
  change the size of SW to minimum;
  show SW on Win with its bottom right corner at the bottom right corner
    of the screen;
  make SW the subworkspace of tracer;
  for TF = each transf-factor-var upon SW do
    change the text of the ref-variable of TF to "[the name of BP]";
```

TABLE 219

Components upon the SW of SCALED-ACTIV-BP-TRANSF-GRAPH-MASTER a velocity-transf-factor

| | |
|---|---|
| Options | do not forward chain, breadth first backward chain |
| Names | none |
| Tracing and breakpoints | default |
| Data type | float |
| Initial value | 0.0 |
| Last recorded value | 0.0, valid indefinitely |
| History keeping spec data | keep history with maximum number of points = 3 |
| Validity interval | supplied |
| Formula | none |
| Simulation details | no simulation formula yet |
| Initial value for simulation | default |
| Data server | inference engine |
| Default update interval | 3 seconds |
| Transform | 0.0 |
| Ref variable | none |
| Label | velocity |
| X | x | a graph

| | |
|---|---|
| Names | none |
| Desired range for horizontal axis | 10 minutes |
| Desired range for vertical axis | 0.0 to 1.1 |
| Scroll continuously? | yes |
| Percentage extra space to leave | 0 |
| Show grid lines? | yes |
| Interval between horizontal grid lines? | compute automatically |
| Extra grid lines? | none |
| Background colors | graph background: slate-blue, grid background: wheat |
| Expressions to display | the transform of the velocity-transf-factor upon this workspace in red using line width 2 |
| Label to display | the name of BP |
| Display update interval | 3 seconds |
| Display wait interval | 2 seconds |
| Display update priority | 2 |
| Show simulated values | no |

TABLE 220

|  |  |
|---|---|
| | a graph |
| Names | none |
| Desired range for horizontal axis | 10 minutes |
| Desired range for vertical axis | 0.0 to 1.1 |
| Scroll continuously? | yes |
| Percentage extra space to leave | 0 |
| Show grid lines? | yes |
| Interval between horizontal grid lines? | compute automatically |
| Extra grid lines? | none |
| Background colors | graph background: medium-aquamarine, grid background: wheat |
| Expressions to display | the transform of the scaled-conc-transf-factor upon this workspace in red using line width 1; the transform of the accum-transf-factor upon this workspace in medium-orchid using line width 1; the transform of the input-transf-factor upon this workspace in sky-blue using line width 1; the transform of the output-transf-factor upon this workspace in lime-green using line width 1 |
| Label to display | the name of BR |
| Display update interval | 3 seconds |
| Display wait interval | 2 seconds |
| Display update priority | 2 |
| Show simulated values | no |

TABLE 221

|  |  |
|---|---|
| | an user-menu-choice |
| Label | hide-s.graph |
| Applicable class | bioreservoir |
| Condition | the subworkspace of the scaled-br-graph-tracer upon the subworkspace of the item exists |
| Action | in order delete the subworkspace of the scaled-br-graph-tracer upon the subworkspace of the item and delete the min-rev-display nearest to the item |

TABLE 222

BR-SCROLL-CALLBACK (tracer: class br-scroll-tracer, win: class window, dlg: class entry-panel)

create a workspace display by cloning the SW of BR-SCROLL;
make display the SW of tracer;
create a text-list BRNL;
for each bioreservoir BR with a name do
    insert "<the name of BR>" at the end of the text list BRNL;
add each message in list BRNL to the scroll-area upon display;
change the size of display to minimum;
show display on win at the bottom right corner of the screen;
delete BRNL;
return

TABLE 223

LIST-EXPER-CALLBACK (button: class pushbutton, win: class window, panel: class entry-panel)

SW = the subworkspace of panel;
M = the model-definition upon SW;
create a experiment-selections-list SL;
transfer SL to SW at (-275, -190);
create a bm-downstream-bp-simulation-list DBPL;
create a down-br-simulation-list DBRL;
create an up-br-simulation-list UBRL;
transfer DBPL to SW at (-370, -260);
transfer DBRL to SW at (-275, -260);
transfer UBRL to SW at (-180, -260);
create a scroll-text-list PSML;
for ES = each experiment-selection upon SW do
  allow other processing;
  if the text of the ref-bioreservoir of ES /= "none" and the text of
     the currently-selected of ES = "true" then
    insert ES at the end of the experiment-selection list SL;
    BR = the bioreservoir named by the ref-bioreservoir of ES;
    call FILL-BR-DOWNSTREAM-LISTS-PROC (BR, DBRL,
        DBPL, UBRL, win);
if there exists a text-pushbutton hi upon SW such that (the id of hi =
    "hi") then disable hi;
if there exists a text-pushbutton ac upon SW such that (the id of ac =
    "ac") then enable ac;
disable button;

TABLE 224

```
DRAW-EXPER-PATHWAY-CALLBACK (button: class button, win:
class window, panel: class entry-panel)

WS = the subworkspace of panel;
EL = the experiment-selections-list upon WS;
DBPL = the bm-downstream-bp-simulation-list upon WS;
init-x: integer = - 50;
if there exists a c-navig-path-tracer upon WS then
   for NT = each c-navig-path-tracer upon WS do
      delete NT;
create a navig-path-tracer NT by cloning MASTER-NAVIG-PATHWAY;
transfer NT to WS at (30, -240);
SW = the subworkspace of NT;
x = the x-pos upon SW;
y = the y-pos upon SW;
conclude that y = 120;
show WS at half scale with its bottom right corner at the bottom right
   corner of the screen;
show SW at three-quarter scale with its top left corner 50 units below the
   top left corner of the screen;
call CONFIGURE-PATH-TRACER-PROC (NT, win);
for E = each experiment-selection in EL do
   allow other processing;
   n = n + 1;
   conclude that x = init-x + 110 * (n - 1);
   conclude that y = y - 100;
   BR = the bioreservoir named by the ref-bioreservoir of E;
   if there exists a bioprocess that is a-down-bioprocess-of BR then
      conclude that the status of BR is selected-for-input;
      BT = the biomodel-title upon SW;
      conclude that the label of BT = "[the label of BT]: [the label of BR]";
      create a bioreservoir LBR by cloning BR;
      transfer LBR to SW at (x, y);
      conclude that y = y - 40;
      for DBP = each bioprocess that is a-down-bioprocess-of BR do
         allow other processing;
         conclude that x = x + 110;
         create a bioprocess LDBP by cloning DBP;
         transfer LDBP to SW at (x, y);
         r = random (3, 35);
         t = random (20, 76);
         create a connection connected between LBR newly locating it at
            right at the position given by r and LDBP newly locating it at
            top at the position given by t with direction output;
         conclude that y = y - 40;
         call CREATE-LOCAL-EXPER-BP-PROC (DBP, LDBP, ,
            SW, win);
change the size of SW to minimum;
disable button;
return
```

TABLE 225
---
CREATE-LOCAL-EXPER-BP-PROC (BP: class bioprocess, LBP: class
  bioprocess, display: class kb-workspace, win: class G2-window)

define four local integers: p, l, r, and t: ;
  x = the x-pos upon display;
  y= the y-pos upon display;
  for each bioreservoir BR that is *a-down-bioreservoir-of* BP do
    for each bioprocess DBP that is *a-down-bioprocess-of* BR do
      if there is a bioprocess MBP upon SW such that the master-
          bioprocess of MBP is equal to the master-bioprocess of DBP then
        go to connect-BP-routine;
      else:
        conclude that x = x + 110;
        create a bioprocess LDBP by cloning DBP;
        transfer LDBP to display at (x, y);
        create a connection connected between LBP newly locating it
          at right at the position given by random (3, 35) and LDBP newly
          locating it at top at the position given by random (20, 76) with
          direction output;
        conclude that y = y - 40;
        call CREATE-LOCAL-EXPER-BP-PROC (DBP, LDBP, display,
          win)
  return;

connect-BP-routine:
  for each connection C connected to LBP do
    if there exists a connection DC connected to MBP such that DC is
        the same object as C then return;
  if the x-position of LBP is lower than the x-position of MBP) then
    create a connection of class c-line connected between LBP newly
      locating it at right at the position given by random (3, 35) and MBP
      newly locating it at bottom at the position given by random (20, 76)
      with direction output, with vertices 6 -60 else
  if the x-position of LBP is higher than the x-position of MBP) then
    create a connection of class c-line connected between LBP newly
      locating it at bottom at the position given by (20, 76) and MBP
      newly locating it at left 52 with direction output, with vertices -60;
  call CREATE-LOCAL-EXPER-BP-PROC (DBP, MBP, display, win);
return
---

TABLE 226

ACTIVATE-EXPER-CALLBACK (button: class pushbutton, win: class window, panel: class entry-panel)

```
WS = the subworkspace of panel;
ESL= the experiment-selections-list upon WS;
DBPL= the bm-downstream-bp-simulation-list upon WS;
val = local text;
if the user-mode of win is simulation then
   for ES = each experiment-selection in ESL do
      if the amount-entry of ES = 0.0 and the factor-entry of ES = 0.0 then
         go to no-value-routine
      else
         go to main-routine;
no-value-routine:
   fd = call create-query-dialog ("fd", "No value for the amount-entry
      or factor-entry of [the label of ES] has been entered. If you want to
      run the simulation with no external input then enter YES in the box
      below and press OK. Otherwise, press OK, enter the desired value
      for this experiment-selection, and press ACTIVATE again.", the
      symbol large, "NO", win, 0, 0);
   val = call get-query-dialog-value (fd);
   if val = "YES" then go to main-routine else return;
main-routine:
   if the number of elements in DBPL = 0 then
      go to no-bp-routine
   else
      call ACTIVATE-SIMULATION-PROC (win, panel);
      disable button;
   return;
no-bp-routine:
   ad = call create-message-dialog ("ad", "There are no bioProcesses that can
      be selected for activation", win, 0, 0);
   return;
```

TABLE 227

START-EXPER-CALLBACK (button: class pushbutton, win: class window, dlg: class entry-panel)

```
panel = the SW of dlg;
call SET-BASAL-DENSITIES-PROC (win, dlg); ESL = the experiment-
selections-list upon panel;
   define three local quantities: EV, FE, and ET;
   M = the model-definition upon panel;
   for ES = each experiment-selection in ESL do
      BR = the bioreservoir named by the ref-bioreservoir of ES;
      EV = the amount-entry of ES;
      FE = the factor-entry of ES;
      ET = the time-entry of ES;
      if EV /= 0.0 then
         if BR is a sol-mol-reservoir or BR is a exp-cell-reservoir then
            start CONC-INPUT-PROC (BR, EV, ET, win, dlg)
         else start DENSITY-INPUT-PROC (BR, EV, ET, win, dlg)
      else start DENSITY-INPUT-PROC (BR, FE, ET, win, dlg);
   start running the model M, conclude that the model-simulation-status
   of M is running, and inform the operator that " The simulation within
      <the items-belonging-to-this-model of M> has started at <the current
      time as a time stamp>";
   enable the button upon panel which id is "pa";
   disable button;
   return
```

TABLE 228

CONC-INPUT-PROC (BR: class bioreservoir, C: float , ET: integer
. win: class window, dlg: class dialog)

PO = the biopool upon the subworkspace of BR;
top = the top-container that is the-container-of-br BR;
define a local float EV:

if BR is a sol-mol-reservoir or BR is a exp-cell-reservoir then
    EV = C {molar} * 6.023e23 {molecules/liter} * the volume of
    top {liters}
t = the current-simulation-time of dlg;
incr = the current-simulation-time-increment of dlg;
wait until t >= ET checking every 1 second;
conclude that the density-entry of PO = EV;
wait until t >= ET + incr checking every 1 second;
conclude that the density-entry of PO = 0.0;
if t > ET + incr then return

TABLE 229

DENSITY-INPUT-PROC (BR: class bioreservoir, D: float , ET: integer,
    win: class window, dlg: class dialog)

PO = the biopool upon the SW of BR;
t = the current-simulation-time of dlg;
incr = the current-simulation-time-increment of dlg;
top = the top-container that is the-container-of-br BR;
wait until t >= ET checking every 1 second;
conclude that the density-entry of PO = D;
wait until t >= ET + incr checking every 1 second;
conclude that the density-entry of PO = 0.0;
if t > ET + incr then return;

TABLE 230

RELATIVE-INPUT-PROC (BR: class bioreservoir, F: float, ET: integer,
    win: class window, dlg: class dialog)

PO = the biopool upon the subworkspace of BR;
top = the top-container that is the-container-of-br BR;
t = the current-simulation-time of dlg;
incr = the current-simulation-time-increment of dlg;
wait until t >= ET checking every 1 second;
conclude that the scaled-entry of PO = F;
wait until t >= ET + incr checking every 1 second;
conclude that the scaled-entry of PO = 0.0;
if t > ET + incr then return;

TABLE 231
---
PAUSE-EXPER-CALLBACK (button: class pushbutton, win: class
window, panel: class entry-panel)

SW = the subworkspace of panel;
M = the model-definition upon SW;
call g2-pause-model (M);
if there exists a text-pushbutton rm upon SW such that (the id of rm =
    "rm") then enable rm;
disable button ;
---
RESUME-EXPER-CALLBACK (button: class pushbutton, win: class
window, panel: class entry-panel)

SW = the subworkspace of panel;
M = the model-definition upon SW;
call g2-resume-model (M);
conclude that the model-simulation-status of M is running;
if there exists a text-pushbutton pa upon SW such that (the id of pa =
    "pa") then enable pa;
disable button;
---

TABLE 232
---
RESET-EXPER-CALLBACK (button: class pushbutton, win: class
window, panel: class entry-panel)

SW = the subworkspace of panel;
M = the model-definition upon SW;
if the g2-user-mode of win is simulation then
    call RESET-SIMUL-PROC (M, panel);
    call g2-reset-model (M);
    conclude that the current-simulation-time of panel = 0 seconds;
    conclude that the current-simulation-time-increment of panel = 0
        seconds;
else
    call RESET-NAVIG-PROC (panel);
if there exists a text-pushbutton st upon SW such that (the id of st =
    "st") then disable st;
if there exists a text-pushbutton pa upon SW such that (the id of pa =
    "pa") then disable pa;
if there exists a text-pushbutton rm upon SW such that (the id of rm =
    "rm") then disable rm;
if there exists a text-pushbutton hi upon SW such that (the id of hi =
    "hi") then enable hi;
for md = each uil-message-dialog upon the subworkspace of DIALOG-
    BIN do
    delete md;
---
HIDE-EXPER-CALLBACK (button: class pushbutton, win: class
window, panel: class entry-panel)

hide the SW of panel on win
---

What is claimed is:

1. A computer system comprising memory means, storage means, program means, and stored means for building virtual-models of complex-systems in said computer system by creating, configuring, and linking instances of prototypes of building-blocks representing different types of components characteristic of said complex-systems, said means comprising:

one or more libraries of prototypes of linkable building-blocks comprising:

one or more different prototypes of reservoir building-blocks, each instance of said prototype(s) to be used to represent a conceptual population of any number of units of entities or entity-complexes of a given type or in a given state or compartment wherein the units of each of said populations represented may be disperse among the units of other populations in said complex-systems, and one or more different prototypes of process building-blocks representing one or more different types of processes characteristic of said complex-systems, each instance of said prototype(s) to be configured to represent a conceptual process in which any number of units from one or more of said populations participate, wherein each of said processes represented may comprise any number of equivalent and cumulative actual processes where subpopulations of said populations participate;

wherein each instance of process building-blocks or their components is to be linked to one or more complementary instances of reservoir building-blocks or their components, said links comprising: links from any number of instances of reservoir building-blocks to represent that input(s) to the represented process are output(s) of the represented populations, and links to any number of instances of reservoir building-blocks to represent that output(s) of said represented process are input(s) to the represented populations, wherein said instances of reservoir building-blocks may also have any number of output-input links from and to any number of instances of said process building-blocks;

wherein models resulting from said linking comprise multidimensional networks where the functional nodes are alternating complementary instances of reservoir building-blocks and process building-blocks, enabling any level of complexity from the possible one to many, many to one, and many to many links, and from the possible forward and feedback loops;

wherein any number of instances of said building-blocks representing processes or populations that provide input(s) to a reference process or population represented by a reference instance of said building-blocks or that may directly or indirectly influence said input(s) in one or more pathways are said to be upstream of said reference instance, and any number of instances of said building-blocks representing processes or populations that receive output(s) from said reference process or population or that may directly or indirectly be influenced by said outputs(s) in one or more pathways are said to be downstream of said reference instance; and wherein said building-blocks may comprise any number of attributes or components which values are either being used to describe characteristics of the types of components of said complex-systems that said types of building-blocks represent, or characteristics of said types of building-blocks in said computer system, or values or data structures used by said program at runtime, or are to be used to more specifically describe or point to characteristics of individual components of said complex-systems that each instance of said types of building-blocks is to represent, or characteristics of each instance of said building-blocks in said computer system, said attributes having values of any type, including but not limited to: character string, integer or real numbers, logical values, fuzzy values, or instances of parameters, variables, lists, arrays, images, or any other data structure, or pointers to other instances of any of said building-blocks, external files, Uniform Resource Locators (URLs), database records, or any other structures, in said computer system or in a network accessible by said computer system; and means for manipulating said building-blocks by domain experts and/or said program means, comprising:

means to make said prototypes of building-blocks available, including-visual means through menus or palettes and/or programmatic means;

means to instantiate said prototypes of building-blocks, including constructor means to create new instances from their definitions and/or means to clone semi-configured instances of said prototypes of building-blocks, interactively and/or programmatically; and means to establish said directional output-input links between said complementary instances of said building-blocks, directly or through their components.

2. A computer system as claimed in claim 1, wherein:

said prototypes of process building-blocks comprise one or more input(s) and output(s) to individually represent the one or more input(s) or output(s) of the pool of entities or characteristic of the type of process represented by any of said prototypes;

the output-input links enabled by said stored means are defined as links between said outputs and instances of reservoir building-block(s) or their components, and links between instances of reservoir building-block(s) or their components and said inputs;

any one of said input(s) of an instance of process building-blocks is to be linked to a complementary instance of said reservoir building-block(s) representing the population that provides the represented input, and any one of said output(s) is to be linked to a complementary instance of said reservoir building-block(s) representing the population that receives the represented output; and said linking results in any instance of said reservoir building-block(s) being linked to any number of instance(s) of said process building-block(s) through any number of input(s) and any number of output(s).

3. A computer system as claimed in claim 2, wherein:

instances of said prototype(s) of reservoir building-blocks are enabled to comprise one or more input(s) and/or output(s) to individually represent the one or more input(s) and/or output(s) of the population represented by each instance;

the output-input links enabled by said stored means are defined as links between outputs of instances of said building-blocks and inputs of instances of complementary building-blocks;

said links are to be established one-to-one between one of said input(s) and one complementary output of an instance of process building-blocks representing the output from the process that provides said input, and between any of said output(s) and one complementary input of an instance of process building-block representing the input to the population that receives said output; and said stored means further comprise means providing functions associated with said building-blocks to be executed upon selection by a user or by said program means, including navigation means associated with said input(s) and output(s) of said building-blocks to successively display a visual representation of the instances of building-blocks linked to any selected input or output.

4. A computer system as claimed in claim 2, further comprising stored means providing functions associated with said building-blocks or their components to be executed for any number of instances upon selection by a user or by said program means, including selection functions.

5. A computer system as claimed in claim 2, wherein the one or more input(s) and output(s) of said prototypes of process building-blocks are of one or more different types further representing the one or more different types of roles said inputs play in each type of process represented by said prototype of process building-blocks, and the one or more different types of outputs from said process, respectively.

6. A computer system as claimed in claim 5, further comprising stored means providing functions associated with said building-blocks or their components to be executed for any number of instances upon selection by a user or by said program means, including query functions for performing queries comprising one or more criteria, including criteria based on said different types of inputs and/or criteria based on said downstream and/or upstream position of instances of reservoir and/or process building-blocks in relation to any of said instances of building-blocks selected as reference(s).

7. A computer system as claimed in claim 5, further comprising stored means to dynamically simulate the quantitative behavior over time of said virtual-models or their subsystems, comprising:

any number of different types of defined quantitative variables and/or parameters characteristic of the components of said complex-systems associated with said prototypes of reservoir building-blocks and with said prototypes of process building-blocks and/or their different types of inputs and outputs, and stored means associated with each of said types of variables to compute during a simulation run the values of the instances of said variables associated with any of the instances of said building blocks comprised in the simulation model selected for said run, said values being dependent on the values of any number of other instances of variables and/or parameters associated with any of the instances of said building blocks comprised in said model.

8. A computer system as claimed in claim 7, wherein:

said types of quantitative variables comprise one or more different types of state variables associated with each of said reservoir building-blocks representing current quantitative measure(s) of the units in the population each instance represents, including one or more of concentration, density, quantity, scaled-quantity, or any other measure; and said stored means comprise simulation means associated with said variables to dynamically compute their value, wherein the values for any instance of said state variables associated with any instance of said reservoir building-blocks is computed by integrating the sum of the rate(s) of input from the output(s) of any number of instances of process building-blocks linked as inputs to said reservoir building-block less the sum of the rate(s) of output to the input(s) of any number of instances of process building-blocks linked as outputs of said reservoir building-block, plus or minus any other optional mathematically modeled inputs or outputs.

9. A computer system as claimed in claim 7, wherein:

said types of quantitative variables comprise one or more different types of dependent variables associated with each of said types of process building-blocks and/or their different types of inputs and outputs; and the stored simulation means enable to dynamically compute the values for any instance of said variables associated with any instance of said process building-blocks and/or its input(s) by incorporating, directly or indirectly, the current value(s) of the corresponding variable(s) of any number of instances of reservoir building-blocks linked to any of the input(s) of said process building-block and/or the values of any number of parameters specific for said instance of process building-blocks and/or its specific input(s).

10. A computer system as claimed in claim 7, further comprising stored means enabling the fitting of the values of one or more of said different types of quantitative parameters, to be used to fit the values of any number of parameters of said types of any number of instances of building-blocks of a virtual-model in order to adapt the behavior of said virtual-model or its subsystems to the experimental observations of said complex systems.

11. A computer system as claimed in claim 4, wherein said stored means comprise navigation functions associated with said building-blocks enabling successive interactive display of visual representations of instance(s) of said building-blocks, including navigation from any selected instance of said building-blocks to any of the instances of complementary building blocks.

12. A computer system as claimed in claim 4, wherein said stored means provide pathways-display functions for dynamically generating at run time visual displays of multidimensional networks of interconnected pathways representing components of the virtual-models of said complex-systems or their subsystems, wherein the nodes of said networks are visually ordered and connected representations of series of said linked instances of building-blocks that are downstream and/or upstream of any number of selected instances of said building-blocks.

13. A computer system as claimed in claim 4, further comprising stored means to dynamically simulate the quantitative behavior over time of said virtual-models or their subsystems, further comprising:

any number of different types of defined quantitative variables and/or parameters characteristic of the components of said complex-systems associated with said prototypes of reservoir building-blocks and with said prototypes of process building-blocks and/or their inputs and outputs; and stored means associated with each of said types of variables to compute during a simulation run the values of the instances of said variables associated with any of the instances of said building blocks comprised in the simulation model selected for said run, said values being dependent on the values of any number of other instances of variables and/or parameters associated with any of the instances of said building blocks comprised in said model.

14. A computer system as claimed in claim 13, further comprising stored means for performing dynamic mixed-type simulations of said virtual-models with data of different degrees of precision for different parts of said complex-systems, wherein:
said building-blocks comprise two corresponding sets of said quantitative variables and parameters, one set to hold absolute values and the other set to hold scaled relative values; and
said stored simulation means further comprise scaling and unscaling functions defined for different types of said variables.

15. A computer system as claimed in claim 1 further enabling the utilization of said virtual-models, further comprising stored means providing functions associated with said building-blocks or their components to be executed for any number of instances of said building-blocks upon selection by a user or by said program means.

16. A computer system as claimed in claim 15, wherein said stored means provide query functions to perform queries wherein at least one of the search criteria is based on said downstream or upstream position of any number of instances of said building-blocks in relation to any of said instances of building-blocks selected as reference.

17. A computer system as claimed in claim 15, wherein said stored means provide pathways-display functions for dynamically generating at run time visual displays of multidimensional networks of interconnected pathways representing components of the virtual-models of said complex-systems or their subsystems, wherein the nodes of said networks are visually ordered and connected representations of series of said linked instances of building-blocks that are downstream and/or upstream of any number of selected instances of said building-blocks.

18. A computer system as claimed in claim 1, wherein:
said stored libraries further comprise prototypes of entity building-blocks representing the composition, structure, or other characteristics of different types of entities, entity-complexes, or entity-components characteristic of said complex-systems;
top-level instances of said prototypes of entity building-blocks are to be used to represent a description of a representative unit of any of the populations represented by said instances of reservoir building-blocks;
instances of said prototypes may be composite, comprising or enabled to comprise instances of other entity building-blocks or other components, without any limits as to how many layers of lower-level entity building-blocks are built into any composite entity building-block;
said reservoir building-blocks comprise an entity-pointer which may be set for any instance to point to the corresponding instance of said top-level entity building-blocks and
said stored means further comprise means providing functions associated with said building-blocks to be executed for any number of instances upon selection by a user or by said program means, including: show-entity functions defined for said reservoir building-blocks to display the instance of entity building-block referred to by a selected instance of reservoir building-blocks, if any, and/or navigation functions defined for composite entity building-blocks to successively display visual representation of the components of selected instances.

19. A computer system as claimed in claim 1, further comprising stored means to dynamically simulate the quantitative behavior over time of said virtual-models or their subsystems, comprising:
one or more different types of defined quantitative variables and/or parameters characteristic of the components of said complex-systems associated with said different prototypes of building-blocks and/or their components, and
simulation means associated with each of said types of variables to compute during a simulation run the values of the instances of said variables associated with any of the instances of said building blocks comprised in the simulation model selected for said run, said values being dependent on the values of any number of other instances of variables and/or parameters associated with any of the instances of said building blocks comprised in said model.

20. A computer system as claimed in claim 19, wherein:
said types of quantitative variables comprise one or more different types of state variables associated with each of said reservoir building-blocks representing current quantitative measures of the units in the population each instance represents, including one or more of concentration, density, quantity, scaled-quantity, or any other measure; and
said stored means comprise simulation means associated with said variables to dynamically compute their value, wherein the values for any instance of said state variables associated with any instance of said reservoir building-blocks is computed by integrating the sum of the rate(s) of input from any number of instances of process building-blocks linked as inputs to said reservoir building-block less the sum of the rate(s) of output to any number of instances of process building-blocks linked as outputs of said reservoir building-block, plus or minus any other optional mathematically modeled inputs or outputs.

21. A computer system as claimed in claim 19, further comprising stored means enabling the fitting of the values of one or more of said different types of quantitative parameters, to be used to fit the values of any number of parameters of said types of any number of instances of building-blocks of a virtual-model in order to adapt the behavior of said virtual-model or its subsystems to the experimental observations of said complex systems.

22. A computer system as claimed in claim 19, wherein:
said types of quantitative variables comprise one or more different types of dependent variables associated with each of said process building-blocks or its components; and
the associated simulation means enable to dynamically compute the value for any instance of said variables associated with any instance of said process building-blocks by incorporating, directly or indirectly, the current value(s) of the corresponding variable(s) of any number of instances of reservoir building-blocks linked as input(s) of said process building-block and/or the values of any number of parameters specific for said instance of process building-block; or its components.

23. A computer system comprising memory means, storage means, and program means, for building virtual-models of complex-systems in said computer system by creating, configuring and linking instances of prototypes of building-blocks stored in said computer-system, said prototypes representing different types of components characteristic of said complex-systems, comprising:

one or more libraries of prototypes of building-blocks comprising:
  one or more different prototypes of reactant building-blocks representing populations of entities that are inputs to different types of processes as well as the different types of roles that the different inputs play in said types of processes,
  one or more different prototypes of product building-blocks representing populations of entities that are outputs of different types in different types of processes, and
  one or more different prototypes of composite process building-blocks representing different types of processes characteristic of said complex-systems, each instance of said prototypes to be configured to represent a conceptual process in which one or more different populations of entities participate, wherein each of said represented processes may comprise any number of equivalent and cumulative actual processes wherein subpopulations of said populations participate, each prototype comprising or enabled to comprise:
    any number of instances of one or more of said prototypes of reactant building-blocks representing the one or more inputs and the one or more different roles each of said inputs play in the represented type of process,
    any number of instances of one or more of said prototypes of product building-blocks representing the one or more outputs and types of outputs from said type of process, and
    wherein each of said inputs and outputs is to represent a population of any number of units of entities or entity complexes of a given type or in a given state or compartment;
  wherein said building-blocks may comprise any number of attributes which values are either being used to describe the characteristics of the types of components of said complex-systems that said types of building-blocks represent, or characteristics of said types of building-blocks in said computer system, or values or data structures used by said program means at runtime, or are to be used to more specifically describe or point to characteristics of individual components of said complex-systems that each instance of said types of building-blocks is to represent, or characteristics of instances of said building-blocks in said computer system, said attributes having values of any type, including but not limited to: character string, integer or real numbers, logical values, fuzzy values, or instances of parameters, variables, lists, arrays, images, or any other data structure, or pointers to other instances of any of said building-blocks, external files, Uniform Resource Locators (URLs), database records, or any other objects, in said computer system or in a network accessible by said computer system;
  wherein each of said instances of product building-block(s) is to be linked to complementary instances of reactant building-block(s) on any number of other instances of process building-blocks, to represent that the represented output from a process provides the represented inputs to other processes, wherein any number of instances of product building-block(s) may be linked to any of said instances of reactant building-blocks;
  wherein virtual-models resulting from said linking comprise multidimensional networks where the functional nodes are alternating complementary instances of process building-blocks or their components enabling any level of complexity from the possible one to many, many to one, and many to many links, and from the possible forward and feedback loops;
  wherein any number of instances of said building-blocks representing components that provide input(s) to a reference component represented by a reference instance of said building-blocks or that may directly or indirectly influence said input(s) in one or more pathways are said to be upstream of said reference instance, and any number of instances of said building-blocks representing components that receive output(s) from said reference component or that directly or indirectly are influenced by said output(s) in one or more pathways are said to be downstream of said reference instance; and
  means for manipulating said building-blocks by domain experts and/or said program means, comprising:
    means to make said prototypes of building-blocks available, including visual means through menus or palettes, and/or programmatic means;
    means to instantiate said prototypes of building-blocks, including constructor means to create new instances from their definitions and/or means to clone semi-configured instances of said prototypes of building-blocks, interactively and/or programmatically; and
    means to establish directional output-input links between said complementary instances of building-blocks, including links between instances of said product building-block(s) and instances of said reactant building-block(s).

24. A computer system as claimed in claim 23 enabling the utilization of said virtual-models, further comprising stored means providing functions associated with said building-blocks or their components to be executed for any number of instances of building-blocks upon selection by a user or by said program means, including selection functions.

25. A computer system as claimed in claim 24, wherein said stored means further provide list functions enabling the listing of instance(s) of process building-blocks that are downstream and/or upstream of a selected instance of said building-blocks in any number of said pathways.

26. A computer system as claimed in claim 24, wherein said stored means further provide query functions for performing queries comprising one or more search criteria, including: criteria based on said downstream or upstream position of instances of said building-blocks in relation to any of said instances of building-blocks selected as reference and/or criteria based on said different types of reactant building-blocks.

27. A computer system as claimed in claim 24, wherein said stored means further provide pathways-display functions for dynamically generating at run time visual displays of multidimensional networks of interconnected pathways representing components of the virtual-models of said complex-systems or their subsystems, wherein the nodes of said networks are visually ordered and connected representations of series of said linked instances of building-blocks that are downstream and/or upstream of any number of selected instance(s) of said building-blocks.

28. A computer system as claimed in claim 24, further comprising stored means enabling to dynamically simulate the quantitative behavior over time of said virtual-models or their subsystems, comprising:

any number of different types of defined quantitative variables and/or parameters characteristic of the components of said complex-systems associated with said prototypes of process building-blocks and/or their different types of reactant and product building-blocks, and stored means associated with each of said types of variables to compute during a simulation run the values of the instances of said variables associated with any of the instances of said building blocks comprised in the simulation model selected for said run, said values being dependent on the values of any number of other instances of variables and/or parameters associated with any of the instances of said building blocks comprised in said model.

29. A computer system as claimed in claim 28, further comprising stored means enabling the fitting of the values of one or more of said different types of quantitative parameters, to be used to fit the values of any number of parameters of said types of any number of instances of building-blocks of a virtual-model in order to adapt the behavior of said virtual-model or its subsystems to the experimental observations of said complex systems.

30. A computer system as claimed in claim 23, wherein:
said libraries further comprise on or more different prototype(s) of reservoir building-block(s), each instance of said prototype(s) to be configured to represent a conceptual population of any number of units of entities or entity-complexes of a given type or in a given state or compartment, wherein the units of each of said represented populations may be disperse among the units of other populations in said complex-systems;

said instances of reservoir building-block(s) are enabled to comprise any number of input(s) and/or output(s) to individually represent the input(s) and/or output(s) of the population represented by any of said instances;

the output-input links enabled by said stored means are defined as one-to-one links between instances of said product building-blocks and inputs of instances of said reservoir building-block(s), and one-to-one links between outputs of instances of said reservoir building-block(s) and instances of said reactant building-blocks;

any one of said input(s) is to be linked to a complementary instance of said product building-block(s) representing the output from a process that provides said input to the represented population, and any one of said output(s) is to be linked to a complementary instance of said reactant building-block(s) representing the input to a process that uses said output from the represented population;

said linking results in any instance of said process building-blocks being linked, through any number of its reactants and/or products building-blocks, to any number of instances of said reservoir building-block(s), and on any instance of said reservoir building-blocks being linked, through any number of its inputs and/or outputs, to any number of instances of said process building-blocks;

virtual-models resulting from said linking comprise multidimensional networks where the functional nodes are alternating complementary instances of reservoir building-blocks and process building-blocks, enabling considerable complexity from the possible one to many, many to one, and many to many links, and from the possible forward and feedback loops; and said stored means further comprise means providing functions associated with said building-blocks or their components to be executed for any number of instances of building-blocks upon selection by a user or by said program means, including selection functions.

31. A computer system as claimed in claim 30, wherein said stored means further provide pathways-display functions for dynamically generating at run time visual displays of multidimensional networks of interconnected pathways representing components of virtual-models of said complex-systems or their subsystems, wherein the nodes of said networks are visually ordered and connected representations of series of said linked instances of building-blocks that are downstream and/or upstream of any number of selected instance(s) of said building-blocks.

32. A computer system as claimed in claim 30, wherein said stored means further provide navigation functions associated with said building-blocks enabling successive interactive display of visual representations of instances of said building-blocks, including navigation from any selected instance of said building-blocks to any of the instances of complementary building blocks linked as input(s) or output(s).

33. A computer system as claimed in claim 30, wherein said stored means further provide simulation functions for dynamically simulating the quantitative behavior over time of said virtual-models or their subsystems, comprising:
any number of different types of defined quantitative variables and/or parameters characteristic of the components of said complex-systems associated with said prototypes of building-blocks and/or their inputs and outputs, and stored means associated with each of said types of variables to dynamically compute during a simulation run the values of the instances of said variables associated with any of the instances of said building blocks comprised in the simulation model selected for said run, said values being dependent on the values of any number of other instances of variables and/or parameters associated with the same instance and/or their inputs and outputs or with instances of said building-blocks linked to said instance as inputs in said model.

34. A computer system as claimed in claim 33, further comprising stored means enabling the fitting of the values of one or more of said different types of quantitative parameters, to be used to fit the values of any number of parameters of said types of any number of instances of building-blocks of a virtual-model in order to adapt the behavior of said virtual-model or its subsystems to the experimental observations of said complex systems.

35. A computer system as claimed in claim 33, wherein said types of quantitative variables comprise one or more different types of state variables associated with each of said reservoir building-blocks representing current quantitative measure(s) of the units in the population it represents, including one or more of concentration, density, quantity, scaled-quantity, or any other measure, with associated simulation means to dynamically integrate the sum of the rate(s) of input from any number of instances of product building-blocks linked to inputs to said reservoir building-block less the sum of the rate(s) of output to any number of instances of reactant building-blocks linked to outputs of said reservoir building-block, plus or minus any other optional mathematically modeled inputs or outputs.

36. A computer system as claimed in claim 33, wherein:
said defined types of quantitative variables comprise any number of different types of dependent variables associated with each of said types of process building-blocks and/or their different types of reactant and product building-blocks, to describe the characteristics of different types of processes and/or their different types of inputs and outputs; and the associated simulation means enable to dynamically compute the values for any instance of said variables associated with any instance of said process building-blocks and/or its instance(s) of reactant building-blocks by directly or indirectly incorporating: the current value(s) of the corresponding variable(s) of any number of instances of reservoir building-blocks linked to any of said instance(s) of reactant building-blocks, and/or the values of any number of parameters specific for said instance of process building-blocks and/or its instance(s) of reactant building-blocks.

37. A computer system as claimed in claim 23, wherein:

said library further comprises prototypes of entity building-blocks representing the composition, structure, or other characteristics of different types of entities, entity-complexes, or entity-components characteristic of said complex-systems;

instances of said prototypes may be composite, comprising instances of other entity building-blocks or other components to be added, without any limits as to how many layers of lower-level entity building-blocks are built into any composite entity building-block;

top-level instances of said prototypes of entity building-blocks are to be used to represent a description of a representative unit of any of the entities or entity-complexes represented by said instances of reactant and product building-blocks:

said reactant and product building-blocks comprise an entity pointer which may be set for any instance to point to the corresponding instance of said top-level entity building-blocks;

said stored means further provide functions associated with said building-blocks or their components to be executed for any number of instances upon selection by a user or by said program means, including: show-entity functions defined for said reactant and product building-blocks to display the top-level instance of entity building-blocks referred to by a selected instance of said reactant and product building-blocks, and/or navigation functions defined for composite entity building-blocks to display visual representations of the components of selected instances.

38. A method for representing virtual-models of complex-systems in a computer system comprising memory means, storage means, and program means, comprising the steps of:

storing in said computer system program means defining prototypes of linkable building-blocks representing components characteristic of said complex-systems, said prototypes comprising:

one or more types of reservoir building-blocks to represent one or more types of conceptual populations of entities characteristic of said complex-systems, wherein the units of each of said populations represented may be disperse among the units of other populations in said complex-systems, and one or more different types of process building-blocks to represent one or more different types of conceptual processes characteristic of said complex-system in which any number of units from one or more of said populations participate, wherein each of said processes represented may comprise any number of equivalent and cumulative actual processes wherein subpopulations of said populations participate, wherein said stored means define any number of attributes and/or components for said building-blocks, which values are either used to describe the characteristics of the types of components of said complex-systems that said types of building-blocks represent, or characteristics of said types of building-blocks in said computer system, or values or data structures used by said program at runtime, or are to be used to more specifically describe or point to characteristics of individual components of said complex-systems that each instance of said types of building-blocks is to represent, or characteristics of instances of said building-blocks in said computer system, said attributes having values of any type, including but not limited to: character string, integer or real numbers, logical values, fuzzy values, instances of parameters, variables, lists, arrays, images, or any other data structure, or pointers to other instances of any of said building-blocks, external files, Uniform Resource Locators (URLs), database records, or any other objects, in said computer system or in a network accessible by said computer system;

storing program means to make said definitions of building-blocks available to the program and/or user, including visual means through menus and/or palettes, and/or programmatic means;

storing program means to instantiate said building blocks, including constructor means in conjunction with said definitions and/or cloning means in conjunction with semi-configured instances of said prototypes;

storing program means to establish directional output-input links between instances of said two complementary kinds of building blocks;

building the different components of a virtual model by instantiating the appropriate types of said building blocks and configuring said instances, wherein:

each instance of said reservoir building-blocks is configured to represent one population of any number of units of entities or entity-complexes of one given type or in a given state or compartment, and each instance of said types of process building-blocks is configured to represent a conceptual process in which any number of units from one or more of said populations participate; and establishing output-input links between individual instances of said process building-blocks and any number of corresponding instances of said reservoir building-blocks to represent that output(s) of a represented process are input(s) to any number of corresponding represented population(s), and links between individual instances of said reservoir building-blocks and any number of instances of said process building-blocks to represent that output(s) of a represented population are input(s) to any number of corresponding represented processes, wherein:

virtual-models resulting from said linking comprise multidimensional networks where the functional nodes are alternating complementary instances of reservoir building-blocks and process building-blocks, enabling any level of complexity from the possible one to many, many to one, or many to many links, and from the possible forward and feedback loops, and any instance(s) of said building-blocks representing populations or processes that provide input(s) to a reference population or process represented by a reference instance of said building-blocks or that directly or indirectly influence said inputs in one or more pathways are said to be upstream of said reference instance, and any instance(s) of said building-blocks representing populations or processes that receive output(s) from said reference population or process or that directly or indirectly are influenced by said output(s) in one or more pathways are said to be downstream of said reference.

39. A method as claimed in claim 38, wherein:

said prototypes of process building-blocks comprise one or more input(s) and/or output(s) to individually represent the one or more input(s) or output(s) characteristic of the type of process represented by any of said prototypes;

the output-input links enabled by said means are defined as links between said outputs and instances of reservoir building-block(s) or their components, and links between instances of reservoir building-block(s) or their components and said inputs;

any of said input(s) of an instances of process building-blocks is to be linked to a complementary instance of said reservoir building-block(s) representing the population that provides the represented input, and any of said output(s) is to be linked to a complementary instance of said reservoir building-block(s) representing the population that receives the represented output; and said linking results in any instance of said reservoir building-block(s) being linked to any number of instance(s) of said process building-block(s) through any number of input(s) and any number of output(s), representing that the represented population provide input(s) to or receive output(s) from any number of the represented processes.

40. A method as claimed in claim 39 wherein the one or more input(s) and output(s) of said prototypes of process building-blocks are of one or more different types further representing the one or more different types of roles said inputs play in each type of process represented by said prototype of process building-blocks, and the one or more different types of outputs from said process, respectively.

41. A method as claimed in claim 39, further representing the dynamic quantitative behavior over time of said virtual-models or their subsystems, further comprising the steps of:

storing means defining one or more different types of quantitative variable(s) and/or parameter(s) characteristic of the components of said complex-systems they represent, in association with the different prototypes of said reservoir building-blocks and of said prototypes of process building-blocks and/or their inputs and outputs; and storing means associated with said different types of variable(s) to relate the dependencies of the values of instances of said types associated with any of the instances of said reservoir building-blocks and process building-blocks to the values of any number of other instances of variable(s) and/or parameter(s) associated with the same instance or with instances of said building-blocks linked to said instance as inputs.

42. A method as claimed in claim 40, further representing the dynamic quantitative behavior over time of said virtual-models or their subsystems, further comprising the steps of:

storing modeling means defining one or more different types of quantitative variable(s) and/or parameter(s) characteristic of the components of said complex-systems they represent, in association with the different prototypes of said reservoir building-blocks and of said prototypes of process building-blocks and/or their different types of inputs and outputs; and storing means associated with said different types of variable(s) to relate the dependencies of the values of instances of said types associated with any of the instances of said reservoir building-blocks and process building-blocks to the values of any number of other instances of variable(s) and/or parameter(s) associated with the same instance or with instances of said building-blocks linked to said instance as inputs.

43. A method as claimed in claim 12, wherein:

said defined variables comprise any number of different types of dependent variables associated with each of said prototypes of process building-blocks and/or their different types of inputs and outputs, describing the characteristics of different types of processes and/or the different roles of their different types of inputs and their different types of outputs; and the modeling means relate directly or indirectly, the values for any instance of said variables associated with any instance of said process building-blocks and/or its different types of input(s) to the current value(s) of the corresponding variable(s) of any number of instances of reservoir building-blocks linked to any of said input(s) and/or to the values of any number of parameters specific for said instance of process building-blocks and/or its specific input(s).

44. A method as claimed in claim 38, further comprising the steps of:

storing in said computer system means to define one or more prototypes of entity building-blocks representing the composition, structure, or other characteristics of different types of entities, entity-complexes, or entity-components characteristic of said complex-systems, wherein:

instances of said entity building-blocks may be used as top-level instances to represent a description of a representative unit of any of the populations represented by said instances of reservoir building-blocks; and certain of said entity building-blocks may be composite and comprise or enabled to comprise instances of other entity building-blocks or other components, without any limits as to how many layers of lower-level entity building-blocks are built into any composite entity building-block; and storing means to relate instances of said building-blocks to other instances of building-blocks, including defining for said prototypes of reservoir building-block(s) entity-pointers which may optionally be set for any instance to reference the corresponding instance of said top-level entity building-blocks.

45. A method as claimed in claim 38, further representing the dynamic quantitative behavior over time of said virtual-models or their subsystems, further comprising the steps of:

storing means defining one or more different types of quantitative variable(s) and/or parameter(s) characteristic of the components of said complex-systems they represent, in association with the different prototypes of said reservoir building-blocks and process building-blocks and storing modeling means associated with said different types of variable(s) to relate the dependencies of the values of instances of said types associated with any of the instances of said building-blocks to the values of any number of other instances of variable(s) and/or parameter(s) associated with the same instance or with instances of said building-blocks linked to said instance as inputs.

46. A method as claimed in claim 45, wherein:

said defined types of quantitative variables comprise one or more different types of state variables associated with each of said prototypes of reservoir building-blocks, representing current quantitative measures of the units in the population it represents, including one or more of concentration, density, quantity, scaled-quantity, or any other measure; and said modeling means relate the value of instance(s) of said different types of state variable(s) of an instance of reservoir building-block to the values of variable(s) of linked complementary instances of process building-blocks by integrating the sum of the current value(s) of the rate(s) of input from any number of said instances of process building-blocks linked as inputs to said instance of reservoir building-block less the sum of the rate(s) of output to any number of said instances of process building-blocks linked as outputs of said instance, plus or minus any other optional mathematically modeled inputs or outputs of said instance.

47. A method as claimed in claim 45, wherein:

said defined types of quantitative variables comprise one or more different types of dependent variables associated with each of said prototypes of process building-blocks, describing the characteristics of different types of processes; and the modeling means relate, directly or indirectly the values for any instance of said variables associated with any instance of said process building-blocks to the current value(s) of the corresponding variable(s) of any number of instance(s) of reservoir building-blocks linked to any of said input(s) and/or to the value(s) of any number of parameters specific for said instance of process building-blocks or its components.

48. A method for representing virtual-models of complex-systems in a computer system comprising memory means, storage means, and program means, comprising the steps of:

storing in said computer system program means to define prototypes of building-blocks representing the components characteristic of said complex-systems, said prototypes comprising:

one or more different type(s) of reactant building-blocks representing populations of entities that are input(s) to different types of processes as well as the different types of roles that the different inputs play in said types of processes;

one or more different type(s) of product building-blocks representing populations of entities that are output(s) of different types in different types of processes; and one or more different types of composite prototypes of process building-blocks representing different types of processes characteristic of said complex-systems, each instance of said prototypes to be configured to represent a conceptual process in which one or more populations of entities participate, wherein each of said represented processes may comprise any number of equivalent and cumulative actual processes wherein subpopulations of said populations participate, each prototype comprising or enabled to comprise:

any number of instances of one or more of said prototype(s) of reactant building-blocks representing the one or more inputs and the one or more different roles each of said inputs play in the represented type of process, any number of instances of one or more of said prototype(s) of product building-blocks representing the one or more output(s) and types of outputs from said type of process, and wherein each of said inputs and outputs implies a population of any number of units of entities or entity-complexes of a given type or in a given state or compartment;

wherein said program means further define any number of attributes and/or components for said building-blocks, which values are either used to describe the characteristics of the types of components of said complex-systems that said types of building-blocks represent, -or characteristics of said types of building-blocks in said computer system, or values or data structures used by said program at runtime, or are to be used to more specifically describe or point to characteristics of individual components of said complex-systems that each instance of said types of building-blocks is to represent, or characteristics of instances of said building-blocks in said computer system, said attributes having values of any type, including but not limited to: character string, integer or real numbers, logical values, fuzzy values, instances of parameters, variables, lists, arrays, images, or any other data structure, or pointers to other instances of any of said building-blocks, external files, Uniform Resource Locators (URLs), database records, or any other objects, in said computer system or in a network accessible by said computer system;

storing program means to make said definitions of building-blocks available to the program and/or user, including visual means through menus and/or palettes, and/or programmatic means;

storing program means to instantiate said building blocks, including constructor means in conjunction with said definitions and/or cloning means in conjunction with semi-configured instances of said prototypes, interactively and/or programmatically;

storing program means to establish directional output-input links between instances of said product building-block(s) and instances of said reactant building-block(s);

building the different components of a virtual model by instantiating the appropriate types of said building blocks and configuring said instances, wherein:

each instance of said types of process building-blocks is configured to represent a conceptual process in which any number of populations of entities participate, and each instance of said reactant or product building-blocks are configured to represent one of the one or more input(s) or output(s), respectively of said process representing populations of any number of entities or entity-complexes of one given type or in a given state or compartment;

establishing output-input links between any instance of product building-block and any number of complementary instances of reactant building-blocks to represent that the output from a process represented by said product building-block provides the input(s) to other processes represented by said linked instances of reactant building-blocks, wherein:
any number of instances of product building-block(s) of different processes building-block(s) may be linked to each of said instances of reactant building-blocks, wherein:
virtual-models resulting from said linking comprise multidimensional networks where the functional nodes are instances of process building-blocks or their reactant and product building-blocks, enabling any level of complexity from the possible one to many, many to one, and many to many links, and from the possible forward and feedback loops, and
any instance(s) of said building-blocks representing components that provide input(s) to a reference component represented by a reference instance of said building-blocks or that may directly or indirectly influence said inputs in one or more pathways are said to be upstream of said reference instance, and any instance(s) of said building-blocks representing components that receive output(s) from said reference component or that directly or indirectly are influenced by said output(s) in one or more pathways are said to be downstream of said reference instance.

49. A method as claimed in claim 48, further comprising the steps of:
storing means to define one or more prototypes of entity building-blocks representing the composition, structure, or other characteristics of different types of entities, entity-complexes, or entity-components characteristic of said complex-systems, wherein:
instances of said entity building-blocks may be used as top-level instances to represent a description of a representative unit of any of the entity populations represented by said instances of reactant and product building-blocks; and
certain of said prototypes of entity building-blocks may be composite and comprise or enabled to comprise instances of other entity building-blocks or other components, without any limits as to how many layers of lower-level entity building-blocks are built into any composite entity building-block; and
storing means to relate instances of said building-block(s) to other instances of building-blocks, including defining for said prototypes of reactant and product building-blocks entity-pointers which may optionally be set for any instance to reference the corresponding instance of said top-level entity building-blocks.

50. A method as claimed in claim 48, further representing the dynamic quantitative behavior over time of said virtual-models or their subsystems, further comprising the steps of:
storing means defining one or more different types of quantitative variable(s) or parameter(s) characteristic of the components of said complex-systems they represent, in association with the different prototypes of said reservoir, process, reactant, and product building-blocks; and
storing means associated with said different types of variables to relate the dependencies of the values of instances of said types associated with any of the instances of said building-blocks to any number of other instances of variable(s) and/or parameter(s) associated with the same instance or with instances of said building-blocks linked to said instance as inputs.

51. A method as claimed in claim 48, wherein:
said stored prototypes further comprise one or more different types of reservoir building-blocks to represent said conceptual populations of entities, wherein the units of each of said represented populations may be disperse among the units of other populations in said complex-systems;
said prototypes enable each instance of said reservoir building-blocks to comprise any number of input(s) and/or output(s) to represent the input(s) and/or output(s) of the represented population;
said means to establish output-input links are defined as links between instances of said product building-blocks and inputs of instances of said reservoir building-block(s), and links between outputs of instances of said reservoir building-block(s) and instances of said reactant building-blocks;
building the components of said virtual model further comprise instantiating the appropriate type(s) of said reservoir building blocks and configuring each instance to represent one population of any number of units of entities or entity-complexes of one given type or in a given state or compartment;
any one of said input(s) is to be linked to a complementary instance of said product building-block(s) representing the output from a process that provides the input represented by said input, and any one of said output(s) is to be linked to a complementary instance of said reactant building-block(s) representing the input to a process that uses the output represented by said output;
said linking results in an instance of said process building-blocks being linked to any number of instances of said reservoir building-block(s) through any number of its reactants(s) or products(s), and any instance of said reservoir building-blocks being linked to any number of instances of said process building-block(s) through any number of its input(s) or output(s)
models resulting from said linking comprise multidimensional networks where the functional nodes are alternating complementary instances of reservoir building-blocks and process building-blocks, enabling considerable complexity from the possible one to many, many to one, or many to many links, and from the possible forward and feedback loops.

52. A method as claimed in claim 51, further representing the dynamic quantitative behavior over time of said virtual-models or their subsystems, further comprising the steps of:
storing means defining one or more different types of quantitative variable(s) and/or parameter(s) characteristic of the components of said complex-systems they represent, in association with the different prototypes of said reservoir, process, reactant, and product building-blocks; and
storing means associated with said different types of variable(s) to relate the dependencies of the values of instances of said types associated with any of the instances of said building-blocks to the values of any number of other distances of variable(s) and/or parameter(s) associated with the same instance or with instances of said building-blocks linked to said instance as inputs.

53. A method for utilizing virtual-models of complex-systems in a computer system comprising memory means, storage means, program means, and stored persistent data sets comprising instances of building-blocks representing the components of said complex-system(s), comprising the steps of:

loading into said memory means one or more of said stored data sets comprising:
  any number of instances of one or more different types of reservoir building-blocks, each instance configured to represent a conceptual population of any number of units of entities or entity-complexes of one given type or in a given state or compartment wherein the units of each of said populations represented may be disperse among the units of other populations in said complex-systems, and
  any number of instances of one or more different types of process building-blocks, each instance configured to represent a conceptual process of one or more different types characteristic of said complex-systems in which any number of units from one or more of said populations participate, wherein each of said processes represented may comprise any number of equivalent and cumulative actual processes wherein subpopulations of said populations participate;
  wherein individual instances of said building-blocks have directional output-input links to instances of complementary building-blocks, including links from any number of instances of said reservoir building-blocks to an instance of said process building-blocks representing that output(s) of the represented population(s), provide input(s) to the represented process, and links from said instance to any number of instances of reservoir building-block (s), representing that output(s) of said process provide input(s) to the represented population(s), wherein said instance(s) of reservoir building-blocks also have any number of output-input links from and to any number of instances of said process building-blocks; and
  wherein said building-blocks comprise any number of attributes which values are either used to describe the characteristics of the types of components of said complex-systems that said types of building-blocks represent, or characteristics of said types or individual instances of building-blocks in said computer system, or values or data structures used by said program at runtime, or more specifically to describe or point to characteristics of individual components of said complex-systems that each instance of said types of building-blocks represents, said attributes having values of any type, including but not limited to: character string, integer or real numbers, logical values, fuzzy values, instances of parameters, variables, lists, arrays, images, or any other data structure, or pointers to other instances of any of said building-blocks, external files, Uniform Resource Locators (URLs), database records, or any other structures, in said computer system or in a network accessible by said computer system;
integrating by said program means said individually linked instances of building-blocks into a multidimensional network of pathways wherein:
  the modes of said network are alternative said instances of reservoir and process building-blocks, each of said nodes being comprised in one or more of said pathways,
  different pathways merge at any of said nodes with multiple input links, and where different pathways branch at any of said nodes with multiple output links,
  any instance(s) of said building-blocks representing processes or populations that provide input(s) to a reference process or population represented by a reference instance of said building-blocks or that directly or indirectly may influence said input(s) are said to be upstream of said reference instance and any instance(s) of said building-blocks representing processes or populations that receive output(s) from said reference process or population or that directly or indirectly may be influenced by said output(s) are said to be downstream of said reference instance; and
  executing by said program means one or more stored functions associated with to said types of building-blocks for any instances of said types of building-blocks selected by a user or by said program.

54. A method as claimed in claim 53, wherein:
each instance of said reservoir or process building-blocks comprises one or more input(s) and/or output(s) representing the one or more input(s) or output(s) of the population or the process, respectively, represented by said instance; and
the complementary instances of said reservoir and process building-blocks are linked through one-to-one output-input links between one of said output(s) of an instance of said building-blocks and one of said input(s) of an instances of a complementary building-block, representing that the inputs represented by said inputs are the outputs represented by said outputs.

55. A method as claimed in claim 54, further enabling to dynamically simulate the quantitative behavior of said virtual-models or their subsystems, wherein said stored instances of reservoir building-blocks and of said process building-blocks and/or their inputs and outputs further comprise one or more quantitative variables and/or parameters of one or more different types characteristic of the components of said complex-systems they represent, further comprising the steps of:
  storing in said computer system means providing simulation functions associated with said different types of variables to compute their values over time, and
  executing said simulation means to run simulations by dynamically computing during a run the values of the instances of said variables associated with any of the instances of said reservoir building-blocks and of said process building-blocks and/or their inputs and outputs comprised in the simulation model selected for said run, said values being dependent on the values of any number of other instances of variables and/or parameters associated with the same instance and/or their inputs and outputs or with instances of said building-blocks linked to said instance as inputs in said model.

56. A method as claimed in claim 55, wherein:
said quantitative variables associated with said instances of reservoir building-blocks comprise
one or more different types of state variables representing current quantitative measures of the units in the population it represents, including one or more of concentration, density, quantity, scaled-quantity, or any other measure; and
said associated simulation means dynamically compute the values for any instance of said state variables associated with any instance of said reservoir building-blocks by integrating the sum of the rate(s) of input from any number of process building-blocks linked as inputs to said reservoir building-block less the sum of the rate(s) of out to any number of process building-blocks linked as outputs of said reservoir building-block, plus or minus any other optional mathematically modeled inputs or outputs.

57. A method as claimed in claim 55 further comprising the steps of:
   storing in said computer system means enabling the fitting of the values of one or more of said different types of quantitative parameters, and
   executing said stored means to fit the values of any number of parameters of said types of any number of instances of building-blocks of a virtual-model in order to adapt the behavior of said virtual-model or its subsystems to the experimental observations of said complex systems.

58. A method as claimed in claim 55, wherein:
   said quantitative variables of said instances of process building-blocks and/or their inputs and outputs comprise any number of instances of one or more different types of dependent variables representing rates of change of the represented processes and/or their different types of inputs and outputs, and
   said associated simulation means dynamically compute the values for any instance of said variables associated with any instance of said process building-blocks and/or its input(s) by directly or indirectly incorporating: the current value(s) of the corresponding variable(s) of one or more instances of reservoir building-blocks linked to input(s) of said instances of process building-blocks, and the values of any number of parameters specific for said instances of process building-blocks and/or their inputs and outputs.

59. A method as claimed in claim 54 wherein:
   the one or more input(s) and output(s) of said prototypes of process building-blocks are of one or more different types further representing he one or more different types of roles said inputs play in each type of process represented by said prototype of process building-blocks, and
   the one or more different types of outputs from said process, respectively;
   said stored means further provide functions associated with said different type(s) of building-blocks or their components to be executed for any number of instances of said building blocks upon selection by a user or by said program means.

60. A method as claimed in claim 59, wherein said stored means provide query-functions further enabling the step of performing queries comprising one or more search criteria based on said different types of inputs and/or based on said downstream or upstream position of said building-blocks in relation to any of said instances selected as reference.

61. A method as claimed in claim 59, wherein said stored means provide pathways-display functions further enabling the steps of
   dynamically generating at run time visual displays of multidimensional networks of interconnected pathways representing components of said virtual models of said complex-systems or their subsystems, wherein the nodes of said networks are visually ordered and connected representations of series of said linked instances of building blocks that are downstream and/or upstream of any number of selected instance(s) of said building blocks.

62. A method as claimed in claim 59, further enabling to dynamically simulate the quantitative behavior of said virtual-models or their subsystems, wherein said stored instances of reservoir building-blocks and of process building-blocks and/or their different types of inputs and outputs further comprise one or more quantitative variables and/or parameters of one or more different types characteristic of the components of said complex-systems they represent, further comprising the steps of:
   storing in said computer system means providing simulation functions associated with said different types of variables to compute their values over time, and
   executing said simulation means run simulations by dynamically computing during a run the values of the instances of said variables associated with any of the instances of said reservoir building-blocks and of said process building-blocks and/or their inputs and outputs comprised in the simulation model selected for said run, said values being dependent on the values of any number of other instances of variables and/or parameters associated with the same instance and/or their inputs and outputs or with instances of said building-blocks linked to said instance as inputs in said model.

63. A method as claimed in claim 62 wherein said stored instances of building-blocks comprise two corresponding sets of said quantitative variables and parameters, one set to hold absolute values and the other set to hold scaled relative values, and said simulation means further comprise scaling and unsealing functions defined for the different types of said variables, further comprising the step of performing dynamic mixed-type simulations of said virtual-models with data of different degrees of precision for different parts of said complex-systems.

64. A method as claimed in claim 54, wherein:
   each instance of said reservoir building-blocks comprises one or more input(s) and/or output(s) to individually represent the one or more input(s) and/or output(s) of the population represented by said instance;
   the complementary instances of said reservoir and process building-blocks are linked through one-to-one output-input links between one of said output(s) of an instance of said building-blocks and one of said input(s) of an instance of a complementary building-block, representing that the inputs represented by said inputs are the outputs represented by said outputs;
   said stored means further provide navigation functions associated with said input(s) and output(s) of said building-blocks enabling the further step of successively displaying visual representations of the instance(s) of complementary building-blocks linked to any selected input or output.

65. A method as claimed in claim 53, further comprising the steps of:
   storing in said computer system means providing functions associated with said different type(s) of building-blocks or their components, including selection functions; and
   executing said means for any number of instances of said building-blocks upon selection by a user or by said program means.

66. A method as claimed in claim 65, wherein said stored means provide navigation functions further enabling the interactive step of successively displaying visual representations of instance(s) of said building-blocks from any selected instance of said building-blocks to any of the instances of complementary building blocks linked as input(s) or output(s).

67. A method as claimed in claim 65, wherein said stored means provide list functions further enabling the step of listing instances of reservoir and/or process building-blocks that are downstream and/or upstream of any selected instance of building-blocks.

68. A method as claimed in claim 65, wherein said stored means provide query functions further enabling the step of performing queries comprising at least one search criteria based on said downstream or upstream position of reservoir or process building-blocks from any of said instances of building-blocks selected as reference.

69. A method as claimed in claim 65, wherein said stored means provide pathways-display functions further enabling the step of dynamically generating at run time visual displays of multidimensional networks of interconnected pathways which visual nodes representing components of said virtual models of said complex-systems or their subsystems, wherein the nodes of said networks are visually ordered and connected representations of series of said linked instances of building blocks that are downstream and/or upstream of any number of selected instance(s) of said building-blocks.

70. A method as claimed in claim 65, further enabling to dynamically simulate the quantitative behavior of said virtual-models or their subsystems, wherein said stored instances of reservoir and process building-blocks further comprise one or more quantitative variables and/or parameters of one or more different types characteristic of the components of said complex-systems they represent, further comprising the steps of;

storing in said computer system means providing simulation functions associated with said different types of variables to compute their values over time, and executing said simulation means to run simulations by dynamically computing during a run the values of the instances of said variables associated with any of the instances of said building-blocks comprised in the simulation model selected for said run, said values being dependent on the values of any number of other instances of variables and/or parameters associated with the same instance or with instances of said building-blocks linked to said instance as inputs in said model.

71. A method as claimed in claim 70 wherein said stored instances of building-blocks comprise two corresponding sets of said quantitative variables and parameters, one set to hold absolute values and the other set to hold scaled relative values, and said simulation means further comprise scaling and unscaling functions defined for the different types of said variables, further comprising the step of performing dynamic mixed-type simulations of said virtual-models with data of different degrees of precision for different parts of said complex-systems.

72. A method for utilizing virtual-models of complex-systems in a computer system comprising processor means, memory means, storage means, program means, and stored persistent data sets comprising instances of building-blocks representing the components of said complex-system(s), comprising the steps of:

loading into said memory means one or more of said stored datasets comprising any number of instances of one or more different types of composite process building-blocks, each representing a conceptual process in which one or more populations of entities participate, the different type(s) of process building-blocks representing one or more different types of processes characteristic of said complex-system, wherein:

each of said represented processes may comprise any number of equivalent and cumulative actual processes where subpopulations of said populations participate;

each instance comprises as components: any number of instances of one or more different type(s)of reactant building-blocks representing one or more different populations of entities that are input(s) to the represented process as well as different types of roles that said inputs play in said process, and any number of instances of one or more different type(s)of product building-blocks representing one or more different populations of entities that are output(s) from the represented process, wherein each of said populations comprise any number of units of entities or entity-complexes of a given type or in a given state or compartment;

individual instances of said product building-blocks have output-input links to one or more instance(s) of said reactant building-blocks of different instances of process building-blocks, representing that an output of a represented process provides input(s) to other processes, wherein an instance of said reactant building-blocks may have output-input links from any number of instance(s) of said product building-blocks; and said building-blocks comprise any number of attributes which values are either used to describe the characteristics of the types of components of said complex-systems that said types of building-blocks represent, or characteristics of said types or individual instances of building-blocks in said computer system, or values or data structures used by said program at runtime, or more specifically to describe or point to characteristics of individual components of said complex-systems that each instance of said types of building-blocks represents, said attributes having values of any type, including but not limited to: character string, integer or real numbers, logical values, fuzzy values, instances of parameters, variables, lists, arrays, images, or any other data structure, or pointers to other instances of any of said building-blocks, external files, Uniform Resource Locators (URLs), database records, or any other structures, in said computer system or in a network accessible by said computer system;

synthesizing said virtual-model(s) by said program means by integrating said individually linked instances of building-blocks into a multidimensional network of pathways wherein:

the nodes of said network are said instances of process building-blocks or their reactant and product building-blocks, each of said nodes being comprised in one or more of said pathways;

different pathways merge at any of said nodes with multiple linked reactants and different pathways branch at any of said nodes with multiple linked products;

said networks may be of many level of complexity due to the possible one to many, many to one, and many to many links, and from the possible forward and feedback loops; and any instance(s) of said building-blocks representing components that provide input(s) to a reference component represented by a reference instance of said building-blocks or that directly or indirectly may influence said input(s) in one or more pathways are said to be upstream of said reference instance, and any instance(s) of said building-blocks that representing components that receive output(s) from said reference component or that directly or indirectly may be influenced by said output(s) in one or more pathways are said to be downstream of said reference instance; and executing by said program means one or more stored means providing functions associated with said types of building-blocks for any instances of said types of building-blocks selected by a user or by said program.

73. A method as claimed in claim 72, wherein said stored means further provide pathways-display functions enabling the further step of:

dynamically generating at run time visual displays of multidimensional networks of interconnected pathways representing components of the virtual-models of said complex-systems or their subsystems, wherein the nodes of said networks are visually ordered and connected representations of series of said linked instances of building blocks that are downstream and/or upstream of any number of selected instance(s) of building blocks.

74. A method as claimed in claim 72, wherein:

said persistent data sets further comprise instances of one or more different types of reservoir building-blocks representing conceptual populations of any number of units of entities or entity-complexes of a given type or in a given state or compartment which may provide inputs to or receive outputs from any number of corresponding processes, wherein the units of each of said represented populations may be disperse among the units of other populations in said complex-systems, each of said instances comprise any number of input(s) and/or output(s) individually representing the input(s) and/or output(s) of the population represented by said instance;

said output-input links are between any one instance of said product building-blocks and the input of a complementary instance of reservoir building-block(s) that represents the input to the population that receives the represented output, and between any one output of an instance of reservoir building-block(s) and the complementary instance of reactant building-blocks that represents the input to the process that receives the represented output;

any instance of said process building-blocks is linked, through any number of its reactants and/or products building-blocks, to any number of instances of said reservoir building-block(s), and in any instance of said reservoir building-blocks is linked, through any number of its inputs and/or outputs, to any number of instances of said process building-blocks;

the functional nodes of the multidimensional networks of said virtual-models are alternating complementary instances of reservoir building-blocks and process building-blocks; and said stored means further provide navigation functions associated with said building-blocks further enabling the step of successively displaying visual representations of any of the instances of complementary building blocks linked to input(s) or output(s) of any selected instance of said building-blocks.

75. A method as claimed in claim 74, wherein said stored instances of reservoir, reactant, product, and process building-blocks further comprise any number of instances of quantitative variables and/or parameters of one or more different types characteristic of the components of said complex-systems they represent, further comprising the steps of:

storing in said computer system means to dynamically simulate the quantitative behavior of said virtual-models or their subsystems over time, comprising simulation functions associated with said different types of variables to compute their values over time, and executing said simulation means to dynamically compute during a simulation run the values of the instances of said different types of variables associated with any of the instances of said building-blocks comprised in the simulation model selected for said run, said values being dependent on the values of any number of other instances of variables and/or parameters associated with the same instance or with instances of said building-blocks linked to said instance as inputs in said model.

76. A method as claimed in claim 75 wherein said stored instances of building-blocks comprise two corresponding sets of said quantitative variables and parameters, one set to hold absolute values and the other set to hold scaled relative values, and said simulation means further comprise scaling and unscaling functions defined for the different types of said variables, further comprising the step of performing dynamic mixed-type simulations of said virtual-models with data of different degrees of precision for different parts of said complex-systems.

* * * * *